(12) United States Patent
Spada et al.

(10) Patent No.: US 7,749,530 B2
(45) Date of Patent: Jul. 6, 2010

(54) KINASE INHIBITORS

(75) Inventors: Lon T. Spada, Walnut, CA (US); Jane Guo Shiah, Irvine, CA (US); Patrick Hughes, Aliso Viejo, CA (US); Thomas C. Malone, Irvine, CA (US); Gerald W. DeVries, San Clemente, CA (US); Jeffrey L. Edelman, Irvine, CA (US); Julie A. Wurster, Irvine, CA (US); Wendy M. Blanda, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/317,469

(22) Filed: Dec. 23, 2008

(65) Prior Publication Data

US 2009/0208557 A1  Aug. 20, 2009

Related U.S. Application Data

(63) Continuation-in-part of application No. 11/456,926, filed on Jul. 12, 2006.

(60) Provisional application No. 60/699,247, filed on Jul. 13, 2005.

(51) Int. Cl.
*A61K 31/404* (2006.01)
(52) U.S. Cl. ............... 424/427; 514/414; 514/419; 514/954
(58) Field of Classification Search ........... 424/427; 514/414, 419, 954
See application file for complete search history.

(56) References Cited

U.S. PATENT DOCUMENTS

| 5,792,783 | A  | 8/1998  | Tang et al. |
| 5,834,504 | A  | 11/1998 | Tang et al. |
| 5,883,113 | A  | 3/1999  | Tang et al. |
| 5,883,116 | A  | 3/1999  | Tang et al. |
| 5,886,020 | A  | 3/1999  | Tang et al. |
| 6,331,313 | B1 | 12/2001 | Wong et al. |
| 6,541,504 | B1 | 4/2003  | Andrews et al. |
| 6,559,173 | B1 | 5/2003  | Andrews et al. |
| 6,699,863 | B1 | 3/2004  | Andrews et al. |
| 6,747,025 | B1 | 6/2004  | Andrews et al. |
| 6,765,012 | B2 | 7/2004  | Andrews et al. |
| 7,005,444 | B2 | 3/2006  | Andrews et al. |
| 7,015,220 | B2 | 3/2006  | Andrews et al. |
| 7,060,844 | B2 | 6/2006  | Andrews et al. |

FOREIGN PATENT DOCUMENTS

| WO | WO99/15500    | 4/1999 |
| WO | WO03/027102   | 4/2003 |
| WO | WO2006/052936 | 5/2006 |

OTHER PUBLICATIONS

Antcliff R., et al Marshall J., *The Pathogenesis Of Edema In Diabetic Maculopathy*, Semin Ophthalmol 1999; 14:223-232.
Plowman et al, "Receptor Tyrosine Kinases as Targets for Drug Intervention", 1994, DN&P 7(6): 334-339.
Bolen, "Nonreceptor tyrosine protein kinases", 1993, Oncogen 8: pp. 2025-2031.

*Primary Examiner*—Kamal A Saeed
*Assistant Examiner*—Samantha L Shterengarts
(74) *Attorney, Agent, or Firm*—Kenton Abel; Debra Condino

(57) ABSTRACT

The present invention relates to drug delivery systems comprising ocular implant, which include organic molecules, capable of modulating tyrosine kinase signal transduction in order to regulate, modulate and/or inhibit abnormal cell proliferation, in combination with a polymer, which polymer serves to control, modify, modulate and/or slow the release of the therapeutic component into the environment of the eye in which said composite is placed.

31 Claims, 3 Drawing Sheets

KINASE INHIBITORS

CROSS REFERENCE TO RELATED APPLICATIONS

Figure 1:
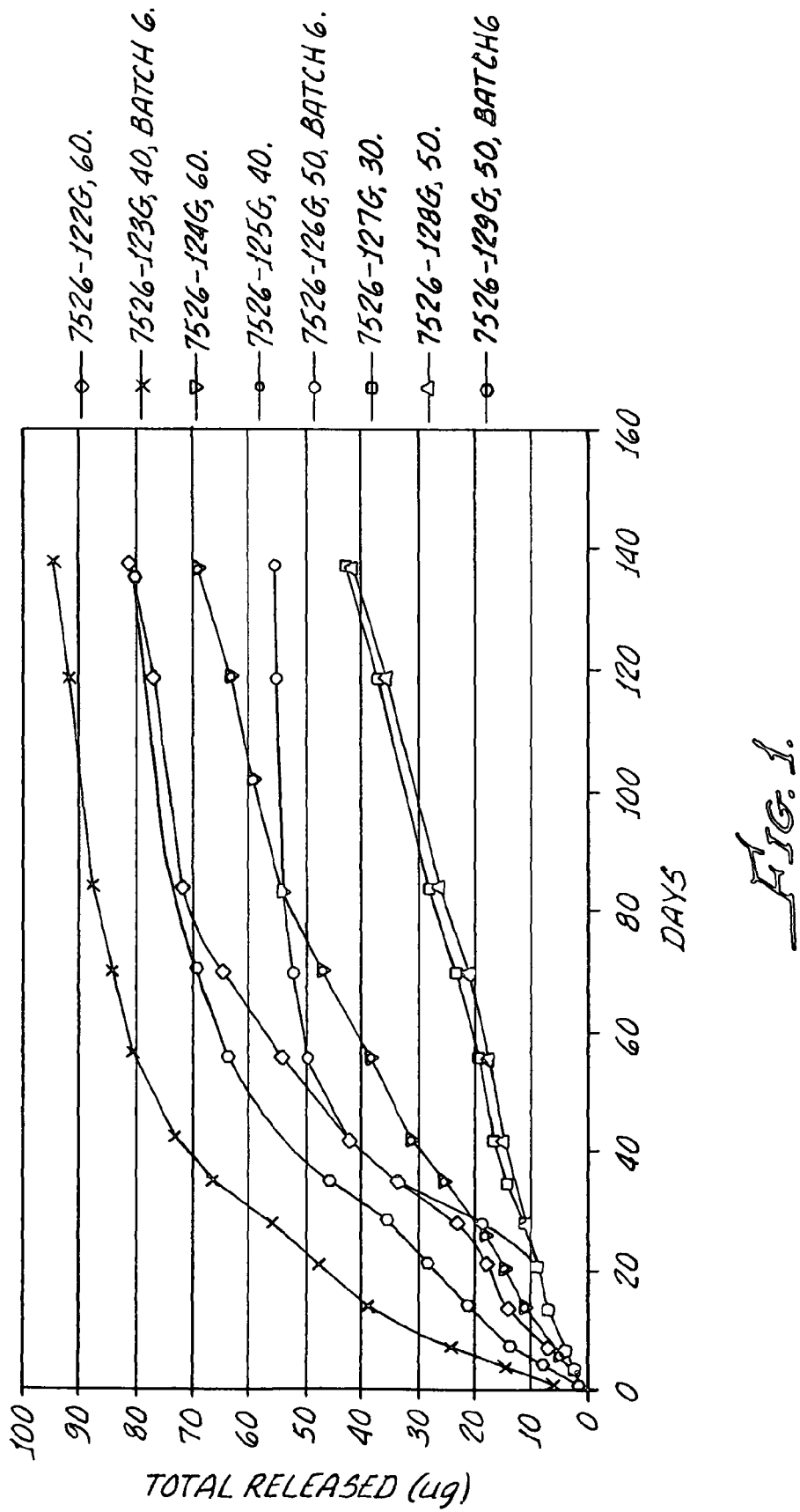

This application is a continuation in part of U.S. patent application Ser. No. 11/456,926 filed on Jul. 12, 2006, in the names of Wurster et al. and entitled KINASE INHIBITORS, which is incorporated herein by reference, which patent application is based on, and claims the benefit of, U.S. Provisional Application No. 60/699,247, filed Jul. 13, 2005, and which is also incorporated herein by reference

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-$\alpha$, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF $\alpha$ and $\beta$ receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands soluble receptors and antibodies RNA ligands and tyrosine kinase inhibitors.

More recently, attempts have been made to identify small molecules which act as tyrosine kinase inhibitors. For example, bis monocyclic, bicyclic or heterocyclic aryl compounds, vinylene-azaindole derivatives and 1-cyclopropyl-4- pyridyl-quinolones have been described generally as tyrosine kinase inhibitors. Styryl compounds, styryl-substituted pyridyl compounds certain quinazoline derivatives seleoindoles and selenides, tricyclic polyhydroxylic compounds and benzylphosphonic acid compounds have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. See also, U.S. Pat. Nos. 6,541,504; 6,559,173; 6,765,012; 6,747,025; 6,699,863; 7,005,444; 7,015,220 and 7,060,844. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

DESCRIPTION OF THE DRAWING FIGURES

FIG. 1 shows the release rate plot for 2,5-Dimethyl-2H-pyrazole-3-carboxylic acid (3-{2-oxo-3-[(4-pyrrolidin-1-yl-methyl-phenylamino)-methylene]-2,3-dihydro-1H-indole-6-carbonyl}-phenyl)-amide in phosphate buffered saline release medium, pH 7.4

Figure 2:
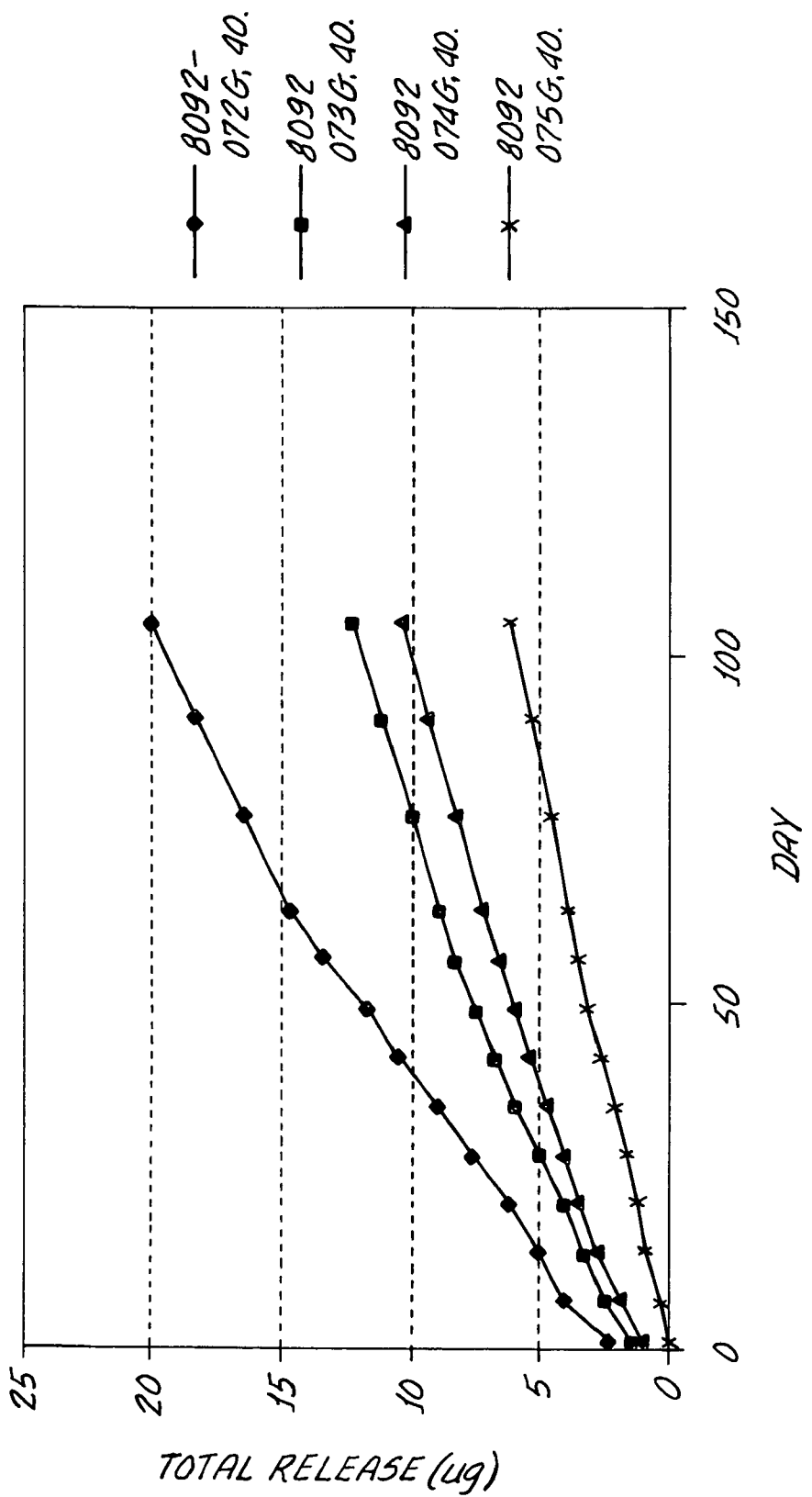

FIG. 2. Shows the release rate plot for 4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid in phosphate buffered saline release medium, pH 7.4

Figure 3:
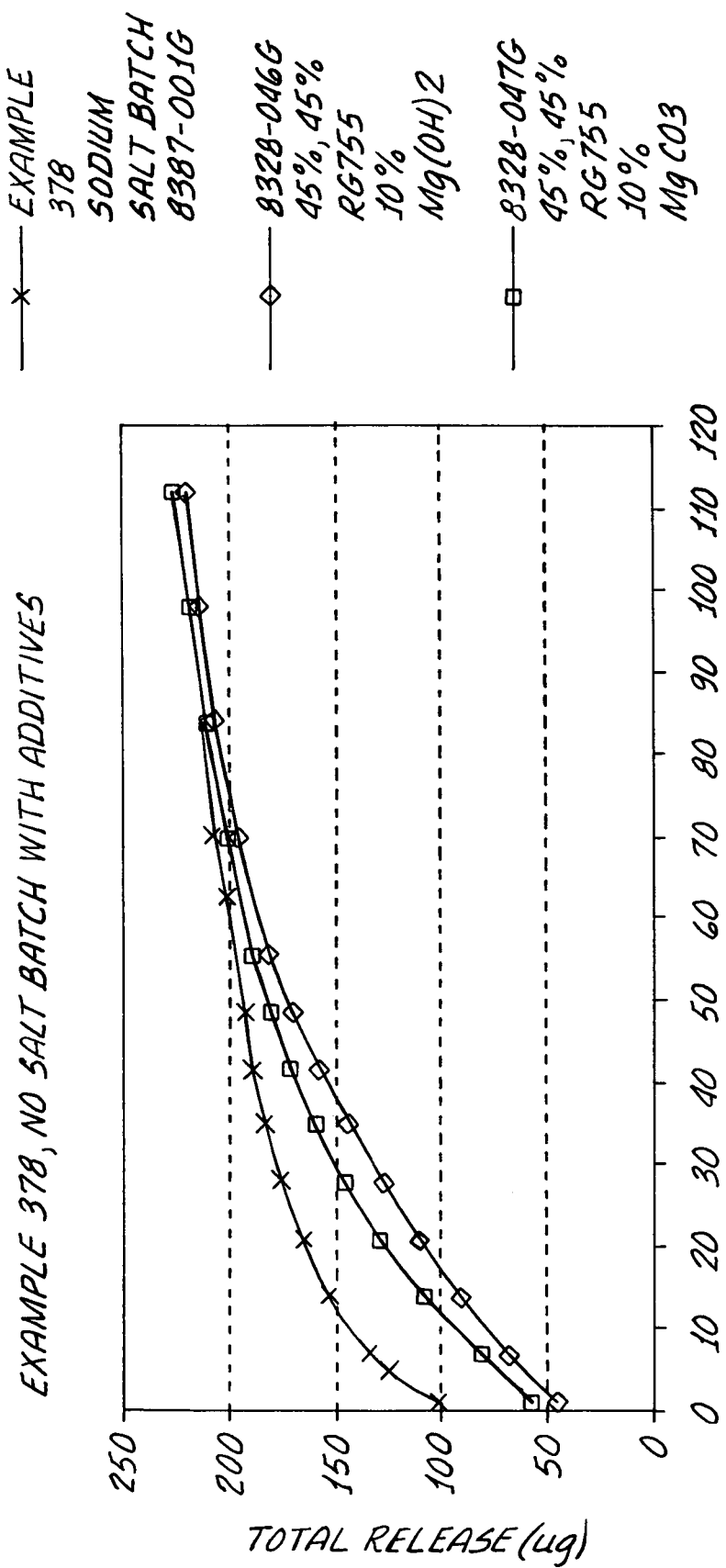

FIG. 3: Shows the release rate plot for 3-{4-[(6-{3-[(3-Methyl-furan-2-carbonyl)-amino]-benzoyl}-2-oxo-1,2-dihydro-indol-3-ylidenemethyl)-amino]-phenyl}-propionic acid in phosphate buffered saline release medium, pH 7.4.

BRIEF SUMMARY OF THE INVENTION

The present invention relates to composites of organic molecules capable of modulating, regulating and/or inhibiting tyrosine kinase signal transduction and a polymer, e.g. a bioerodible polymer. Such composites are useful for the treatment of diseases related to unregulated TKS transduction, including cell proliferative diseases such as cancer, restenosis, conditions associated with metabolic diseases such as diabetes, inflammatory diseases vascular proliferative disorders such as diabetic retinopathy, age-related macular degeneration and retinopathy of prematurity, autoimmune diseases and transplant rejection. The TKI compounds utilized in the composites, i.e. the ocular implants, of this invention are selected from the compounds represented by formula I and II, below:

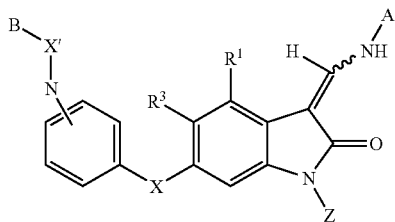

I

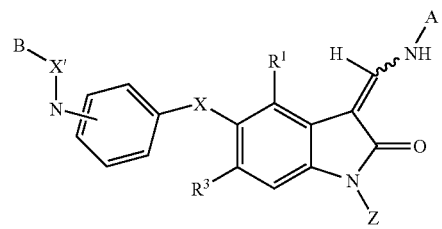

II

Wherein substitutents listed are illustrated but not limited to the illustrative list set forth below:

wherein X is selected from the group consisting of C=O, C=S, $CR^4R^5$, O, S, NH, and $NR^4$;

Z is selected from the group consisting of hydrogen, $C_1$ to $C_8$ alkyl, phenyl, hydroxymethyl, —$CH_2$—N(—$CH_2CH_2W$ $CH_2CH_2$—), $COCH_3$, $CH_2CH_2OH$, and $CH_2CH_2CH_2OH$;

W is selected from the group consisting of O, S, $CH_2$ and $NCH_3$;

$R^1$ is selected from the group consisting of hydrogen and $CH_3$;

$R^3$ is selected from the group consisting of hydrogen, $C_1$ to $C_8$ alkyl, phenyl, hydroxymethyl, $COCH_3$, $CH_2CH_2OH$, $CH_2CH_2CH_2OH$ and $[C(R^2)_2]_cN(R^2)_2$, wherein $R^2$ is selected from the group consisting of hydrogen, halogen, $NO_2$, CN, $C_1$ to $C_4$ alkyl or aryl, and $N(R^2)_2$ may form a 3 to 7 membered heterocyclic ring, for example pyrrolidine, 3-fluoropyrrolidine, piperidine, 4-fluoropiperidine, N-methylpiperazine, morpholine, 2,6-dimethylmorpholine, thiomorpholine; and said heterocyclic ring may be substituted with one or more of $R^2$; and $[C(R^2)_2]_c$ may form a 3 to 7 membered carbocyclic or heterocyclic ring;

$R^4$ and $R^5$ may be selected from the group consisting of hydrogen, halogen, $NO_2$, CN, $C_1$ to $C_8$ alkyl and aryl; or $CR^4R^5$ may form a 3 to 7 membered carbocyclic or heterocyclic ring;

A is

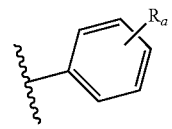

wherein,

R is selected from the group consisting of hydrogen, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, HN—$C(O)OR^2$, $(CR^7R^8)_cOC(O)(CR^7R^8)$ $N(R^2)_2$, $(CR^7R^8)_cN(R^2)_2$, $SO_2$ $(CR^7R^8)_cN(R^2)_2$, $OP(O)$ $(OR^2)_2$, $OC(O)OR^2$, $OCH_2O$, HN—CH=CH, —$N(COR^2)CH_2CH_2$, HC=N—NH, N=CH—S, $O(CR^7R^8)_d$—$R^6$, $(CR^7R^8)_c$—$R^6$ and $(CR^7R^8)_cNR_2$ $(CR^7R^8)_dR^6$ wherein $R^6$ is selected from the group consisting of halogen, 3-fluoropyrrolidinyl, piperidinyl, 4-fluoropiperidinyl, N-methylpiperazinyl, 2,6-dimethylmorpholinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, ethanolamine and alkyl-substituted derivatives thereof; provided said alkyl or phenyl radicals may be substituted with one or two halo, hydroxy or lower alkyl amino radicals or said alkyl radicals may include enchained nitrogen or oxygen atoms, i.e. oxa or imino radicals, as, for example, in polyethylene(oxy)radicals and wherein $R^7$ and $R^8$ may be selected from the group consisting of H, hydroxyl, halogen, e.g. F, and $C_1$ to $C_4$ alkyl and $CR^7R^8$ may form a carbocyclic ring of from 3 to 6 carbons;

X' is selected from the group consisting of

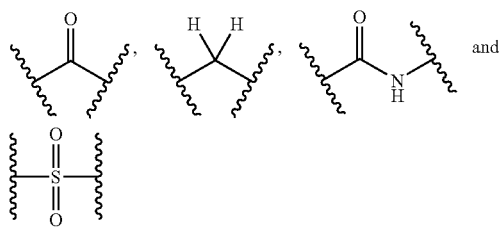

and

B may be selected from the group consisting of hydrogen, hydroxy, $C_1$ to $C_8$ alkyl, aryl and $CR^4R^5$ wherein $CR^4R^5$ may form a 3 to 7 membered carbocyclic or heterocyclic ring, e.g B may be a 5 or 6 membered aryl radical represented by formula III below:

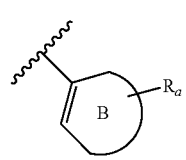

III wherein said aryl is selected from the group consisting of:

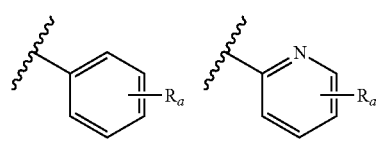

-continued

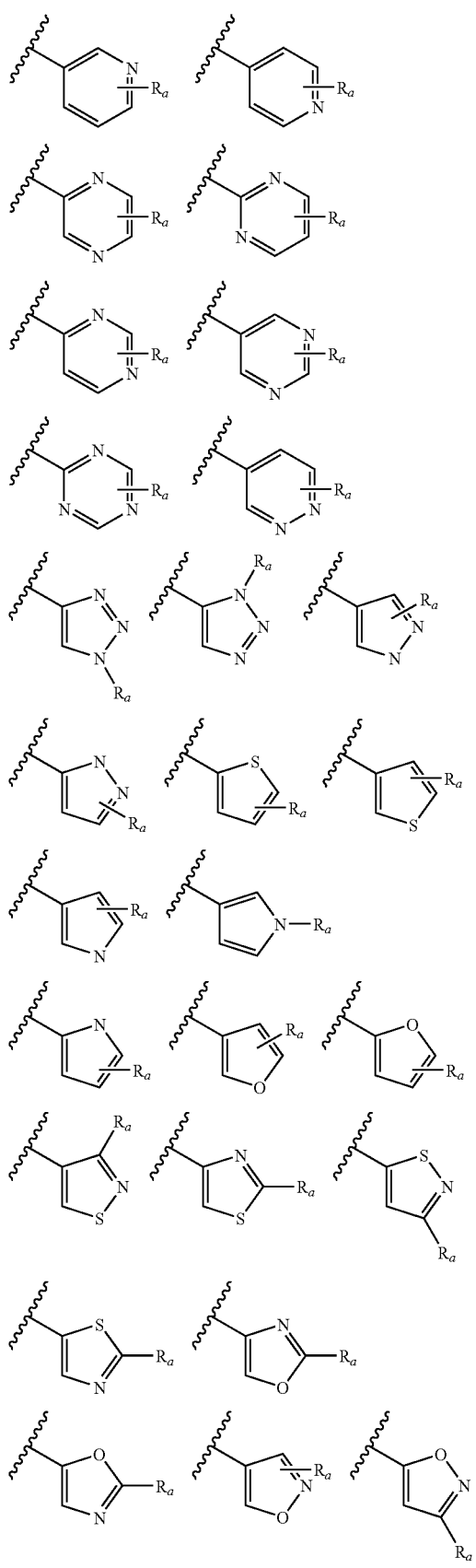

-continued

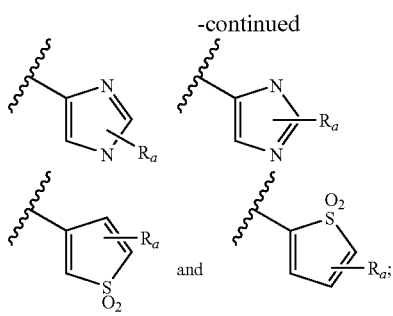

a is 0 or an integer of from 1 to 5, preferably 1 to 3;
c is 0 or an integer of from 1 to 4,
d is an integer of from 2 to 5;

the wavy line represents a E or Z bond and pharmaceutically acceptable salts thereof

DETAILED DESCRIPTION OF THE INVENTION

Compounds of the general formulas I and II are useful as kinase inhibitors in the composites of this invention. As such, said composites will be useful for treating ocular diseases, i.e. diseases of the eye, related to unregulated tyrosine kinase signal transduction.

Broadly speaking, the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (anterior to the retina but posterior to the posterior wall of the lens capsule), the lens or the lens capsule and blood vessels and nerve which vascularize or innervate an anterior ocular region or site.

A condition of the posterior segment (posterior ocular condition) of the eye is a disease, ailment or condition which significantly affects or involves a tissue or cell type in a posterior ocular region or site (that is, in a position posterior to a plane through the posterior wall of the lens capsule), such as the accordingly located parts of the choroid or sclera, vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection). The infiltrative growth of new blood vessels can disrupt or destroy nervous tissue; thus the inhibition of angiogenesis can also be considered to provide protection to affected neurons.

Macular edema is a major cause of visual loss in patients, and can accompany a number of pathological conditions, including, without limitation, diabetes, central retinal vein occlusion (CRVO) and branch retinal vein occlusion (BRVO). Although laser photocoagulation can reduce further vision loss in patients with diabetic macular edema (DME), vision that has already been decreased by macular edema through neural cell death usually does not improve appreciably by use of laser photocoagulation. Currently, there is no FDA (U.S. Food and Drug Administration) approved treatment for macular edema associated with CRVO. For macular edema associated with BRVO, grid laser photocoagulation may be an effective treatment for some patients.

Diabetic macular edema is characterized abnormal leakage of macromolecules, such as lipoproteins, from retinal capillaries into the extravascular space followed by an oncotic influx of water into the extravascular space. The leakage may be caused by or exacerbated by the growth of new blood vessels (angiogenesis). Abnormalities in the retinal pigment epithelium (RPE) may also cause or contribute to diabetic macular edema. These abnormalities can allow increased fluid from the choriocapillaries to enter the retina or they may decrease the normal efflux of fluid from the retina to the choriocapillaries. The breakdown of the blood-retina barrier at the level of the retinal capillaries and the retinal pigment epithelium may also be accompanied or caused by changes to tight junction proteins. Antcliff R., et al Marshall J., *The Pathogenesis Of Edema In Diabetic Maculopathy*, Semin Opthalmol 1999; 14:223-232.

Macular edema from venous occlusive disease can result from thrombus formation at the lamina cribrosa or at an arteriovenous crossing. These changes can result in an increase in retinal capillary permeability and accompanying retinal edema. The increase in retinal capillary permeability and subsequent retinal edema can ensue from of a breakdown of the blood retina barrier mediated in part by vascular endothelial growth factor (VEGF), a 45 kD glycoprotein. It is known that VEGF can increase vascular permeability; possibly by increasing phosphorylation of tight junction proteins such as occludin and zonula occluden. Similarly, in human non-ocular disease states such as ascites, VEGF has been characterized as a potent vascular permeability factor (VPF).

Ocular conditions which can be treated or addressed in accordance with the present invention include, without limitation, the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior veal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

As stated above, the TKI compounds utilized in the composites, i.e. the ocular implants, of this invention are selected from the compounds represented by formula I and II, below:

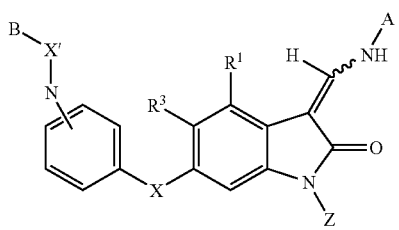

I

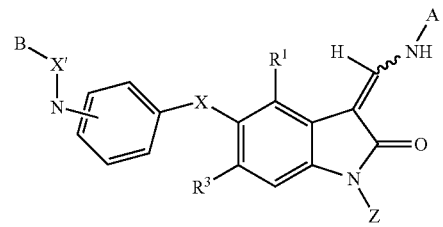

II

Wherein the substitutents may be as set forth below:
wherein X is selected from the group consisting of C=O, C=S, $CR^4R^5$, O, S, NH, and $NR^4$;
Z is selected from the group consisting of hydrogen, $C_1$ to $C_8$ alkyl, phenyl, hydroxymethyl, —$CH_2$—N(—$CH_2CH_2W$ $CH_2CH_2$—), $COCH_3$, $CH_2CH_2OH$, and $CH_2CH_2CH_2OH$;
W is selected from the group consisting of O, S, $CH_2$ and $NCH_3$;
$R^1$ is selected from the group consisting of hydrogen and $CH_3$;
$R^3$ is selected from the group consisting of hydrogen, $C_1$ to $C_8$ alkyl, phenyl, hydroxymethyl, $COCH_3$, $CH_2CH_2OH$, $CH_2CH_2CH_2OH$ and $[C(R^2)_2]_cN(R^2)_2$, wherein $R^2$ is selected from the group consisting of hydrogen, halogen, $NO_2$, CN, $C_1$ to $C_4$ alkyl or aryl, and $N(R^2)_2$ may form a 3 to 7 membered heterocyclic ring, for example pyrrolidine, 3-fluoropyrrolidine, piperidine, 4-fluoropiperidine, N-methylpiperazine, morpholine, 2,6-dimethylmorpholine, thiomorpholine; and said heterocyclic ring may be substituted with one or more of $R^2$; and $[C(R^2)_2]_c$ may form a 3 to 7 membered carbocyclic or heterocyclic ring;
$R^4$ and $R^5$ may be selected from the group consisting of hydrogen, halogen, $NO_2$, CN, $C_1$ to $C_8$ alkyl and aryl; or $CR^4R^5$ may form a 3 to 7 membered carbocyclic or heterocyclic ring;
A is

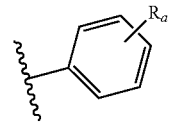

wherein,
R is selected from the group consisting of hydrogen, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, HN—$C(O)OR^2$, $(CR^7R^8)_cOC(O)(CR^7R^8)_cN(R^2)_2$, $(CR^7R^8)_cN(R^2)_2$, $SO_2$ $(CR^7R^8)_cN(R^2)_2$, $OP(O)(OR^2)_2$, $OC(O)OR^2$, $OCH_2O$, HN—CH=CH, —N($COR^2$)$CH_2CH_2$, HC=N—NH, N=CH—S, $O(CR^7R^8)_d$—$R^6$, $(CR^7R^8)_c$—$R^6$ and $(CR^7R^8)_cNR_2$ $(CR^7R^8)_dR^6$ wherein $R^6$ is selected from the group consisting of halogen, 3-fluoropyrrolidinyl, piperidinyl, 4-fluoropiperidinyl, N-methylpiperazinyl, 2,6-dimethylmorpholinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, ethanolamine and alkyl-substituted derivatives thereof; provided said alkyl or phenyl radicals may be substituted with one or two halo, hydroxy or lower alkyl amino radicals or said alkyl radicals may include enchained nitrogen or oxygen atoms, i.e. oxa or imino radicals, as, for example, in polyethylene(oxy)radicals and wherein $R^7$ and $R^8$ may be selected from the group consisting of H, hydroxyl, halogen, e.g. F, and $C_1$ to $C_4$ alkyl and $CR^7R^8$ may form a carbocyclic ring of from 3 to 6 carbons;

X' is selected from the group consisting of

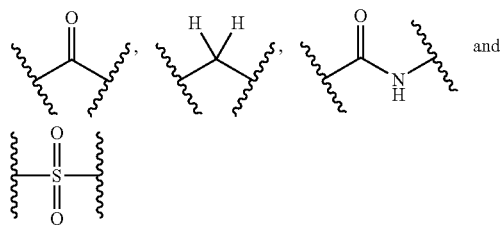

and

B may be selected from the group consisting of hydrogen, hydroxy, $C_1$ to $C_8$ alkyl, aryl and $CR^4R^5$ wherein $CR^4R^5$ may form a 3 to 7 membered carbocyclic or heterocyclic ring, e.g B may be a 5 or 6 membered aryl radical represented by formula III below:

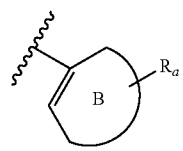

III wherein said aryl is selected from the group consisting of:

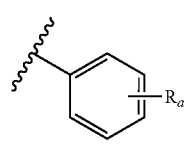 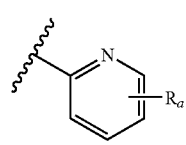

-continued

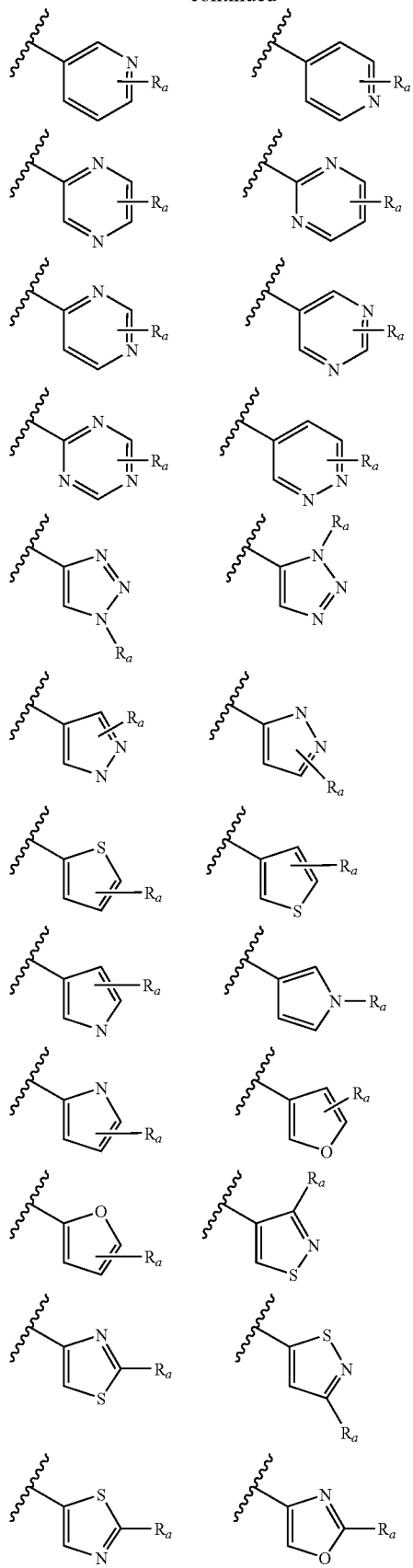

-continued

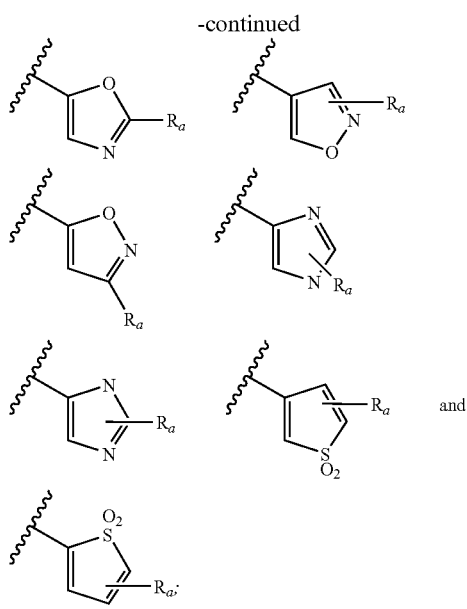

a is 0 or an integer of from 1 to 5, preferably 1 to 3;
c is 0 or an integer of from 1 to 4,
d is an integer of from 2 to 5;
the wavy line represents a E or Z bond and pharmaceutically acceptable salts thereof.
Preferably Z, $R^1$ and $R^3$ are H.
Preferably X' is selected from the group consisting of

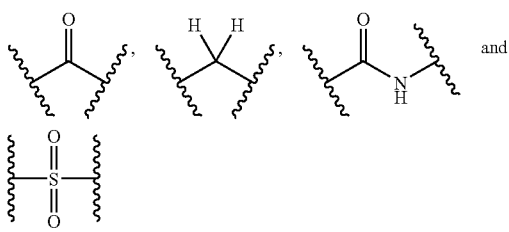

Preferably B is selected from the group consisting of 5-membered heterocyclic aryl radicals and 6-membered carbocyclic aryl radicals.

More preferably, X is

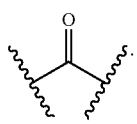

More preferably, X' is

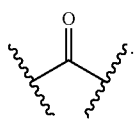

More preferably, B is a 5-membered heterocyclic aryl radical wherein the heterocyclic ring comprises one oxygen or sulfur atom or two nitrogen atoms.

More preferably, said heterocyclic aryl radical is substituted with a lower alkyl group or a halogen radical.

In another embodiment, B is phenyl and said phenyl radical may be substituted with a lower alkyl radical.

Preferably a is 1 or 2 and at least one R is H or OH or a is 1 and R is selected from the group consisting of carboxylic acid radicals, and 5 or 6 membered heterocyclic radicals wherein the heterocyclic ring includes a first enchained nitrogen atom and optionally, an enchained oxygen atom or a second enchained nitrogen atom.

Preferably R includes a carboxylic acid radical which is covalently bonded to a phenyl group through a polymethylene group, e.g. an ethenylenyl or a propenylenyl group.

Preferably R includes a heterocyclic ring which is directly bonded to the phenyl group or indirectly through a polymethylene group wherein, in either case, said bond is through an enchained nitrogen atom in said heterocyclic ring.

More preferably, said heterocyclic ring is selected from the group consisting of pyrrolidine, morpholine, piperazine and piperidine and said heterocyclic ring is substituted with a lower alkyl or a hydroxyl radical.

R may be

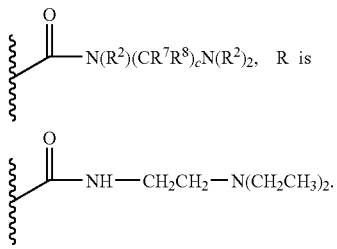

In another embodiment, B is selected from the group consisting of furyl, thienyl, pyrazole and imidazole.

In the present invention there is provided a drug delivery system comprising a therapeutic component, comprising one or more of the above compounds, in combination with a polymer to form a composite of said therapeutic component and said polymer, said composite being configured and suitable for insertion into the eye of a patient suffering from an ocular disease or condition, wherein said polymer serves to control, modify, modulate and/or slow the release of the therapeutic component into the environment of the eye in which said composite is placed.

Intraocular Implant

In a first aspect of the ocular composite of this invention there is provided an intraocular implant in accordance with the disclosure herein which comprises a therapeutic component, i.e. a tyrosine kinase inhibitor, and a drug release sustaining polymer component associated with the therapeutic component. The implants may be solid, semisolid, or viscoelastic. In accordance with the present invention, the therapeutic component comprises, consists essentially of, or consists of, a tyrosine kinase inhibitor (TKI), for example, an agent or compound that inhibits or reduces the activity of tyrosine kinase. The TKI may also be understood to be a small molecule TKI. The drug release sustaining component is associated with the therapeutic component to sustain release of an amount of the TKI into an eye in which the implant is placed. TKIs may be released from the implant by diffusion, erosion, dissolution or osmosis. The drug release sustaining component may comprise one or more biodegradable polymers or one or more non-biodegradable polymers. Examples of biodegradable polymers of the present implants may include poly-lactide-co-glycolide (PLGA and PLA), polyesters, poly (ortho ester), poly(phosphazine), poly(phosphate ester), polycaprolactone, natural polymers such as gelatin or collagen, or polymeric blends. The amount of the TKI is released into the eye for a period of time greater than about one week after the implant is placed in the eye and is effective in reducing or treating an ocular condition.

In one embodiment, the intraocular implants comprise a TKI and a biodegradable polymer matrix. The TKI is associated with a biodegradable polymer matrix that degrades at a rate effective to sustain release of an amount of the TKI from the implant effective to treat an ocular condition. The intraocular implant is biodegradable or bioerodible and provides a sustained release of the TKI in an eye for extended periods of time, such as for more than one week, for example for about one month or more and up to about six months or more. The implants may be configured to provide release of the therapeutic agent in substantially one direction, or the implants may provide release of the therapeutic agent from all surfaces of the implant.

The biodegradable polymer matrix of the foregoing implants may be a mixture of biodegradable polymers or the matrix may comprise a single type of biodegradable polymer. For example, the matrix may comprise a polymer selected from the group consisting of polylactides, poly(lactide-co-glycolides), polycaprolactones, and combinations thereof.

In another embodiment, intraocular implants comprise a therapeutic component that comprises a TKI, and a polymeric outer layer covering the therapeutic component. The polymeric outer layer includes one or more orifices or openings or holes that are effective to allow a liquid to pass into the implant, and to allow the TKI to pass out of the implant. The therapeutic component is provided in a core or interior portion of the implant, and the polymeric outer layer covers or coats the core. The polymeric outer layer may include one or more non-biodegradable portions. The implant can provide an extended release of the TKI for more than about two months, and for more than about one year, and even for more than about five or about ten years. One example of such a polymeric outer layer covering is disclosed in U.S. Pat. No. 6,331,313.

Advantageously, the present implants provide a sustained or controlled delivery of therapeutic agents at a maintained level despite the rapid elimination of the TKIs from the eye. For example, the present implants are capable of delivering therapeutic amounts of a TKI for a period of at least about 30 days to about a year despite the short intraocular half-lives associated with TKIs. Plasma TKI levels obtained after implantation are extremely low, thereby reducing issues or risks of systemic toxicity. The controlled delivery of the TKIs from the present implants permits the TKIs to be administered into an eye with reduced toxicity or deterioration of the blood-aqueous and blood-retinal barriers, which may be associated with intraocular injection of liquid formulations containing TKIs.

A method of making the present implants involves combining or mixing the TKI with a biodegradable polymer or polymers. The mixture may then be extruded or compressed to form a single composition. The single composition may then be processed to form individual implants suitable for placement in an eye of a patient.

Another method of making the present implants involves providing a polymeric coating around a core portion containing a TKI, wherein the polymeric coating has one or more holes.

The implants may be placed in an ocular region to treat a variety of ocular conditions, such as treating, preventing, or reducing at least one symptom associated with non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, retinitis pigmentosa, ocular tumors, ocular neoplasms, and the like.

Kits in accordance with the present invention may comprise one or more of the present implants, and instructions for using the implants. For example, the instructions may explain how to administer the implants to a patient, and types of conditions that may be treated with the implants.

Intravitreal Implant

In a second aspect of the present invention, there is provided a biodegradable intravitreal implant comprising: a plurality of biodegradable polymer microspheres encapsulating a tyrosine kinase inhibitor (TKI), the microspheres releasing the TKI at a rate effective to sustain release of the TKI from the microspheres for at least about one week after the implant is placed in the vitreous of an eye. By encapsulating it is meant that the active agent is associated with, dispersed within, mixed with and/or embedded in the polymer.

The microspheres of this biodegradable intravitreal implant can release the TKI at a rate effective to sustain release of an amount of the TKI from the implant for more than one month from the time the implant is placed in the vitreous of the eye. The TKI can be present in the implant (i.e. the plurality of microspheres) in an amount of from about 5% by weight to about 70% by weight, preferably from about 40% by weight to about 60% by weight of the implant, and the biodegradable polymer matrix can comprise a poly(lactide-co-glycolide) in an amount from about 30% by weight to about 95% by weight, preferably from about 40% by weight to about 60% by weight of the implant.

A process for making biodegradable active agent microspheres includes the following steps:

(a) preparing an organic phase, which comprises, an active agent, a biodegradable polymer, and a solvent for the active agent and the polymer;

(b) preparing a first aqueous phase; containing at least one emulsifier, e.g. the emulsifier can be polyvinyl alcohol (PVA), polysorbate, poloxamer, etc.

(c) combining the organic and the aqueous phase to form an emulsion;

(d) preparing a second aqueous phase;

(e) adding the second aqueous phase to the emulsion to form a solution (f) stirring the solution, and;

(g) evaporating the solvent, thereby making biodegradable active agent microspheres.

The organic phase can be a viscous fluid. This method can also have the step of crystallizing active agent in the organic phase and/or the further step of crystallizing active agent in the emulsion.

Preferably, the pH of the first aqueous phase is between about pH 6 and about pH 8 and the pH of the second aqueous phase is between about pH 4 and about pH 9.

A detailed process for making biodegradable active agent microspheres can have the steps of:

(a) preparing a viscous organic phase, which comprises, a TKI, a biodegradable PLGA (or PLA) polymer, and a solvent for the active agent and the PLGA (or PLA) polymer;

(b) crystallizing active agent in the viscous organic phase (c) preparing a first aqueous phase with a pH between about pH 6 and about pH 8;

(d) combining the organic and the aqueous phase to form an emulsion;

(e) crystallizing active agent in the emulsion;

(f) preparing a second aqueous phase with a pH between about pH 4 and about pH 9;

(g) adding the second aqueous phase to the emulsion to form a suspension (h) stirring the suspension, and;

(i) evaporating the solvent, thereby making biodegradable active agent microspheres. The active agent can be a TKI.

The presently disclosed invention also encompasses a method for treating an ocular condition of an eye of a patient by placing biodegradable intraocular microspheres into the vitreous of an eye of the patient, the microspheres comprising a TKI and a biodegradable polymer, wherein the microspheres degrades at a rate effective to sustain release of an amount of the TKI from the microspheres effective to treat the ocular condition. The ocular condition can be, for example, a retinal ocular, glaucoma or a proliferative vitreoretinopathy.

In an alternative embodiment a biodegradable intravitreal implant comprising a tyrosine kinase inhibitor (TKI) and a biodegradable polymer can be prepared by a method comprising the step of: extruding a mixture of a TKI and a biodegradable polymer to form a biodegradable implant that degrades at a rate effective to sustain release of an amount of the TKI from the implant for at least about one week after the implant is placed in the vitreous of an eye. The mixture can consist essentially of the TKI and the biodegradable polymer. The polymer can be a polylactide, poly(lactide-co-glycolide), polycaprolactone, or a derivative thereof, or a mixture thereof. The polymer can release the TKI at a rate effective to sustain release of an amount of the TKI from the implant for more than one month from the time the implant is placed in the vitreous of the eye. The TKI can be provided in an amount from about 5% by weight to about 70% by weight, preferably from about 30% by weight to about 70% by weight of the implant, and the biodegradable polymer matrix can comprise a poly(lactide-co-glycolide) in an amount from about 30% by weight to about 95% by weight, preferably from about 30% by weight to about 70% by weight of the implant. More preferably, the TKI can be provided in an amount from about 40% by weight to about 60% by weight of the implant, and the biodegradable polymer matrix can comprise a poly(lactide-co-glycolide) in an amount from about 40% by weight to about 60% by weight of the implant.

The microspheres of the present invention may range in size from 1-100 um and may include additives, e.g. cholesterol, PEG, etc, to modify the release rate of the TKI from the microsphere or reduce inflammation etc.

The TKI can be present in the microspheres in various forms, e.g. in a dispersed molecular form, or as crystalline aggregates.

The microspheres of the present invention can be administered by injection, i.e. as a suspension in an appropriate vehicle, e.g. a viscous vehicle, such as a hyaluronic acid gel, containing up to 30% by weight of the microspheres, by means of a 22 G-30 G needle, preferably to form a depot comprising said microspheres.

Finally, the polymer may be selected to have a degradation rate, whereby The microparticles partially or completely disappear before next injection.

The most preferred TKIs for utilization in the ocular implants of this invention are:

Example 206

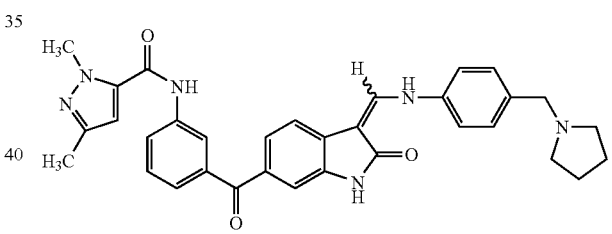

2,5-Dimethyl-2H-pyrazole-3-carboxylic acid (3-{2-oxo-3-[(4-pyrrolidin-1-ylmethyl-phenylamino)-methylene]-2,3-dihydro-1H-indole-6-carbonyl}-phenyl)-amide.

Example 324

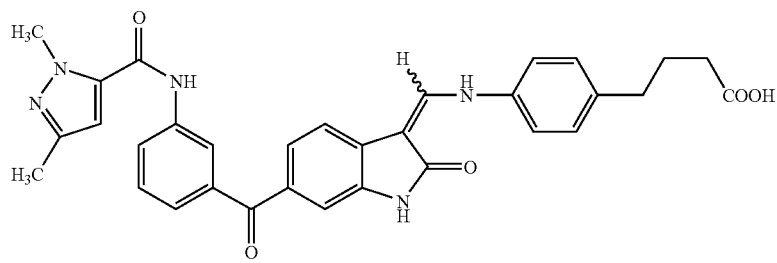

4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid.

Example 355

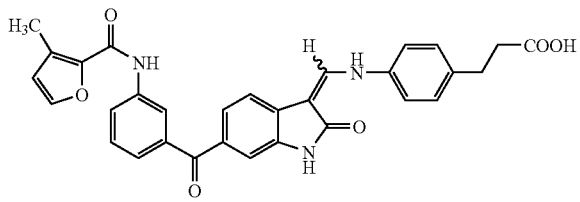

3-{4-[(6-{3-[(3-Methyl-furan-2-carbonyl)-amino]-benzoyl}-2-oxo-1,2-dihydro-indol-3-ylidenemethyl)-amino]-phenyl}-propionic acid.

The following abbreviations may be used throughout this specification.

"Ac" refers to acetyl.
"Ar" refers to aryl.
"Tf" refers to triflate.
"Me" refers to methyl.
"Et" refers to ethyl.
"tBu" refers to t-butyl.
"iPr" refers to I-propyl.
"Ph" refers to phenyl.

Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salt" may also refer to those salts which retain the biological effectiveness and properties of the free acid and which are obtained by reaction with inorganic bases such as sodium hydroxide, potassium hydroxide or calcium hydroxide and the like or organic bases such as lysine, arginine, ethanolamine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, $CH_2CN$, alkyaryl, sulfonamide, NH-alkyl, NH-alkylaryl, or NH-aryl.

Illustrative routes to compounds of the present invention are illustrated in Schemes I, II, III, IV and V set forth below and are not intended to limit the scope of the invention.

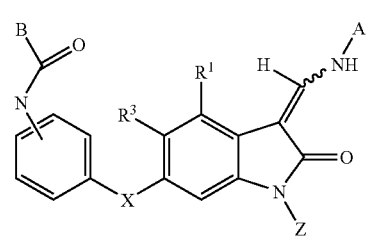

I

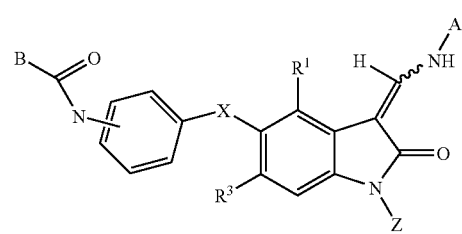

II

Scheme I:
Preparation of IIIa & IIIb (5-(3, and 4-Amino-benzoyl)-1,3-dihydro-indol-2-one) and
IVa & IVb (5-(3, and 4-Amino-benzoyl)-1,3-dihydro-indol-2-one).
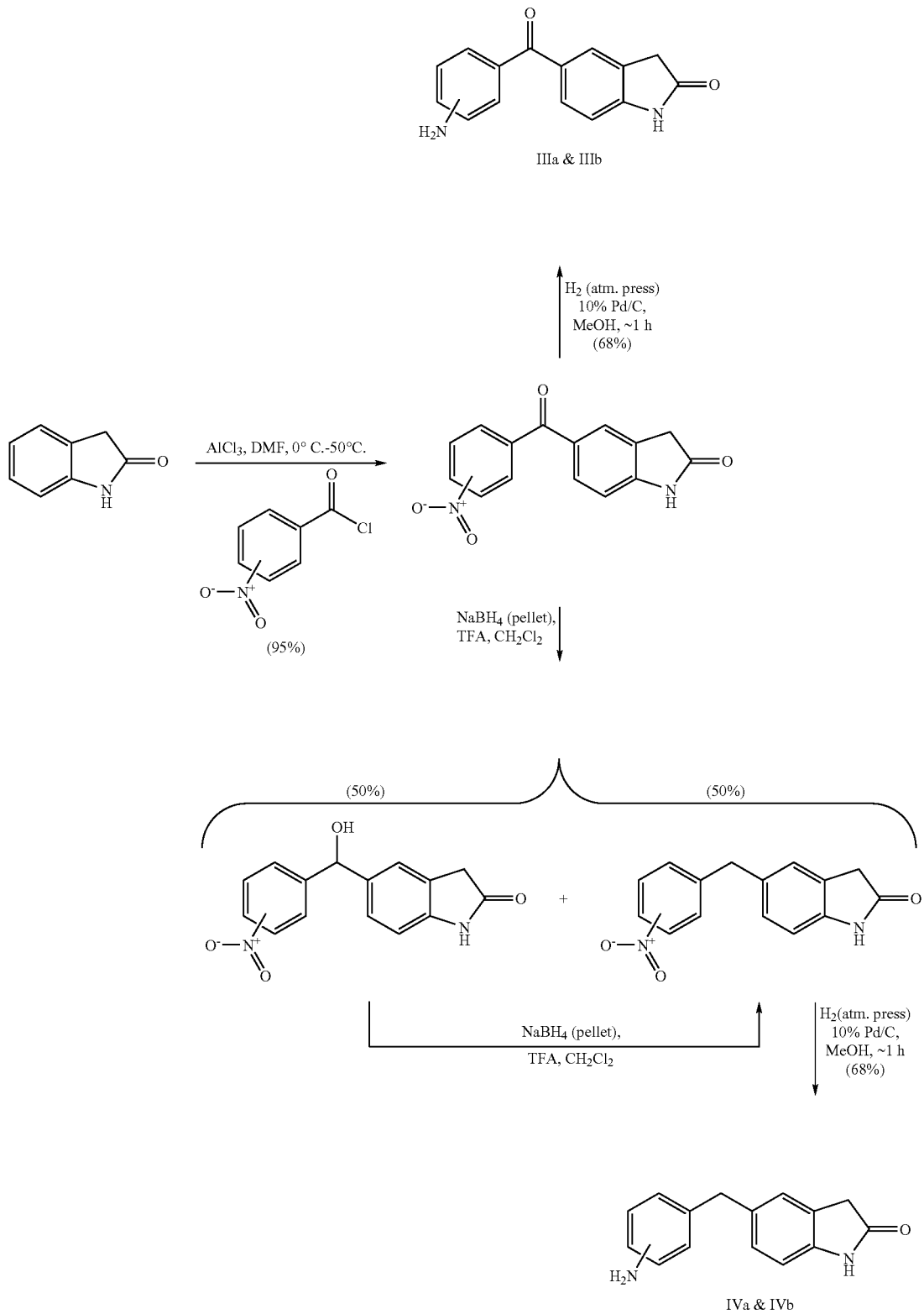

Wherein IVa & IVb are specific embodiments of Formula II in which X=CH₂;
Scheme II:
Preparation of Ia: 6-(4-Amino-benzoyl)-1,3-dihydro-indol-2-one.
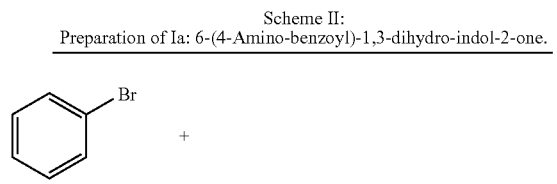
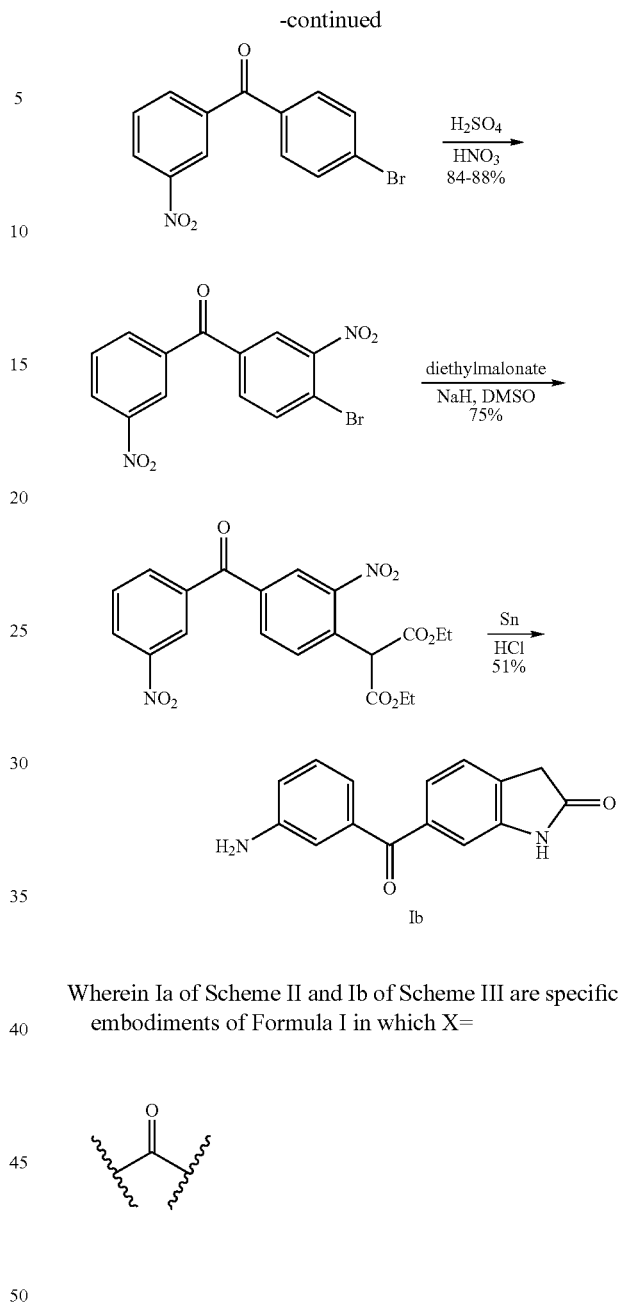
Wherein Ia of Scheme II and Ib of Scheme III are specific embodiments of Formula I in which X=
Scheme III:
Preparation of Ib: 6-(3-Amino-benzoyl)-1,3-dihydro-indol-2-one.
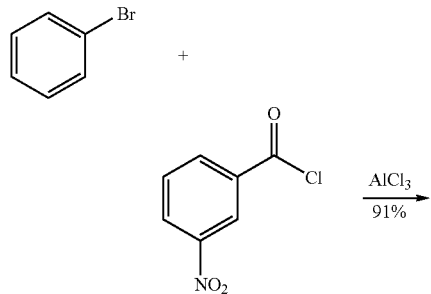
Scheme IV:
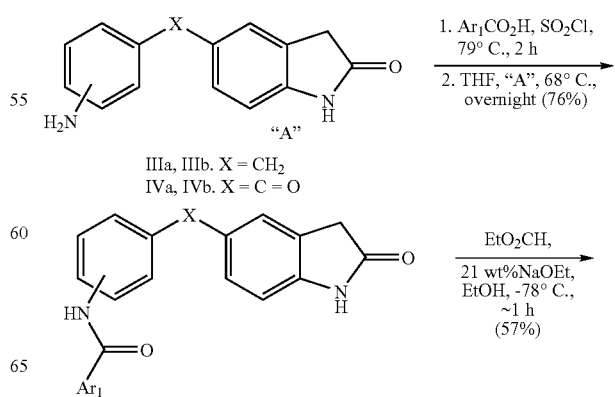

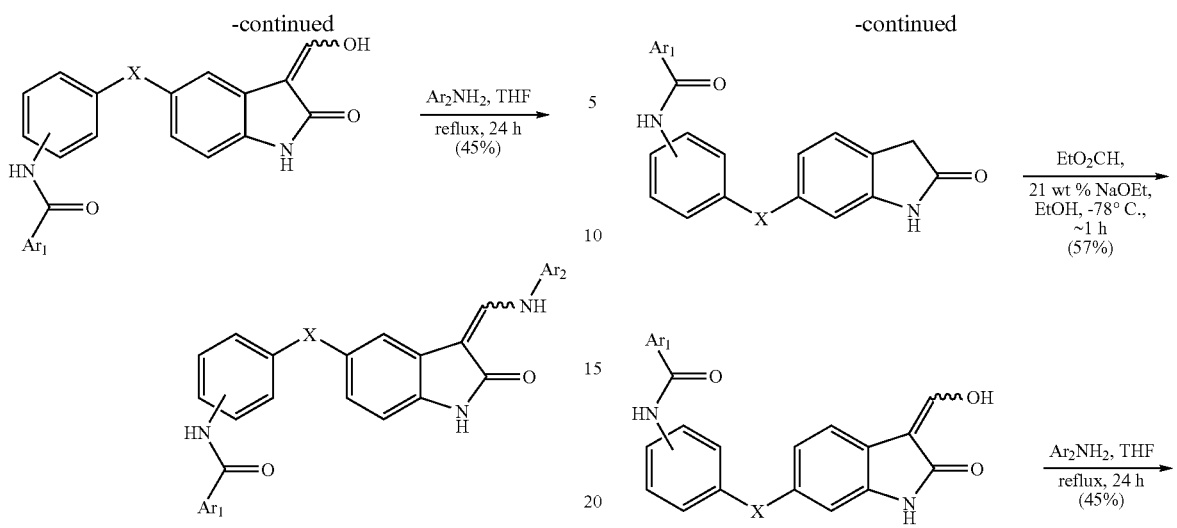

Wherein X in Scheme IV represents X in Formula II, Ar$_2$ of Scheme IV represents A in Formula II, and COAr$_1$ of Scheme IV represents X'B in Formula II.

Scheme V:

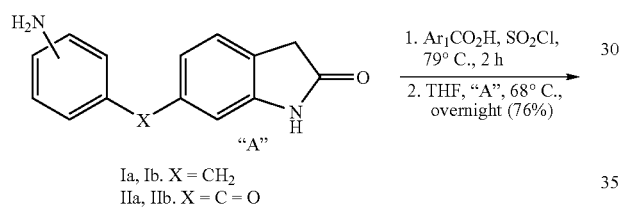

Ia, Ib. X = CH$_2$
IIa, IIb. X = C=O

Wherein X of Scheme V represents X in Formula I, COAr$_1$ of Scheme V represents X'B of Formula I Specific compounds within the scope of the present invention are as set forth below in Table 1:

TABLE 1

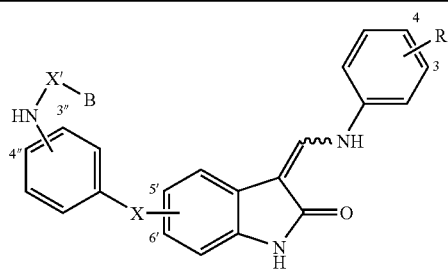

(The above structure is what Table 1 refers to and represents Formulae I and II wherein X'-B represents X'-B in Formulae I and II, X above represents X in Formulae I and II, and

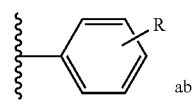

above represents A in Formulae I and II)

| Example # | R substitution | | X (position) | X' | HN X'B position | B |
|---|---|---|---|---|---|---|
| | 3 | 4 | | | | |
| 1 | H | ⟜N⟋O (morpholine) | C=O (5') | C=O | 3" | Et-pyrazole-Me |

TABLE 1-continued

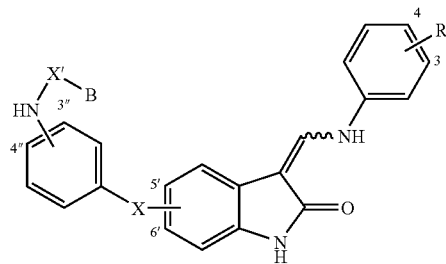

(The above structure is what Table 1 refers to and represents Formulae I and II wherein X′-B represents X′-B in Formulae I and II, X above represents X in Formulae I and II, and

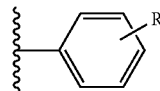

above represents A in Formulae I and II)

| Example # | R substitution 3 | R substitution 4 | X (position) | X' | HN X'B position | B |
|---|---|---|---|---|---|---|
| 2 | H | ⸺N(piperazine)N—CH₃ | C=O (5') | C=O | 3" | Et-pyrazole-Me |
| 3 | OH | H | C=O (5') | C=O | 3" | Et-pyrazole-Me |
| 4 | OH | CH₃ | C=O (5') | C=O | 3" | Et-pyrazole-Me |
| 5 | H | CH₂CO₂H | C=O (5') | C=O | 3" | Et-pyrazole-Me |
| 6 | H | ⸺N(morpholine)O | C=O (5') | C=O | 3" | CH₃ |
| 7 | H | ⸺N(morpholine)O | C=O (5') | C=O | 4" | Et-pyrazole-Me |
| 8 | H | ⸺N(piperazine)N—CH₃ | C=O (5') | C=O | 4" | Et-pyrazole-Me |

TABLE 1-continued

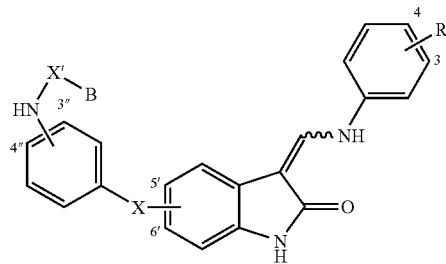

(The above structure is what Table 1 refers to and represents Formulae I and II wherein X'-B represents X'-B in Formulae I and II, X above represents X in Formulae I and II, and

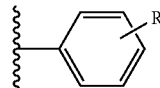 above represents A in Formulae I and II)

| Example # | R substitution 3 | R substitution 4 | X (position) | X' | HN X'B position | B |
|---|---|---|---|---|---|---|
| 9 | OH | H | C=O (5') | C=O | 4" | 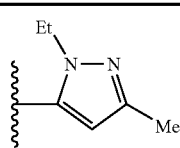 Et, N—N, Me (pyrazole) |
| 10 | OH | CH₃ | C=O (5') | C=O | 4" | 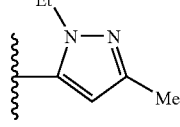 Et, N—N, Me (pyrazole) |
| 11 | H | 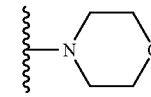 morpholine-N | C=O (5') | C=O | 4" | CH₃ |
| 12 | H | 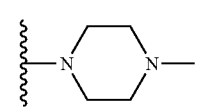 N-methylpiperazine | C=O (5') | C=O | 4" | CH₃ |
| 13 | OH | CH₃ | C=O (5') | C=O | 4" | CH₃ |
| 14 | H | 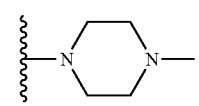 N-methylpiperazine | C=O (5') | C=O | 4" | 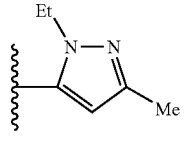 Et, N—N, Me |
| 15 | H | 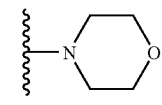 morpholine-N | C=O (6') | C=O | 4" | 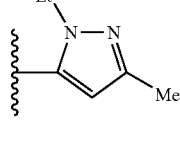 Et, N—N, Me |
| 16 | H | 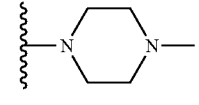 N-methylpiperazine | C=O (6') | C=O | 4" | 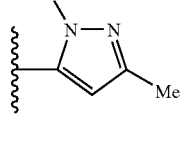 Et, N—N, Me |

TABLE 1-continued

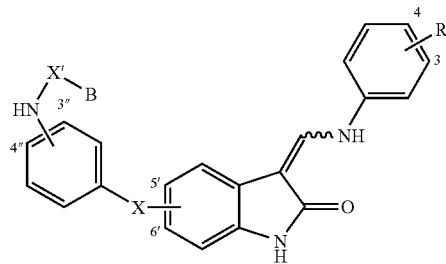

(The above structure is what Table 1 refers to and represents Formulae I and II wherein X'-
B represents X'-B in Formulae I and II, X above represents X in Formulae I and II, and

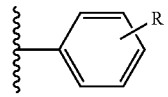

above represents A in Formulae I and II)

| Example # | R substitution 3 | R substitution 4 | X (position) | X' | HN X'B position | B |
|---|---|---|---|---|---|---|
| 17 |  | —N—N═CH— | C═O (6') | C═O | 4" | 1-Et, 3-Me pyrazole |
| 18 | OH | H | C═O (6') | C═O | 4" | 1-Et, 3-Me pyrazole |
| 19 | OH | CH₃ | C═O (6') | C═O | 4" | 1-Et, 3-Me pyrazole |
| 20 | H | —N(morpholine) | C═O (6') | C═O | 4" | thiophene |
| 21 | H | —N(N-methylpiperazine) | C═O (6') | C═O | 4" | thiophene |
| 22 | OH | H | C═O (6') | C═O | 4" | thiophene |
| 23 | OH | CH₃ | C═O (6') | C═O | 4" | thiophene |
| 24 | OH | OCH₃ | C═O (6') | C═O | 4" | thiophene |

TABLE 1-continued

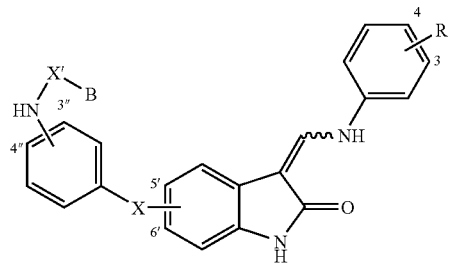

(The above structure is what Table 1 refers to and represents Formulae I and II wherein X'-B represents X'-B in Formulae I and II, X above represents X in Formulae I and II, and

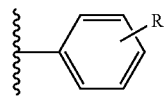

above represents A in Formulae I and II)

| Example | R substitution | | X | | HN X'B | |
|---|---|---|---|---|---|---|
| # | 3 | 4 | (position) | X' | position | B |
| 25 | H | ![morpholine] | C=O (6') | C=O | 4" | Me-pyrazole-Me |
| 26 | H | ![N-methylpiperazine] | C=O (6') | C=O | 4" | Me-pyrazole-Me |
| 27 | OH | CH$_3$ | C=O (6') | C=O | 4" | Me-pyrazole-Me |
| 28 | OH | H | C=O (6') | C=O | 4" | Me-pyrazole-Me |
| 29 | H | ![morpholine] | C=O (6') | C=O | 4" | CH$_3$ |
| 30 | H | ![N-methylpiperazine] | C=O (6') | C=O | 4" | CH$_3$ |
| 31 | OH | OCH$_3$ | C=O (6') | C=O | 4" | CH$_3$ |
| 32 | OH | H | C=O (6') | C=O | 4" | CH$_3$ |
| 33 | OH | CH$_3$ | C=O (6') | C=O | 4" | CH$_3$ |

TABLE 1-continued

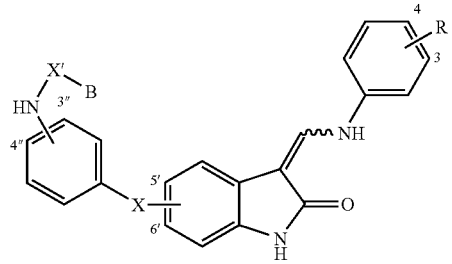

(The above structure is what Table 1 refers to and represents Formulae I and II wherein X'-B represents X'-B in Formulae I and II, X above represents X in Formulae I and II, and

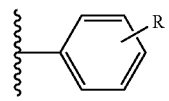

above represents A in Formulae I and II)

| Example # | R substitution 3 | R substitution 4 | X (position) | X' | HN X'B position | B |
|---|---|---|---|---|---|---|
| 34 | H | ⸾-N(morpholine)O | C=O (6') | C=O | 4" | 5-acetylthiophen-2-yl |
| 35 | OH | CH₃ | C=O (6') | C=O | 4" | 5-acetylthiophen-2-yl |
| 36 | H | ⸾-N(piperazine)N-Me | C=O (6') | C=O | 4" | 5-acetylthiophen-2-yl |
| 37 | OH | OCH₃ | C=O (6') | C=O | 4" | 5-acetylthiophen-2-yl |
| 38 | OH | H | C=O (6') | C=O | 4" | 5-acetylthiophen-2-yl |
| 39 | OH | OCH₃ | C=O (6') | C=O | 4" | 1,3-dimethyl-1H-pyrazol-5-yl |

TABLE 1-continued

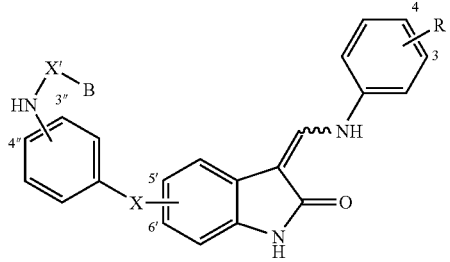

(The above structure is what Table 1 refers to and represents Formulae I and II wherein X'-B represents X'-B in Formulae I and II, X above represents X in Formulae I and II, and

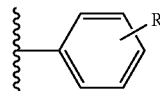

above represents A in Formulae I and II)

| Example # | R substitution 3 | R substitution 4 | X (position) | X' | HN X'B position | B |
|---|---|---|---|---|---|---|
| 40 | OH | OCH$_3$ | C=O (6') | C=O | 3" | CH$_3$ |
| 41 | H | -N(morpholine) | C=O (6') | C=O | 3" | CH$_3$ |
| 42 | H | -N(N-methylpiperazine) | C=O (6') | C=O | 3" | CH$_3$ |
| 43 | OH | CH$_3$ | C=O (6') | C=O | 3" | CH$_3$ |
| 44 | OH | H | C=O (6') | C=O | 3" | CH$_3$ |
| 45 | OH | CH$_3$ | C=O (6') | C=O | 3" | thiophene |
| 46 | H | -N(N-methylpiperazine) | C=O (6') | C=O | 3" | thiophene |
| 47 | OH | OCH$_3$ | C=O (6') | C=O | 3" | thiophene |
| 48 | OH | H | C=O (6') | C=O | 3" | thiophene |
| 49 | H | -N(morpholine) | C=O (6') | C=O | 3" | thiophene |
| 50 | OH | CH$_3$ | C=O (6') | C=O | 3" | tBu-N-N-Me pyrazole |

TABLE 1-continued

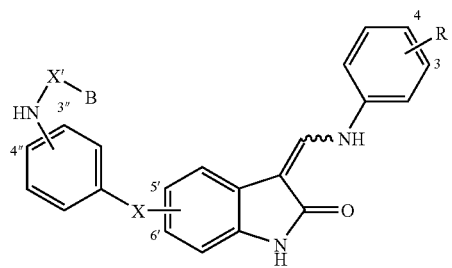

(The above structure is what Table 1 refers to and represents Formulae I and II wherein X'-B represents X'-B in Formulae I and II, X above represents X in Formulae I and II, and

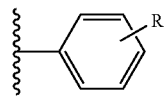

above represents A in Formulae I and II)

| Example # | R substitution 3 | R substitution 4 | X (position) | X' | HN X'B position | B |
|---|---|---|---|---|---|---|
| 51 | OH | OCH₃ | C=O (6') | C=O | 3" | tBu-pyrazole-Me |
| 52 | OH | H | C=O (6') | C=O | 3" | tBu-pyrazole-Me |
| 53 | H | morpholine-N | C=O (6') | C=O | 3" | tBu-pyrazole-Me |
| 54 | OH | OCH₃ | C=O (6') | C=O | 3" | acetylthiophene |
| 55 | OH | CH₃ | C=O (6') | C=O | 3" | acetylthiophene |
| 56 | H | morpholine-N | C=O (6') | C=O | 3" | acetylthiophene |

TABLE 1-continued

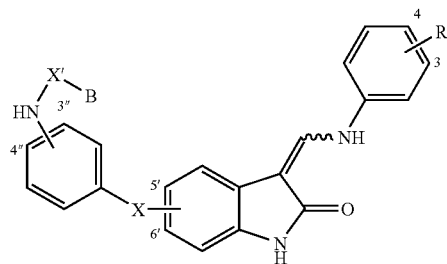

(The above structure is what Table 1 refers to and represents Formulae I and II wherein X'-B represents X'-B in Formulae I and II, X above represents X in Formulae I and II, and

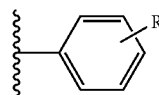 above represents A in Formulae I and II)

| Example # | R substitution | | X | | HN X'B | |
|---|---|---|---|---|---|---|
| | 3 | 4 | (position) | X' | position | B |
| 57 | OH | H | C=O (6') | C=O | 3" | (5-acetylthiophen-2-yl) |
| 58 | H | N-methylpiperazin-1-yl | C=O (6') | C=O | 3" | (5-acetylthiophen-2-yl) |
| 59 | H | N-methylpiperazin-1-yl | C=O (6') | C=O | 3" | 1-tBu-3-Me-pyrazol-5-yl |
| 60 | OH | CH₃ | C=O (6') | C=O | 3" | 1,3-dimethylpyrazol-5-yl |
| 61 | H | N-methylpiperazin-1-yl | C=O (6') | C=O | 3" | 1,3-dimethylpyrazol-5-yl |
| 62 | OH | OCH₃ | C=O (6') | C=O | 3" | 1,3-dimethylpyrazol-5-yl |

TABLE 1-continued

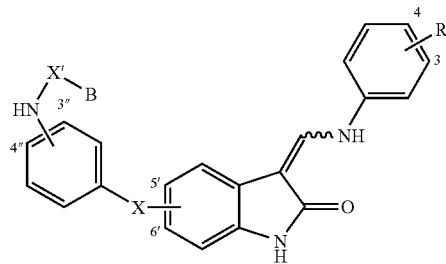

(The above structure is what Table 1 refers to and represents Formulae I and II wherein X'-B represents X'-B in Formulae I and II, X above represents X in Formulae I and II, and

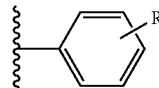

above represents A in Formulae I and II)

| Example # | R substitution 3 | R substitution 4 | X (position) | X' | HN X'B position | B |
|---|---|---|---|---|---|---|
| 63 | OH | H | C=O (6') | C=O | 3" | Me-N-N pyrazole-Me |
| 64 | H | morpholine-N | C=O (6') | C=O | 3" | Me-N-N pyrazole-Me |
| 65 | H | morpholine-N | C=O (6') | C=O | 4" | tBu-N-N pyrazole-Me |
| 66 | H | N-methylpiperazine-N | C=O (6') | C=O | 4" | tBu-N-N pyrazole-Me |
| 67 | OH | H | C=O (6') | C=O | 4" | tBu-N-N pyrazole-Me |
| 68 | OH | OCH₃ | C=O (6') | C=O | 4" | tBu-N-N pyrazole-Me |
| 69 | H | morpholine-N | C=O (6') | C=O | 3" | Et-N-N pyrazole-Me |

TABLE 1-continued

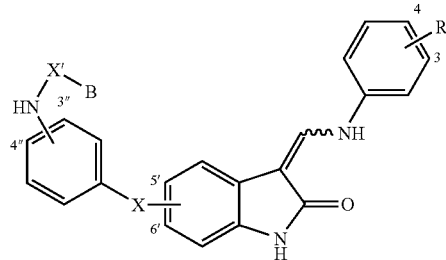

(The above structure is what Table 1 refers to and represents Formulae I and II wherein X'-
B represents X'-B in Formulae I and II, X above represents X in Formulae I and II, and

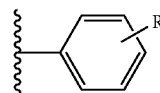

above represents A in Formulae I and II)

| Example # | R substitution | | X (position) | X' | HN X'B position | B |
|---|---|---|---|---|---|---|
| | 3 | 4 | | | | |
| 70 | H | ![piperazine]  —N⌒N—Me | C=O (6') | C=O | 3" | Et-pyrazole-Me |
| 71 | OH | H | C=O (6') | C=O | 3" | Et-pyrazole-Me |
| 72 | OH | CH₃ | C=O (6') | C=O | 3" | Et-pyrazole-Me |
| 73 | OH | OCH₃ | C=O (6') | C=O | 3" | Et-pyrazole-Me |
| 74 | H | O(CH₂)₃NEt₂ | C=O (6') | C=O | 3" | thiophene |
| 75 | H | CO₂H | C=O (6') | C=O | 3" | thiophene |
| 76 | H | —(CH₂)₂CO₂H | C=O (6') | C=O | 3" | thiophene |
| 77 | H | CO₂H | C=O (6') | C=O | 3" | Me-pyrazole-Me |

TABLE 1-continued

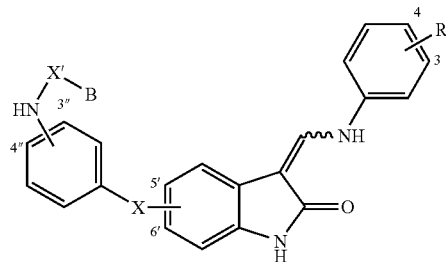

(The above structure is what Table 1 refers to and represents Formulae I and II wherein X'-B represents X'-B in Formulae I and II, X above represents X in Formulae I and II, and

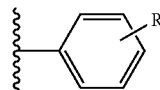

above represents A in Formulae I and II)

| Example | R substitution | | X | | HN X'B | |
|---|---|---|---|---|---|---|
| # | 3 | 4 | (position) | X' | position | B |
| 78 | H | O(CH₂)₂N(CH₂)₄ | C=O (6') | C=O | 3" | Me-pyrazole-Me |
| 79 | H | O(CH₂)₂N(CH₂)₅ | C=O (6') | C=O | 3" | Me-pyrazole-Me |
| 80 | H | NCH(CH₃)CH₂NMe₂ | C=O (6') | C=O | 3" | Me-pyrazole-Me |
| 81 | H | —CH₂CO₂H | C=O (6') | C=O | 3" | Me-pyrazole-Me |
| 82 | H | —(CH₂)₂CO₂H | C=O (6') | C=O | 3" | Me-pyrazole-Me |
| 83 | H | O(CH₂)₃NEt₂ | C=O (6') | C=O | 3" | Me-pyrazole-Me |
| 84 | H | O(CH₂)₃N(CH₂)₅ | C=O (6') | C=O | 3" | Me-pyrazole-Me |

TABLE 1-continued

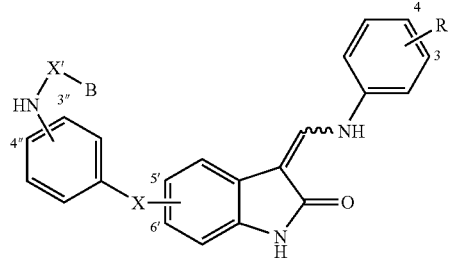

(The above structure is what Table 1 refers to and represents Formulae I and II wherein X'-B represents X'-B in Formulae I and II, X above represents X in Formulae I and II, and

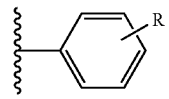

above represents A in Formulae I and II)

| Example # | R substitution 3 | R substitution 4 | X (position) | X' | HN X'B position | B |
|---|---|---|---|---|---|---|
| 85 | H | OCH$_2$CH(OH)CH$_2$NEt$_2$ | C=O (6') | C=O | 3" | Me-N-N, Me (pyrazole) |
| 86 | H | piperazine-N-Me | C=O (6') | C=O | 3" | N-Me pyrazole with CF$_3$ |
| 87 | H | piperazine-N-Me | C=O (6') | C=O | 3" | Me-N-N, Me, Cl pyrazole |
| 88 | H | O(CH$_2$)$_2$NEt$_2$ | C=O (6') | C=O | 3" | Me-N-N, Me pyrazole |
| 89 | H | piperazine-N-Me | C=O (6') | C=O | 3" | Me-N-N pyrazole |
| 90 | H | piperazine-N-Me | C=O (6') | C=O | 3" | Me-N-N, Cl pyrazole |
| 91 | H | piperazine-N-Me | C=O (6') | C=O | 3" | thiophene |

TABLE 1-continued

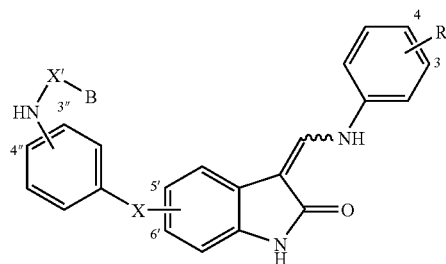

(The above structure is what Table 1 refers to and represents Formulae I and II wherein X'-B represents X'-B in Formulae I and II, X above represents X in Formulae I and II, and

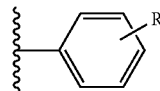

above represents A in Formulae I and II)

| Example # | R substitution 3 | R substitution 4 | X (position) | X' | HN X'B position | B |
|---|---|---|---|---|---|---|
| 92 | H | ⸾-N(piperazine)N-Me | C=O (6') | C=O | 3" | Me-N-N / pyrazole / Me |
| 93 | H | ⸾-N(morpholine)O | C=O (5') | C=O | 3" | Me-N / imidazole |
| 94 | H | ⸾-N(piperazine)N-Me | C=O (5') | C=O | 3" | Me-N / imidazole |
| 95 | OH | OCH₃ | C=O (5') | C=O | 3" | Me-N / imidazole |
| 96 | OH | CH₃ | C=O (5') | C=O | 3" | Me-N / imidazole |
| 97 | OH | OCH₃ | C=O (5') | C=O | 3" | Et-N-N / pyrazole / Me |
| 98 | H | ⸾-N(morpholine)O | C=O (5') | C=O | 3" | Me-N / pyrazole |

TABLE 1-continued

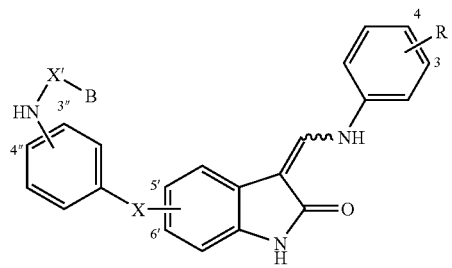

(The above structure is what Table 1 refers to and represents Formulae I and II wherein X'-B represents X'-B in Formulae I and II, X above represents X in Formulae I and II, and

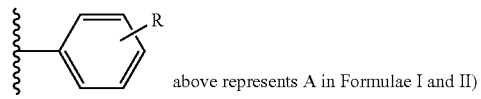

above represents A in Formulae I and II)

| Example | R substitution | | X | | HN X'B | |
|---|---|---|---|---|---|---|
| # | 3 | 4 | (position) | X' | position | B |
| 99 | H | ξ-N(piperazine)N-Me | C=O (5') | C=O | 3" | N-methylpyrazol-4-yl |
| 100 | OH | H | C=O (5') | C=O | 3" | N-methylpyrazol-4-yl |
| 101 | H | ξ-N(piperazine)N-Me | C=O (5') | C=O | 3" | CH₃ |
| 102 | OH | OCH₃ | C=O (5') | C=O | 3" | CH₃ |
| 103 | H | ξ-N(morpholine)O | C=O (5') | C=O | 3" | thien-2-yl |
| 104 | H | ξ-N(piperazine)N-Me | C=O (5') | C=O | 3" | thien-2-yl |
| 105 | OH | OCH₃ | C=O (5') | C=O | 3" | thien-2-yl |
| 106 | H | ξ-N(morpholine)O | C=O (5') | C=O | 3" | 5-acetylthien-2-yl |

TABLE 1-continued

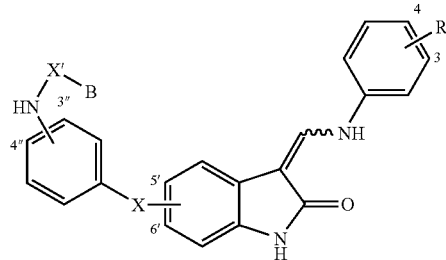

(The above structure is what Table 1 refers to and represents Formulae I and II wherein X'-B represents X'-B in Formulae I and II, X above represents X in Formulae I and II, and

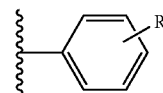 above represents A in Formulae I and II)

| Example # | R substitution 3 | R substitution 4 | X (position) | X' | HN X'B position | B |
|---|---|---|---|---|---|---|
| 107 | H | -N(piperazinyl)N-Me | C=O (5') | C=O | 3" | 5-acetyl-thiophen-2-yl |
| 108 | H | -N(morpholinyl) | C=O (5') | C=O | 3" | 1,3-dimethyl-pyrazol-5-yl |
| 109 | H | -N(piperazinyl)N-Me | C=O (5') | C=O | 3" | 1,3-dimethyl-pyrazol-5-yl |
| 110 | OH | OCH$_3$ | C=O (5') | C=O | 3" | 1,3-dimethyl-pyrazol-5-yl |
| 111 | H | -N(morpholinyl) | C=O (5') | C=O | 3" | 1-tBu-3-methyl-pyrazol-5-yl |
| 112 | H | -N(piperazinyl)N-Me | C=O (5') | C=O | 3" | 1-tBu-3-methyl-pyrazol-5-yl |
| 113 | OH | OCH$_3$ | C=O (5') | C=O | 3" | 1-tBu-3-methyl-pyrazol-5-yl |

TABLE 1-continued

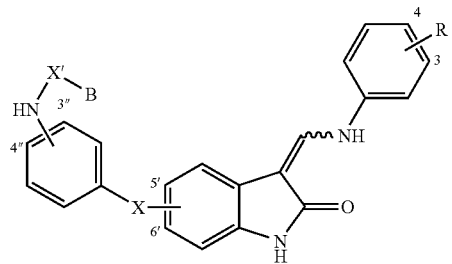

(The above structure is what Table 1 refers to and represents Formulae I and II wherein X'-B represents X'-B in Formulae I and II, X above represents X in Formulae I and II, and

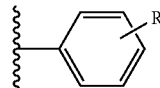

above represents A in Formulae I and II)

| Example # | R substitution 3 | R substitution 4 | X (position) | X' | HN X'B position | B |
|---|---|---|---|---|---|---|
| 114 | OH | CH₃ | C=O (5') | C=O | 3" | tBu-N-N pyrazole-Me |
| 115 | OH | H | C=O (5') | C=O | 3" | tBu-N-N pyrazole-Me |
| 116 | OH | OCH₃ | C=O (5') | C=O | 4" | Et-N-N pyrazole-Me |
| 117 | H | morpholine (N-) | C=O (5') | C=O | 4" | N-Me pyrazole |
| 118 | H | N-methylpiperazine | C=O (5') | C=O | 4" | N-Me pyrazole |
| 119 | H | morpholine (N-) | C=O (5') | C=O | 4" | thiophene |
| 120 | H | N-methylpiperazine | C=O (5') | C=O | 4" | thiophene |
| 121 | OH | OCH₃ | C=O (5') | C=O | 4" | thiophene |

TABLE 1-continued

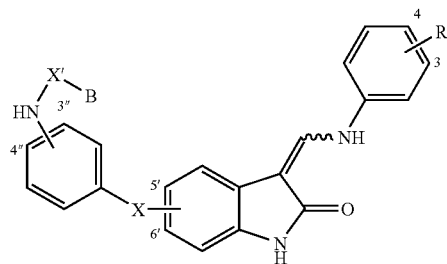

(The above structure is what Table 1 refers to and represents Formulae I and II wherein X'-B represents X'-B in Formulae I and II, X above represents X in Formulae I and II, and

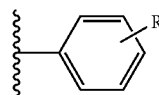 above represents A in Formulae I and II)

| Example # | R substitution 3 | R substitution 4 | X (position) | X' | HN X'B position | B |
|---|---|---|---|---|---|---|
| 122 | H | -N(morpholine) | C=O (5') | C=O | 4" | 2-acetylthiophen-5-yl |
| 123 | H | -N(N-methylpiperazine) | C=O (5') | C=O | 4" | 2-acetylthiophen-5-yl |
| 124 | H | -N(morpholine) | C=O (5') | C=O | 4" | 1,3-dimethylpyrazol-5-yl |
| 125 | H | -N(N-methylpiperazine) | C=O (5') | C=O | 4" | 1,3-dimethylpyrazol-5-yl |
| 126 | H | -N(morpholine) | C=O (5') | C=O | 4" | 1-tBu-3-methylpyrazol-5-yl |
| 127 | H | -N(N-methylpiperazine) | C=O (5') | C=O | 4" | 1-tBu-3-methylpyrazol-5-yl |

TABLE 1-continued

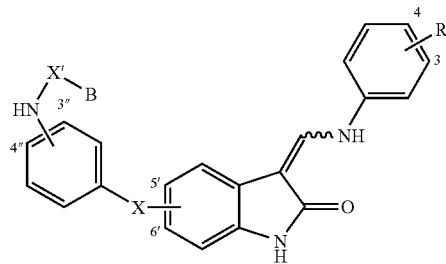

(The above structure is what Table 1 refers to and represents Formulae I and II wherein X'-B represents X'-B in Formulae I and II, X above represents X in Formulae I and II, and

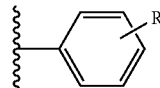

above represents A in Formulae I and II)

| Example # | R substitution | | X | | HN X'B | |
|---|---|---|---|---|---|---|
| | 3 | 4 | (position) | X' | position | B |
| 128 | OH | OCH₃ | C=O (5') | C=O | 4" | tBu-pyrazole-Me |
| 129 | OH | H | C=O (5') | C=O | 4" | tBu-pyrazole-Me |
| 130 | H | morpholine | CH₂ (5') | C=O | 3" | Me-imidazole |
| 131 | H | N-methylpiperazine | CH₂ (5') | C=O | 3" | Me-imidazole |
| 132 | OH | OCH₃ | CH₂ (5') | C=O | 3" | Me-imidazole |
| 133 | OH | CH₃ | CH₂ (5') | C=O | 3" | Me-imidazole |
| 134 | OH | H | CH₂ (5') | C=O | 3" | Me-imidazole |

TABLE 1-continued

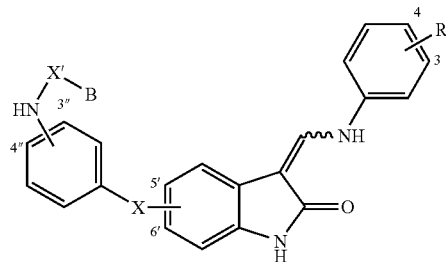

(The above structure is what Table 1 refers to and represents Formulae I and II wherein X'-B represents X'-B in Formulae I and II, X above represents X in Formulae I and II, and

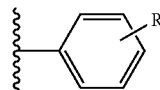

above represents A in Formulae I and II)

| Example # | R substitution 3 | R substitution 4 | X (position) | X' | HN X'B position | B |
|---|---|---|---|---|---|---|
| 135 | H | 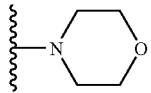 N-morpholine | CH₂ (5') | C=O | 3" | 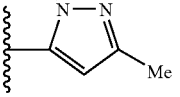 Et-pyrazole-Me |
| 136 | H | 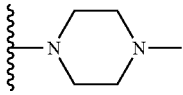 N-methylpiperazine | CH₂ (5') | C=O | 3" | 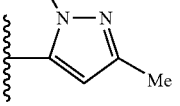 Et-pyrazole-Me |
| 137 | OH | OCH₃ | CH₂ (5') | C=O | 3" | 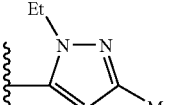 Et-pyrazole-Me |
| 138 | H | 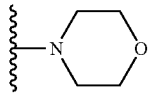 N-morpholine | CH₂ (5') | C=O | 3" | 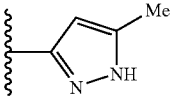 pyrazole-Me NH |
| 139 | H |  N-methylpiperazine | CH₂ (5') | C=O | 3" | 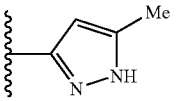 pyrazole-Me NH |
| 140 | OH | OCH₃ | CH₂ (5') | C=O | 3" | 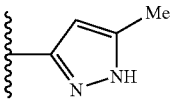 pyrazole-Me NH |
| 141 | OH | CH₃ | CH₂ (5') | C=O | 3" | 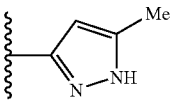 pyrazole-Me NH |
| 142 | OH | H | CH₂ (5') | C=O | 3" | 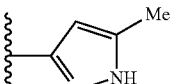 pyrazole-Me NH |

TABLE 1-continued

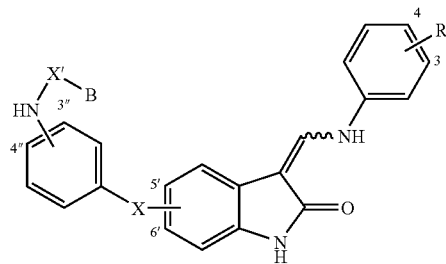

(The above structure is what Table 1 refers to and represents Formulae I and II wherein X'-B represents X'-B in Formulae I and II, X above represents X in Formulae I and II, and

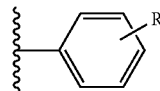

above represents A in Formulae I and II)

| Example # | R substitution 3 | R substitution 4 | X (position) | X' | HN X'B position | B |
|---|---|---|---|---|---|---|
| 143 | H | ⁓N(morpholine) | CH₂ (5') | C=O | 3" | 1-Me-pyrazol-4-yl |
| 144 | H | ⁓N(N-Me-piperazine) | CH₂ (5') | C=O | 3" | 1-Me-pyrazol-4-yl |
| 145 | OH | OCH₃ | CH₂ (5') | C=O | 3" | 1-Me-pyrazol-4-yl |
| 146 | OH | H | CH₂ (5') | C=O | 3" | 1-Me-pyrazol-4-yl |
| 147 | H | ⁓N(morpholine) | CH₂ (5') | C=O | 3" | 1H-pyrazol-4-yl |
| 148 | H | ⁓N(N-Me-piperazine) | CH₂ (5') | C=O | 3" | 1H-pyrazol-4-yl |
| 149 | OH | CH₃ | CH₂ (5') | C=O | 3" | 1H-pyrazol-4-yl |
| 150 | OH | H | CH₂ (5') | C=O | 3" | 1H-pyrazol-4-yl |
| 151 | H | ⁓N(morpholine) | CH₂ (5') | C=O | 3" | CH₃ |

TABLE 1-continued

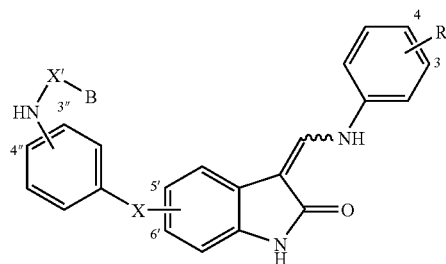

(The above structure is what Table 1 refers to and represents Formulae I and II wherein X'-B represents X'-B in Formulae I and II, X above represents X in Formulae I and II, and

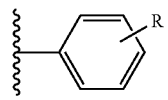

above represents A in Formulae I and II)

| Example # | R substitution 3 | R substitution 4 | X (position) | X' | HN X'B position | B |
|---|---|---|---|---|---|---|
| 152 | H | ![piperazine-N]—N⌒N— | CH₂ (5') | C=O | 3" | CH₃ |
| 153 | OH | OCH₃ | CH₂ (5') | C=O | 3" | CH₃ |
| 154 | OH | CH₃ | CH₂ (5') | C=O | 3" | CH₃ |
| 155 | OH | H | CH₂ (5') | C=O | 3" | CH₃ |
| 156 | H | —N⌒O (morpholine) | CH₂ (5') | C=O | 3" | thiophen-2-yl |
| 157 | H | —N⌒N— (N-methylpiperazine) | CH₂ (5') | C=O | 3" | thiophen-2-yl |
| 158 | OH | OCH₃ | CH₂ (5') | C=O | 3" | thiophen-2-yl |
| 159 | OH | CH₃ | CH₂ (5') | C=O | 3" | thiophen-2-yl |
| 160 | OH | H | CH₂ (5') | C=O | 3" | thiophen-2-yl |
| 161 | H | —N⌒O (morpholine) | CH₂ (5') | C=O | 3" | 5-acetyl-thiophen-2-yl |

TABLE 1-continued

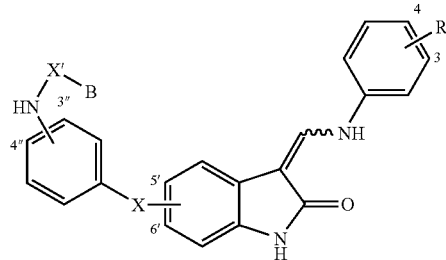

(The above structure is what Table 1 refers to and represents Formulae I and II wherein X'-B represents X'-B in Formulae I and II, X above represents X in Formulae I and II, and

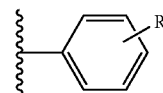 above represents A in Formulae I and II)

| Example # | R substitution 3 | R substitution 4 | X (position) | X' | HN X'B position | B |
|---|---|---|---|---|---|---|
| 162 | H | N-piperazinyl-N-Me | CH₂ (5') | C=O | 3" | 5-acetyl-thiophen-2-yl |
| 163 | H | morpholino | CH₂ (5') | C=O | 3" | 1,3-dimethyl-1H-pyrazol-5-yl |
| 164 | H | N-piperazinyl-N-Me | CH₂ (5') | C=O | 3" | 1,3-dimethyl-1H-pyrazol-5-yl |
| 165 | OH | OCH₃ | CH₂ (5') | C=O | 3" | 1,3-dimethyl-1H-pyrazol-5-yl |
| 166 | OH | CH₃ | CH₂ (5') | C=O | 3" | 1,3-dimethyl-1H-pyrazol-5-yl |
| 167 | OH | H | CH₂ (5') | C=O | 3" | 1,3-dimethyl-1H-pyrazol-5-yl |
| 168 | H | N-piperazinyl-N-Me | CH₂ (5') | C=O | 3" | 1-tBu-3-Me-1H-pyrazol-5-yl |

TABLE 1-continued

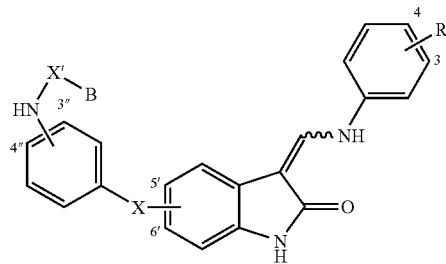

(The above structure is what Table 1 refers to and represents Formulae I and II wherein X'-B represents X'-B in Formulae I and II, X above represents X in Formulae I and II, and

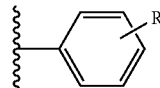

above represents A in Formulae I and II)

| Example # | R substitution 3 | R substitution 4 | X (position) | X' | HN X'B position | B |
|---|---|---|---|---|---|---|
| 169 | OH | H | CH₂ (5') | C=O | 3" | tBu-pyrazole-Me |
| 170 | H | morpholine-N | CH₂ (5') | C=O | 4" | Me-imidazole |
| 171 | OH | OCH₃ | CH₂ (5') | C=O | 4" | Me-imidazole |
| 172 | OH | H | CH₂ (5') | C=O | 4" | Me-imidazole |
| 173 | H | morpholine-N | CH₂ (5') | C=O | 4" | Et-pyrazole-Me |
| 174 | OH | OCH₃ | CH₂ (5') | C=O | 4" | Et-pyrazole-Me |
| 175 | OH | H | CH₂ (5') | C=O | 4" | Et-pyrazole-Me |

TABLE 1-continued

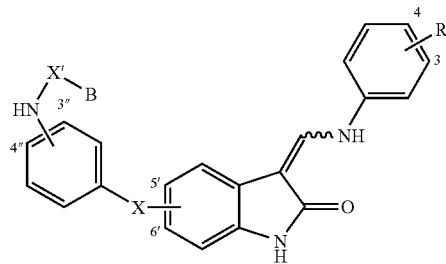

(The above structure is what Table 1 refers to and represents Formulae I and II wherein X'-B represents X'-B in Formulae I and II, X above represents X in Formulae I and II, and

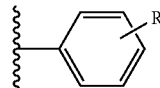 above represents A in Formulae I and II)

| Example # | R substitution 3 | R substitution 4 | X (position) | X' | HN X'B position | B |
|---|---|---|---|---|---|---|
| 176 | H | ⟳-N(piperazine)N-Me | CH₂ (5') | C=O | 4″ | 3-Me-pyrazole (NH) |
| 177 | OH | OCH₃ | CH₂ (5') | C=O | 4″ | 3-Me-pyrazole (NH) |
| 178 | H | ⟳-N(piperazine)N-Me | CH₂ (5') | C=O | 4″ | N-Me-pyrazole |
| 179 | OH | OCH₃ | CH₂ (5') | C=O | 4″ | N-Me-pyrazole |
| 180 | OH | CH₃ | CH₂ (5') | C=O | 4″ | N-Me-pyrazole |
| 181 | OH | H | CH₂ (5') | C=O | 4″ | N-Me-pyrazole |
| 182 | H | ⟳-N(morpholine)O | CH₂ (5') | C=O | 4″ | pyrazole (NH) |
| 183 | H | ⟳-N(piperazine)N-Me | CH₂ (5') | C=O | 4″ | pyrazole (NH) |
| 184 | H | ⟳-N(morpholine)O | CH₂ (5') | C=O | 4″ | CH₃ |

TABLE 1-continued

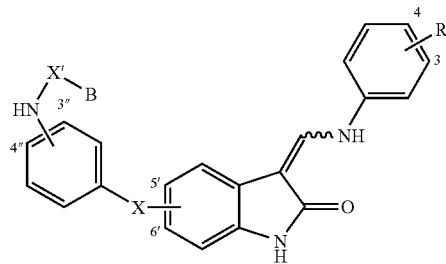

(The above structure is what Table 1 refers to and represents Formulae I and II wherein X'-B represents X'-B in Formulae I and II, X above represents X in Formulae I and II, and

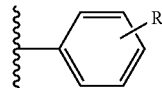

above represents A in Formulae I and II)

| Example # | R substitution 3 | R substitution 4 | X (position) | X' | HN X'B position | B |
|---|---|---|---|---|---|---|
| 185 | H | ⟨N-piperazine-N-Me⟩ | CH₂ (5') | C=O | 4" | CH₃ |
| 186 | OH | H | CH₂ (5') | C=O | 4" | CH₃ |
| 187 | H | ⟨N-piperazine-N-Me⟩ | CH₂ (5') | C=O | 4" | thiophene |
| 188 | OH | OCH₃ | CH₂ (5') | C=O | 4" | thiophene |
| 189 | OH | CH₃ | CH₂ (5') | C=O | 4" | thiophene |
| 190 | H | ⟨N-morpholine⟩ | CH₂ (5') | C=O | 4" | acetyl-thiophene |
| 191 | H | ⟨N-piperazine-N-Me⟩ | CH₂ (5') | C=O | 4" | acetyl-thiophene |
| 192 | H | ⟨N-morpholine⟩ | CH₂ (5') | C=O | 4" | 1,3-dimethylpyrazole |

TABLE 1-continued

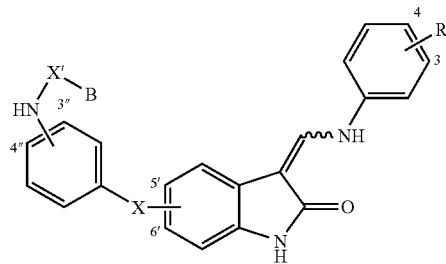

(The above structure is what Table 1 refers to and represents Formulae I and II wherein X'-B represents X'-B in Formulae I and II, X above represents X in Formulae I and II, and

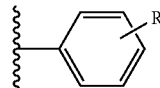

above represents A in Formulae I and II)

| Example # | R substitution | | X (position) | X' | HN X'B position | B |
|---|---|---|---|---|---|---|
| | 3 | 4 | | | | |
| 193 | H | ⸙-N(piperazine)N-Me | CH₂ (5') | C=O | 4" | Me-N-N / pyrazole / Me |
| 194 | OH | OCH₃ | CH₂ (5') | C=O | 4" | Me-N-N / pyrazole / Me |
| 195 | OH | CH₃ | CH₂ (5') | C=O | 4" | Me-N-N / pyrazole / Me |
| 196 | H | ⸙-N(morpholine)O | CH₂ (5') | C=O | 4" | tBu-N-N / pyrazole / Me |
| 197 | H | ⸙-N(piperazine)N-Me | CH₂ (5') | C=O | 4" | tBu-N-N / pyrazole / Me |
| 198 | OH | OCH₃ | CH₂ (5') | C=O | 4" | tBu-N-N / pyrazole / Me |
| 199 | OH | CH₃ | CH₂ (5') | C=O | 4" | tBu-N-N / pyrazole / Me |

TABLE 1-continued

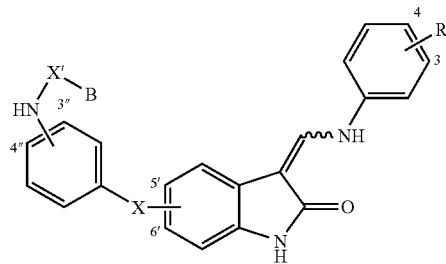

(The above structure is what Table 1 refers to and represents Formulae I and II wherein X'-B represents X'-B in Formulae I and II, X above represents X in Formulae I and II, and

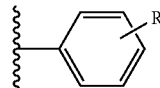

above represents A in Formulae I and II)

| Example # | R substitution | | X | | HN X'B | |
|---|---|---|---|---|---|---|
| | 3 | 4 | (position) | X' | position | B |
| 200 | OH | H | CH$_2$ (5') | C=O | 4" | tBu-pyrazole-Me |
| 201 | H | (3-fluoropyrrolidin-1-yl)propoxy | C=O (6') | C=O | 3" | Me-pyrazole-Me |
| 202 | F | —O(CH$_2$)$_3$NEt$_2$ | C=O (6') | C=O | 3" | Me-pyrazole-Me |
| 203 | H | —CH$_2$NHCO$_2$(t-Bu) | C=O (6') | C=O | 3" | Me-pyrazole-Me |
| 204 | H | —CH$_2$CH$_2$NMe$_2$ | C=O (6') | C=O | 3" | Me-pyrazole-Me |
| 205 | H | 3-(pyrrolidin-1-yl)propyl | C=O (6') | C=O | 3" | Me-pyrazole-Me |
| 206 | H | pyrrolidin-1-ylmethyl | C=O (6') | C=O | 3" | Me-pyrazole-Me |

TABLE 1-continued

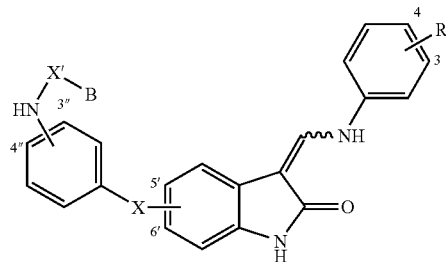

(The above structure is what Table 1 refers to and represents Formulae I and II wherein X'-B represents X'-B in Formulae I and II, X above represents X in Formulae I and II, and

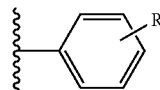

above represents A in Formulae I and II)

| Example # | R substitution 3 | R substitution 4 | X (position) | X' | HN X'B position | B |
|---|---|---|---|---|---|---|
| 207 | H | ⤳-CH₂-N(-)-CH₂CH₂-N(pyrrolidine) | C=O (6') | C=O | 3" | 1,3-dimethyl-pyrazol-5-yl |
| 208 | H | 4-methylpiperazin-1-yl | C=O (6') | C=O | 3" | 5-chloro-1,3-dimethyl-pyrazol-4-yl |
| 209 | H | 4-methylpiperazin-1-yl | C=O (6') | C=O | 3" | furan-3-yl |
| 210 | H | 4-methylpiperazin-1-yl | C=O (6') | C=O | 3" | 3-methylfuran-2-yl |
| 211 | H | 4-methylpiperazin-1-yl | C=O (6') | C=O | 3" | 5-methoxyfuran-2-yl |
| 212 | H | 4-methylpiperazin-1-yl | C=O (6') | C=O | 3" | 5-methylfuran-2-yl |
| 213 | H | 4-methylpiperazin-1-yl | C=O (6') | C=O | 3" | 4-methoxythiophen-3-yl |

TABLE 1-continued

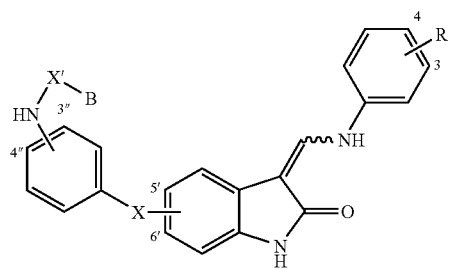

(The above structure is what Table 1 refers to and represents Formulae I and II wherein X'-B represents X'-B in Formulae I and II, X above represents X in Formulae I and II, and

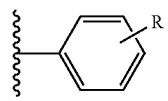

above represents A in Formulae I and II)

| Example # | R substitution 3 | R substitution 4 | X (position) | X' | HN X'B position | B |
|---|---|---|---|---|---|---|
| 214 | H | —N(piperazine)N— | C=O (6') | C=O | 3" | thiophene-SMe |
| 215 | H | —N(piperazine)N— | C=O (6') | C=O | 3" | thiophene-Cl |
| 216 | H | —N(piperazine)N— | C=O (6') | C=O | 3" | thiophene-Me |
| 217 | H | —N(piperazine)N— | C=O (6') | C=O | 3" | thiophene-OEt |
| 218 | H | —N(piperazine)N— | C=O (6') | C=O | 3" | oxazole |
| 219 | H | —N(piperazine)N— | C=O (6') | C=O | 3" | oxazole |
| 220 | H | —N(piperazine)N— | C=O (6') | C=O | 3" | isoxazole-OMe |

TABLE 1-continued

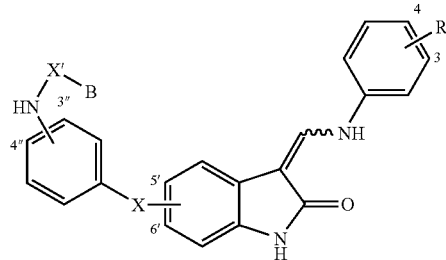

(The above structure is what Table 1 refers to and represents Formulae I and II wherein X′-B represents X′-B in Formulae I and II, X above represents X in Formulae I and II, and

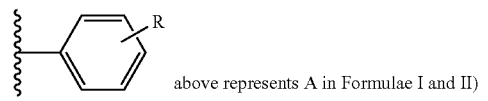

above represents A in Formulae I and II)

| Example # | R substitution 3 | R substitution 4 | X (position) | X' | HN X'B position | B |
|---|---|---|---|---|---|---|
| 221 | H | —N(piperazine)N— | C=O (6') | C=O | 3" | 2,4-dimethyl-thiazol-5-yl (Me, S, N, Me) |
| 222 | H | —N(piperazine)N— | C=O (6') | C=O | 3" | 4-methyl-thiazol-5-yl (S, N, Me) |
| 223 | H | —N(piperazine)N— | C=O (6') | C=O | 3" | 2-methyl-thiazol-4-yl (Me, N, S) |
| 224 | H | —N(piperazine)N— | C=O (6') | C=O | 3" | thiazol-4-yl (N, S) |
| 225 | H | —N(piperazine)N— | C=O (6') | C=O | 3" | thiazol-2-yl (S, N) |
| 226 | H | —N(piperazine)N— | C=O (6') | C=O | 3" | thiazol-5-yl (S, N) |
| 227 | H | —N(piperazine)N— | C=O (6') | C=O | 3" | 1-methyl-imidazol-2-yl (Me, N, N) |
| 228 | H | —N(piperazine)N— | C=O (6') | C=O | 3" | 1-methyl-imidazol-4-yl (N, N-Me) |

TABLE 1-continued

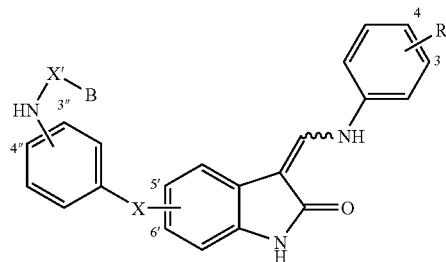

(The above structure is what Table 1 refers to and represents Formulae I and II wherein X'-B represents X'-B in Formulae I and II, X above represents X in Formulae I and II, and

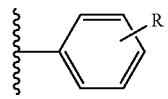

above represents A in Formulae I and II)

| Example # | R substitution 3 | R substitution 4 | X (position) | X' | HN X'B position | B |
|---|---|---|---|---|---|---|
| 229 | H | N-piperazinyl-N-Me | C=O (6') | C=O | 3" | imidazo[2,1-b]thiazol-5-yl, 6-Me |
| 230 | H | N-piperazinyl-N-Me | C=O (6') | C=O | 3" | imidazo[2,1-b]thiazol-6-yl |
| 231 | H | N-piperazinyl-N-Me | C=O (6') | C=O | 3" | pyrimidin-5-yl |
| 232 | H | N-piperazinyl-N-Me | C=O (6') | C=O | 3" | 2,5-dimethoxyphenyl |
| 233 | H | N-piperazinyl-N-Me | C=O (6') | C=O | 3" | 2-(dimethylamino)phenyl |
| 234 | H | N-piperazinyl-N-Me | C=O (6') | C=O | 3" | 2-methoxypyridin-3-yl |

TABLE 1-continued

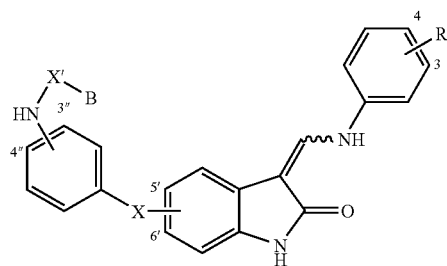

(The above structure is what Table 1 refers to and represents Formulae I and II wherein X'-B represents X'-B in Formulae I and II, X above represents X in Formulae I and II, and

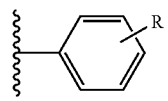

above represents A in Formulae I and II)

| Example # | R substitution 3 | R substitution 4 | X (position) | X' | HN X'B position | B |
|---|---|---|---|---|---|---|
| 235 | H | ⟜–N⌒N– | C=O (6') | C=O | 3" | pyridine, 2-Me, 5-linked |
| 236 | H | ⟜–N⌒N– | C=O (6') | C=O | 3" | pyridine, 2-Me, 3-linked |
| 237 | H | ⟜–N⌒N– | C=O (6') | C=O | 3" | pyridine, 2,6-diMe |
| 238 | H | ⟜–N⌒N– | C=O (6') | C=O | 3" | pyridine, 3-Me, 2-linked |
| 239 | H | ⟜–N⌒N– | C=O (6') | C=O | 3" | pyridine, 3-Cl, 4-linked |
| 240 | H | ⟜–N⌒N– | C=O (6') | C=O | 3" | pyridine, 5-Me, 3-linked |

TABLE 1-continued

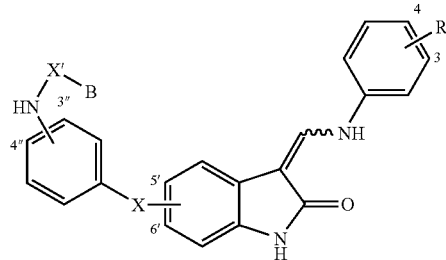

(The above structure is what Table 1 refers to and represents Formulae I and II wherein X'-
B represents X'-B in Formulae I and II, X above represents X in Formulae I and II, and

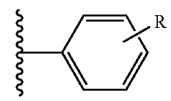

above represents A in Formulae I and II)

| Example # | R substitution 3 | R substitution 4 | X (position) | X' | HN X'B position | B |
|---|---|---|---|---|---|---|
| 241 | H | —N(piperazine)N— | C=O (6') | C=O | 3" | 4-chloropyridin-2-yl |
| 242 | H | —N(piperazine)N— | C=O (6') | C=O | 3" | pyridazin-4-yl |
| 243 | H | —N(piperazine)N— | C=O (6') | C=O | 3" | pyrazin-2-yl |
| 244 | H | —N(piperazine)N— | C=O (6') | C=O | 3" | 5-methylpyrazin-2-yl |
| 245 | H | —N(piperazine)N— | C=O (6') | C=O | 3" | furan-2-yl |
| 246 | H | —N(piperazine)N— | C=O (6') | C=O | 3" | 2,5-dimethylfuran-3-yl |
| 247 | H | —N(piperazine)N— | C=O (6') | C=O | 3" | 5-methylfuran-3-yl |

TABLE 1-continued

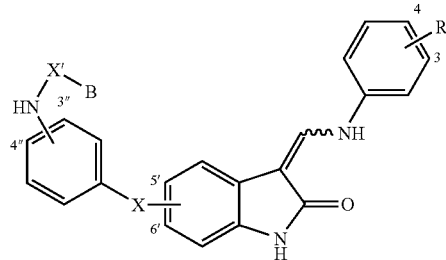

(The above structure is what Table 1 refers to and represents Formulae I and II wherein X'-B represents X'-B in Formulae I and II, X above represents X in Formulae I and II, and

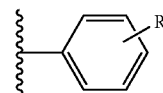

above represents A in Formulae I and II)

| Example # | R substitution | | X (position) | X' | HN X'B position | B |
|---|---|---|---|---|---|---|
| | 3 | 4 | | | | |
| 248 | H | —N(piperazine)N— | C=O (6') | C=O | 3" | thiophen-3-yl |
| 249 | H | —N(piperazine)N— | C=O (6') | C=O | 3" | 1,3-dimethyl-thieno[2,3-c]pyrazol-5-yl |
| 250 | H | —N(piperazine)N— | C=O (6') | C=O | 3" | 3-methylthiophen-2-yl |
| 251 | H | —N(piperazine)N— | C=O (6') | C=O | 3" | 5-methylthiophen-2-yl |
| 252 | H | —N(piperazine)N— | C=O (6') | C=O | 3" | 3,5-dimethylisoxazol-4-yl |
| 253 | H | —N(piperazine)N— | C=O (6') | C=O | 3" | 5-methylisoxazol-3-yl |
| 254 | H | —N(piperazine)N— | C=O (6') | C=O | 3" | 1-methyl-1H-imidazol-5-yl |

TABLE 1-continued

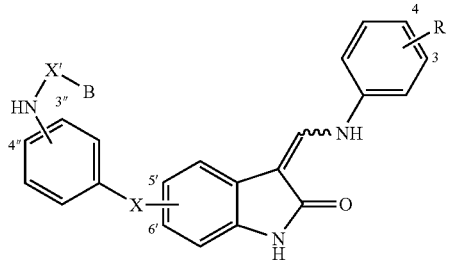

(The above structure is what Table 1 refers to and represents Formulae I and II wherein X'-B represents X'-B in Formulae I and II, X above represents X in Formulae I and II, and

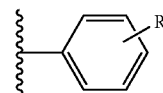

above represents A in Formulae I and II)

| Example # | R substitution 3 | R substitution 4 | X (position) | X' | HN X'B position | B |
|---|---|---|---|---|---|---|
| 255 | H | —N(piperazine)N— | C=O (6') | C=O | 3" | 5-(4-methyl-1,2,3-thiadiazolyl) |
| 256 | H | —N(piperazine)N— | C=O (6') | C=O | 3" | 1-methylpyrrol-2-yl |
| 257 | H | —N(piperazine)N—N(piperazine)N— | C=O (6') | C=O | 3" | phenyl |
| 258 | H | —N(piperazine)N— | C=O (6') | C=O | 3" | 3,5-difluorophenyl |
| 259 | H | —N(piperazine)N— | C=O (6') | C=O | 3" | 2-chlorophenyl |
| 260 | H | —N(piperazine)N— | C=O (6') | C=O | 3" | 3-chlorophenyl |
| 261 | H | —N(piperazine)N— | C=O (6') | C=O | 3" | 4-chlorophenyl |

TABLE 1-continued

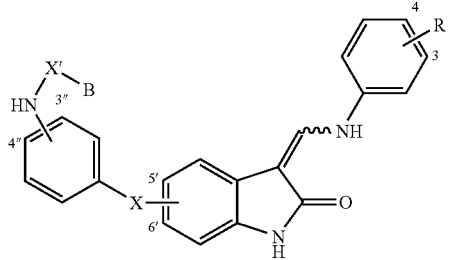

(The above structure is what Table 1 refers to and represents Formulae I and II wherein X'-B represents X'-B in Formulae I and II, X above represents X in Formulae I and II, and

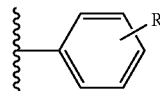

above represents A in Formulae I and II)

| Example # | R substitution 3 | R substitution 4 | X (position) | X' | HN X'B position | B |
|---|---|---|---|---|---|---|
| 262 | H | —N(piperazine)N— | C=O (6') | C=O | 3" | 2-MeO-phenyl |
| 263 | H | —N(piperazine)N— | C=O (6') | C=O | 3" | 3-OMe-phenyl |
| 264 | H | —N(piperazine)N— | C=O (6') | C=O | 3" | 4-OMe-phenyl |
| 265 | H | —N(piperazine)N— | C=O (6') | C=O | 3" | 3,5-(OMe)₂-phenyl |
| 266 | H | —N(piperazine)N— | C=O (6') | C=O | 3" | 3,4-(OMe)₂-phenyl |
| 267 | H | —N(piperazine)N— | C=O (6') | C=O | 3" | 2-Me-phenyl |
| 268 | H | —N(piperazine)N— | C=O (6') | C=O | 3" | 3-Me-phenyl |

TABLE 1-continued

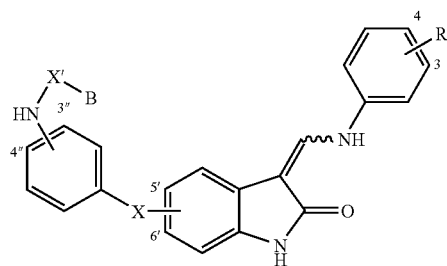

(The above structure is what Table 1 refers to and represents Formulae I and II wherein X'-B represents X'-B in Formulae I and II, X above represents X in Formulae I and II, and

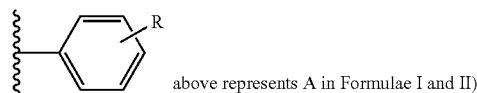

above represents A in Formulae I and II)

| Example # | R substitution 3 | R substitution 4 | X (position) | X' | HN X'B position | B |
|---|---|---|---|---|---|---|
| 269 | H | ⟨piperazine⟩ | C=O (6') | C=O | 3" | 4-Me-phenyl |
| 270 | H | ⟨piperazine⟩ | C=O (6') | C=O | 3" | 4-CN-phenyl |
| 271 | H | ⟨piperazine⟩ | C=O (6') | C=O | 3" | N-Me-benzoxazine |
| 272 | H | ⟨piperazine⟩ | C=O (6') | C=O | 3" | 2-F-6-Cl-phenyl |
| 273 | H | ⟨piperazine⟩ | C=O (6') | C=O | 3" | 2,4-diOMe-phenyl |
| 274 | H | ⟨piperazine⟩ | C=O (6') | C=O | 3" | 3-CN-phenyl |

TABLE 1-continued

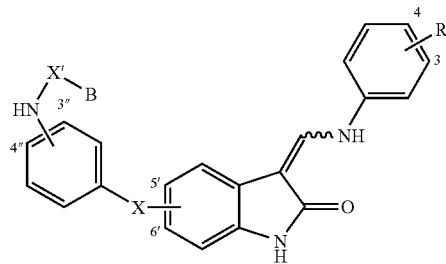

(The above structure is what Table 1 refers to and represents Formulae I and II wherein X′-B represents X′-B in Formulae I and II, X above represents X in Formulae I and II, and

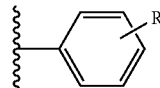

above represents A in Formulae I and II)

| Example # | R substitution 3 | R substitution 4 | X (position) | X′ | HN X′B position | B |
|---|---|---|---|---|---|---|
| 275 | H | –N(piperazine)N– | C=O (6′) | C=O | 3″ | benzothiadiazole |
| 276 | H | –N(piperazine)N– | C=O (6′) | C=O | 3″ | 2-F, 4-Cl phenyl |
| 277 | H | –N(piperazine)N– | C=O (6′) | C=O | 3″ | 3-pyridyl |
| 278 | H | –N(piperazine)N– | C=O (6′) | C=O | 3″ | 4-pyridyl |
| 279 | H | –N(piperazine)N– | C=O (6′) | C=O | 3″ | 6-chloro-3-pyridyl |
| 280 | H | –N(piperazine)N– | C=O (6′) | C=O | 3″ | 2-pyridyl |
| 281 | H | –N(piperazine)N– | C=O (6′) | C(=O)NH | 3″ | 2-thienyl |

TABLE 1-continued

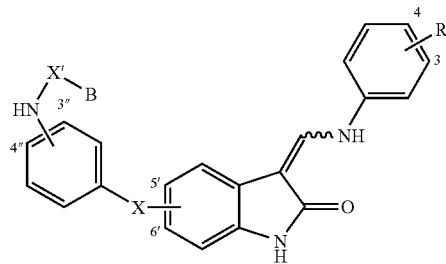

(The above structure is what Table 1 refers to and represents Formulae I and II wherein X'-B represents X'-B in Formulae I and II, X above represents X in Formulae I and II, and

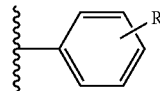

above represents A in Formulae I and II)

| Example # | R substitution | | X (position) | X' | HN X'B position | B |
|---|---|---|---|---|---|---|
| | 3 | 4 | | | | |
| 282 | H | —N(piperazine)N— | C=O (6') | —C(O)NH— | 3" | 3-thienyl |
| 283 | H | —N(piperazine)N— | C=O (6') | —C(O)NH— | 3" | phenyl |
| 284 | H | —N(piperazine)N— | C=O (6') | —C(O)NH— | 3" | 2,6-difluorophenyl |
| 285 | H | —N(piperazine)N— | C=O (6') | —C(O)NH— | 3" | 2-chlorophenyl |
| 286 | H | —N(piperazine)N— | C=O (6') | —C(O)NH— | 3" | 3-chlorophenyl |
| 287 | H | —N(piperazine)N— | C=O (6') | —C(O)NH— | 3" | 4-chlorophenyl |
| 288 | H | —N(piperazine)N— | C=O (6') | —C(O)NH— | 3" | 2-methoxyphenyl |

TABLE 1-continued

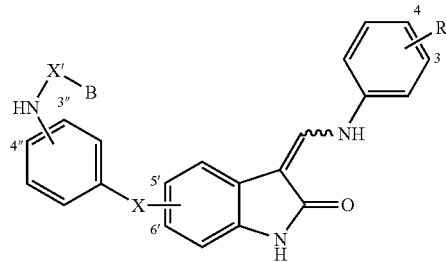

(The above structure is what Table 1 refers to and represents Formulae I and II wherein X′-B represents X′-B in Formulae I and II, X above represents X in Formulae I and II, and

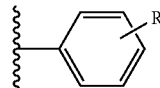

above represents A in Formulae I and II)

| Example # | R substitution | | X (position) | X′ | HN X′B position | B |
|---|---|---|---|---|---|---|
| | 3 | 4 | | | | |
| 289 | H | -N(piperazine)N- | C=O (6′) | -C(=O)NH- | 3″ | phenyl-3-OMe |
| 290 | H | -N(piperazine)N- | C=O (6′) | -C(=O)NH- | 3″ | phenyl-4-OMe |
| 291 | H | -N(piperazine)N- | C=O (6′) | -C(=O)NH- | 3″ | phenyl-3-OMe,4-OMe |
| 292 | H | -N(piperazine)N- | C=O (6′) | -C(=O)NH- | 3″ | phenyl-2-Me |
| 293 | H | -N(piperazine)N- | C=O (6′) | -C(=O)NH- | 3″ | phenyl-3-Me |
| 294 | H | -N(piperazine)N- | C=O (6′) | -C(=O)NH- | 3″ | phenyl-4-Me |
| 295 | H | -N(piperazine)N- | C=O (6′) | -C(=O)NH- | 3″ | phenyl-3-CN |

TABLE 1-continued

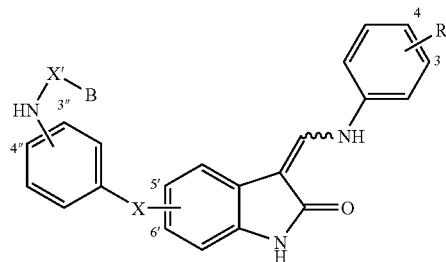

(The above structure is what Table 1 refers to and represents Formulae I and II wherein X'-
B represents X'-B in Formulae I and II, X above represents X in Formulae I and II, and

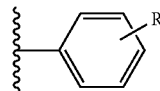

above represents A in Formulae I and II)

| Example # | R substitution 3 | R substitution 4 | X (position) | X' | HN X'B position | B |
|---|---|---|---|---|---|---|
| 296 | H | piperazinyl-Me | C=O (6') | –C(O)NH– | 3" | 4-CN-phenyl |
| 297 | H | piperazinyl-Me | C=O (6') | –C(O)NH– | 3" | 4-NMe₂-phenyl |
| 298 | H | piperazinyl-Me | C=O (6') | –C(O)NH– | 3" | 3,5-diF-phenyl |
| 299 | H | piperazinyl-Me | C=O (6') | –C(O)NH– | 3" | 3,5-diOMe-phenyl |
| 300 | H | piperazinyl-Me | C=O (6') | –C(O)NH– | 3" | 3,4-diOMe-phenyl |
| 301 | H | piperazinyl-Me | C=O (6') | –C(O)NH– | 3" | 2-F-4-Cl-phenyl |

TABLE 1-continued

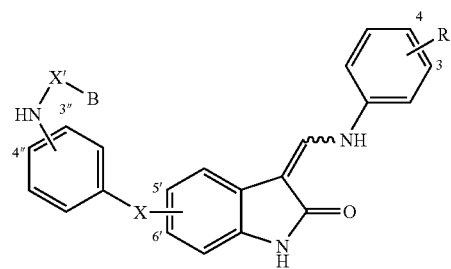

(The above structure is what Table 1 refers to and represents Formulae I and II wherein X'-B represents X'-B in Formulae I and II, X above represents X in Formulae I and II, and

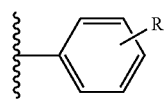

above represents A in Formulae I and II)

| Example # | R substitution 3 | R substitution 4 | X (position) | X' | HN X'B position | B |
|---|---|---|---|---|---|---|
| 302 | H | piperazinyl | C=O (6') | C(=O)NH amide | 3" | 2,5-dimethoxyphenyl |
| 303 | H | piperazinyl | C=O (6') | C(=O)NH amide | 3" | 2,6-dimethoxyphenyl |
| 304 | H | piperazinyl | C=O (6') | SO₂ | 3" | 2,5-dimethylfuran-3-yl |
| 305 | H | piperazinyl | C=O (6') | SO₂ | 3" | thiophen-2-yl |
| 306 | H | piperazinyl | C=O (6') | SO₂ | 3" | thiophen-3-yl |
| 307 | H | piperazinyl | C=O (6') | SO₂ | 3" | 5-chlorothiophen-2-yl |

TABLE 1-continued

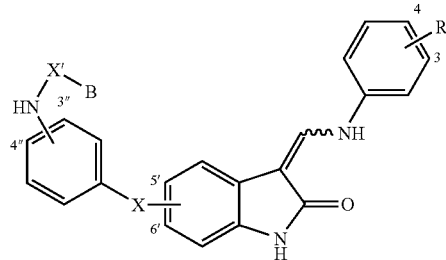

(The above structure is what Table 1 refers to and represents Formulae I and II wherein X'-B represents X'-B in Formulae I and II, X above represents X in Formulae I and II, and

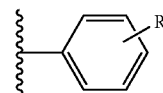

above represents A in Formulae I and II)

| Example # | R substitution 3 | R substitution 4 | X (position) | X' | HN X'B position | B |
|---|---|---|---|---|---|---|
| 308 | H | —N(piperazine)N— | C=O (6') | —S(=O)₂— | 3" | 3,5-dimethylisoxazol-4-yl (Me, Me) |
| 309 | H | —N(piperazine)N— | C=O (6') | —S(=O)₂— | 3" | 1-methylimidazol-5-yl |
| 310 | H | —N(piperazine)N— | C=O (6') | —S(=O)₂— | 3" | 1,3,5-trimethylpyrazol-4-yl |
| 311 | H | —N(piperazine)N— | C=O (6') | —S(=O)₂— | 3" | 2-chlorophenyl |
| 312 | H | —N(piperazine)N— | C=O (6') | —S(=O)₂— | 3" | 3-chlorophenyl |
| 313 | H | —N(piperazine)N— | C=O (6') | —S(=O)₂— | 3" | 4-chlorophenyl |
| 314 | H | —N(piperazine)N— | C=O (6') | —S(=O)₂— | 3" | 4-methoxyphenyl |

TABLE 1-continued

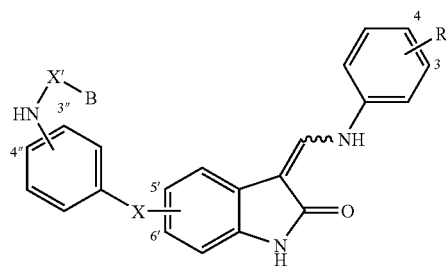

(The above structure is what Table 1 refers to and represents Formulae I and II wherein X'-B represents X'-B in Formulae I and II, X above represents X in Formulae I and II, and

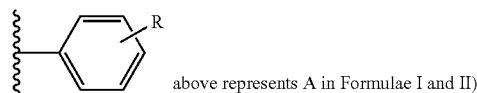

above represents A in Formulae I and II)

| Example # | R substitution | | X | | HN X'B | |
|---|---|---|---|---|---|---|
| | 3 | 4 | (position) | X' | position | B |
| 315 | H | ⸺N⌒N⸺ | C=O (6') | —S(O)(O)— | 3" | 4-Me-phenyl |
| 316 | H | ⸺N⌒N⸺ | C=O (6') | —S(O)(O)— | 3" | 2-CN-phenyl |
| 317 | H | ⸺N⌒N⸺ | C=O (6') | —S(O)(O)— | 3" | 3-CN-phenyl |
| 318 | H | ⸺N⌒N⸺ | C=O (6') | —S(O)(O)— | 3" | 4-CN-phenyl |
| 319 | H | ⸺N⌒N⸺ | C=O (6') | —S(O)(O)— | 3" | 2-Me-phenyl |
| 320 | H | ⸺N⌒N⸺ | C=O (6') | —S(O)(O)— | 3" | 3,5-diF-phenyl |

TABLE 1-continued

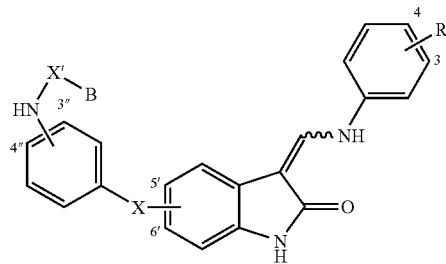

(The above structure is what Table 1 refers to and represents Formulae I and II wherein X'-B represents X'-B in Formulae I and II, X above represents X in Formulae I and II, and

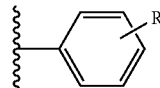

above represents A in Formulae I and II)

| Example # | R substitution 3 | R substitution 4 | X (position) | X' | HN X'B position | B |
|---|---|---|---|---|---|---|
| 321 | H | ⟶N⟶N—Me (piperazine) | C═O (6') | —S(O)₂— | 3″ | 3-OMe-phenyl |
| 322 | H | ⟶N⟶N—Me (piperazine) | C═O (6') | —S(O)₂— | 3″ | 3-Me-phenyl |
| 323 | H | ⟶N⟶N—Me (piperazine) | C═O (6') | —C(O)N(Me)— | 3″ | phenyl |
| 324 | H | —(CH₂)₃CO₂H | C═O (6') | C═O | 3″ | 1,3-dimethylpyrazol-5-yl |
| 325 | H | ⟶N(H)CH₂CH₂CH₂—N(piperazine)—Me | C═O (6') | C═O | 3″ | 1,3-dimethylpyrazol-5-yl |
| 326 | H | ⟶N(H)CH₂CH₂—N(morpholine) | C═O (6') | C═O | 3″ | 1,3-dimethylpyrazol-5-yl |
| 327 | H | ⟶N(H)CH₂CH₂—N(pyrrolidine) | C═O (6') | C═O | 3″ | 1,3-dimethylpyrazol-5-yl |

TABLE 1-continued

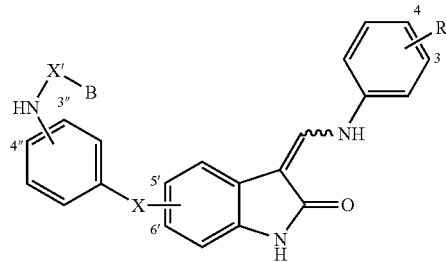

(The above structure is what Table 1 refers to and represents Formulae I and II wherein X'-B represents X'-B in Formulae I and II, X above represents X in Formulae I and II, and

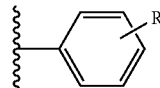 above represents A in Formulae I and II)

| Example # | R substitution 3 | R substitution 4 | X (position) | X' | HN X'B position | B |
|---|---|---|---|---|---|---|
| 328 | H | N-piperazinyl-N'-Me | C=O (6') | C=O | 3" | 5-Cl-1-Me-pyrazol-4-yl |
| 329 | H | —CH₂NH₂ | C=O (6') | C=O | 3" | 1-Me-3-Me-pyrazol-5-yl |
| 330 | H | —CH₂CH₂OH | C=O (6') | C=O | 3" | 1-Me-3-Me-pyrazol-5-yl |
| 331 | H | —CH₂OH | C=O (6') | C=O | 3" | 1-Me-3-Me-pyrazol-5-yl |
| 332 | H | —CH₂OC(O)CH₂NMe₂ | C=O (6') | C=O | 3" | 1-Me-3-Me-pyrazol-5-yl |
| 333 | H | 4-hydroxypiperidin-1-yl | C=O (6') | C=O | 3" | 1-Me-3-Me-pyrazol-5-yl |
| 334 | H | —C(O)NHOH | C=O (6') | C=O | 3" | 1-Me-3-Me-pyrazol-5-yl |

TABLE 1-continued

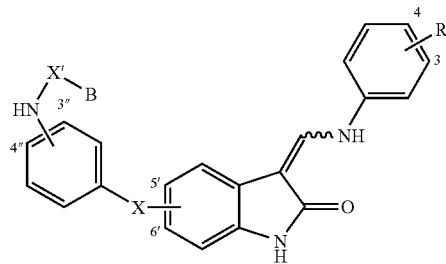

(The above structure is what Table 1 refers to and represents Formulae I and II wherein X'-B represents X'-B in Formulae I and II, X above represents X in Formulae I and II, and

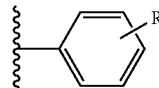

above represents A in Formulae I and II)

| Example # | R substitution | | X (position) | X' | HN X'B position | B |
|---|---|---|---|---|---|---|
| | 3 | 4 | | | | |
| 335 | H | —(CH₂)₃CO₂CH(CH₃)₂ | C=O (6') | C=O | 3" | Me-N-N, Me (pyrazole) |
| 336 | H | —(CH₂)₃CONHOCH₃ | C=O (6') | C=O | 3" | Me-N-N, Me (pyrazole) |
| 337 | H | N-piperazine-N— | C=O (6') | C=O | 3" | Et-N-N (pyrazole) |
| 338 | H | N-piperazine-N— | C=O (6') | C=O | 3" | Ph-N-N (pyrazole) |
| 339 | H | N-piperazine-N— | C=O (6') | C=O | 3" | Et, Me pyrazole |
| 340 | H | N-piperazine-N— | C=O (6') | C=O | 3" | Me, Me, Me pyrazole |
| 341 | H | N-piperazine-N— | C=O (6') | C=O | 3" | Me, tBu pyrazole |

TABLE 1-continued

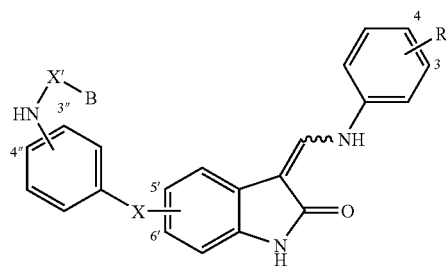

(The above structure is what Table 1 refers to and represents Formulae I and II wherein X'-B represents X'-B in Formulae I and II, X above represents X in Formulae I and II, and

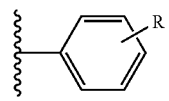  above represents A in Formulae I and II)

| Example # | R substitution 3 | R substitution 4 | X (position) | X' | HN X'B position | B |
|---|---|---|---|---|---|---|
| 342 | H | piperazine-N-Me | C=O (6') | C=O | 3″ | 4-Cl-1-Et-pyrazol-3-yl |
| 343 | H | —(CH$_2$)$_3$CO$_2$H | C=O (6') | C=O | 3″ | 4-Cl-1-Et-pyrazol-3-yl |
| 344 | H | CH$_2$-pyrrolidin-1-yl | C=O (6') | C=O | 3″ | 4-Cl-1-Et-pyrazol-3-yl |
| 345 | H | piperazine-N-Me | C=O (6') | C=O | 3″ | 5-Et-1-Me-pyrazol-3-yl |
| 346 | H | —(CH$_2$)$_2$CO$_2$H | C=O (6') | C=O | 3″ | 5-Et-1-Me-pyrazol-3-yl |
| 347 | H | CH$_2$-pyrrolidin-1-yl | C=O (6') | C=O | 3″ | 5-Et-1-Me-pyrazol-3-yl |
| 348 | H | piperazine-N-Me | C=O (6') | C=O | 3″ | 1-Me-3-tBu-pyrazol-5-yl |

TABLE 1-continued

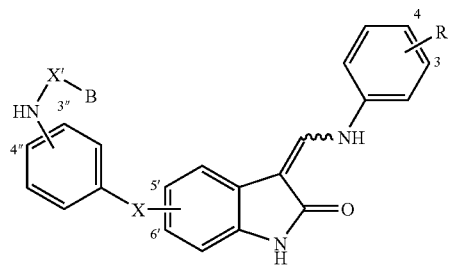

(The above structure is what Table 1 refers to and represents Formulae I and II wherein X′-B represents X′-B in Formulae I and II, X above represents X in Formulae I and II, and

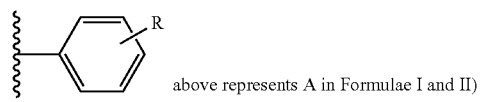

above represents A in Formulae I and II)

| Example | R substitution | | X | | HN X'B | |
|---|---|---|---|---|---|---|
| # | 3 | 4 | (position) | X' | position | B |
| 349 | H | piperazine-N-Me | C=O (6') | C=O | 3" | iPr-pyrazole |
| 350 | H | piperazine-N-Me | C=O (6') | C=O | 3" | 1,5-diMe-pyrazole (N-Me) |
| 351 | H | piperazine-N-Me | C=O (6') | C=O | 3" | 5-Me-1-Et-pyrazole |
| 352 | H | CH₂-pyrrolidine | C=O (6') | C=O | 3" | 3-Me-thiophene |
| 353 | H | —(CH₂)₃CO₂H | C=O (6') | C=O | 3" | 3-Me-thiophene |
| 354 | H | (CH₂)₃-pyrrolidine | C=O (6') | C=O | 3" | 3-Me-furan |
| 355 | H | —(CH₂)₂CO₂H | C=O (6') | C=O | 3" | 3-Me-furan |

TABLE 1-continued

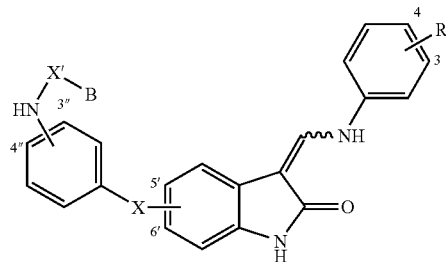

(The above structure is what Table 1 refers to and represents Formulae I and II wherein X'-B represents X'-B in Formulae I and II, X above represents X in Formulae I and II, and

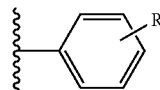

above represents A in Formulae I and II)

| Example # | R substitution | | X (position) | X' | HN X'B position | B |
|---|---|---|---|---|---|---|
| | 3 | 4 | | | | |
| 356 | H | ⸺CH₂-pyrrolidinyl | C=O (6') | C=O | 3" | 3-methylfuran-2-yl |
| 357 | H | —(CH₂)₂CO₂H | C=O (6') | C=O | 3" | 5-chloro-1-methyl-1H-pyrazol-4-yl |
| 358 | H | ⸺(CH₂)₂-pyrrolidinyl | C=O (6') | C=O | 3" | 5-chloro-1-methyl-1H-pyrazol-4-yl |
| 359 | H | —(CH₂)₂CO₂H | C=O (6') | C=O | 3" | 3-methylisoxazol-4-yl |
| 360 | H | ⸺(CH₂)₂-pyrrolidinyl | C=O (6') | C=O | 3" | 3-methylisoxazol-4-yl |
| 361 | H | ⸺CH₂-pyrrolidinyl | C=O (6') | C=O | 3" | 2-methylphenyl |
| 362 | H | —(CH₂)₃CO₂H | C=O (6') | C=O | 3" | 2-methylphenyl |

TABLE 1-continued

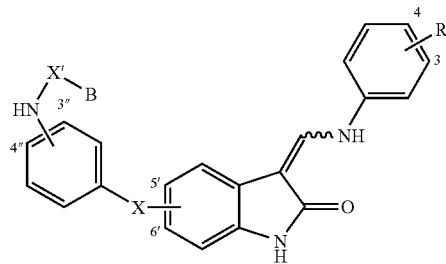

(The above structure is what Table 1 refers to and represents Formulae I and II wherein X'-B represents X'-B in Formulae I and II, X above represents X in Formulae I and II, and

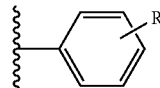

above represents A in Formulae I and II)

| Example # | R substitution 3 | R substitution 4 | X (position) | X' | HN X'B position | B |
|---|---|---|---|---|---|---|
| 363 | H | (CH₂-pyrrolidine) | C=O (6') | C=O | 3" | Et-pyrazole-Me |
| 364 | H | —(CH₂)₃CO₂H | C=O (6') | C=O | 3" | Et-pyrazole-Me |
| 365 | H | (N-methylpiperazine) | C=O (6') | CH₂ | 3" | Me-pyrazole-Me |
| 366 | H | (N-methylpiperazine) | C=O (6') | CH₂ | 3" | phenyl |
| 367 | H | —CH₂NEt₂ | C=O (6') | C=O | 3" | Me-pyrazole-Me |
| 368 | H | (CH₂-4-hydroxypiperidine) | C=O (6') | C=O | 3" | Me-pyrazole-Me |
| 369 | H | —NH(CH₂)₂NEt₂ | C=O (6') | C=O | 3" | Me-pyrazole-Me |

TABLE 1-continued

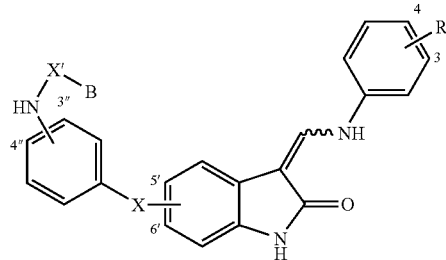

(The above structure is what Table 1 refers to and represents Formulae I and II wherein X'-B represents X'-B in Formulae I and II, X above represents X in Formulae I and II, and

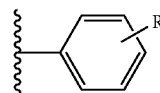

above represents A in Formulae I and II)

| Example # | R substitution 3 | R substitution 4 | X (position) | X' | HN X'B position | B |
|---|---|---|---|---|---|---|
| 370 | H | ⸺N(piperazine)N⸺CH₂CH₂OCH₂CH₂OH | C=O (6') | C=O | 3" | 1-Me,3-Me pyrazol-5-yl |
| 371 | H | —CONHCH₂CH₂NEt₂ | C=O (6') | C=O | 3" | 1-Me,3-Me pyrazol-5-yl |
| 372 | H | —CONHCH₂CH₂NEt₂ | C=O (6') | C=O | 3" | 3-Me-furan-2-yl |
| 373 | H | —CH₂CONHCH₂CH₂NEt₂ | C=O (6') | C=O | 3" | 1-Me,3-Me pyrazol-5-yl |
| 374 | H | —CH₂CH₂NEt₂ | C=O (6') | C=O | 3" | 1-Me,3-Me pyrazol-5-yl |
| 375 | H | —CH₂CH₂CH₂NEt₂ | C=O (6') | C=O | 3" | 1-Me,3-Me pyrazol-5-yl |
| 376 | H | —CH₂CH₂-N(piperidin-4-ol) | C=O (6') | C=O | 3" | 1-Me,3-Me pyrazol-5-yl |

TABLE 1-continued

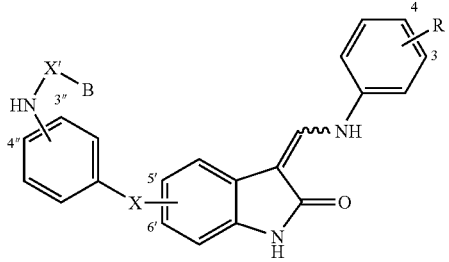

(The above structure is what Table 1 refers to and represents Formulae I and II wherein X'-B represents X'-B in Formulae I and II, X above represents X in Formulae I and II, and

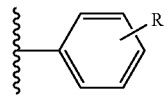

above represents A in Formulae I and II)

| Example # | R substitution 3 | R substitution 4 | X (position) | X' | HN X'B position | B |
|---|---|---|---|---|---|---|
| 377 | H | —CH(OH)CH(OH)CH$_2$OH | C=O (6') | C=O | 3" | Me, N—N, Me (pyrazole) |

In the table below, certain general reaction schemes are set forth. The symbols utilized in such schemes relate to the above formula I and II as follows:

Scheme

Formula I and II

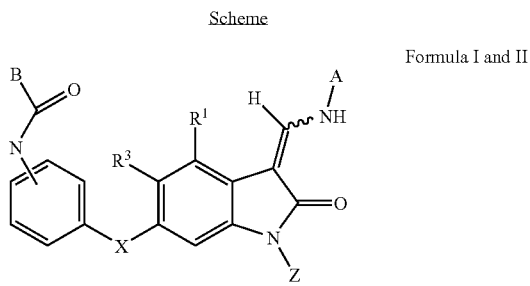

I

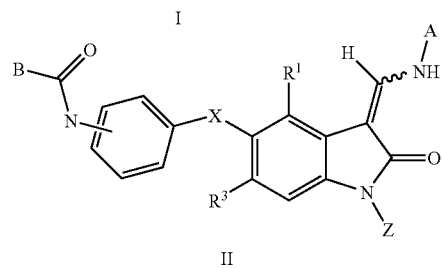

II

The compounds of the above Table 1 are prepared as follows:

Example 1

2-Ethyl-5-methyl-2H-pyrazole-3-carboxylic acid (3-{3-[(4-morpholin-4-yl-phenylamino)-methylene]-2-oxo-2,3-dihydro-1H-indole-5-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-5-carbonyl)-phenyl]-amide (prepared below, 30 mg, 0.072 mmol) and THF (1 mL). To the resulting solution was added N-(4-aminophenyl)morpholine (19.3 mg, 0.1082 mmol), and the mixture was stirred for 24 h at 65° C. Subsequently, the reaction mixture was cooled to room temperature, concentrated in vacuo and redissolved in EtOAc. Hexanes were added to the reaction mixture. The solid precipitate that formed was filtered and washed with ~1 mL of ice cold THF yielding 36% (15 mg, 0.026 mmol) of the title compound.

The 2-Ethyl-5-methyl-2H-pyrazole-3-carboxylic acid [3-(3-hydroxymethylene-2-oxo-2,3-dihydro-1H-indole-5-carbonyl)-phenyl]-amide was prepared from oxindole using the following multiple step procedure:

Step 1: 5-(3-Nitro-benzoyl)-1,3-dihydro-indol-2-one

AlCl$_3$ (20.0 g, 150 mmol) was placed in a dry 250 mL round bottom flask and DMF (3.30 mL) was added dropwise at 0° C. During the addition of DMF care was taken to ensure that the reaction was allowed to vent to the outside as this addition caused an exotherm to occur. Additionally as the DMF was added a white suspension formed. This suspension was allowed to stir for 30 min at room temperature. The room temperature reaction mixture was then treated with 3-nitrobenzoyl chloride (3.70 g, 19.5 mmol) and oxindole (2.051 g, 15 mmol), respectively. The resulting reaction mixture was heated to 70° C. and allowed to stir for 6 hours during which the reaction mixture transitioned from a white suspension, to a thick yellow oil and finally to a black wax. The reaction was cooled to room temperature. Water (25 mL) was added directly to the reaction mixture followed by 1M HCl$_{(aq)}$ (5 mL), turning the black wax into a white solid. The white solid was collected via vacuum filtration. The crude white solid was purified by washing with sat. NaHCO$_{3(aq)}$ providing pure, solid 5-(3-Nitro-benzoyl)-1,3-dihydro-indol-2-one (4.05 g, 14.4 mmol, 95%).

Step 2: 5-(3-Amino-benzoyl)-1,3-dihydro-indol-2-one 5-(3-Nitro-benzoyl)-1,3-dihydro-indol-2-one (2.0 g, 7.09 mmol) was dissolved in MeOH (600 mL). 10% Pd/C (0.20 g) was added to the flask and then placed under vacuum to remove any $O_{2(g)}$. The reaction mixture was kept under reduced pressure for ~5 min and was then charged with $H_{2(g)}$ at atmospheric pressure. This evacuation/$H_{2(g)}$ fill procedure was repeated twice. The reaction mixture was stirred for 2 h at which point the starting material had been completely consumed. As the desired ketone product was prone to over-reduction to the alcohol, stopping the reaction immediately upon complete consumption of the starting material limited the amount over-reduction that occurred. The reaction mixture was filtered over celite and the filtrate was concentrated in vacuo resulting in a solid that contained the desired keto-aniline product plus ~5% of the overreduced alcohol-aniline. Flash silica gel chromatography (5% MeOH/CHCl$_3$) of the crude solid provided pure 5-(3-Amino-benzoyl)-1,3-dihydro-indol-2-one in 72% (0.957 g, 3.80 mmol) yield.

Step 3: 2-Ethyl-5-methyl-2H-pyrazole-3-carboxylic acid [3-(2-oxo-2,3-dihydro-1H-indole-5-carbonyl)-phenyl]-amide A dry 25 mL flask was charged with 2-Ethyl-5-methyl-2H-pyrazole-3-carboxylic acid (0.802 g, 4.67 mmol) and thionyl chloride (10 mL) and allowed to stir at 79° C. for 2 h. The thionyl chloride was then removed by distillation. The crude acid chloride was cooled to room temperature, and then dissolved in THF (5 mL). 5-(3-Amino-benzoyl)-1,3-dihydro-indol-2-one (0.905 g, 3.59 mmol) was added to the THF solution of the acid chloride, and the mixture was allowed to reflux for 2 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The tan solids were filtered to afford the pure 2-Ethyl-5-methyl-2H-pyrazole-3-carboxylic acid [3-(2-oxo-2,3-dihydro-1H-indole-5-carbonyl)-phenyl]-amide (1.05 g, 2.73 mmol, 76%).

Step 4: 2-Ethyl-5-methyl-2H-pyrazole-3-carboxylic acid [3-(3-hydroxymethylene-2-oxo-2,3-dihydro-1H-indole-5-carbonyl)-phenyl]-amide 2-Ethyl-5-methyl-2H-pyrazole-3-carboxylic acid [3-(2-oxo-2,3-dihydro-1H-indole-5-carbonyl)-phenyl]-amide (1.12 g, 2.89 mmol) and ethyl formate (0.700 mL, 8.67 mmol) were dissolved in anhydrous ethanol (5.78 mL). The resulting solution was treated in dropwise fashion with a 21 wt % solution of sodium ethoxide in ethanol (5.40 mL, 14.50 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure product (0.609 g, 1.47 mmol, 57%).

Example 2

2-Ethyl-5-methyl-2H-pyrazole-3-carboxylic acid [3-(3-{[4-(4-methyl-piperazin-1-yl)-phenylamino]-methylene}-2-oxo-2,3-dihydro-1H-indole-5-carbonyl)-phenyl]-amide A small screw cap test tube was charged with 2-Ethyl-5-methyl-2H-pyrazole-3-carboxylic acid [3-(3-hydroxymethylene-2-oxo-2,3-dihydro-1H-indole-5-carbonyl)-phenyl]-amide (as prepared in Example 1, 30 mg, 0.072 mmol) and THF (1 mL). To the resulting solution was added 4-(4-methyl-piperazin-1-yl)-phenylamine (20.7 mg, 0.1082 mmol), and the mixture was stirred for 24 h at 65° C. Subsequently, the reaction mixture was cooled to room temperature. The reaction mixture was concentrated in vacuo and purified via flash silica gel chromatography (5% MeOH/95% CHCl$_3$) providing the title compound in 57% yield (24 mg, 0.0407 mmol).

Example 3

2-Ethyl-5-methyl-2H-pyrazole-3-carboxylic acid (3-{3-[(3-hydroxy-phenylamino)-methylene]-2-oxo-2,3-dihydro-1H-indole-5-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-5-carbonyl)-phenyl]-amide (as prepared in Example 1, 30 mg, 0.072 mmol) and THF (1 mL). To the resulting solution was added 3-aminophenol (11.8 mg, 0.1082 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 79% (29 mg, 0.057 mmol) of the title compound.

Example 4

2-Ethyl-5-methyl-2H-pyrazole-3-carboxylic acid (3-{3-[(3-hydroxy-4-methyl-phenylamino)-methylene]-2-oxo-2,3-dihydro-1H-indole-5-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-5-carbonyl)-phenyl]-amide (as prepared in Example 1, 30 mg, 0.072 mmol) and THF (1 mL). To the resulting solution was added 5-amino-2-methoxyphenol (13.3 mg, 0.1082 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 67% (25 g, 0.048 mmol) of the title compound.

Example 5

{4-[(5-{3-[(2-Ethyl-5-methyl-2H-pyrazole-3-carbonyl)-amino]-benzoyl}-2-oxo-1,2-dihydro-indol-3-ylidenemethyl)-amino]-phenyl}-acetic acid A small screw cap test tube was charged with 2-Ethyl-5-methyl-2H-pyrazole-3-carboxylic acid [3-(3-hydroxymethylene-2-oxo-2,3-dihydro-1H-indole-5-carbonyl)-phenyl]-amide (as prepared in Example 1, 30 mg, 0.072 mmol) and THF (1 mL). To the resulting solution was added 4-aminophenylacetic acid (16.4 mg, 0.1082 mmol), and the mixture was stirred for 24 h at 65° C. Subsequently, the reaction mixture was cooled to room temperature. Hexanes were added to the reaction mixture. The solid precipitate that formed was washed with ~1 mL of ice cold THF yielding 42% (16.7 mg, 0.030 mmol) of the title compound.

Example 6

N-(3-{3-[(4-Morpholin-4-yl-phenylamino)-methylene]-2-oxo-2,3-dihydro-1H-indole-5-carbonyl}-phenyl)-acetamide A small screw cap test tube was charged with N-[3-(3-Hydroxymethylene-2-oxo-2,3-dihydro-1H-indole-5-carbonyl)-phenyl]-acetamide (prepared below, 52 mg, 0.161 mmol) and THF (2 mL). To the resulting solution was added N-(4-aminophenyl)morpholine (43 mg, 0.242 mmol), and the mixture was stirred for 24 h at 65° C. Subsequently, the reaction mixture was cooled to room temperature. Hexanes were added to the reaction mixture.

The solid precipitate that formed was washed with ~1 mL of i-prOH yielding 69% (54 mg, 0.111 mmol) of the title compound.

The N-[3-(3-Hydroxymethylene-2-oxo-2,3-dihydro-1H-indole-5-carbonyl)-phenyl]-acetamide was prepared from oxindole using the following multiple step procedure:

Step 1: N-[3-(2-Oxo-2,3-dihydro-1H-indole-5-carbonyl)-phenyl]-acetamide

A dry 25 mL flask was charged with acetyl chloride (0.273 g, 3.48 mmol) and THF (5 mL). 5-(3-Amino-benzoyl)-1,3-dihydro-indol-2-one (as prepared in Example 1, 0.675 g, 2.67 mmol) was added to the THF solution of the acid chloride, and the mixture was allowed to reflux for 3 h. The reaction mixture was then allowed to cool to room temperature. The tan precipitate was filtered to afford N-[3-(2-Oxo-2,3-dihydro-1H-indole-5-carbonyl)-phenyl]-acetamide (0.478 g, 1.48 mmol, 61%).

Step 2: N-[3-(3-Hydroxymethylene-2-oxo-2,3-dihydro-1H-indole-5-carbonyl)-phenyl]-acetamide N-[3-(2-Oxo-2,3-dihydro-1H-indole-5-carbonyl)-phenyl]-acetamide (0.452 g, 1.54 mmol) and ethyl formate (0.370 mL, 4.60 mmol) were dissolved in anhydrous ethanol (6.50 mL). The resulting solution was treated in dropwise fashion with a 21 wt % solution of sodium ethoxide in ethanol (2.90 mL, 7.69 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding pure N-[3-(3-Hydroxymethylene-2-oxo-2,3-dihydro-1H-indole-5-carbonyl)-phenyl]-acetamide (0.415 g, 1.29 mmol, 84%).

Example 7

2-Ethyl-5-methyl-2H-pyrazole-3-carboxylic acid (4-{3-[(4-morpholin-4-yl-phenylamino)-methylene]-2-oxo-2,3-dihydro-1H-indole-5-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-5-carbonyl)-phenyl]-amide (prepared below, 70 mg, 0.168 mmol) and THF (2 mL). To the resulting solution was added N-(4-aminophenyl)morpholine (32.9 mg, 0.184 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 49% (48 mg, 0.083 mmol) of the title compound.

The 2-Ethyl-5-methyl-2H-pyrazole-3-carboxylic acid [4-(3-hydroxymethylene-2-oxo-2,3-dihydro-1H-indole-5-carbonyl)-phenyl]-amide was prepared from oxindole using the following multiple step procedure:

Step 1: 5-(4-Nitro-benzoyl)-1,3-dihydro-indol-2-one

AlCl$_3$ (20.0 g, 150 mmol) was placed in a dry 200 mL round bottom flask and DMF (3.30 mL) was added dropwise at 0° C. During the addition of DMF care was taken to ensure that the reaction was allowed to vent to the outside as this addition caused an exotherm to occur. Additionally as the DMF was added a white suspension formed. This suspension was allowed to stir for 30 min at room temperature, after which 4-nitrobenzoyl chloride (2.984 g, 16 mmol) was added. The mixture was warmed to 50° C. and stirred for 15 min at that temperature. The 50° C. mixture then was treated with oxindole (2.051 g, 15 mmol). The resulting reaction mixture was heated to 90° C. and allowed to stir for 5 hours during which the reaction mixture turned from a yellowish suspension to a thick black oil. The reaction was cooled to room temperature. Ice was added directly to the flask followed by water, turning the black oil into a pale yellow/white precipitate. Concentrated HCl$_{(aq)}$ (3 mL) was added to the reaction and the contents were stirred at room temperature for 15 min. The precipitate was collected via vacuum filtration. The crude solid was purified by washing with sat. NaHCO$_{3(aq)}$ providing 5-(4-Nitro-benzoyl)-1,3-dihydro-indol-2-one as a gray solid (4.05 g, 14.4 mmol, 95%).

Step 2: 5-(4-Amino-benzoyl)-1,3-dihydro-indol-2-one 5-(4-Nitro-benzoyl)-1,3-dihydro-indol-2-one (1.51 g, 5.28 mmol) was dissolved in MeOH (600 mL). 10% Pd/C (0.150 g) was added to the flask and then placed under vacuum to remove any O$_{2(g)}$. The reaction mixture was kept under reduced pressure for ~5 min and was then charged with H$_{2(g)}$. This evacuation/H$_{2(g)}$ fill procedure was repeated twice. The reaction mixture changed from a cloudy grayish/black color to a translucent dark green/black color, signifying complete consumption of the starting material. As the desired ketone product was prone to over-reduction to the alcohol, stopping the reaction immediately upon complete consumption of the starting material limited the amount over-reduction that occurred. The reaction was allowed to run for 0.75-1.0 hours after which, the reaction mixture was filtered over celite and concentrated in vacuo resulting in a yellowish solid that contained the desired keto-aniline product plus ~5% of the overreduced alcohol-aniline. The crude solid was purified by triturating with MeOH. The desired keto-aniline product, 5-(3-Amino-benzoyl)-1,3-dihydro-indol-2-one was soluble in MeOH and was filtered away from the insoluble over reduced alcohol by-product. In vacuo concentration of the methanolic filtrate provided pure 5-(3-Amino-benzoyl)-1,3-dihydro-indol-2-one in 72% (0.957 g, 3.80 mmol) yield.

Step 3: 2-Ethyl-5-methyl-2H-pyrazole-3-carboxylic acid [4-(2-oxo-2,3-dihydro-1H-indole-5-carbonyl)-phenyl]-amide A dry 25 mL flask was charged with 2-Ethyl-5-methyl-2H-pyrazole-3-carboxylic acid (0.608 mg, 3.53 mmol) and thionyl chloride (10 mL) and allowed to stir at 79° C. for 2 h. The thionyl chloride was then removed by distillation. The crude acid chloride was cooled to room temperature, and then dissolved in THF (5 mL). 5-(4-Amino-benzoyl)-1,3-dihydro-indol-2-one (0.685 g, 2.72 mmol) was added to the THF solution of the acid chloride, and the mixture was allowed to reflux for 2 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The tan solids were filtered to afford pure 2-Ethyl-5-methyl-2H-pyrazole-3-carboxylic acid [4-(2-oxo-2,3-dihydro-1H-indole-5-carbonyl)-phenyl]-amide (0.760 g, 1.96 mmol, 72%).

Step 4: 2-Ethyl-5-methyl-2H-pyrazole-3-carboxylic acid [4-(3-hydroxymethylene-2-oxo-2,3-dihydro-1H-indole-5-carbonyl)-phenyl]-amide 2-Ethyl-5-methyl-2H-pyrazole-3-carboxylic acid [4-(2-oxo-2,3-dihydro-1H-indole-5-carbonyl)-phenyl]-amide (0.735 g, 1.89 mmol) and ethyl formate (0.454 mL, 3.78 mmol) were dissolved in anhydrous ethanol (3.80 mL). The resulting solution was treated in dropwise fashion with a 21 wt % solution of sodium ethoxide in ethanol (3.53 mL, 9.46 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 2-Ethyl-5-methyl-2H-pyrazole-3-carboxylic acid [4-(3-hydroxymethylene-2-oxo-2,3-dihydro-1H-indole-5-carbonyl)-phenyl]-amide (0.594 g, 1.42 mmol, 75%).

Example 8

2-Ethyl-5-methyl-2H-pyrazole-3-carboxylic acid [4-(3-{[4-(4-methyl-piperazin-1-yl)-phenylamino]-methylene}-2-oxo-2,3-dihydro-1H-indole-5-carbonyl)-phenyl]-amide A small screw cap test tube was charged with 2-Ethyl-5-methyl-2H-pyrazole-3-carboxylic acid [4-(3-hydroxymethylene-2-oxo-2,3-dihydro-1H-indole-5-carbonyl)-phenyl]-amide (as prepared in Example 7, 70 mg, 0.168 mmol) and THF (2 mL). To the resulting solution was added 4-(4-methyl-piperazin-1-yl)-phenylamine (35.4 mg, 0.184 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 46% (45 mg, 0.076 mmol) of the title compound.

Example 9

2-Ethyl-5-methyl-2H-pyrazole-3-carboxylic acid (4-{3-[(3-hydroxy-phenylamino)-methylene]-2-oxo-2,3-dihydro-1H-indole-5-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-5-carbonyl)-phenyl]-amide (as prepared in Example 7, 70 mg, 0.168 mmol) and THF (2 mL). To the resulting solution was added 3-aminophenol (20.2 mg, 0.184 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 25% (21 mg, 0.0414 mmol) of the title compound.

Example 10

2-Ethyl-5-methyl-2H-pyrazole-3-carboxylic acid (4-{3-[(3-hydroxy-4-methyl-phenylamino)-methylene]-2-oxo-2,3-dihydro-1H-indole-5-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-5-carbonyl)-phenyl]-amide (as prepared in Example 7, 70 mg, 0.168 mmol) and THF (2 mL). To the resulting solution was added 5-amino-2-methoxyphenol (22.8 mg, 0.184 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 62% (56 mg, 0.104 mmol) of the title compound.

Example 11

N-(4-{3-[(4-Morpholin-4-yl-phenylamino)-methylene]-2-oxo-2,3-dihydro-1H-indole-5-carbonyl}-phenyl)-acetamide A small screw cap test tube was charged with N-[4-(3-Hydroxymethylene-2-oxo-2,3-dihydro-1H-indole-5-carbonyl)-phenyl]-acetamide (prepared below, 50 mg, 0.155 mmol) and THF (2 mL). To the resulting solution was added N-(4-aminophenyl)morpholine (30.4 mg, 0.170 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 41% (31 mg, 0.075 mmol) of the title compound.

The N-[4-(3-Hydroxymethylene-2-oxo-2,3-dihydro-1H-indole-5-carbonyl)-phenyl]-acetamide was prepared from oxindole using the following multiple step procedure:

Step 1: N-[4-(2-Oxo-2,3-dihydro-1H-indole-5-carbonyl)-phenyl]-acetamide

A dry 25 mL flask was charged with acetyl chloride (0.209 g, 2.67 mmol) and THF (10 mL). 5-(4-Amino-benzoyl)-1,3-dihydro-indol-2-one (as prepared in Example 7, 0.512 g, 2.06 mmol) was added to the THF solution of the acid chloride, and the mixture was allowed to reflux for 3 h. The reaction mixture was then allowed to cool to room temperature. The precipitate that formed was filtered and washed with THF affording N-[4-(2-Oxo-2,3-dihydro-1H-indole-5-carbonyl)-phenyl]-acetamide (0.503 g, 1.56 mmol, 83%).

Step 2: N-[4-(3-Hydroxymethylene-2-oxo-2,3-dihydro-1H-indole-5-carbonyl)-phenyl]-acetamide N-[4-(2-Oxo-2,3-dihydro-1H-indole-5-carbonyl)-phenyl]-acetamide (0.330 g, 1.12 mmol) and ethyl formate (0.269 mL, 3.37 mmol) were dissolved in anhydrous ethanol (3.80 mL). The resulting solution was treated in dropwise fashion with a 21 wt % solution of sodium ethoxide in ethanol (2.09 mL, 5.61 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure N-[4-(3-Hydroxymethylene-2-oxo-2,3-dihydro-1H-indole-5-carbonyl)-phenyl]-acetamide (0.272 g, 0.838 mmol, 75%).

Example 12

N-[4-(3-{[4-(4-Methyl-piperazin-1-yl)-phenylamino]-methylene}-2-oxo-2,3-dihydro-1H-indole-5-carbonyl)-phenyl]-acetamide A small screw cap test tube was charged with N-[4-(3-Hydroxymethylene-2-oxo-2,3-dihydro-1H-indole-5-carbonyl)-phenyl]-acetamide (as prepared in Example 11, 50 mg, 0.155 mmol) and THF (2 mL). To the resulting solution was added 4-(4-methyl-piperazin-1-yl)-phenylamine (32.6 mg, 0.170 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 62% (48 mg, 0.097 mmol) of the title compound.

Example 13

N-(4-{3-[(3-Hydroxy-4-methyl-phenylamino)-methylene]-2-oxo-2,3-dihydro-1H-indole-5-carbonyl}-phenyl)-acetamide A small screw cap test tube was charged with N-[4-(3-Hydroxymethylene-2-oxo-2,3-dihydro-1H-indole-5-carbonyl)-phenyl]-acetamide (as prepared in Example 11, 50 mg, 0.155 mmol) and THF (2 mL). To the resulting solution was added 5-Amino-2-methoxy-phenol (21.0 mg, 0.170 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 63% (42 mg, 0.098 mmol) of the title compound.

Example 14

2-Ethyl-5-methyl-2H-pyrazole-3-carboxylic acid [4-(3-{[4-(4-methyl-piperazin-1-yl)-phenylamino]-methylene}-2-oxo-2,3-dihydro-1H-indol-5-ylmethyl)-phenyl]-amide A small screw cap test tube was charged with 2-Ethyl-5-methyl-2H-pyrazole-3-carboxylic acid [4-(3-hydroxymethylene-2-oxo-2,3-dihydro-1H-indol-5-ylmethyl)-phenyl]-amide (prepared below, 70 mg, 0.175 mmol) and THF (1 mL). To the resulting solution was added 4-(4-Methyl-piperazin-1-yl)-phenylamine (66.8 mg, 0.349 mmol), and the mixture was stirred for 24 h at 65° C. Subsequently, the reaction mixture was cooled to room temperature and then diluted with EtOAc (2 mL). The solution was washed with water (2 mL) and the water layer was re-washed with additional EtOAc (2 mL). The combined organic layers were then concentrated in vacuo affording the crude product. The crude product was further purified by silica gel column chromatography with 5% methanol in chloroform as eluant to give the desired product as a solid in 55% yield (55 mg, 0.96 mmol).

The 2-Ethyl-5-methyl-2H-pyrazole-3-carboxylic acid [4-(3-hydroxymethylene-2-oxo-2,3-dihydro-1H-indol-5-ylmethyl)-phenyl]-amide was prepared from oxindole using the following multiple step procedure:

Step 1: 5-(4-Nitro-benzyl)-1,3-dihydro-indol-2-one

In a dried 250 mL round bottom flask, 20.73 mL of trifluoroacetic acid was added and then cooled to 0° C. under $Ar_{(g)}$. $NaBH_4$ in pellet form (1.35 g, 35.71 mmol, ~1.5 pellets) was added to the flask. 5-(4-Nitro-benzoyl)-1,3-dihydro-indol-2-one (as prepared in Example 7, 1.0 g, 3.55 mmol) was then added in slowly over 15 min. After the addition was completed, the reaction was allowed to warm to room temperature and was stirred for 36 hours forming a yellow foamy mixture. The mixture was poured over ice-water and allowed to warm to room temperature, during which a tan solid precipitated out of solution. The tan solid was collected by filtration and washed with water affording 5-(4-Nitro-benzyl)-1,3-dihydro-indol-2-one in 61% yield (0.589 g, 2.165 mmol).

Step 2: 5-(4-Amino-benzyl)-1,3-dihydro-indol-2-one 5-(4-Nitro-benzyl)-1,3-dihydro-indol-2-one (0.524 g, 1.94 mmols) was suspended in 35 ml of MeOH. 5% Pd/C (50 mg) was added to the flask which then was placed on a PARR apparatus. The flask was evacuated then charged with $H_{2(g)}$ (55 psi). This evacuation/$H_{2(g)}$ fill procedure was repeated 3 times (to degas the reaction mixture). The reaction vessel charged with $H_{2(g)}$ (55 psi) was shaken on the PARR apparatus for 2.5 hours after which the contents were filtered through celite. The organic solution was then concentrated in vacuo affording 5-(4-Amino-benzyl)-1,3-dihydro-indol-2-one at 58% yield (0.267 g, 1.12 mmol).

Step 3: 2-Ethyl-5-methyl-2H-pyrazole-3-carboxylic acid [4-(2-oxo-2,3-dihydro-1H-indol-5-ylmethyl)-phenyl]-amide A dry 25 mL flask was charged with 2-Ethyl-5-methyl-2H-pyrazole-3-carboxylic acid (0.168 g, 1.09 mmol) and thionyl chloride (4 mL) and allowed to stir at 79° C. for 2 h. The thionyl chloride was then removed by distillation. The crude acid chloride was cooled to 65° C., and then dissolved in THF (5 mL). 5-(4-Amino-benzyl)-1,3-dihydro-indol-2-one (0.200 g, 0.840 mmol) was added to the THF solution of the acid chloride, and the mixture was allowed to reflux overnight. Subsequently, the reaction mixture was allowed to cool to room temperature. The room temperature reaction mixture was concentrated in vacuo, and the crude residue was dissolved in EtOH (5 mL). The ethanolic solution was treated with 1M $NaOH_{(aq)}$ (2 mL) and stirred for 30 min. The basic solution was acidified to a pH of 1 with 1M $HCl_{(aq)}$ yielding a pale yellow precipitate. The pale yellow solids were filtered to afford the pure product (0.141 g, 0.377 mmol, 34.5%).

Step 4: 2-Ethyl-5-methyl-2H-pyrazole-3-carboxylic acid [4-(3-hydroxymethylene-2-oxo-2,3-dihydro-1H-indol-5-ylmethyl)-phenyl]-amide 2-Ethyl-5-methyl-2H-pyrazole-3-carboxylic acid [4-(2-oxo-2,3-dihydro-1H-indol-5-ylmethyl)-phenyl]-amide (0.140 g, 0.374 mmol) and ethyl formate (0.060 mL, 0.816 mmol) were dissolved in anhydrous ethanol (0.250 mL). The resulting solution was treated in dropwise fashion with a 21 wt % solution of sodium ethoxide in ethanol (0.42 mL, 1.12 mmol). This reaction mixture was heated at 78° C. for 0.5-1 h, producing a viscous, dark reddish colored oil. Subsequently, the reaction mixture was cooled to room temperature, and then the reaction pH was adjusted to pH 3 with dropwise addition of 1M $HCl_{(aq)}$ causing the formation of a grey precipitate. The suspension was filtered yielding a grey solid as the pure product (0.070 g, 0.175 mmol, 47%).

Example 15

2-Ethyl-5-methyl-2H-pyrazole-3-carboxylic acid (4-{3-[(4-morpholin-4-yl-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-6-carbonyl)-phenyl]-amide (prepared below, 100 mg, 0.240 mmol) and THF (1 mL). To the resulting solution was added N-(4-aminophenyl) morpholine (47.08 mg, 0.264 mmol), and the mixture was stirred for 24 h at 65° C. Subsequently, the reaction mixture was cooled to room temperature and concentrated in vacuo. The crude residue was purified via flash silica gel chromatography (5% MeOH/95% CHCl₃) yielding 67% (94 mg, 0.163 mmol) of the title compound.

The 2-Ethyl-5-methyl-2H-pyrazole-3-carboxylic acid [4-(3-hydroxymethylene-2-oxo-2,3-dihydro-1H-indole-6-carbonyl)-phenyl]-amide was prepared from 4-nitrobenzoyl chloride using the following multiple step procedure:

Step 1:
(4-Bromo-phenyl)-(4-nitro-phenyl)-methanone

Anhydrous aluminum chloride (7.05 g, 54 mmol) was added to a mixture of 4-nitrobenzoyl chloride (10 g, 54 mmol) and bromobenzene (16.9 g, 107 mmol). The reaction was allowed to stir at 60° C. for 4 hours. The reaction was quenched in 200 mL of ice water and allowed to stir. The mixture was then diluted with EtOAc (200 mL) and the aqueous layer was extracted with EtOAc (3×200 mL). The combined organic layers were dried over anhydrous Na₂SO₄ and concentrated in vacuo affording a mixture of the expected coupling products [(4-Bromo-phenyl)-(4-nitro-phenyl)-methanone and ((2-Bromo-phenyl)-(4-nitro-phenyl)-methanone)] in 91% yield (15 g, 49 mmol) as a white solid. By ¹H NMR, the product mixture appeared to contain ~94% of the desired (4-Bromo-phenyl)-(4-nitro-phenyl)-methanone and ~6% of the minor isomer (2-Bromo-phenyl)-(4-nitro-phenyl)-methanone. The mixture was carried on without further purification.

Step 2: (4-Bromo-3-nitro-phenyl)-(-4-nitro-phenyl)-methanone

The crude (4-Bromo-phenyl)-(4-nitro-phenyl)-methanone (15 g, 49 mmol) was dissolved in 45 mL of dichloroethane and added dropwise via addition funnel to a mixture of concentrated $H_2SO_{4(aq)}$ (2 mL, 392 mmol) and fuming $HNO_{3(aq)}$ (15.7 mL, 392 mmol). The mixture was stirred at 60° C. overnight. Subsequently the mixture was poured over ice water and allowed to stir resulting in precipitation of the product. The product was filtered and dried affording 78% yield of the desired (4-Bromo-3-nitro-phenyl)-(-4-nitro-phenyl)-methanone (13.1 g, 38 mmol).

Step 3:
2-[2-Nitro-4-(4-nitro-benzoyl)-phenyl]-malonic acid diethyl ester

NaH, 60% dispersion in mineral oil, (1.27 g, 31.7 mmol) was washed with petroleum ether then suspended in anhydrous DMSO (30 mL). Diethyl malonate (4.85 mL, 31.7 mmol) was dissolved in 8 mL of anhydrous DMSO and added dropwise to the NaH suspension. The mixture was allowed to stir for 15 min at 100° C., during which time the reaction mixture became homogeneous. (4-Bromo-3-nitro-phenyl)-(-4-nitro-phenyl)-methanone (5.15 g, 14.4 mmol) was dissolved in anhydrous DMSO (15 mL) and subsequently added via syringe to the malonate solution. The mixture was allowed to stir at 100° C. for 2 h after which the reaction was cooled to room temperature and poured into water (~300 mL). The mixture was extracted with EtOAc (3×300 mL) and dried over anhydrous Na₂SO₄. The organic layers were then concentrated in vacuo affording a crude black oil. The crude oil was then flashed through a plug of silica with 30% EtOAc/Hexanes. The solution was then concentrated in vacuo yielding a pale yellow solid that contained the desired product contaminated with excess diethyl malonate. The impure solid was washed with Hexanes, filtered and dried affording diethyl [2-nitro-4-(4-nitrobenzoyl)phenyl] malonate in 75% yield (4.64 g, 10.8 mmol).

Step 4:
6-(4-Amino-benzoyl)-1,3-dihydro-indol-2-one

[2-Nitro-4-(4-nitrobenzoyl)phenyl] malonate (4.15 g, 9.61 mmol) was dissolved in EtOH (24 mL) after which Sn powder (9.16 g, 77 mmol) was added followed by dropwise addition of concentrated $HCl_{(aq)}$ (26 mL). The reaction mixture was allowed to reflux for 3 hours, filtered while hot and then allowed to cool to room temperature. The cooled reaction mixture was diluted with CHCl₃ (400 mL) and then extracted once with H₂O (400 mL). The aqueous layer was then neutralized with NaHCO₃ (pH=7) and then extracted with a 95% EtOAc/5% i-prOH solution (3×400 mL). The organic layers were combined and dried over anhydrous Na₂SO₄. The solution was then concentrated in vacuo affording the 6-(4-Amino-benzoyl)-1,3-dihydro-indol-2-one in 51% yield (1.24 g, 4.90 mmol).

Step 5: 2-Ethyl-5-methyl-2H-pyrazole-3-carboxylic acid [4-(2-oxo-2,3-dihydro-1H-indole-6-carbonyl)-phenyl]-amide A dry 25 mL flask was charged with 2-Ethyl-5-methyl-2H-pyrazole-3-carboxylic acid (0.887 g, 5.16 mmol) and thionyl chloride (5 mL) and allowed to stir at 79° C. for 2 h. The thionyl chloride then was removed by concentration in vacuo. The crude acid chloride was cooled to room temperature, and then dissolved in THF (5 mL). 6-(4-Amino-benzoyl)-1,3-dihydro-indol-2-one (1.00 g, 3.97 mmol) was added to the THF solution of the acid chloride, and the mixture was allowed to reflux for 4 h. The reaction mixture was then allowed to cool to room temperature. The room temperature reaction mixture was concentrated in vacuo, and the crude residue was dissolved in EtOH (5 mL). The ethanolic solution was treated with 1M $NaOH_{(aq)}$ (2 mL) and stirred for 30 min. The basic solution was acidified to a pH of 1 with 1M $HCl_{(aq)}$ yielding a precipitate. The solids were filtered to afford the pure 2-Ethyl-5-methyl-2H-pyrazole-3-carboxylic acid [4-(2-oxo-2,3-dihydro-1H-indole-6-carbonyl)-phenyl]-amide (0.741 g, 1.94 mmol, 49%).

Step 6: 2-Ethyl-5-methyl-2H-pyrazole-3-carboxylic acid [4-(3-hydroxymethylene-2-oxo-2,3-dihydro-1H-indole-6-carbonyl)-phenyl]-amide 2-Ethyl-5-methyl-2H-pyrazole-3-carboxylic acid [4-(2-oxo-2,3-dihydro-1H-indole-6-carbonyl)-phenyl]-amide (0.758 g, 1.95 mmol) and ethyl formate (0.468 mL, 5.85 mmol) were dissolved in anhydrous ethanol (5.78 mL). The resulting solution was treated in dropwise fashion with a 21 wt % solution of sodium ethoxide in ethanol (3.64 mL, 9.76 mmol). This reaction mixture was heated at 78° C. for 1 h, producing a black oil.

Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 2-Ethyl-5-methyl-2H-pyrazole-3-carboxylic acid [4-(3-hydroxymethylene-2-oxo-2,3-dihydro-1H-indole-6-carbonyl)-phenyl]-amide (0.752 g, 1.47 mmol, 75%).

Example 16

2-Ethyl-5-methyl-2H-pyrazole-3-carboxylic acid [4-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-Ethyl-5-methyl-2H-pyrazole-3-carboxylic acid [4-(3-hydroxymethylene-2-oxo-2,3-dihydro-1H-indole-6-carbonyl)-phenyl]-amide (as prepared in Example 15, 100 mg, 0.240 mmol) and THF (2 mL). To the resulting solution was added 4-(4-methyl-piperazin-1-yl)-phenylamine (50.5 mg, 0.264 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 60% (85 mg, 0.144 mmol) of the title compound.

Example 17

2-Ethyl-5-methyl-2H-pyrazole-3-carboxylic acid (4-{3-[(1H-indazol-6-ylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-6-carbonyl)-phenyl]-amide (as prepared in Example 15, 100 mg, 0.240 mmol) and THF (2 mL). To the resulting solution was added 1H-Indazol-6-ylamine (36 mg, 0.264 mmol), and the mixture was stirred for 24 h at 65° C. Subsequently, the reaction mixture was cooled to room temperature and concentrated in vacuo. The crude residue was purified over silica (5% MeOH/95% CHCl$_3$) yielding 16% (20 mg, 0.038 mmol) of the title compound.

Example 18

2-Ethyl-5-methyl-2H-pyrazole-3-carboxylic acid (4-{3-[(3-hydroxy-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-6-carbonyl)-phenyl]-amide (as prepared in Example 15, 100 mg, 0.240 mmol) and THF (2 mL). To the resulting solution was added 3-aminophenol (28.8 mg, 0.264 mmol), and the mixture was stirred for 24 h at 65° C. Subsequently, the reaction mixture was cooled to room temperature. The solid precipitate that formed was washed with ~1 mL of i-prOH yielding 20% (24 mg, 0.047 mmol) of the title compound.

Example 19

2-Ethyl-5-methyl-2H-pyrazole-3-carboxylic acid (4-{3-[(3-hydroxy-4-methyl-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [4-(3-hydroxymethylene-2-oxo-2,3-dihydro-1H-indole-6-carbonyl)-phenyl]-amide (as prepared in Example 15, 100 mg, 0.240 mmol) and THF (2 mL). To the resulting solution was added 5-amino-2-methylphenol (32.5 mg, 0.1082 mmol), and the mixture was stirred for 24 h at 65° C. Subsequently, the reaction mixture was cooled to room temperature. The solid precipitate that formed was washed with ~1 mL of i-prOH yielding 44% (55 mg, 44 mmol) of the title compound.

Example 20

Thiophene-2-carboxylic acid (4-{3-[(4-morpholin-4-yl-phenylamino)-methylene]-2-oxo-2,3-dihydro-1H-indole-6-carbonyl}-phenyl)-amide A small screw cap test tube was charged with Thiophene-2-carboxylic acid [4-(3-hydroxymethylene-2-oxo-2,3-dihydro-1H-indole-6-carbonyl)-phenyl]-amide (100 mg, 0.257 mmol) and THF (2 mL). To the resulting solution was added N-(4-aminophenyl)morpholine (50.2 mg, 0.282 mmol), and the mixture was stirred for 24 h at 65° C. Subsequently, the reaction mixture was cooled to room temperature. EtOAc and Hexanes were added to the reaction mixture. The solid precipitate that formed was washed with ~1 mL of i-prOH yielding 71% (100 mg, 0.181 mmol) of the title compound.

The Thiophene-2-carboxylic acid [4-(3-hydroxymethylene-2-oxo-2,3-dihydro-1H-indole-6-carbonyl)-phenyl]-amide was prepared from 4-nitrobenzoyl chloride using the following multiple step procedure:

Step 1: Thiophene-2-carboxylic acid [4-(2-oxo-2,3-dihydro-1H-indole-6-carbonyl)-phenyl]-amide A dry 25 mL flask was charged with Thiophene-2-carbonyl chloride (0.756 g, 5.16 mmol) and THF (10 mL). 6-(4-Amino-benzoyl)-1,3-dihydro-indol-2-one (as prepared in Example 15, 1.02 g, 3.98 mmol) was added to the THF solution of the acid chloride, and the mixture was allowed to reflux for 3 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The tan solids were filtered to afford the pure Thiophene-2-carboxylic acid [4-(2-oxo-2,3-dihydro-1H-indole-6-carbonyl)-phenyl]-amide (0.924 g, 2.53 mmol, 64%).

Step 2: Thiophene-2-carboxylic acid [4-(3-hydroxymethylene-2-oxo-2,3-dihydro-1H-indole-6-carbonyl)-phenyl]-amide Thiophene-2-carboxylic acid [4-(2-oxo-2,3-dihydro-1H-indole-6-carbonyl)-phenyl]-amide (0.857 g, 2.36 mmol) and ethyl formate (0.567 mL, 7.09 mmol) were dissolved in anhydrous ethanol (4.73 mL). The resulting solution was treated in dropwise fashion with a 21 wt % solution of sodium ethoxide in ethanol (4.4 mL, 11.83 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure Thiophene-2-carboxylic acid [4-(3-hydroxymethylene-2-oxo-2,3-dihydro-1H-indole-6-carbonyl)-phenyl]-amide (0.695 g, 1.78 mmol, 75%).

Example 21

Thiophene-2-carboxylic acid [4-(3-{[4-(4-methyl-piperazin-1-yl)-phenylamino]-methylene}-2-oxo-2,3-dihydro-1H-indole-6-carbonyl)-phenyl]-amide A small screw cap test tube was charged with Thiophene-2-carboxylic acid [4-(3-hydroxymethylene-2-oxo-2,3-dihydro-1H-indole-6-carbonyl)-phenyl]-amide (as prepared in Example 20, 100 mg, 0.257 mmol) and THF (2 mL). To the resulting solution was added 4-(4-methyl-piperazin-1-yl)-phenylamine (53.9 mg, 0.282 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 59% (86 mg, 0.153 mmol) of the title compound.

Example 22

Thiophene-2-carboxylic acid (4-{3-[(3-hydroxy-phenylamino)-methylene]-2-oxo-2,3-dihydro-1H-indole-6-carbonyl}-phenyl)-amide A small screw cap test tube was charged with Thiophene-2-carboxylic acid [4-(3-hydroxymethylene-2-oxo-2,3-dihydro-1H-indole-6-carbonyl)-phenyl]-amide (as prepared in Example 20, 100 mg, 0.257 mmol) and THF (2 mL). To the resulting solution was added 3-aminophenol (30.7 mg, 0.282 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 61% (75 mg, 0.156 mmol) of the title compound.

Example 23

Thiophene-2-carboxylic acid (4-{3-[(3-hydroxy-4-methyl-phenylamino)-methylene]-2-oxo-2,3-dihydro-1H-indole-6-carbonyl}-phenyl)-amide A small screw cap test tube was charged with Thiophene-2-carboxylic acid [4-(3-hydroxymethylene-2-oxo-2,3-dihydro-1H-indole-6-carbonyl)-phenyl]-amide (as prepared in Example 20, 100 mg, 0.257 mmol) and THF (2 mL). To the resulting solution was added 5-amino-2-methylphenol (34.7 mg, 0.282 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 70% (89 mg, 0.180 mmol) of the title compound.

Example 24

Thiophene-2-carboxylic acid (4-{3-[(3-hydroxy-4-methoxy-phenylamino)-methylene]-2-oxo-2,3-dihydro-1H-indole-6-carbonyl}-phenyl)-amide A small screw cap test tube was charged with Thiophene-2-carboxylic acid [4-(3-hydroxymethylene-2-oxo-2,3-dihydro-1H-indole-6-carbonyl)-phenyl]-amide (as prepared in Example 20, 100 mg, 0.257 mmol) and THF (2 mL). To the resulting solution was added 5-amino-2-methoxyphenol (39.2 mg, 0.282 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 57% (75 mg, 0.147 mmol) of the title compound.

Example 25

2,5-Dimethyl-2H-pyrazole-3-carboxylic acid (4-{3-[(4-morpholin-4-yl-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [4-(3-hydroxymethylene-2-oxo-2,3-dihydro-1H-indole-6-carbonyl)-phenyl]-amide (prepared below, 100 mg, 0.248 mmol) and THF (2 mL). To the resulting solution was added N-(4-aminophenyl)morpholine (48.7 mg, 0.248 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 36% (50 mg, 0.089 mmol) of the title compound.

The 2,5-Dimethyl-2H-pyrazole-3-carboxylic acid [4-(3-hydroxymethylene-2-oxo-2,3-dihydro-1H-indole-6-carbonyl)-phenyl]-amide was prepared from 4-nitrobenzoyl chloride using the following multiple step procedure:

Step 1: 2,5-Dimethyl-2H-pyrazole-3-carboxylic acid [4-(2-oxo-2,3-dihydro-1H-indole-6-carbonyl)-phenyl]-amide A dry 25 mL flask was charged with 2,5-Dimethyl-2H-pyrazole-3-carbonyl chloride (0.820 g, 5.15 mmol) and THF (10 mL). 6-(4-Amino-benzoyl)-1,3-dihydro-indol-2-one (as prepared in Example 15, 1.00 g, 3.97 mmol) was added to the THF solution of the acid chloride, and the mixture was allowed to reflux for 4 h. The reaction mixture was then allowed to cool to room temperature. The room temperature reaction mixture was concentrated in vacuo, and the crude residue was dissolved in EtOH (5 mL). The ethanolic solution was treated with 1M $NaOH_{(aq)}$ (2 mL) and stirred for 30 min. The basic solution was acidified to a pH of 1 with 1M $HCl_{(aq)}$ yielding a tan precipitate. The solids were filtered to afford the pure 2,5-Dimethyl-2H-pyrazole-3-carboxylic acid [4-(2-oxo-2,3-dihydro-1H-indole-6-carbonyl)-phenyl]-amide (1.35 g, 3.60 mmol, 91%).

Step 2: 2,5-Dimethyl-2H-pyrazole-3-carboxylic acid [4-(3-hydroxymethylene-2-oxo-2,3-dihydro-1H-indole-6-carbonyl)-phenyl]-amide 2,5-Dimethyl-2H-pyrazole-3-carboxylic acid [4-(2-oxo-2,3-dihydro-1H-indole-6-carbonyl)-phenyl]-amide (1.345 g, 3.59 mmol) and ethyl formate (0.862 mL, 10.77 mmol) were dissolved in anhydrous ethanol (7.19 mL). The resulting solution was treated in dropwise fashion with a 21 wt % solution of sodium ethoxide in ethanol (6.70 mL, 17.9 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure 2,5-Dimethyl-2H-pyrazole-3-carboxylic acid [4-(3-hydroxymethylene-2-oxo-2,3-dihydro-1H-indole-6-carbonyl)-phenyl]-amide (1.358 g, 3.37 mmol, 94%).

Example 26

2,5-Dimethyl-2H-pyrazole-3-carboxylic acid [4-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [4-(3-hydroxymethylene-2-oxo-2,3-dihydro-1H-indole-6-carbonyl)-phenyl]-amide (as prepared in Example 25, 100 mg, 0.248 mmol) and THF (2 mL). To the resulting solution was added 4-(4-methyl-piperazin-1-yl)-phenylamine (52.2 mg, 0.248 mmol), and the mixture was stirred for 24 h at 65° C. Subsequently, the reaction mixture was cooled to room temperature. Hexanes were added to the reaction mixture. The solid precipitate that formed was washed with ~1 mL of ice cold THF yielding 33% (48 mg, 0.083 mmol) of the title compound.

Example 27

2,5-Dimethyl-2H-pyrazole-3-carboxylic acid (4-{3-[(3-hydroxy-4-methyl-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [4-(3-hydroxymethylene-2-oxo-2,3-dihydro-1H-indole-6-carbonyl)-phenyl]-amide (as prepared in Example 25, 100 mg, 0.248 mmol) and THF (2 mL). To the resulting solution was added 5-amino-2-methylphenol (33.7 mg, 0.248 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 54% (68 mg, 0.134 mmol) of the title compound.

Example 28

2,5-Dimethyl-2H-pyrazole-3-carboxylic acid (4-{3-[(3-hydroxy-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [4-(3-hydroxymethylene-2-oxo-2,3-dihydro-1H-indole-6-carbonyl)-phenyl]-amide (as prepared in Example 25, 100 mg, 0.248 mmol) and THF (1.5 mL). To the resulting solution was added 3-aminophenol (29.8 mg, 0.273 mmol), and the mixture was stirred for 24 h at 65° C. Subsequently, the reaction mixture was cooled to room temperature. The solid precipitate that formed was filtered and washed with THF yielding 70% (86 mg, 0.174 mmol) of the title compound.

Example 29

N-(4-{3-[(4-Morpholin-4-yl-phenylamino)-methylene]-2-oxo-2,3-dihydro-1H-indole-6-carbonyl}-phenyl)-acetamide A dry 50 mL flask was charged with N-[4-(3-Hydroxymethylene-2-oxo-2,3-dihydro-1H-indole-6-carbonyl)-phenyl]-acetamide (prepared below, 70 mg, 0.217 mmol) and Dioxane (10 mL). To the resulting solution was added N-(4-aminophenyl)morpholine (200 mg, 1.122 mmol), and the mixture was stirred for 24 h at 100° C. Subsequently, the reaction mixture was cooled to room temperature. The resulting suspension was concentrated in vacuo and the resulting solid residue was recrystallized from iPrOH (~5 mL). The solid recovered through filtration then was subjected to flash silica gel chromatography using a 5% $MeOH/CHCl_3$ eluant mixture to afford the title compound in 33% yield (35 mg, 0.072 mmol).

The N-[4-(3-Hydroxymethylene-2-oxo-2,3-dihydro-1H-indole-6-carbonyl)-phenyl]-acetamide was prepared from 4-nitrobenzoyl chloride using the following multiple step procedure:

Step 1: N-[4-(2-Oxo-2,3-dihydro-1H-indole-6-carbonyl)-phenyl]-acetamide

A dry 100 mL flask was charged with acetyl chloride (0.408 g, 5.20 mmol) and THF (40 mL). 6-(4-Amino-benzoyl)-1,3-dihydro-indol-2-one (as prepared in Example 15, 1.00 g, 3.96 mmol) was added to the THF solution of the acid chloride, and the reaction was allowed to reflux for 3 h. The reaction mixture was then allowed to cool to room temperature. The room temperature reaction mixture was concentrated in vacuo. The brown solid residue was suspended in boiling EtOAc. The suspension was allowed to cool to room temperature before filtering to afford the N-[4-(2-Oxo-2,3-dihydro-1H-indole-6-carbonyl)-phenyl]-acetamide as a tan solid (1.16 g, 3.94 mmol, 99%).

Step 2: N-[4-(3-Hydroxymethylene-2-oxo-2,3-dihydro-1H-indole-6-carbonyl)-phenyl]-acetamide N-[4-(2-Oxo-2,3-dihydro-1H-indole-6-carbonyl)-phenyl]-acetamide (1.15 g, 3.90 mmol) and ethyl formate (0.95 mL, 11.70 mmol) were dissolved in anhydrous ethanol (8.00 mL). The resulting solution was treated in dropwise fashion with a 21 wt % solution of sodium ethoxide in ethanol (4.40 mL, 11.70 mmol). This reaction mixture was heated at 78° C. for 1 h, producing a black oil. Subsequently, the reaction mixture was cooled to room temperature, and then the reaction pH was adjusted to pH 3 with dropwise addition of 1M $HCl_{(aq)}$. The dark orange precipitate that formed was filtered then re-dissolved in EtOH (25 mL). The ethanolic solution was made basic with the addition of 1 M $NaOH_{(aq)}$ (4 mL). The basic solution then was re-acidified to pH 1 with 1 M $HCl_{(aq)}$ (10 mL) causing the formation of a pale orange precipitate. This suspension was filtered yielding an orange solid as the pure N-[4-(3-Hydroxymethylene-2-oxo-2,3-dihydro-1H-indole-6-carbonyl)-phenyl]-acetamide (0.852 g, 2.64 mmol, 68%).

Example 30

N-[4-(3-{[4-(4-Methyl-piperazin-1-yl)-phenylamino]-methylene}-2-oxo-2,3-dihydro-1H-indole-6-carbonyl)-phenyl]-acetamide A small screw cap test tube was charged with N-[4-(3-Hydroxymethylene-2-oxo-2,3-dihydro-1H-indole-6-carbonyl)-phenyl]-acetamide (as prepared in Example 29, 70 mg, 0.217 mmol) and THF (2 mL). To the resulting solution was added 4-(4-methyl-piperazin-1-yl)-phenylamine (20.7 mg, 0.1082 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 82% yield (0.088 g, 0.178 mmol).

Example 31

N-(4-{3-[(3-Hydroxy-4-methoxy-phenylamino)-methylene]-2-oxo-2,3-dihydro-1H-indole-6-carbonyl}-phenyl)-acetamide A small screw cap test tube was charged with N-[4-(3-Hydroxymethylene-2-oxo-2,3-dihydro-1H-indole-6-carbonyl)-phenyl]-acetamide (as prepared in Example 29, 70 mg, 0.217 mmol) and THF (2 mL). To the resulting solution was added 5-amino-2-methoxyphenol (26.0 mg, 0.258 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 72% yield (0.069 g, 0.1555 mmol).

Example 32

N-(4-{3-[(3-Hydroxy-phenylamino)-methylene]-2-oxo-2,3-dihydro-1H-indole-6-carbonyl}-phenyl)-acetamide A small screw cap test tube was charged with N-[4-(3-Hydroxymethylene-2-oxo-2,3-dihydro-1H-indole-6-carbonyl)-phenyl]-acetamide (as prepared in Example 29, 70 mg, 0.217 mmol) and THF (2 mL). To the resulting solution was added 3-aminophenol (28 mg, 0.257 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 76% yield (0.068 g, 0.1645 mmol).

Example 33

N-(4-{3-[(3-Hydroxy-4-methyl-phenylamino)-methylene]-2-oxo-2,3-dihydro-1H-indole-6-carbonyl}-phenyl)-acetamide A small screw cap test tube was charged with 2,5-Dimethyl-2H-pyrazole-3-carboxylic acid [4-(3-hydroxymethylene-2-oxo-2,3-dihydro-1H-indole-6-carbonyl)-phenyl]-amide (as prepared in Example 29, 70 mg, 0.217 mmol) and THF (2 mL). To the resulting solution was added 5-amino-2-methylphenol (32 mg, 0.260 mmol), and the mixture was stirred for 24 h at 65° C. Subsequently, the reaction mixture was cooled to room temperature and concentrated in vacuo. The solid residue was recrystallized with ~2 mL of i-prOH affording the title compound in 69% yield (0.064 g, 0.1497 mmol).

Example 34

5-Acetyl-thiophene-2-carboxylic acid (4-{3-[(4-morpholin-4-yl-phenylamino)-methylene]-2-oxo-2,3-dihydro-1H-indole-6-carbonyl}-phenyl)-amide A small screw cap test tube was charged with 5-Acetyl-thiophene-2-carboxylic acid [4-(3-hydroxymethylene-2-oxo-2,3-dihydro-1H-indole-6-carbonyl)-phenyl]-amide (prepared below, 50 mg, 0.116 mmol) and THF (2 mL). To the resulting solution was added N-(4-aminophenyl)morpholine (20.0 mg, 0.1122 mmol), and the mixture was stirred for 24 h at 65° C. Subsequently, the reaction mixture was cooled to room temperature and concentrated in vacuo. The solid residue was recrystallized with ~2 mL of i-prOH affording the title compound in 64% yield (0.044 g, 0.0742 mmol).

The 5-Acetyl-thiophene-2-carboxylic acid [4-(3-hydroxymethylene-2-oxo-2,3-dihydro-1H-indole-6-carbonyl)-phenyl]-amide was prepared from 4-nitrobenzoyl chloride using the following multiple step procedure:

Step 1: 5-Acetyl-thiophene-2-carboxylic acid [4-(2-oxo-2,3-dihydro-1H-indole-6-carbonyl)-phenyl]-amide A dry 100 mL flask was charged with 5-Acetyl-thiophene-2-carboxylic acid (0.9339 g, 5.49 mmol) and thionyl chloride (6 mL) and allowed to stir at 79° C. for 2 h. The thionyl chloride was then removed by concentration in vacuo. The crude acid chloride was cooled to room temperature, and then dissolved in THF (80 mL). 6-(4-Amino-benzoyl)-1,3-dihydro-indol-2-one (as prepared in Example 15, 1.00 g, 3.97 mmol) was added to the THF solution of the acid chloride, and the mixture was allowed to reflux for 4 h. The reaction mixture was then allowed to cool to room temperature. The room temperature reaction mixture was concentrated in vacuo. The solid residue was suspended in boiling EtOAc. The suspension was allowed to cool to room temperature before filtering to afford the 5-Acetyl-thiophene-2-carboxylic acid [4-(2-oxo-2,3-dihydro-1H-indole-6-carbonyl)-phenyl]-amide as a solid (1.16 g, 3.94 mmol, 99%).

Step 2: 5-Acetyl-thiophene-2-carboxylic acid [4-(3-hydroxymethylene-2-oxo-2,3-dihydro-1H-indole-6-carbonyl)-phenyl]-amide 5-Acetyl-thiophene-2-carboxylic acid [4-(2-oxo-2,3-dihydro-1H-indole-6-carbonyl)-phenyl]-amide (0.959 g, 2.37 mmol) and ethyl formate (0.60 mL, 7.43 mmol) were dissolved in anhydrous ethanol (10 mL). The resulting solution was treated in dropwise fashion with a 21 wt % solution of sodium ethoxide in ethanol (2.8 mL, 7.50 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure 5-Acetyl-thiophene-2-carboxylic acid [4-(3-hydroxymethylene-2-oxo-2,3-dihydro-1H-indole-6-carbonyl)-phenyl]-amide (0.666 g, 1.54 mmol, 65%).

Example 35

5-Acetyl-thiophene-2-carboxylic acid (4-{3-[(3-hydroxy-4-methyl-phenylamino)-methylene]-2-oxo-2,3-dihydro-1H-indole-6-carbonyl}-phenyl)-amide A small screw cap test tube was charged with 5-Acetyl-thiophene-2-carboxylic acid [4-(3-hydroxymethylene-2-oxo-2,3-dihydro-1H-indole-6-carbonyl)-phenyl]-amide (as prepared in Example 34, 40 mg, 0.093 mmol) and THF (2 mL). To the resulting solution was added 5-amino-2-methylphenol (14 mg, 0.1137 mmol), and the mixture was stirred for 24 h at 65° C. Subsequently, the reaction mixture was cooled to room temperature and concentrated in vacuo. The solid residue was recrystallized with ~2 mL of i-prOH affording the title compound in 36% yield (0.028 g, 0.0521 mmol).

Example 36

5-Acetyl-thiophene-2-carboxylic acid [4-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 5-Acetyl-thiophene-2-carboxylic acid [4-(3-hydroxymethylene-2-oxo-2,3-dihydro-1H-indole-6-carbonyl)-phenyl]-amide (as prepared in Example 34, 40 mg, 0.093 mmol) and THF (2 mL). To the resulting solution was added 4-(4-methyl-piperazin-1-yl)-phenylamine (22 mg, 0.1150 mmol), and the mixture was stirred for 24 h at 65° C. Subsequently, the reaction mixture was cooled to room temperature and concentrated in vacuo. The solid residue was recrystallized with 2 mL of i-prOH affording the title compound in 57% yield (0.032 g, 0.0528 mmol).

Example 37

5-Acetyl-thiophene-2-carboxylic acid (4-{3-[(3-hydroxy-4-methoxy-phenylamino)-methylene]-2-oxo-2,3-dihydro-1H-indole-6-carbonyl}-phenyl)-amide A small screw cap test tube was charged with 5-Acetyl-thiophene-2-carboxylic acid [4-(3-hydroxymethylene-2-oxo-2,3-dihydro-1H-indole-6-carbonyl)-phenyl]-amide (as prepared in Example 34, 40 mg, 0.093 mmol) and THF (2 mL). To the resulting solution was added 5-amino-2-methoxyphenol (16 mg, 0.115 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 74% yield (0.038 g, 0.0686 mmol).

Example 38

5-Acetyl-thiophene-2-carboxylic acid (4-{3-[(3-hydroxy-phenylamino)-methylene]-2-oxo-2,3-dihydro-1H-indole-6-carbonyl}-phenyl)-amide A small screw cap test tube was charged with 5-Acetyl-thiophene-2-carboxylic acid [4-(3-hydroxymethylene-2-oxo-2,3-dihydro-1H-indole-6-carbonyl)-phenyl]-amide (as prepared in Example 34, 40 mg, 0.093 mmol) and THF (2 mL). To the resulting solution was added 3-aminophenol (13 mg, 0.1191 mmol), and the mixture was stirred for 24 h at 65° C. Subsequently, the reaction mixture was cooled to room temperature and concentrated in vacuo. The solid residue was recrystallized with ~2 mL of i-prOH affording the title compound in 64% yield (0.031 g, 0.0592 mmol).

Example 39

2,5-Dimethyl-2H-pyrazole-3-carboxylic acid (4-{3-[(3-hydroxy-4-methoxy-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [4-(3-hydroxymethylene-2-oxo-2,3-dihydro-1H-indole-6-carbonyl)-phenyl]-amide (as prepared in Example 25, 100 mg, 0.240 mmol) and THF (1.5 mL). To the resulting solution was added 5-amino-2-methoxyphenol (39 mg, 0.274 mmol), and the mixture was stirred for 24 h at 65° C. Subsequently, the reaction mixture was cooled to room temperature. The solid precipitate that formed was filtered and washed with ~1 mL of ice cold THF yielding 61% (34 mg, 0.065 mmol) of the title compound.

Example 40

N-(3-{3-[(3-Hydroxy-4-methoxy-phenylamino)-methylene]-2-oxo-2,3-dihydro-1H-indole-6-carbonyl}-phenyl)-acetamide A small screw cap test tube was charged with N-[3-(3-Hydroxymethylene-2-oxo-2,3-dihydro-1H-indole-6-carbonyl)-phenyl]-acetamide (prepared below, 100 mg, 0.310 mmol) and THF (2 mL). To the resulting solution was added 5-amino-2-methoxyphenol (47.49 mg, 0.341 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 73% (100 mg, 0.22 mmol) of the title compound.

The N-[3-(3-Hydroxymethylene-2-oxo-2,3-dihydro-1H-indole-6-carbonyl)-phenyl]-acetamide was prepared from 3-nitrobenzoyl chloride using the following multiple step procedure:

Step 1: (4-Bromo-phenyl)-(3-nitro-phenyl)-methanone

Anhydrous aluminum chloride (5.75 g, 43.2 mmol) was added to a mixture of 3-nitrobenzoyl chloride (8 g, 43.2 mmol) and bromobenzene (13.57 g, 86.4 mmol). The reaction was allowed to stir at 60° C. for 4 hours. The reaction was quenched in 200 mL of ice water and allowed to stir. The mixture was then diluted with EtOAc (200 mL) and the aqueous layer was extracted with EtOAc (3×200 mL). The combined organic layers were dried over anhydrous $Na_2SO_4$ and concentrated in vacuo affording a mixture of the expected coupling products [(4-Bromo-phenyl)-(3-nitro-phenyl)-methanone and ((2-Bromo-phenyl)-(3-nitro-phenyl)-methanone)] in 86% yield (11.37 g, 37.2 mmol) as a white solid. By $^1$H NMR, the white solid collected showed a ~16:1 ratio of the desired, (4-Bromo-phenyl)-(3-nitro-phenyl)-methanone (major isomer) to the (2-Bromo-phenyl)-(3-nitro-phenyl)-methanone (minor isomer) present. The mixture was carried on without further purification.

Step 2: (4-Bromo-3-nitro-phenyl)-(3-nitro-phenyl)-methanone

The crude (4-bromo-phenyl)-(3-nitro-phenyl)-methanone (11.1 g, 36.27 mmol) was dissolved in dichloroethane (35 mL) and added dropwise via addition funnel to a mixture of concentrated H$_2$SO$_{4(aq)}$ (16 mL, 290 mmol) and fuming HNO$_{3(aq)}$ (13 mL, 290 mmol). The mixture was stirred at 60° C. overnight. Subsequently the mixture was poured over ice water and allowed to stir resulting in precipitation of the product. The product was filtered and dried affording 72% yield of the (4-Bromo-3-nitro-phenyl)-(3-nitro-phenyl)-methanone (9.17 g, 26.1 mmol).

Step 3: 2-[2-Nitro-4-(3-nitro-benzoyl)-phenyl]-malonic acid diethyl ester

NaH, 60% dispersed in mineral oil, (0.912 g, 22.8 mmol) was washed with petroleum ether after which the NaH was suspended in anhydrous DMSO (23 mL). Diethyl malonate (3.65 mL, 22.8 mmol) was dissolved in 5.7 mL of anhydrous DMSO and added dropwise to the NaH suspension. The mixture was allowed to stir for 15 min at 100° C., during which time the reaction mixture became homogeneous. (4-Bromo-3-nitro-phenyl)-(4-nitro-phenyl)-methanone (4 g, 11.4 mmol) was dissolved in anhydrous DMSO (12.2 mL) and subsequently added via syringe to the malonate solution. The mixture was allowed to stir at 100° C. for 2 h after which the reaction was cooled to room temperature and poured into water (250 mL). The mixture was extracted with EtOAc (3×250 mL) and dried over anhydrous Na$_2$SO$_4$. The organic layers were then concentrated in vacuo affording a crude black oil. The crude oil was then flashed through a plug of silica with 30% EtOAc/Hexanes. The solution was then concentrated in vacuo yielding a pale yellow solid that contained the desired product contaminated with excess diethyl malonate. The impure solid was washed with Hexanes, filtered and dried affording [2-nitro-4-(3-nitro-benzoyl)-phenyl]-malonic acid diethyl ester in 81% yield (4.01 g, 9.31 mmol).

Step 4: 6-(3-Amino-benzoyl)-1,3-dihydro-indol-2-one

[2-Nitro-4-(3-nitro-benzoyl)-phenyl]-malonic acid diethyl ester (2.00 g, 4.65 mmol) was dissolved in EtOH (11.5 mL) after which Sn powder (4.42 g, 37.2 mmol) was added followed by dropwise addition of concentrated HCl$_{(aq)}$ (13 mL). The mixture was allowed to reflux for 3 hours, filtered while hot and then allowed to cool to room temperature. The mixture was diluted with CHCl$_3$ (200 mL) and then extracted once with H$_2$O (200 mL). The aqueous layer was then neutralized with NaHCO$_3$ (pH=7) and then the aqueous layer was extracted with a 95% EtOAc/5% i-prOH solution (3×200 mL). The organic layers were combined and dried over anhydrous Na$_2$SO$_4$. The solution was then concentrated in vacuo affording the 6-(3-Amino-benzoyl)-1,3-dihydro-indol-2-one in 44% yield (0.516 g, 2.05 mmol).

Step 5: N-[3-(2-Oxo-2,3-dihydro-1H-indole-6-carbonyl)-phenyl]-acetamide

A dry 25 mL flask was charged with acetyl chloride (0.405 g, 5.15 mmol) and THF (10 mL). 6-(3-Amino-benzoyl)-1,3-dihydro-indol-2-one (0.905 g, 3.59 mmol) was added to the THF solution of the acid chloride, and the mixture was allowed to reflux for 4 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The precipitate that formed was filtered and washed with THF affording the N-[3-(2-Oxo-2,3-dihydro-1H-indole-6-carbonyl)-phenyl]-acetamide (0.957 g, 3.22 mmol, 81%).

Step 6: N-[3-(3-Hydroxymethylene-2-oxo-2,3-dihydro-1H-indole-6-carbonyl)-phenyl]-acetamide N-[3-(2-Oxo-2,3-dihydro-1H-indole-6-carbonyl)-phenyl]-acetamide (0.957 g, 3.25 mmol) and ethyl formate (0.78 mL, 9.75 mmol) were dissolved in anhydrous ethanol (6.50 mL). The resulting solution was treated in dropwise fashion with a 21 wt % solution of sodium ethoxide in ethanol (6.07 mL, 16.26 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure N-[3-(3-Hydroxymethylene-2-oxo-2,3-dihydro-1H-indole-6-carbonyl)-phenyl]-acetamide (0.752 g, 2.33 mmol, 71%).

Example 41

N-(3-{3-[(4-Morpholin-4-yl-phenylamino)-methylene]-2-oxo-2,3-dihydro-1H-indole-6-carbonyl}-phenyl)-acetamide A small screw cap test tube was charged with N-[3-(3-Hydroxymethylene-2-oxo-2,3-dihydro-1H-indole-6-carbonyl)-phenyl]-acetamide (as prepared in Example 40, 100 mg, 0.310 mmol) and THF (2 mL). To the resulting solution was added N-(4-aminophenyl)morpholine (60.83 mg, 0.341 mmol), and the mixture was stirred for 24 h at 65° C. Subsequently, the reaction mixture was cooled to room temperature and concentrated in vacuo. The crude residue was purified via flash silica gel chromatography (5% MeOH, 95% CHCl$_3$) providing the title compound in 50% yield (75 mg, 0.155 mmol).

Example 42

N-[3-(3-{[4-(4-Methyl-piperazin-1-yl)-phenylamino]-methylene}-2-oxo-2,3-dihydro-1H-indole-6-carbonyl)-phenyl]-acetamide A small screw cap test tube was charged with N-[3-(3-Hydroxymethylene-2-oxo-2,3-dihydro-1H-indole-6-carbonyl)-phenyl]-acetamide (as prepared in Example 40, 100 mg, 0.310 mmol) and THF (2 mL). To the resulting solution was added 4-(4-methyl-piperazin-1-yl)-phenylamine (65.27 mg, 0.341 mmol), and the mixture was stirred for 24 h at 65° C. Subsequently, the reaction mixture was cooled to room temperature and concentrated in vacuo. The crude residue was purified over silica (5% MeOH/CHCl$_3$) providing the title compound in 53% yield (81 mg, 0.163 mmol).

Example 43

N-(3-{3-[(3-Hydroxy-4-methyl-phenylamino)-methylene]-2-oxo-2,3-dihydro-1H-indole-6-carbonyl}-phenyl)-acetamide A small screw cap test tube was charged with N-[3-(3-Hydroxymethylene-2-oxo-2,3-dihydro-1H-indole-6-carbonyl)-phenyl]-acetamide (as prepared in Example 40, 100 mg, 0.310 mmol) and THF (2 mL). To the resulting solution was added 5-amino-2-methylphenol (42.03 mg, 0.341 mmol), and the mixture was stirred for 24 h at 65° C. Subsequently, the reaction mixture was cooled to room temperature. Hexanes were added to the reaction mixture. The solid precipitate that formed was washed with ˜1 mL of i-prOH yielding 73% (100 mg, 0.225 mmol) of the title compound.

Example 44

N-(3-{3-[(3-Hydroxy-phenylamino)-methylene]-2-oxo-2,3-dihydro-1H-indole-6-carbonyl}-phenyl)-acetamide A small screw cap test tube was charged with N-[3-(3-Hydroxymethylene-2-oxo-2,3-dihydro-1H-indole-6-carbonyl)-phenyl]-acetamide (as prepared in Example 40, 100 mg, 0.310 mmol) and THF (2 mL). To the resulting solution was added 3-aminophenol (37.24 mg, 0.341 mmol), and the mixture was stirred for 24 h at 65° C. Subsequently, the reaction mixture was cooled to room temperature and concentrated in vacuo. Ethyl acetate and Hexanes were added to the reaction mixture. The solid precipitate that formed was washed with ~1 mL of i-prOH yielding 45% (58 mg, 0.140 mmol) of the title compound.

Example 45

Thiophene-2-carboxylic acid (4-{3-[(3-hydroxy-4-methyl-phenylamino)-methylene]-2-oxo-2,3-dihydro-1H-indole-6-carbonyl}-phenyl)-amide A small screw cap test tube was charged with Thiophene-2-carboxylic acid [3-(3-hydroxymethylene-2-oxo-2,3-dihydro-1H-indole-6-carbonyl)-phenyl]-amide (prepared below, 100 mg, 0.256 mmol) and THF (2 mL). To the resulting solution was added 5-amino-2-methylphenol (38 mg, 0.309 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 84% yield (0.107 g, 0.2159 mmol).

The Thiophene-2-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: Thiophene-2-carboxylic acid [3-(2-oxo-2,3-dihydro-1H-indole-6-carbonyl)-phenyl]-amide A dry 250 mL flask was charged with Thiophene-2-carbonyl chloride (1.14 g, 7.77 mmol) and THF (60 mL). 6-(3-Amino-benzoyl)-1,3-dihydro-indol-2-one (as prepared in Example 40, 1.508 g, 5.978 mmol) was added to the THF solution of the acid chloride, and the mixture was allowed to reflux for 3 h. The reaction mixture was then allowed to cool to room temperature. The room temperature reaction mixture was concentrated in vacuo. The solid residue was suspended in boiling EtOAc. The suspension was allowed to cool to room temperature before filtering to afford the Thiophene-2-carboxylic acid [3-(2-oxo-2,3-dihydro-1H-indole-6-carbonyl)-phenyl]-amide as a tan solid (1.82 g, 5.02 mmol, 84%).

Step 2: Thiophene-2-carboxylic acid [3-(3-hydroxymethylene-2-oxo-2,3-dihydro-1H-indole-6-carbonyl)-phenyl]-amide Thiophene-2-carboxylic acid [3-(2-oxo-2,3-dihydro-1H-indole-6-carbonyl)-phenyl]-amide (1.27 g, 3.504 mmol) and ethyl formate (0.85 mL, 10.52 mmol) were dissolved in anhydrous ethanol (10 mL). The resulting solution was treated in dropwise fashion with a 21 wt % solution of sodium ethoxide in ethanol (3.90 mL, 10.45 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure Thiophene-2-carboxylic acid [3-(3-hydroxymethylene-2-oxo-2,3-dihydro-1H-indole-6-carbonyl)-phenyl]-amide (0.971 g, 2.487 mmol, 71%).

Example 46

Thiophene-2-carboxylic acid [3-(3-{[4-(4-methyl-piperazin-1-yl)-phenylamino]-methylene}-2-oxo-2,3-dihydro-H-indole-6-carbonyl)-phenyl]-amide A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 100 mg, 0.256 mmol) and THF (2 mL). To the resulting solution was added 4-(4-methyl-piperazin-1-yl)-phenylamine (60 mg, 0.3137 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 76% yield (0.110 g, 0.1951 mmol).

Example 47

Thiophene-2-carboxylic acid (3-{3-[(3-hydroxy-4-methoxy-phenylamino)-methylene]-2-oxo-2,3-dihydro-1H-indole-6-carbonyl}-phenyl)-amide A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 100 mg, 0.256 mmol) and THF (2 mL). To the resulting solution was added 5-amino-2-methoxyphenol (43 mg, 0.309 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 75% yield (0.098 g, 0.1916 mmol).

Example 48

Thiophene-2-carboxylic acid (3-{3-[(3-hydroxy-phenylamino)-methylene]-2-oxo-2,3-dihydro-1H-indole-6-carbonyl}-phenyl)-amide A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 100 mg, 0.256 mmol) and THF (2 mL). To the resulting solution was added 3-aminophenol (34 mg, 0.3116 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 84% yield (0.104 g, 0.2159 mmol).

Example 49

Thiophene-2-carboxylic acid (3-{3-[(4-morpholin-4-yl-phenylamino)-methylene]-2-oxo-2,3-dihydro-1H-indole-6-carbonyl}-phenyl)-amide A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 100 mg, 0.256 mmol) and THF (2 mL). To the resulting solution was added N-(4-aminophenyl)morpholine (55 mg, 0.3086 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 82% yield (0.116 g, 0.2107 mmol).

Example 50

2-tert-Butyl-5-methyl-2H-pyrazole-3-carboxylic acid (3-{3-[(3-hydroxy-4-methyl-phenylamino)-methylene]-2-oxo-2,3-dihydro-1H-indole-6-carbonyl}-phenyl)-amide A small screw cap test tube was charged with 2-tert-Butyl 1-5-methyl-2H-pyrazole-3-carboxylic acid [3-(3-hydroxymethylene-2-oxo-2,3-dihydro-1H-indole-6-carbonyl)-phenyl]-amide (prepared below, 70 mg, 0.157 mmol) and THF (2 mL). To the resulting solution was added 5-amino-2-methylphenol (24 mg, 0.1949 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 66% yield (0.057 g, 0.1037 mmol).

The 2-tert-Butyl 1-5-methyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-tert-Butyl-5-methyl-2H-pyrazole-3-carboxylic acid [3-(2-oxo-2,3-dihydro-1H-indole-6-carbonyl)-phenyl]-amide A dry 250 mL flask was charged with 2-tert-Butyl-5-methyl-2H-pyrazole-3-carbonyl chloride (1.00 g, 4.98 mmol) and THF (40 mL). 6-(3-Amino-benzoyl)-1,3-dihydro-indol-2-one (as prepared in Example 40, 1.0 g, 3.96 mmol) was added to the THF solution of the acid chloride, and the mixture was allowed to reflux for 3 h. The reaction mixture was then allowed to cool to room temperature. The room temperature reaction mixture was concentrated in vacuo. The solid residue was suspended in boiling EtOAc. The suspension was allowed to cool to room temperature before filtering to afford the 2-tert-Butyl-5-methyl-2H-pyrazole-3-carboxylic acid [3-(2-oxo-2,3-dihydro-1H-indole-6-carbonyl)-phenyl]-amide as a tan solid (0.984 g, 2.363 mmol, 60%).

Step 2: 2-tert-Butyl-5-methyl-2H-pyrazole-3-carboxylic acid [3-(3-hydroxymethylene-2-oxo-2,3-dihydro-1H-indole-6-carbonyl)-phenyl]-amide 2-tert-Butyl-5-methyl-2H-pyrazole-3-carboxylic acid [3-(2-oxo-2,3-dihydro-1H-indole-6-carbonyl)-phenyl]-amide (0.715 g, 1.717 mmol) and ethyl formate (0.43 mL, 5.32 mmol) were dissolved in anhydrous ethanol (5.00 mL). The resulting solution was treated in dropwise fashion with a 21 wt % solution of sodium ethoxide in ethanol (2 mL, 5.357 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 2-tert-Butyl-5-methyl-2H-pyrazole-3-carboxylic acid [3-(3-hydroxymethylene-2-oxo-2,3-dihydro-1H-indole-6-carbonyl)-phenyl]-amide (0.412 g, 0.927 mmol, 54%).

Example 51

2-tert-Butyl-5-methyl-2H-pyrazole-3-carboxylic acid (3-{3-[(3-hydroxy-4-methyl-phenylamino)-methylene]-2-oxo-2,3-dihydro-1H-indole-6-carbonyl}-phenyl)-amide A small screw cap test tube was charged with 2-tert-Butyl-5-methyl-2H-pyrazole-3-carboxylic acid [3-(3-hydroxymethylene-2-oxo-2,3-dihydro-1H-indole-6-carbonyl)-phenyl]-amide (as prepared in Example 50, 70 mg, 0.157 mmol) and THF (2 mL). To the resulting solution was added 5-amino-2-methoxyphenol (26 mg, 0.1868 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 71% yield (0.063 g, 0.111 mmol).

Example 52

2-tert-Butyl-5-methyl-2H-pyrazole-3-carboxylic acid (3-{3-[(3-hydroxy-phenylamino)-methylene]-2-oxo-2,3-dihydro-1H-indole-6-carbonyl}-phenyl)-amide A small screw cap test tube was charged with 2-tert-Butyl-5-methyl-2H-pyrazole-3-carboxylic acid [3-(3-hydroxymethylene-2-oxo-2,3-dihydro-1H-indole-6-carbonyl)-phenyl]-amide (as prepared in Example 50, 70 mg, 0.157 mmol) and THF (2 mL). To the resulting solution was added 3-aminophenol (21 mg, 0.1924 mmol), and the mixture was stirred for 24 h at 65° C. Subsequently, the reaction mixture was cooled to room temperature and concentrated in vacuo. The solid residue was recrystallized with ~5 μmL of i-prOH affording the title compound in 67% yield (0.056 g, 0.1046 mmol).

Example 53

2-tert-Butyl-5-methyl-2H-pyrazole-3-carboxylic acid (3-{3-[(4-morpholin-4-yl-phenylamino)-methylene]-2-oxo-2,3-dihydro-1H-indole-6-carbonyl}-phenyl)-amide A small screw cap test tube was charged with 2-tert-Butyl-5-methyl-2H-pyrazole-3-carboxylic acid [3-(3-hydroxymethylene-2-oxo-2,3-dihydro-1H-indole-6-carbonyl)-phenyl]-amide (as prepared in Example 50, 70 mg, 0.157 mmol) and THF (2 mL). To the resulting solution was added N-(4-aminophenyl)morpholine (34 mg, 0.1907 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 73% yield (0.069 g, 0.1141 mmol).

Example 54

5-Acetyl-thiophene-2-carboxylic acid (3-{3-[(3-hydroxy-4-methoxy-phenylamino)-methylene]-2-oxo-2,3-dihydro-1H-indole-6-carbonyl}-phenyl)-amide A small screw cap test tube was charged with 5-Acetyl-thiophene-2-carboxylic acid [3-(3-hydroxymethylene-2- oxo-2,3-dihydro-1H-indole-6-carbonyl)-phenyl]-amide (prepared below, 100 mg, 0.231 mmol) and THF (2 mL). To the resulting solution was added 5-amino-2-methoxyphenol (35.39 mg, 0.254 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 59% (75 mg, 0.136 mmol) of the title compound.

The 5-Acetyl-thiophene-2-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 5-Acetyl-thiophene-2-carboxylic acid [3-(2-oxo-2,3-dihydro-1H-indole-6-carbonyl)-phenyl]-amide A dry 25 mL flask was charged with 5-Acetyl-thiophene-2-carboxylic acid (0.880 g, 5.15 mmol) and thionyl chloride (5 mL) and allowed to stir at 79° C. for 2 h. The thionyl chloride was then removed by concentration in vacuo. The crude acid chloride was cooled to room temperature, and then dissolved in THF (5 mL). 6-(3-Amino-benzoyl)-1,3-dihydro-indol-2-one (as prepared in Example 40, 1.01 g, 3.97 mmol) was added to the THF solution of the acid chloride, and the mixture was allowed to reflux for 3 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The tan solids were filtered to afford the pure 5-Acetyl-thiophene-2-carboxylic acid [3-(2-oxo-2,3-dihydro-1H-indole-6-carbonyl)-phenyl]-amide (1.275 g, 3.05 mmol, 77%).

Step 2: 5-Acetyl-thiophene-2-carboxylic acid [3-(3-hydroxymethylene-2-oxo-2,3-dihydro-1H-indole-6-carbonyl)-phenyl]-amide 5-Acetyl-thiophene-2-carboxylic acid [3-(2-oxo-2,3-dihydro-1H-indole-6-carbonyl)-phenyl]-amide (1.245 g, 3.077 mmol) and ethyl formate (0.739 mL, 9.23 mmol) were dissolved in anhydrous ethanol (6.16 mL). The resulting solution was treated in dropwise fashion with a 21 wt % solution of sodium ethoxide in ethanol (5.75 mL, 15.38 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 5-Acetyl-thiophene-2-carboxylic acid [3-(3-hydroxymethylene-2-oxo-2,3-dihydro-1H-indole-6-carbonyl)-phenyl]-amide (0.864 g, 1.99 mmol, 65%).

Example 55

5-Acetyl-thiophene-2-carboxylic acid (3-{3-[(3-hydroxy-4-methyl-phenylamino)-methylene]-2-oxo-2,3-dihydro-1H-indole-6-carbonyl}-phenyl)-amide A small screw cap test tube was charged with 5-Acetyl-thiophene-2-carboxylic acid [3-(3-hydroxymethylene-2-oxo-2,3-dihydro-1H-indole-6-carbonyl)-phenyl]-amide (as prepared in Example 54, 100 mg, 0.231 mmol) and THF (2 mL). To the resulting solution was added 5-amino-2-methylphenol (31.33 mg, 0.254 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 72% (89 mg, 0.166 mmol) of the title compound.

Example 56

5-Acetyl-thiophene-2-carboxylic acid (3-{3-[(4-morpholin-4-yl-phenylamino)-methylene]-2-oxo-2,3-dihydro-1H-indole-6-carbonyl}-phenyl)-amide A small screw cap test tube was charged with 5-Acetyl-thiophene-2-carboxylic acid [3-(3-hydroxymethylene-2-oxo-2,3-dihydro-1H-indole-6-carbonyl)-phenyl]-amide (as prepared in Example 54, 100 mg, 0.231 mmol) and THF (2 mL). To the resulting solution was added N-(4-aminophenyl) morpholine (45.34 mg, 0.254 mmol), and the mixture was stirred for 24 h at 65° C. Subsequently, the reaction mixture was cooled to room temperature. Hexanes (5 mL) were added to the reaction mixture. The crude mixture was concentrated in vacuo and then dissolved into hot EtOAc. Hexanes (~5 mL) were added causing a precipitate to crash out. The precipitate was filtered and washed with ~1 mL of i-prOH yielding 69% (95 mg, 0.160 mmol) of the title compound.

Example 57

5-Acetyl-thiophene-2-carboxylic acid (3-{3-[(3-hydroxy-phenylamino)-methylene]-2-oxo-2,3-dihydro-1H-indole-6-carbonyl}-phenyl)-amide A small screw cap test tube was charged with 5-Acetyl-thiophene-2-carboxylic acid [3-(3-hydroxymethylene-2-oxo-2,3-dihydro-1H-indole-6-carbonyl)-phenyl]-amide (as prepared in Example 54, 100 mg, 0.231 mmol) and THF (2 mL). To the resulting solution was added 3-aminophenol (27.76 mg, 0.254 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 82% (99 mg, 0.189 mmol) of the title compound.

Example 58

5-Acetyl-thiophene-2-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 5-Acetyl-thiophene-2-carboxylic acid [3-(3-hydroxymethylene-2-oxo-2,3-dihydro-1H-indole-6-carbonyl)-phenyl]-amide (as prepared in Example 54, 100 mg, 0.231 mmol) and THF (2 mL). To the resulting solution was added 4-(4-methyl-piperazin-1-yl)-phenylamine (48.65 mg, 0.254 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 46% (65 g, 0.107 mmol) of the title compound.

Example 59

2-tert-Butyl-5-methyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-tert-Butyl-5-methyl-2H-pyrazole-3-carboxylic acid [3-(3-hydroxymethylene-2-oxo-2,3-dihydro-1H-indole-6-carbonyl)-phenyl]-amide (as prepared in Example 50, 70 mg, 0.157 mmol) and THF (2 mL). To the resulting solution was added 4-(4-methyl-piperazin-1-yl)-phenylamine (36 mg, 0.1882 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 50% yield (0.051 g, 0.078 mmol).

Example 60

2,5-Dimethyl-2H-pyrazole-3-carboxylic acid (3-{3-[(3-hydroxy-4-methyl-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (prepared below, 120 mg, 0.298 mmol) and THF (2 mL). To the resulting solution was added 5-amino-2-methylphenol (44 mg, 0.357 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 56% yield (0.084 g, 0.1655 mmol).

The 2,5-Dimethyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2,5-Dimethyl-2H-pyrazole-3-carboxylic acid [3-(2-oxo-2,3-dihydro-1H-indole-6-carbonyl)-phenyl]-amide A dry 250 mL flask was charged with 2,5-Dimethyl-2H-pyrazole-3-carboxylic acid (0.989 g, 7.057 mmol) and thionyl chloride (5 mL) and allowed to stir at 79° C. for 2 h. The thionyl chloride was then removed by concentration in vacuo. The crude acid chloride was cooled to room temperature, and then dissolved in THF (40 mL). 6-(3-Amino-benzoyl)-1,3-dihydro-indol-2-one (as prepared in Example 40, 1.26 g, 4.994 mmol) was added to the THF solution of the acid chloride, and the mixture was allowed to reflux for 4 h. The reaction mixture was then allowed to cool to room temperature. The room temperature reaction mixture was concentrated in vacuo. The solid residue was suspended in boiling EtOAc. The suspension was allowed to cool to room temperature before filtering to afford the 2,5-Dimethyl-2H-pyrazole-3-carboxylic acid [3-(2-oxo-2,3-dihydro-1H-indole-6-carbonyl)-phenyl]-amide as a tan solid (1.4 g, 3.74 mmol, 75%).

Step 2: 2,5-Dimethyl-2H-pyrazole-3-carboxylic acid [3-(3-hydroxymethylene-2-oxo-2,3-dihydro-1H-indole-6-carbonyl)-phenyl]-amide 2,5-Dimethyl-2H-pyrazole-3-carboxylic acid [3-(2-oxo-2,3-dihydro-1H-indole-6-carbonyl)-phenyl]-amide (1.2 g, 3.205 mmol) and ethyl formate (0.800 mL, 9.903 mmol) were dissolved in anhydrous ethanol (10 mL). The resulting solution was treated in dropwise fashion with a 21 wt % solution of sodium ethoxide in ethanol (3.6 mL, 9.643 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 2,5-Dimethyl-2H-pyrazole-3-carboxylic acid [3-(3-hydroxymethylene-2-oxo-2,3-dihydro-1H-indole-6-carbonyl)-phenyl]-amide (0.887 g, 2.204 mmol, 69%).

Example 61

2,5-Dimethyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 120 mg, 0.298 mmol) and THF (2 mL). To the resulting solution was added 4-(4-methyl-piperazin-1-yl)-phenylamine (68 mg, 0.3555 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 64% yield (0.109 g, 0.1893 mmol).

Example 62

2,5-Dimethyl-2H-pyrazole-3-carboxylic acid (3-{3-[(3-hydroxy-4-methoxy-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 120 mg, 0.298 mmol) and THF (2 mL). To the resulting solution was added 5-amino-2-methoxyphenol (50 mg, 0.3593 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 74% yield (0.115 g, 0.1965 mmol).

Example 63

2,5-Dimethyl-2H-pyrazole-3-carboxylic acid (3-{3-[(3-hydroxy-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 120 mg, 0.298 mmol) and THF (2 mL). To the resulting solution was added 3-aminophenol (40 mg, 0.3665 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 70% yield (0.103 g, 0.2087 mmol).

Example 64

2,5-Dimethyl-2H-pyrazole-3-carboxylic acid (3-{3-[(4-morpholin-4-yl-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 120 mg, 0.298 mmol) and THF (2 mL). To the resulting solution was added N-(4-aminophenyl)morpholine (64 mg, 0.3591 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 58% yield (0.097 g, 0.1724 mmol).

Example 65

2-tert-Butyl-5-methyl-2H-pyrazole-3-carboxylic acid (4-{3-[(4-morpholin-4-yl-phenylamino)-methylene]-2-oxo-2,3-dihydro-1H-indole-6-carbonyl}-phenyl)-amide A small screw cap test tube was charged with 2-tert-Butyl-5-methyl-2H-pyrazole-3-carboxylic acid [4-(3-hydroxymethylene-2-oxo-2,3-dihydro-1H-indole-6-carbonyl)-phenyl]-amide (prepared below, 100 mg, 2.25 mmol) and THF (2 mL). To the resulting solution was added N-(4-aminophenyl)morpholine (44 mg, 2.48 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 49% (67 mg, 0.111 mmol) of the title compound.

The 2-tert-Butyl-5-methyl-2H-pyrazole-3-carboxylic acid [4-(3-hydroxymethylene-2-oxo-2,3-dihydro-1H-indole-6-carbonyl)-phenyl]-amide was prepared from 4-nitrobenzoyl chloride using the following multiple step procedure:

Step 1: 2-tert-Butyl-5-methyl-2H-pyrazole-3-carboxylic acid [4-(2-oxo-2,3-dihydro-1H-indole-6-carbonyl)-phenyl]-amide A dry 25 mL flask was charged with 2-tert-Butyl-5-methyl-2H-pyrazole-3-carbonyl chloride (1.03 g, 5.17 mmol) and THF (10 mL). 6-(4-Amino-benzoyl)-1,3-dihydro-indol-2-one (as prepared in Example 15, 1.0 g, 3.97 mmol) was added to the THF solution of the acid chloride, and the mixture was allowed to reflux for 4 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The tan solids were filtered to afford the pure 2-tert-Butyl-5-methyl-2H-pyrazole-3-carboxylic acid [4-(2-oxo-2,3-dihydro-1H-indole-6-carbonyl)-phenyl]-amide (0.654 g, 1.68 mmol, 42%).

Step 2: 2-tert-Butyl-5-methyl-2H-pyrazole-3-carboxylic acid [4-(3-hydroxymethylene-2-oxo-2,3-dihydro-1H-indole-6-carbonyl)-phenyl]-amide 2-tert-Butyl-5-methyl-2H-pyrazole-3-carboxylic acid [4-(2-oxo-2,3-dihydro-1H-indole-6-carbonyl)-phenyl]-amide (0.634 g, 1.63 mmol) and ethyl formate (0.39 mL, 4.89 mmol) were dissolved in anhydrous ethanol (3.50 mL). The resulting solution was treated in dropwise fashion with a 21 wt % solution of sodium ethoxide in ethanol (3.05 mL, 8.16 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 2-tert-Butyl-5-methyl-2H-pyrazole-3-carboxylic acid [4-(3-hydroxymethylene-2-oxo-2,3-dihydro-1H-indole-6-carbonyl)-phenyl]-amide (0.548 g, 1.32 mmol, 81%).

Example 66

2-tert-Butyl-5-methyl-2H-pyrazole-3-carboxylic acid [4-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-tert-Butyl-5-methyl-2H-pyrazole-3-carboxylic acid [4-(3-hydroxymethylene-2-oxo-2,3-dihydro-1H-indole-6-carbonyl)-phenyl]-amide (as prepared in Example 65, 100 mg, 0.225 mmol) and THF (2 mL). To the resulting solution was added 4-(4-methyl-piperazin-1-yl)-phenylamine (47 mg, 0.25 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 42% (59 mg, 0.0955 mmol) of the title compound.

Example 67

2-tert-Butyl-5-methyl-2H-pyrazole-3-carboxylic acid (4-{3-[(3-hydroxy-phenylamino)-methylene]-2-oxo-2,3-dihydro-1H-indole-6-carbonyl}-phenyl)-amide A small screw cap test tube was charged with 2-tert-Butyl-5-methyl-2H-pyrazole-3-carboxylic acid [4-(3-hydroxymethylene-2-oxo-2,3-dihydro-1H-indole-6-carbonyl)-phenyl]-amide (as prepared in Example 65, 100 mg, 0.225 mmol) and THF (2 mL). To the resulting solution was added 3-aminophenol (27 mg, 0.25 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 31% (42 mg, 0.0954 mmol) of the title compound.

Example 68

2-tert-Butyl-5-methyl-2H-pyrazole-3-carboxylic acid (4-{3-[(3-hydroxy-4-methyl-phenylamino)-methylene]-2-oxo-2,3-dihydro-1H-indole-6-carbonyl}-phenyl)-amide A small screw cap test tube was charged with 2-tert-Butyl-5-methyl-2H-pyrazole-3-carboxylic acid [4-(3-hydroxymethylene-2-oxo-2,3-dihydro-1H-indole-6-carbonyl)-phenyl]-amide (as prepared in Example 65, 100 mg, 0.225 mmol) and THF (2 mL). To the resulting solution was added 5-amino-2-methoxyphenol (34 mg, 0.25 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 32% (38 mg, 0.071 mmol) of the title compound.

Example 69

2-Ethyl-5-methyl-2H-pyrazole-3-carboxylic acid (3-{3-[(4-morpholin-4-yl-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]-amide (prepared below, 100 mg, 0.240 mmol) and THF (2 mL). To the resulting solution was added N-(4-aminophenyl)morpholine (47.08 mg, 0.264 mmol), and the mixture was stirred for 24 h at 65° C. Subsequently, the reaction mixture was cooled to room temperature and concentrated in vacuo. The crude residue was purified via flash silica gel chromatography (5% MeOH/CHCl$_3$) providing the title compound in 18% yield (25 mg, 0.043 mmol).

The 2-Ethyl-5-methyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-Ethyl-5-methyl-2H-pyrazole-3-carboxylic acid [3-(2-oxo-2,3-dihydro-1H-indole-6-carbonyl)-phenyl]-amide A dry 25 mL flask was charged with 2-Ethyl-5-methyl-2H-pyrazole-3-carboxylic acid (0.891 g, 5.16 mmol) and thionyl chloride (15 mL) and allowed to stir at 79° C. for 2 h. The thionyl chloride was then removed by concentration in vacuo. The crude acid chloride was cooled to room temperature, and then dissolved in THF (5 mL). 6-(3-Amino-benzoyl)-1,3-dihydro-indol-2-one (as prepared in Example 40, 1.0 g, 3.97 mmol) was added to the THF solution of the acid chloride, and the mixture was allowed to reflux for 3 h. The reaction mixture was then allowed to cool to room temperature. The room temperature reaction mixture was concentrated in vacuo, and the crude residue was dissolved in EtOH (5 mL). The ethanolic solution was treated with 1M NaOH$_{(aq)}$ (2 mL) and stirred for 30 min. The basic solution was acidified to a pH of 1 with 1M HCl$_{(aq)}$ yielding a tan precipitate. The tan solids were filtered to afford the pure 2-Ethyl-5-methyl-2H-pyrazole-3-carboxylic acid [3-(2-oxo-2,3-dihydro-1H-indole-6-carbonyl)-phenyl]-amide (1.354 g, 3.49 mmol, 88%).

Step 2: 2-Ethyl-5-methyl-2H-pyrazole-3-carboxylic acid [3-(3-hydroxymethylene-2-oxo-2,3-dihydro-1H-indole-6-carbonyl)-phenyl]-amide 2-Ethyl-5-methyl-2H-pyrazole-3-carboxylic acid [3-(2-oxo-2,3-dihydro-1H-indole-6-carbonyl)-phenyl]-amide (1.00 g, 2.57 mmol) and ethyl formate (0.619 mL, 7.72 mmol) were dissolved in anhydrous ethanol (5.20 mL). The resulting solution was treated in dropwise fashion with a 21 wt % solution of sodium ethoxide in ethanol (4.80 mL, 12.80 mmol). This reaction mixture was heated at 78° C. for 1 h, producing a black oil.

Subsequently, the reaction mixture was cooled to room temperature, and then the reaction pH was adjusted to pH 1 with dropwise addition of 1M HCl$_{(aq)}$ causing the formation of a pale orange precipitate. The suspension was filtered yielding an orange solid as the pure 2-Ethyl-5-methyl-2H-pyrazole-3-carboxylic acid [3-(3-hydroxymethylene-2-oxo-2,3-dihydro-1H-indole-6-carbonyl)-phenyl]-amide (0.786 g, 1.88 mmol, 73%).

Example 70

2-Ethyl-5-methyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]-amide (as prepared in Example 69, 100 mg, 0.240 mmol) and THF (2 mL). To the resulting solution was added 4-(4-methyl-piperazin-1-yl)-phenylamine (50.53 mg, 0.264 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~1 mL of i-prOH yielding 32% (45 mg, 0.076 mmol) of the title compound.

Example 71

2-Ethyl-5-methyl-2H-pyrazole-3-carboxylic acid (3-{3-[(3-hydroxy-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]-amide (as prepared in Example 69, 100 mg, 0.240 mmol) and THF (2 mL). To the resulting solution was added 3-aminophenol (28.83 mg, 0.264 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 37% (45 mg, 0.089 mmol) of the title compound.

Example 72

2-Ethyl-5-methyl-2H-pyrazole-3-carboxylic acid (3-{3-[(3-hydroxy-4-methyl-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]-amide (as prepared in Example 69, 100 mg, 0.240 mmol) and THF (2 mL). To the resulting solution was added 5-amino-2-methylphenol (32.5, 0.264 mmol), and the mixture was stirred for 24 h at 65° C. Subsequently, the reaction mixture was cooled to room temperature. Hexanes were added to the reaction mixture. The solid precipitate that formed was washed with ~1 mL of i-prOH yielding 27% (34 g, 0.065 mmol) of the title compound.

Example 73

2-Ethyl-5-methyl-2H-pyrazole-3-carboxylic acid (3-{3-[(3-hydroxy-4-methyl-phenylamino)-methylene]-2-oxo-2,3-dihydro-1H-indole-6-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]-amide (as prepared in Example 69, 100 mg, 0.240 mmol) and THF (2 mL). To the resulting solution was added 5-amino-2-methylphenol (36.76 mg, 0.264 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~1 mL of i-prOH yielding 66% (85 g, 0.158 mmol) of the title compound.

Example 74

Thiophene-2-carboxylic acid [3-(3-{[4-(3-diethylamino-propoxy)-phenylamino]-methylene}-2-oxo-2,3-dihydro-1H-indole-6-carbonyl)-phenyl]-amide A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 130 mg, 0.333 mmol) and THF (2 mL). To the resulting solution was added 4-(3-Diethylamino-propoxy)-phenylamine[1] (151.3 mg, 0.681 mmol), and the mixture was stirred for 24 h at 65° C. Subsequently, the reaction mixture was cooled to room temperature. The room temperature reaction mixture was concentrated in vacuo. The solid residue was recrystallized from EtOAc (5 mL) and Hexanes (2 mL) yielding the title compound in 39% yield (0.078 g, 0.131 mmol).

Example 75

4-[(2-Oxo-6-{3-[(thiophene-2-carbonyl)-amino]-benzoyl}-1,2-dihydro-indol-3-ylidenemethyl)-amino]-benzoic acid A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 80 mg, 0.2049 mmol) and THF (2 mL). To the resulting solution was added 4-Amino-benzoic acid (34 mg, 0.248 mmol), and the mixture was stirred for 24 h at 65° C. Subsequently, the reaction mixture was cooled to room temperature. The room temperature reaction mixture was concentrated in vacuo. The solid residue was recrystallized from EtOAc (5 mL) and Hexanes (2 mL) yielding the title compound in 81% yield (0.085 g, 0.1668 mmol).

Example 76

3-{4-[(2-Oxo-6-{3-[(thiophene-2-carbonyl)-amino]-benzoyl}-1,2-dihydro-indol-3-ylidenemethyl)-amino]-phenyl}-propionic acid A small screw cap test tube was charged with Thiophene-2-carboxylic acid [3-(3-hydroxymethylene-2-oxo-2,3-dihydro-1H-indole-6-carbonyl)-phenyl]-amide (as prepared in Example 45, 80 mg, 0.2049 mmol) and THF (2 mL). To the resulting solution was added 3-(4-Amino-phenyl)-propionic acid (41 mg, 0.2482 mmol), and the mixture was stirred for 24 h at 65° C. Subsequently, the reaction mixture was cooled to room temperature. The room temperature reaction mixture was concentrated in vacuo. The solid residue was recrystallized from EtOAc (5 mL) and Hexanes (2 mL) yielding the title compound in 74% yield (0.082 g, 0.1525 mmol).

Example 77

4-[(6-{3-[(2,5-Dimethyl-2H-pyrazole-3-carbonyl)-amino]-benzoyl}-2-oxo-1,2-dihydro-indol-3-ylidenemethyl)-amino]-benzoic acid A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-Amino-benzoic acid (37.5 mg, 0.274 mmol), and the mixture was stirred for 24 h at 65° C. Subsequently, the reaction mixture was cooled to room temperature. The yellow solid was dissolved into a solution of 98% EtOAc/2% i-prOH (3 mL) and washed with water (3×2 mL). The organic layers were combined and dried over anhydrous $Na_2SO_4$ affording 47.8% (0.062 g, 0.119 mmol) of the title compound.

Example 78

2,5-Dimethyl-2H-pyrazole-3-carboxylic acid [3-(2-oxo-3-{[4-(2-pyrrolidin-1-yl-ethoxy)-phenylamino]-methylene}-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 121 mg, 0.298 mmol) and THF (2 mL). To the resulting solution was added 4-(2-Pyrrolidin-1-yl-ethoxy)-phenylamine[1] (67.7 mg, 0.329 mmol), and the mixture was stirred for 24 h at 65° C. Subsequently, the reaction mixture was cooled to room temperature. Hexanes were added to the reaction mixture, and the resulting suspension was filtered. The filtrate then was concentrated in vacuo. The residue was redissolved into EtOAc then diluted with Hexanes causing a precipitate to form. This precipitate was filtered and washed with ~1 mL of i-prOH yielding 62% (0.109 g, 0.185 mmol) of the title compound.

Example 79

2,5-Dimethyl-2H-pyrazole-3-carboxylic acid [3-(2-oxo-3-{[4-(2-piperidin-1-yl-ethoxy)-phenylamino]-methylene}-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-(2-Piperidin-1-yl-ethoxy)-phenylamine[1] (60.3 mg, 0.274 mmol), and the mixture was stirred for 24 h at 65° C. Subsequently, the reaction mixture was cooled to room temperature. Hexanes were added to the reaction mixture and the reaction mixture was vacuum filtered. The black solid collected was set aside. The filtrate was then concentrated in vacuo and then redissolved into EtOAc and then Hexanes were added causing a precipitate to form. The precipitate was then filtered and washed with ~1 mL of i-prOH yielding 33.2% (0.050 g, 0.083 mmol) of the title compound.

Example 80

2,5-Dimethyl-2H-pyrazole-3-carboxylic acid [3-(3-{[4-(2-dimethylamino-1-methyl-ethylamino)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 116 mg, 0.288 mmol) and THF (2 mL). To the resulting solution was added N-(2-Dimethylamino-1-methyl-ethyl)-benzene-1,4-diamine (prepared below, 61.4 mg, 0.314 mmol), and the mixture was stirred for 24 h at 65° C. Subsequently, the reaction mixture was cooled to room temperature. Hexanes were added to the reaction mixture and the reaction mixture was vacuum filtered. The black solid collected was set aside. The filtrate was then concentrated in vacuo and then redissolved into EtOAc and then Hexanes were added causing a precipitate to form. The precipitate was then filtered and washed with ~1 mL of i-prOH yielding 40% (0.067 g, 0.116 mmol) of the title compound.

N-(2-Dimethylamino-1-methyl-ethyl)-benzene-1,4-diamine was prepared from 1-fluoro-4-nitrobenzene using the following multiple step procedure:

Step 1: N1,N1-Dimethyl-N2-(4-nitro-phenyl)-propane-1,2-diamine

A solution of N1,N1-Dimethyl-propane-1,2-diamine (10 mL, 77.4 mmol) in DMF (40 mL) at room temperature was treated with potassium carbonate (15.26 g, 1.5 equiv.) and 1-fluoro-4-nitrobenzene (8.2 mL, 1 equiv.). The reaction mixture was stirred at 110° C. overnight. The reaction mixture was cooled to room temperature, filtered to remove remaining solid potassium carbonate and diluted with $CH_2Cl_2$ (500 mL). The reaction mixture was extracted with $H_2O$ (3×500 mL) and dried over anhydrous $MgSO_4$. Following filtration and concentration in vacuo the gelatinous red residue was purified by flash silica gel chromatography ($CHCl_3$ to 1:4 MeOH: $CHCl_3$ gradient eluant) to give N1,N1-Dimethyl-N2-(4-nitro-phenyl)-propane-1,2-diamine as a light brown oil (81.4%).

Step 2: N-(2-Dimethylamino-1-methyl-ethyl)-benzene-1,4-diamine

To a solution of N1,N1-Dimethyl-N2-(4-nitro-phenyl)-propane-1,2-diamine (446 mg, 2 mmol) in absolute ethanol (20 mL) was added hydrazine monohydrate (0.78 mL, 8 equiv.) followed by the addition of a small portion of Raney nickel. The reaction mixture was heated to 50° C. with stirring for 2 h at which point all gas evolution had ceased. The reaction mixture was filtered through celite to remove the Raney nickel. The filtrate was concentrated under reduced pressure to give the N-(2-Dimethylamino-1-methyl-ethyl)-benzene-1,4-diamine as a brown oil. This material was carried on in subsequent steps without purification.

Example 81

{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-acetic acid

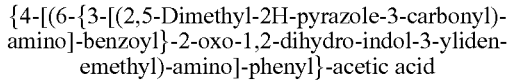

A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added (4-Aminophenyl)-acetic acid (41.4 mg, 0.274 mmol), and the mixture was stirred for 24 h at 65° C. Subsequently, the reaction mixture was cooled to room temperature. EtOAc (3 mL) was added to the mixture and was washed with 5% $HCl_{(aq)}$ (2 mL) and $H_2O$ (2×2 mL). The organic layers were combined dried over anhydrous $Na_2SO_4$, filtered and concentrated in vacuo The solid was then recrystallized from EtOAc/Hexanes affording 51% (0.068 g, 0.127 mmol) of the title compound.

Example 82

3-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-propionic acid

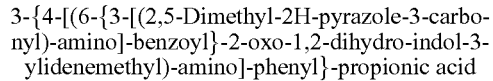

A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 3-(4-Amino-phenyl)-propionic acid (45.2 mg, 0.274 mmol), and the mixture was stirred for 24 h at 65° C. Subsequently, the reaction mixture was cooled to room temperature and concentrated in vacuo. The resulting residue was redissolved into EtOAc. Hexanes were added to the EtOAc solution causing a precipitate to form. The solid precipitate that formed was washed with ~1 mL of i-prOH yielding 15.4% (0.021 g, 0.038 mmol) of the title compound.

Example 83

2,5-Dimethyl-2H-pyrazole-3-carboxylic acid [3-(3-{[4-(3-diethylamino-propoxy)-phenylamino]-methylene}-2-oxo-2,3-dihydro-1H-indole-6-carbonyl)-phenyl]-amide

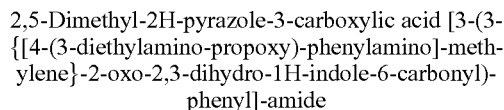

A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 144.3 mg, 0.3586 mmol) and THF (2 mL). To the resulting solution was added 4-(3-Diethylamino-propoxy)-phenylamine[1] (98.2 mg, 0.4417 mmol), and the mixture was stirred for 24 h at 65° C. Subsequently, the reaction mixture was cooled to room temperature. The room temperature reaction mixture was concentrated in vacuo. The solid residue was recrystallized from EtOAc (5 mL) and Hexanes (2 mL) yielding the title compound in 30% yield (0.066 g, 0.1088 mmol).

Example 84

2,5-Dimethyl-2H-pyrazole-3-carboxylic acid [3-(2-oxo-3-{[4-(3-piperidin-1-yl-propoxy)-phenylamino]-methylene}-2,3-dihydro-1H-indole-6-carbonyl)-phenyl]-amide

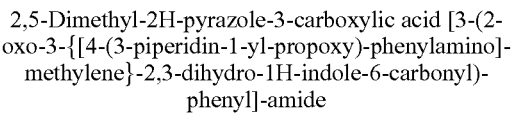

A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 135.1 mg, 0.3357 mmol) and THF (1 mL). To the resulting solution was added 4-(3-Piperidin-1-yl-propoxy)-phenylamine[1] (95.2 mg, 0.4062 mmol), and the mixture was stirred for 24 h at 65° C. Subsequently, the reaction mixture was cooled to room temperature. The room temperature reaction mixture was concentrated in vacuo. The solid residue was recrystallized from EtOAc (5 mL) and Hexanes (2 mL) yielding the title compound in 28% yield (0.058 g, 0.0937 mmol).

Example 85

2,5-Dimethyl-2H-pyrazole-3-carboxylic acid [3-(3-{[4-(3-diethylamino-2-hydroxy-propoxy)-phenylamino]-methylene}-2-oxo-2,3-dihydro-1H-indole-6-carbonyl)-phenyl]-amide

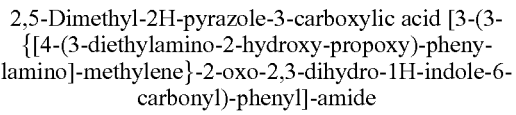

A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 132.3 mg, 0.3288 mmol) and THF (2 mL). To the resulting solution was added 1-(4-Amino-phenoxy)-3-diethylamino-propan-2-ol (prepared below; 95.7 mg, 0.4015 mmol), and the mixture was stirred for 24 h at 65° C. Subsequently, the reaction mixture was cooled to room temperature. The room temperature reaction mixture was concentrated in vacuo. The solid residue was recrystallized from EtOAc (5 mL) and Hexanes (2 mL) yielding the title compound in 35% yield (0.072 g, 0.1156 mmol).

The 1-(4-Amino-phenoxy)-3-diethylaminopropan-2-ol was prepared from 2-(4-nitro-phenoxymethyl)-oxirane using the following multiple step procedure:

Step 1:
1-Diethylamino-3-(4-nitro-phenoxy)-propan-2-ol

A solution of 2-(4-nitro-phenoxymethyl)-oxirane (9.75 g, 50 mmol) in absolute EtOH (100 mL) was heated at 70° C. until 2-(4-nitro-phenoxymethyl)-oxirane is dissolved then the solution was allowed to cool to room temperature. Subsequently the room temperature solution was treated with diethylamine (5.2 mL, 1.0 equiv.) in one portion. The reaction mixture is stirred at room temperature for 15 min during which time starting material (oxirane) began to precipitate out of solution. The reaction mixture was heated to 50° C. and an additional amount of diethylamine (2.6 mL) was added to achieve complete dissolution of starting oxirane. The reaction mixture was heated for an additional 5 h at 55° C. at which point thin layer chromatography (9:1, chloroform:methanol) indicated complete consumption of the starting oxirane. The reaction mixture was cooled to room temperature and concentrated in vacuo. The oily light brown residue obtained after evaporation, was purified by flash silica gel chromatography, ($CHCl_3$ to 1:9, $MeOH:CHCl_3$ gradient eluant) to give the 1-diethylamino-3-(4-nitro-phenoxy)-propan-2-ol as a yellow oil (11.9 g, 89%).

Step 2:
1-(4-Amino-phenoxy)-3-diethylaminopropan-2-ol

A suspension of 1-diethylamino-3-(4-nitro-phenoxy)-propan-2-ol (2.41 g, 8.99 mmol) in absolute ethanol (60 mL) was heated to 50° C. To the resulting solution was added hydrazine monohydrate (2.62 mL, 6 equiv.) followed by addition of a small portion of Raney nickel. The reaction mixture was heated at 50° C. with stirring for 1 h at which point all gas evolution had ceased. The reaction mixture was filtered through celite to remove the Raney nickel. The filtrate was concentrated in vacuo to give the 1-(4-Amino-phenoxy)-3-diethylaminopropan-2-ol as a light yellow oil (2.13 g).

Example 86

1-Methyl-3-trifluoromethyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 1-Methyl-3-trifluoromethyl-1H-pyrazole-4-carboxylic acid [3-(3-hydroxymethylene-2-oxo-2,3-dihydro-1H-indole-6-carbonyl)-phenyl]-amide (prepared below, 100 mg, 0.249 mmol) and THF (2 mL). To the resulting solution was added 4-(4-methyl-piperazin-1-yl)-phenylamine (47.5 mg, 0.249 mmol), and the mixture was stirred for 24 h at 65° C. Subsequently, the reaction mixture was cooled to room temperature and concentrated in vacuo. The crude residue was dissolved in EtOAc.

The resulting solution was diluted with Hexanes to initiate the precipitation of the product. The solid precipitate that formed was filtered then washed with ~3 mL of acetone yielding 32% (45 mg, 0.076 mmol) of the title compound.

The 1-Methyl-3-trifluoromethyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 1-Methyl-3-trifluoromethyl-1H-pyrazole-4-carboxylic acid [3-(2-oxo-2,3-dihydro-1H-indole-6-carbonyl)-phenyl]-amide A dry 25 mL flask was charged with 1-Methyl-3-trifluoromethyl-1H-pyrazole-4-carbonyl chloride (0.186 g, 0.873 mmol) and THF (2 mL). 6-(4-Amino-benzoyl)-1,3-dihydro-indol-2-one (as prepared in Example 40, 0.200 g, 0.794 mmol) was added to the THF solution of the acid chloride, and the mixture was allowed to reflux for 2 h. The reaction mixture was then allowed to cool to room temperature. The room temperature reaction mixture was concentrated in vacuo. The light yellow solids were washed with THF (~3 mL) and filtered to afford the pure product 1-Methyl-3-trifluoromethyl-1H-pyrazole-4-carboxylic acid [3-(2-oxo-2,3-dihydro-1H-indole-6-carbonyl)-phenyl]-amide (0.235 g, 0.627 mmol, 79%).

Step 2: 1-Methyl-3-trifluoromethyl-1H-pyrazole-4-carboxylic acid [3-(3-hydroxymethylene-2-oxo-2,3-dihydro-1H-indole-6-carbonyl)-phenyl]-amide 1-Methyl-3-trifluoromethyl-1H-pyrazole-4-carboxylic acid [3-(2-oxo-2,3-dihydro-1H-indole-6-carbonyl)-phenyl]-amide (0.205 g, 0.548 mmol) and ethyl formate (0.132 mL, 1.64 mmol) were dissolved in anhydrous ethanol (1.1 mL). The resulting solution was treated in dropwise fashion with a 21 wt % solution of sodium ethoxide in ethanol (1.00 mL, 2.74 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure 1-Methyl-3-trifluoromethyl-1H-pyrazole-4-carboxylic acid [3-(3-hydroxymethylene-2-oxo-2,3-dihydro-1H-indole-6-carbonyl)-phenyl]-amide (0.178 g, 0.444 mmol, 81%).

Example 87

4-Chloro-2,5-dimethyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 4-Chloro-2,5-dimethyl-2H-pyrazole-3-carboxylic acid [3-(3-hydroxymethylene-2-oxo-2,3-dihydro-1H-indole-6-carbonyl)-phenyl]-amide (prepared below, 70 mg, 0.160 mmol) and THF (1.5 mL). To the resulting solution was added 4-(4-methyl-piperazin-1-yl)-phenylamine (30.6 mg, 0.160 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~3 mL of acetone yielding 58% (56.7 mg, 0.093 mmol) of the title compound.

The 4-Chloro-2,5-dimethyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 4-Chloro-2,5-dimethyl-2H-pyrazole-3-carboxylic acid [3-(2-oxo-2,3-dihydro-1H-indole-6-carbonyl)-phenyl]-amide A dry 25 mL flask was charged with 4-Chloro-2,5-dimethyl-2H-pyrazole-3-carbonyl chloride (0.152 g, 0.794 mmol) and THF (2 mL). 6-(4-Amino-benzoyl)-1,3-dihydro-indol-2-one (as prepared in Example 40, 0.200 g, 0.794 mmol) was added to the THF solution of the acid chloride, and the mixture was allowed to reflux for 4 h. The reaction mixture was then allowed to cool to room temperature. The room temperature reaction mixture was concentrated in vacuo. The tan solids were washed with THF (~3 mL) and filtered to afford the pure 4-Chloro-2,5-dimethyl-2H-pyrazole-3-carboxylic acid [3-(2-oxo-2,3-dihydro-1H-indole-6-carbonyl)-phenyl]-amide (0.187 g, 0.458 mmol, 58%).

Step 2: 4-Chloro-2,5-dimethyl-2H-pyrazole-3-carboxylic acid [3-(3-hydroxymethylene-2-oxo-2,3-dihydro-1H-indole-6-carbonyl)-phenyl]-amide 4-Chloro-2,5-dimethyl-2H-pyrazole-3-carboxylic acid [3-(2-oxo-2,3-dihydro-1H-indole-6-carbonyl)-phenyl]-amide (0.167 g, 0.409 mmol) and ethyl formate (0.098 mL, 1.23 mmol) were dissolved in anhydrous ethanol (0.810 mL). The resulting solution was treated in dropwise fashion with a 21 wt % solution of sodium ethoxide in ethanol (0.76 mL, 2.05 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure 4-Chloro-2,5-dimethyl-2H-pyrazole-3-carboxylic acid [3-(3-hydroxymethylene-2-oxo-2,3-dihydro-1H-indole-6-carbonyl)-phenyl]-amide (0.127 g, 0.290 mmol, 71%).

Example 88

2,5-Dimethyl-2H-pyrazole-3-carboxylic acid [3-(3-{[4-(2-diethylamino-ethoxy)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-(2-Diethylamino-ethoxy)-phenylamine[1] (51.7 mg, 0.249 mmol), and the mixture was stirred for 24 h at 65° C. The reaction mixture was cooled to room temperature. Hexanes were added to the reaction mixture. The filtrate was then concentrated in vacuo and then redissolved into EtOAc and then Hexanes were added causing a precipitate to form. The precipitate was then filtered and washed with ~1 mL of i-prOH yielding 8.8% (0.013 g, 0.022 mmol) of the title compound.

Example 89

2-Methyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-Methyl-2H-pyrazole-3-carboxylic acid [3-(3-hydroxymethylene-2-oxo-2,3-dihydro-1H-indole-6-carbonyl)-phenyl]-amide (prepared below, 50 mg, 0.129 mmol) and THF (1 mL). To the resulting solution was added 4-(4-methyl-piperazin-1-yl)-phenylamine (50.53 mg, 0.264 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~1 mL of i-prOH yielding 32% (45 mg, 0.076 mmol) of the title compound.

The 2-Methyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-Methyl-2H-pyrazole-3-carboxylic acid [3-(2-oxo-2,3-dihydro-1H-indole-6-carbonyl)-phenyl]-amide A dry 25 mL flask was charged with 2-Methyl-2H-pyrazole-3-carboxylic acid (0.110 g, 0.873 mmol) and thionyl chloride (5 mL) and allowed to stir at 79° C. for 2 h. The thionyl chloride was then removed by concentration in vacuo. The crude acid chloride was cooled to room temperature, and then dissolved in THF (5 mL). 6-(3-Amino-benzoyl)-1,3-dihydro-indol-2-one (as prepared in Example 40, 0.200 g, 0.794 mmol) was added to the THF solution of the acid chloride, and the mixture was allowed to reflux for 2 h. The reaction mixture was then allowed to cool to room temperature. The room temperature reaction mixture was concentrated in vacuo, and the crude residue was dissolved in EtOH (5 mL). The ethanolic solution was treated with 1M $NaOH_{(aq)}$ (2 mL) and stirred for 30 min. The basic solution was acidified to a pH of 1 with 1M $HCl_{(aq)}$ yielding a tan precipitate. The tan solids were filtered to afford the pure 2-Methyl-2H-pyrazole-3-carboxylic acid [3-(2-oxo-2,3-dihydro-1H-indole-6-carbonyl)-phenyl]-amide (0.160 g, 0.444 mmol, 56%).

Step 2: 2-Methyl-2H-pyrazole-3-carboxylic acid [3-(3-hydroxymethylene-2-oxo-2,3-dihydro-1H-indole-6-carbonyl)-phenyl]-amide 2-Methyl-2H-pyrazole-3-carboxylic acid [3-(2-oxo-2,3-dihydro-1H-indole-6-carbonyl)-phenyl]-amide (0.142 g, 0.394 mmol) and ethyl formate (0.095 mL, 1.18 mmol) were dissolved in anhydrous ethanol (4.73 mL). The resulting solution was treated in dropwise fashion with a 21 wt % solution of sodium ethoxide in ethanol (0.18 mL, 1.97 mmol).

This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure 2-Methyl-2H-pyrazole-3-carboxylic acid [3-(3-hydroxymethylene-2-oxo-2,3-dihydro-1H-indole-6-carbonyl)-phenyl]-amide (0.093 g, 0.241 mmol, 61%).

Example 90

4-Chloro-2-methyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 4-Chloro-2-methyl-2H-pyrazole-3-carboxylic acid [3-(3-hydroxymethylene-2-oxo-2,3-dihydro-1H-indole-6-carbonyl)-phenyl]-amide (prepared below, 100 mg, 0.240 mmol) and THF (2 mL). To the resulting solution was added 4-(4-methyl-piperazin-1-yl)-phenylamine (50.53 mg, 0.264 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~1 mL of i-prOH yielding 32% (45 mg, 0.076 mmol) of the title compound.

The 4-Chloro-2-methyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 4-Chloro-2-methyl-2H-pyrazole-3-carboxylic acid [3-(2-oxo-2,3-dihydro-1H-indole-6-carbonyl)-phenyl]-amide A dry 25 mL flask was charged with 4-Chloro-2-methyl-2H-pyrazole-3-carboxylic acid (0.139 g, 0.873 mmol) and thionyl chloride (5 mL) and allowed to stir at 79° C. for 2 h. The thionyl chloride was then removed by concentration in vacuo. The crude acid chloride was cooled to room temperature, and then dissolved in THF (5 mL). 6-(3-Amino-benzoyl)-1,3-dihydro-indol-2-one (as prepared in Example 40, 0.200 g, 0.794 mmol) was added to the THF solution of the acid chloride, and the mixture was allowed to reflux for 2 h. The reaction mixture was then allowed to cool to room temperature. The tan solids were filtered and washed with ~3 mL of THF to afford the pure 4-Chloro-2-methyl-2H-pyrazole-3-carboxylic acid [3-(2-oxo-2,3-dihydro-1H-indole-6-carbonyl)-phenyl]-amide (0.264 g, 0.667 mmol, 84%).

Step 2: 4-Chloro-2-methyl-2H-pyrazole-3-carboxylic acid [3-(3-hydroxymethylene-2-oxo-2,3-dihydro-1H-indole-6-carbonyl)-phenyl]-amide 4-Chloro-2-methyl-2H-pyrazole-3-carboxylic acid [3-(2-oxo-2,3-dihydro-1H-indole-6-carbonyl)-phenyl]-amide (0.250 g, 0.633 mmol) and ethyl formate (0.148 mL, 1.90 mmol) were dissolved in anhydrous ethanol (1.3 mL). The resulting solution was treated in dropwise fashion with a 21 wt % solution of sodium ethoxide in ethanol (2.48 mL, 3.17 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale orange precipitate. The suspension was filtered yielding an orange solid as the pure 4-Chloro-2-methyl-2H-pyrazole-3-carboxylic acid [3-(3-hydroxymethylene-2-oxo-2,3-dihydro-1H-indole-6-carbonyl)-phenyl]-amide (0.187 g, 0.443 mmol, 70%).

Example 91

Thiophene-2-carboxylic acid [3-(3-{[4-(4-methyl-piperazin-1-yl)-phenylamino]-methylene}-2-oxo-2, 3-dihydro-1H-indol-6-ylmethyl)-phenyl]-amide A small screw cap test tube was charged with Thiophene-2-carboxylic acid [3-(3-hydroxymethylene-2-oxo-2,3-dihydro-1H-indol-6-ylmethyl)-phenyl]-amide (prepared below, 50 mg, 0.133 mmol) and THF (1 mL). To the resulting solution was added 4-(4-methyl-piperazin-1-yl)-phenylamine (25.4 mg, 0.133 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~3 mL of i-prOH yielding 31% (22.6 mg, 0.041 mmol) of the title compound.

The Thiophene-2-carboxylic acid [3-(3-hydroxymethylene-2-oxo-2,3-dihydro-1H-indol-6-ylmethyl)-phenyl]-amide was prepared from 3-nitrobenzoyl chloride using the following multiple step procedure:

Step 1:
(4-Bromo-phenyl)-(3-nitro-phenyl)-methanone

A 5 L, 3-necked round bottomed flask equipped with an overhead stirrer, dropping funnel, $N_{2(g)}$ inlet was charged with $AlCl_3$ (432.5 g, 3.24 mol). The solids were cooled to 0° C. with an ice-$H_2O$ bath. DMF (71 ml) was added dropwise over a period of 35 min and the temperature was kept under 32° C. during the addition. The reaction mixture was heated to 50° C. and treated with 3-Nitrobenzoyl chloride (63.2 g, 0.34 mol). The reaction that ensued was exothermic and caused the internal reaction temperature to rise to 65° C. The reaction was stirred for 50 min then bromobenzene (33.5 ml, 0.32 mol) was added. The reaction was heated at 90° C. for 3 h. Thin layer chromatographic analysis (Hexanes/ethylacetate 1:1) indicated completion of reaction. The reaction was cooled and ice-$H_2O$ (3 L) was added dropwise over a period of 1.5 h. The reaction was allowed to stir overnight. The solids were filtered, washed with $H_2O$ (1 L), saturated $NaHCO_{3(aq)}$ (1 L), another portion of $H_2O$ (500 mL) and Hexanes (500 mL). The product was dried in the vacuum oven at 40° C., 28 in Hg for 30 hours to yield (4-Bromo-phenyl)-(3-nitro-phenyl)-methanone in 88% (85.34 g, 0.28 mol).

Step 2: (4-Bromo-3-nitro-phenyl)-(3-nitro-phenyl)-methanone

A 2 L, 3 necked round bottomed flask equipped with a mechanical stirrer, thermocouple and ice-bath was charged with concentrated $H_2SO_{4(aq)}$ (635 mL) and concentrated $HNO_{3(aq)}$ (62 mL). The flask and its contents were cooled to 0° C. (4-Bromo-phenyl)-(3-nitro-phenyl)-methanone (127 g, 0.42 mol) was added over a period of 1 h and the temperature was kept under 10° C. Thirty minutes later, the reaction was complete by thin layer chromatographic analysis (Hexanes/EtOAc 6:4). The reaction was poured into ice-$H_2O$ (2 L). The solids were filtered, washed with $H_2O$ (4 L), saturated $NaHCO_{3(aq)}$ (1 L) and an additional portion of $H_2O$ (1 L). The product was dried at 45° C., for 48 h yielding (4-Bromo-3-nitro-phenyl)-(3-nitro-phenyl)-methanone in 95% (138.4 g, 0.39 mol).

Step 3:
2-[2-Nitro-4-(3-nitro-benzoyl)-phenyl]-malonic acid diethyl ester

A 3 L round bottomed flask equipped with an overhead stirrer, condenser, thermocouple, and heating mantle was charged with (4-Bromo-3-nitro-phenyl)-(3-nitro-phenyl)-methanone (134 g, 0.38 mol), $Cs_2CO_3$ (149 g, 0.46 mol), DMF (670 ml), and diethylmalonate (64 mL, 0.42 mol). The reaction was heated at 90° C. for 6 h. The reaction was complete by thin layer chromatographic (TLC) Analysis (Hexanes/Ethyl Acetate 7:3). The TLC plate was viewed with short wavelength UV. The reaction was cooled to room temperature and Cs₂CO₃ was filtered from the reaction mixture. The filtrate was diluted with EtOAc (2 L) then washed with brine (3×2 L). The aqueous extracts were back extracted with EtOAc (2 L). The combined organic extracts were dried over Na₂SO₄ and concentrated to give a purple solid. The product was washed with methanol (2.5 L) thereby removing the purple impurity and yielding 76% of pure 2-[2-Nitro-4-(3-nitro-benzoyl)-phenyl]-malonic acid diethyl ester (124 g, 0.29 mol).

Step 4: [2-Nitro-4-(3-nitro-benzoyl)-phenyl]-acetic acid ethyl ester

A 2 L, 3-necked round bottomed flask equipped with a heating mantle, condenser, overhead stirrer, thermocouple, and $N_{2(g)}$ inlet was charged with 2-[2-Nitro-4-(3-nitro-benzoyl)-phenyl]-malonic acid diethyl ester (105 g, 0.24 mol), DMSO (1 L) and H₂O (87 mL) The reaction was heated at 110° C. for 11 h. Thin layer chromatographic analysis (Hexanes/ethylacetate 6:4) indicated completion of reaction. The reaction mixture was cooled to room temperature and was diluted with ethyl acetate (4 L). The organic layer was washed with brine (3×4 L), dried over Na₂SO₄ and concentrated. Methyl t-butyl ether (1 L) was added to the solids and stirred. The product was filtered and washed with Methyl t-butyl ether (2×250 mL). The solids collected were dried in the vacuum oven at 45° C. for 24 hours to yield 89% of pure [2-Nitro-4-(3-nitro-benzoyl)-phenyl]-acetic acid ethyl ester (77 g, 0.21 mol).

Step 5: [2-Amino-4-(3-amino-benzoyl)-phenyl]-acetic acid ethyl ester

A 2 L metal reactor was charged with [2-Nitro-4-(3-nitro-benzoyl)-phenyl]-acetic acid ethyl ester (65 g, 181.4 mmol) in ethanol (1.3 L) was added Pt(IV)O₂ (6.5 g). The reactor was evacuated, purged with $N_{2(g)}$ then filled with $H_{2(g)}$ (15 psi). The temperature of the reaction was controlled with a H₂O coiled condenser and the maximum allowable temperature was 26° C. After 1 h and 15 min, the reaction was determined to be complete by thin layer chromatographic analysis (TLC) (Hexanes/EtOAc 1:1). The TLC was viewed with short wavelength UV and I₂ stain. At the end of the reaction, the reactor was evacuated and purged with $N_{2(g)}$. The reaction was filtered through celite and the celite was washed with THF (1 L). The filtrates were concentrated and the solids were dried in a vacuum oven under 28 mmHg at 45° C. to afford [2-Amino-4-(3-amino-benzoyl)-phenyl]-acetic acid ethyl ester in quantitative yield (54 g, 181.0 mmol).

Step 6: 6-(3-Amino-benzoyl)-1,3-dihydro-indol-2-one

A 2 L round bottomed flask equipped with an overhead stirrer, condenser, thermocouple and heating mantle was charged with [2-Amino-4-(3-amino-benzoyl)-phenyl]-acetic acid ethyl ester (48 g, 160.9 mmol) in of ethanol (960 mL). Concentrated $HCl_{(aq)}$ (67 mL) was added dropwise at 21° C. The reaction was exothermic causing a rise in reaction temperature from 21° C. to 28° C. The reaction was heated at 67° C. for 1.5 h and was determined to be complete by thin layer chromatographic analysis (ethylacetate/Hexanes 8:2). The thin layer chromatography plate was viewed with short wavelength UV and I₂ stain. Following ethanol evaporation, H₂O (480 mL) and saturated $NaHCO_{3(aq)}$ (500 mL) were added to the crude product, and the resulting mixture was stirred for 15 hours. The solids were filtered and washed with H₂O (2×200 mL) and methyl t-butyl ether (300 mL). The product was dried at 40° C. for 24 h to afford 6-(3-Amino-benzoyl)-1,3-dihydro-indol-2-one in 95% yield (38.6 g, 153.0 mmol).

Step 7: 6-(3-Amino-benzyl)-1,3-dihydro-indol-2-one

A 2 L, 3-necked round bottomed flask equipped with a condenser, heating mantle, overhead stirrer and a thermocouple was charged with 6-(3-Amino-benzoyl)-1,3-dihydro-indol-2-one (47 g, 0.19 mol) then trifluoroacetic acid (TFA, 294 mL). The initial reaction was exothermic raising the reaction temperature from 20° C. to 32° C. Triethylsilane (148 mL) was added and the reaction mixture was heated at 55° C. for 3 d. During this period, additional triethylsilane (518 mL total, by 2.5 equivalents at a time) was added until the reaction was complete by thin layer chromatographic analysis (ethylacetate/Hexanes 8:2). The thin layer chromatography plate was viewed with short wavelength UV and I₂ stain.

The reaction mixture was concentrated to remove the TFA and the remaining solids were washed with methyl t-butyl ether (500 mL) and THF (1 L). The solids were then suspended in water (500 mL) and saturated sodium bicarbonate (500 mL) and allowed to stir overnight. The suspension was then filtered and the solids collected were washed with water (300 mL). Subsequently the solids were dried in the vacuum oven at 40° C. to afford pure 6-(3-Amino-benzyl)-1,3-dihydro-indol-2-one in 75% yield (33.4 g, 0.14 mol).

Step 8: Thiophene-2-carboxylic acid [3-(2-oxo-2,3-dihydro-1H-indol-6-ylmethyl)-phenyl]-amide A dry 25 mL flask was charged with Thiophene-2-carbonyl chloride (0.136 g, 0.924 mmol) and THF (2 mL). 6-(3-Amino-benzyl)-1,3-dihydro-indol-2-one (0.200 g, 0.840 mmol) was added to the THF solution of the acid chloride, and the mixture was allowed to reflux for 3 h. The reaction mixture was then allowed to cool to room temperature. The room temperature reaction mixture was concentrated in vacuo. The solid residue was dissolved in ethanol. The ethanolic solution was treated with 1M $NaOH_{(aq)}$ (1 mL) and stirred for 30 min. The basic solution was acidified to a pH of 1 with 1M $HCl_{(aq)}$ yielding a tan precipitate. The precipitate that formed was filtered and washed with 2 mL of THF affording the Thiophene-2-carboxylic acid [3-(2-oxo-2,3-dihydro-1H-indol-6-ylmethyl)-phenyl]-amide (0.139 g, 0.387 mmol, 46%).

Step 9: Thiophene-2-carboxylic acid [3-(3-hydroxymethylene-2-oxo-2,3-dihydro-1H-indol-6-ylmethyl)-phenyl]-amide Thiophene-2-carboxylic acid [3-(2-oxo-2,3-dihydro-1H-indol-6-ylmethyl)-phenyl]-amide (0.110 g, 0.306 mmol) and ethyl formate (0.075 mL, 0.918 mmol) were dissolved in anhydrous ethanol (0.6 mL). The resulting solution was treated in dropwise fashion with a 21 wt % solution of sodium ethoxide in ethanol (2.85 mL, 1.53 mmol). This reaction mixture was heated at 78° C. for 1 h, producing a black oil. Subsequently, the reaction mixture was cooled to room temperature, and then the reaction pH was adjusted to pH 1 with dropwise addition of 1M $HCl_{(aq)}$ causing the formation of a pale brown precipitate. The suspension was filtered yielding a tan solid as the pure Thiophene-2-carboxylic acid [3-(3-hydroxymethylene-2-oxo-2,3-dihydro-1H-indol-6-ylmethyl)-phenyl]-amide (0.061 g, 0.162 mmol, 53%).

Example 92

2,5-Dimethyl-2H-pyrazole-3-carboxylic acid [3-(3-{[4-(4-methyl-piperazin-1-yl)-phenylamino]-methylene}-2-oxo-2,3-dihydro-1H-indol-6-ylmethyl)-phenyl]-amide A small screw cap test tube was charged with 2,5-Dimethyl-2H-pyrazole-3-carboxylic acid [3-(3-hydroxymethylene-2-oxo-2,3-dihydro-1H-indol-6-ylmethyl)-phenyl]-amide (prepared below, 50 mg, 0.129 mmol) and THF (1 mL). To the resulting solution was added 4-(4-methyl-piperazin-1-yl)-phenylamine (24.6 mg, 0.129 mmol), and the mixture was stirred for 24 h at 65° C. Subsequently, the reaction mixture was cooled to room temperature and concentrated in vacuo. The crude residue was dissolved in EtOAc. The resulting solution was diluted with Hexanes to initiate the precipitation of the product. The solid precipitate that formed was filtered then washed with ~3 mL of i-prOH yielding 35% (25.3 mg, 0.045 mmol) of the title compound.

The 2,5-Dimethyl-2H-pyrazole-3-carboxylic acid [3-(3-hydroxymethylene-2-oxo-2,3-dihydro-1H-indol-6-ylmethyl)-phenyl]-amide was prepared from 3-nitrobenzoyl chloride using the following multiple step procedure:

Step 1: 2,5-Dimethyl-2H-pyrazole-3-carboxylic acid [3-(2-oxo-2,3-dihydro-1H-indol-6-ylmethyl)-phenyl]-amide A dry 25 mL flask was charged with 2,5-Dimethyl-2H-pyrazole-3-carbonyl chloride (0.146 g, 0.924 mmol) and THF (2 mL). 6-(3-Amino-benzyl)-1,3-dihydro-indol-2-one (as prepared in Example 91, 0.200 g, 0.840 mmol) was added to the THF solution of the acid chloride, and the mixture was allowed to reflux for 3 h. The reaction mixture was then allowed to cool to room temperature. The room temperature reaction mixture was concentrated in vacuo, and the crude residue was dissolved in EtOH (2 mL). The ethanolic solution was treated with 1M NaOH$_{(aq)}$ (1 mL) and stirred for 30 min. The basic solution was acidified to a pH of 1 with 1M HCl$_{(aq)}$ yielding a tan precipitate. The precipitate that formed was filtered and washed with THF (~2 mL) affording the 2,5-Dimethyl-2H-pyrazole-3-carboxylic acid [3-(2-oxo-2,3-dihydro-1H-indol-6-ylmethyl)-phenyl]-amide (0.115 g, 0.319 mmol, 38%).

Step 2: 2,5-Dimethyl-2H-pyrazole-3-carboxylic acid [3-(3-hydroxymethylene-2-oxo-2,3-dihydro-1H-indol-6-ylmethyl)-phenyl]-amide 2,5-Dimethyl-2H-pyrazole-3-carboxylic acid [3-(2-oxo-2,3-dihydro-1H-indol-6-ylmethyl)-phenyl]-amide (0.100 g, 0.278 mmol) and ethyl formate (0.068 mL, 0.834 mmol) were dissolved in anhydrous ethanol (0.55 mL). The resulting solution was treated in dropwise fashion with a 21 wt % solution of sodium ethoxide in ethanol (0.519 mL, 1.39 mmol). This reaction mixture was heated at 78° C. for 1 h, producing a black oil. Subsequently, the reaction mixture was cooled to room temperature, and then the reaction pH was adjusted to pH 1 with dropwise addition of 1M HCl$_{(aq)}$ causing the formation of a brown precipitate. The suspension was filtered yielding an light brown solid as the pure 2,5-Dimethyl-2H-pyrazole-3-carboxylic acid [3-(3-hydroxymethylene-2-oxo-2,3-dihydro-1H-indol-6-ylmethyl)-phenyl]-amide (0.072 g, 0.186 mmol, 67%).

Example 201

2,5-Dimethyl-2H-pyrazole-3-carboxylic acid {3-[3-({4-[3-(3-fluoro-pyrrolidin-1-yl)-propoxy]-phenylamino}-methylene)-2-oxo-2,3-dihydro-1H-indole-6-carbonyl]-phenyl}-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-[3-(3-Fluoro-pyrrolidin-1-yl)-propoxy]-phenylamine (prepared below, 59.3 mg, 0.249 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~3 mL of EtOAc. Hexanes were added causing a yellow precipitate to form. The precipitate was then filtered and washed with 1 mL of i-prOH yielding 39% (0.060 g, 0.097 mmol) of the title compound.

The 4-[3-(3-Fluoro-pyrrolidin-1-yl)-propoxy]-phenylamine was prepared from 3-Hydroxy-pyrrolidine-1-carboxylic acid tert-butyl ester using the following multiple step procedure:

Step 1: 3-Fluoro-pyrrolidine-1-carboxylic acid tert-butyl ester

A −70° C. solution of (R)-(−)-3-Hydroxy-pyrrolidine-1-carboxylic acid tert-butyl ester (5 g, 26.7 mmol) in anhydrous EtOAc (250 mL) was treated dropwise with DAST (4.6 mL, 1.3 equiv.) and stirred for 1.5 h. The reaction was allowed to warm to room temperature over a period of 3 h. The reaction mixture was poured into ice cold saturated aqueous sodium bicarbonate solution (300 mL). The EtOAc layer was separated and washed with additional saturated aqueous sodium bicarbonate solution (2×300 mL) and then with brine (300 mL). The organics were dried over anhydrous Na$_2$SO$_4$, filtered and evaporated in vacuo. The crude residue was purified by silica gel chromatography (Hexanes to 1:9 EtOAc:Hexanes, gradient eluant) to yield 3-Fluoro-pyrrolidine-1-carboxylic acid tert-butyl ester as an oil (1.7 g).

Step 2: 3-Fluoro-pyrrolidine dihydrochloride salt

To pure 3-Fluoro-pyrrolidine-1-carboxylic acid tert-butyl ester (1.3 g, 6.88 mmol) was added a 4 M solution of HCl in Dioxane (10 mL, 5.8 equiv.). The reaction mixture was stirred overnight. The white crystals that had precipitated out of solution were then isolated by filtration to yield pure 3-Fluoro-pyrrolidine dihydrochloride salt (723 mg, 84%).

Step 3: 1-[3-(tert-Butyl-dimethyl-silanyloxy)-propyl]-3-fluoro-pyrrolidine

A solution of 3-Fluoro-pyrrolidine dihydrochloride salt (448 mg, 3.584 mmol) in anhydrous acetonitrile (24 mL) was treated with bromopropoxy-tert-butyldimethyl silane (0.83 mL) and then with K$_2$CO$_3$ (2.5 g, 5 equiv.). The reaction mixture was heated to 50° C. and stirred overnight. The reaction mixture was subsequently diluted with water (75 mL) and extracted with a 6:1 mixture of Hexane and diethyl ether (2×100 mL). The organic layer was washed with NaHCO$_{3(aq)}$ (100 mL) and brine (100 mL) then dried over anhydrous K$_2$CO$_3$. Following filtration and concentration of the filtrate in vacuo the crude product was purified by flash silica gel chromatography (MeOH:EtOAc, 1:20). By $^1$H NMR the resulting clear oil (0.8 g) was the desired 1-[3-(tert-Butyl-dimethyl-silanyloxy)-propyl]-3-fluoro-pyrrolidine in a 10:1 ratio with the t-butyldimethylsilanol by-product. This residue was carried on without further purification.

Step 4: 3-(3-Fluoro-pyrrolidin-1-yl)-propan-1-ol

Crude 1-[3-(tert-Butyl-dimethyl-silanyloxy)-propyl]-3-fluoro-pyrrolidine (0.8 g, 3.06 mmol) was treated with a freshly prepared 3:1:1 mixture of AcOH:H$_2$O:THF (15 mL). The resulting reaction mixture was heated to 55° C. and stirred overnight. The solvents then were removed in vacuo to provide, in apparent quantitative yield, a light brown oil that contained the desired 3-(3-Fluoro-pyrrolidin-1-yl)-propan-1-ol contaminated with t-butyldimethylsilanol by-product.

Step 5: 3-Fluoro-1-[3-(4-nitro-phenoxy)-propyl]-pyrrolidine

The crude 3-(3-Fluoro-pyrrolidin-1-yl)-propan-1-ol (assumed 3.06 mmol) was dissolved in THF (8 mL) and was cooled to 0° C. The 0° C. solution was treated consecutively with KOtBu (1.5 g, 13.5 mmol) then 4-fluoronitrobenzene (423.3 mg, 3 mmol). The resulting reaction mixture was allowed to warm to room temperature and stir for an additional 4.5 h. The reaction mixture was quenched with the addition of ice water (50 mL) followed by extraction with EtOAc (75 mL). The organics were subsequently washed with room temperature H$_2$O (75 mL), then saturated NaHCO$_3$ (aq) (75 mL), and finally with brine (75 mL). The organics then were dried over anhydrous sodium sulfate, decanted and concentrated in vacuo to yield crude 3-Fluoro-1-[3-(4-nitro-phenoxy)-propyl]-pyrrolidine (660 mg) as a yellow oil. This material was carried on without further purification.

Step 6: 4-[3-(3-Fluoro-pyrrolidin-1-yl)-propoxy]-phenylamine

A solution of crude 3-Fluoro-1-[3-(4-nitro-phenoxy)-propyl]-pyrrolidine (6.316 g, ~24 mmol) was dissolved in absolute ethanol (180 mL) and to this solution was added hydrazine monohydrate (~7.9 mL) followed by the addition of a small portion of Raney nickel (~1 mL). The reaction mixture was heated to 50° C. with stirring for ~2 h at which point all gas evolution had ceased. The reaction mixture was filtered through celite to remove the Raney nickel. The filtrate was concentrated in vacuo to give 4-[3-(3-Fluoro-pyrrolidin-1-yl)-propoxy]-phenylamine as a brown oil which was subjected to flash silica gel chromatography (CHCl$_3$ to CHCl$_3$:MeOH, 1:40 gradient eluant). Pure 4-[3-(3-Fluoro-pyrrolidin-1-yl)-propoxy]-phenylamine was isolated as a reddish oil (4.033 g, 79%).

Example 202

2,5-Dimethyl-2H-pyrazole-3-carboxylic acid [3-(3-{[4-(3-diethylamino-propoxy)-3-fluoro-phenylamino]-methylene}-2-oxo-2,3-dihydro-1H-indole-6-carbonyl)-phenyl]-amide tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-(3-Diethylamino-propoxy)-3-fluoro-phenylamine[1] (59.8 mg, 0.249 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~3 mL of EtOAc. Hexanes were added causing a yellow precipitate to form. The precipitate was then filtered and washed with ~1 mL of i-prOH yielding 35% (0.054 g, 0.087 mmol) of the title compound.

Example 203

{4-[(6-{3-[(2,5-Dimethyl-2H-pyrazole-3-carbonyl)-amino]-benzoyl}-2-oxo-1,2-dihydro-indol-3-ylidenemethyl)-amino]-benzyl}-carbamic acid tert-butyl ester charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added (4-Amino-benzyl)-carbamic acid tert-butyl ester (55.3 mg, 0.249 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~3 mL of EtOAc. Hexanes were added causing a yellow precipitate to form. The precipitate was then filtered and washed with ~1 mL of i-prOH yielding 48% (0.072 g, 0.119 mmol) of the title compound.

Example 204

2,5-Dimethyl-2H-pyrazole-3-carboxylic acid [3-(3-{[4-(2-dimethylamino-ethyl)-phenylamino]-methylene}-2-oxo-2,3-dihydro-1H-indole-6-carbonyl)-phenyl]-amide test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-(2-Dimethylamino-ethyl)-phenylamine (40.9 mg, 0.249 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~3 mL of EtOAc. Hexanes were added causing a light brown precipitate to form. The precipitate was then filtered and washed with ~1 mL of i-prOH yielding 12% (0.016 g, 0.029 mmol) of the title compound.

Example 205

2,5-Dimethyl-2H-pyrazole-3-carboxylic acid [3-(2-oxo-3-{[4-(2-pyrrolidin-1-yl-ethyl)-phenylamino]-methylene}-2,3-dihydro-1H-indole-6-carbonyl)-phenyl]-amide was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-(2-Pyrrolidin-1-yl-ethyl)-phenylamine (47.3 mg, 0.249 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~3 mL of EtOAc. Hexanes were added causing a yellow precipitate to form. The precipitate was then filtered and washed with ~1 mL of i-prOH yielding 41% (0.058 g, 0.102 mmol) of the title compound.

Example 206

2,5-Dimethyl-2H-pyrazole-3-carboxylic acid (3-{2-oxo-3-[(4-pyrrolidin-1-ylmethyl-phenylamino)-methylene]-2,3-dihydro-1H-indole-6-carbonyl}-phenyl)-amide was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2 mL). To the resulting solution was added 4-Pyrrolidin-1-ylmethyl-phenylamine (43.8 mg, 0.249 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~3 mL of EtOAc. Hexanes were added causing a yellow precipitate to form. The precipitate was then filtered and washed with ~1 mL of i-prOH yielding 15% (0.021 g, 0.067 mmol) of the title compound.

Example 207

2,5-Dimethyl-2H-pyrazole-3-carboxylic acid {3-[2-oxo-3-({4-[(2-pyrrolidin-1-yl-ethylamino)-methyl]-phenylamino}-methylene)-2,3-dihydro-1H-indole-6-carbonyl]-phenyl}-amide small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 200 mg, 0.498 mmol) and THF (4 mL). To the resulting solution was added 4-[(2-Pyrrolidin-1-yl-ethylamino)-methyl]-phenylamine (prepared below; 109.2 mg, 0.498 mmol), and the mixture was stirred for 24 h at 65° C. The reaction mixture was cooled to room temperature. Hexanes were added to the reaction mixture causing a black precipitate to form. The precipitate was vacuum filtered and the filtrate was then concentrated in vacuo and redissolved into ~5 mL of EtOAc. Hexanes were added causing a yellow precipitate to form. The precipitate was then filtered and washed with ~1 mL of i-prOH yielding 31% (0.092 g, 0.152 mmol) of the title compound.

4-[(2-Pyrrolidin-1-yl-ethylamino)-methyl]-phenylamine was prepared from 4-nitrobenzaldehyde using the following multiple step procedure:

Step 1: (4-Nitro-benzyl)-(2-pyrrolidin-1-yl-ethyl)-amine

4-Nitrobenzaldehyde (0.5 g, 3.31 mmol) was dissolved in MeOH (1 mL) then treated with 2-pyrrolidin-1-yl-ethyl)-amine (0.567 g, 4.97 mmol). NaBH$_3$CN (0.520 g, 8.28 mmol) was then added followed by AcOH (0.2 mL). The mixture was allowed to stir at room temperature for 2 h. Saturated NaHCO$_3$ $_{(aq)}$ was then added to the reaction mixture until bubbling stopped. The mixture was then extracted with EtOAc (2×~50 mL) and with brine (2×~30 mL). The combined organic layers were dried over anhydrous Na$_2$SO$_4$ and then concentrated in vacuo. The crude product was then purified via flash silica gel chromatography (5% MeOH/95% CHCl$_3$) providing the pure (4-Nitro-benzyl)-(2-pyrrolidin-1-yl-ethyl)-amine (0.503 g, 2.02 mmol, 61% yield).

Step 2: 4-[(2-Pyrrolidin-1-yl-ethylamino)-methyl]-phenylamine

The (4-Nitro-benzyl)-(2-pyrrolidin-1-yl-ethyl)-amine (0.503 g, 2.02 mmol) was dissolved in EtOH (10 mL) under Ar$_{(g)}$, and hydrazine hydrate (0.439 mL, 14.14 mmol) was added. Subsequently, excess RaNi was added in dropwise until the solution stopped bubbling. The suspension was then allowed to stir for an additional 45 minutes at 65° C. The suspension was cooled to r.t. and then filtered over celite. The celite was washed with MeOH and the combined organic solutions were then concentrated in vacuo affording a pure 4-[(2-Pyrrolidin-1-yl-ethylamino)-methyl]-phenylamine as a light purple oil (0.331 g, 1.52 mmol, 75% yield).

Example 208

5-Chloro-1,3-dimethyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 5-Chloro-1,3-dimethyl-1H-pyrazole-4-carboxylic acid [3-(3-hydroxymethylene-2-oxo-2,3-dihydro-1H-indole-6-carbonyl)-phenyl]-amide (prepared below, 100 mg, 0.244 mmol) and THF (2 mL). To the resulting solution was added 4-(4-Methyl-piperazin-1-yl)-phenylamine (46.7 mg, 0.244 mmol), and the mixture was stirred for 24 h at 65° C. The reaction mixture was cooled to room temperature and concentrated in vacuo. The crude mixture was redissolved into ~2 mL of EtOAc and then Hexanes were added to causing a precipitate to form. The precipitate was then filtered yielding 45% (0.067 g, 0.109 mmol) of the title compound.

The 5-Chloro-1,3-dimethyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 5-Chloro-1,3-dimethyl-1H-pyrazole-4-carboxylic acid [3-(2-oxo-2,3-dihydro-1H-indole-6-carbonyl)-phenyl]-amide A dry 25 mL flask was charged with 5-Chloro-1,3-dimethyl-1H-pyrazole-4-carboxylic acid (0.180 g, 0.873 mmol) and thionyl chloride (10 mL) and allowed to stir at 79° C. for 2 h. The thionyl chloride was then removed by rotary evaporation. The crude acid chloride dissolved in THF (5 mL). 6-(3-Amino-benzoyl)-1,3-dihydro-indol-2-one (as prepared in Example 40, 0.200 g, 0.794 mmol) was added to the THF solution of the acid chloride, and the mixture was allowed to reflux for 2 h. The reaction mixture was then allowed to cool to room temperature and the precipitate was filtered and washed with THF (~5 mL) affording pure 5-Chloro-1,3-dimethyl-1H-pyrazole-4-carboxylic acid [3-(2-oxo-2,3-dihydro-1H-indole-6-carbonyl)-phenyl]-amide (0.233 g, 0.571 mmol, 72%).

Step 2: 5-Chloro-1,3-dimethyl-1H-pyrazole-4-carboxylic acid [3-(3-hydroxymethylene-2-oxo-2,3-dihydro-1H-indole-6-carbonyl)-phenyl]-amide 5-Chloro-1,3-dimethyl-1H-pyrazole-4-carboxylic acid [3-(2-oxo-2,3-dihydro-1H-indole-6-carbonyl)-phenyl]-amide (0.233 g, 0.571) and ethyl formate (0.140 mL, 1.71 mmol) were dissolved in anhydrous ethanol (1.10 mL). The resulting solution was treated in dropwise fashion with a 21 wt % solution of sodium ethoxide in ethanol (1.10 mL, 2.85 mmol). This reaction mixture was heated at 78° C. for 1 h, turning the reaction mixture to a brownish red color. The reaction mixture was cooled to room temperature, and then the reaction pH was adjusted to pH 1 with dropwise addition of 1M HCl$_{(aq)}$ causing the formation of a pale brown precipitate. The suspension was filtered yielding a tan solid as pure 5-Chloro-1,3-dimethyl-1H-pyrazole-4-carboxylic acid [3-(3-hydroxymethylene-2-oxo-2,3-dihydro-1H-indole-6-carbonyl)-phenyl]-amide (0.147 g, 0.337 mmol, 59%).

Procedures for Library I: the Library of Compounds Examples 93 through 200.

General Synthetic Procedure: The general synthetic route to the compounds prepared in the Library was similar in all cases to the procedures followed in the preparation of the individually prepared compounds (Examples 1-14, see General Scheme for overview).

General Scheme:

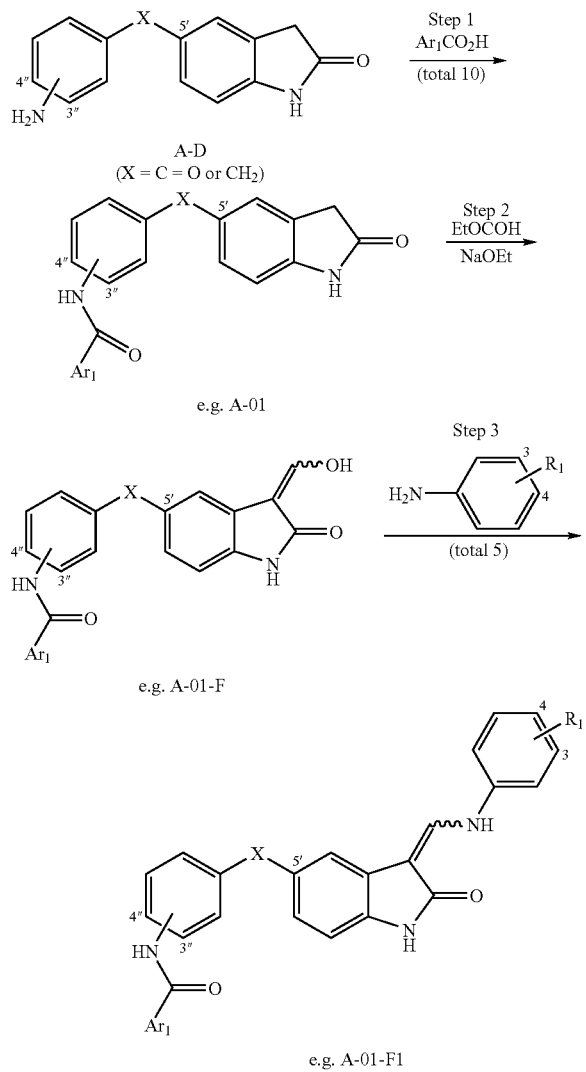

(Wherein X in the General Scheme above represents X in Formula II, COAr$_1$ in the General Scheme above represents X'B in Formula II, and

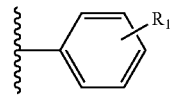

in the General Scheme above represents A in Formula II)

The General Stepwise Procedures and Reagent Tables for the Preparation of Library I (not limited to but including, Examples 93-200).

Tables of Reagents:

Library Reagent Table 1

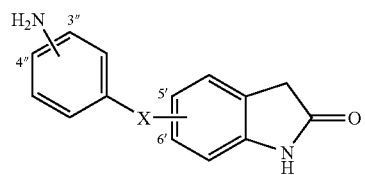

| Library ID # | X (position) | NH$_2$ (position) | As Prepared in Example # |
|---|---|---|---|
| A | C=O (5') | 3" | 1 |
| B | C=O (5') | 4" | 7 |
| C | CH$_2$ (5') | 3" | See Below |
| D | CH$_2$ (5') | 4" | 14 |
| 1 | C=O (6') | 3" | 40 |

5-(3-Amino-benzyl)-1,3-dihydro-indol-2-one was prepared from oxindole using the following method:

5-(3-Nitro-benzoyl)-1,3-dihydro-indol-2-one. A 3 L, 3 necked round bottomed flask equipped with a mechanical stirrer, thermocouple and was charged with AlCl$_3$ (256 g, 1.92 mol). The solids were cooled to 0° C. with an ice-H$_2$O bath. DMF (42 ml) was added dropwise over a period of 35 min. The temperature was stirred at 0° C. for 2 h then was warmed to room temperature. The reaction mixture was treated with 3-Nitrobenzoyl chloride (37.3 g, 0.2 mol) and the resulting slurry was heated to 41° C. Subsequently, oxindole (25 g, 0.19 mol) was added over a period of 10 min. The reaction that ensued was exothermic and caused the internal reaction temperature to rise to 60° C. The reaction was heated at 90° C. for 3.5 h. Thin layer chromatographic analysis (Hexanes/ethylacetate 1:1) indicated completion of reaction. The reaction was cooled and ice-H$_2$O (1.5 L) was added dropwise over a period of 1.5 h. The solids were filtered, washed with saturated NaHCO$_{3(aq)}$ (2×300 mL), H$_2$O (300 mL) and Methyl-t-Butyl Ether (500 mL) to yield 5-(3-Nitro-benzoyl)-1,3-dihydro-indol-2-one in quantitative yield (53.63 g, 0.19 mol).

5-(3-Amino-benzyl)-1,3-dihydro-indol-2-one. The PARR apparatus was charged with was charged with 5-(3-Nitrobenzoyl)-1,3-dihydro-indol-2-one (50 g, 0.18 mol), 10%

Pd/C (5 g) and DMF (500 mL). The reactor was evacuated, purged with N$_{2(g)}$ then filled with H$_{2(g)}$ (60 psi) at room temperature. After hydrogenating at 60 psi for 45 min thin layer chromatographic analysis (TLC) (Hexanes/EtOAc 1:1) indicated that the reaction had caused the reduction of the nitro group to an amine and the reduction of the keto group to the alcohol. Subsequently, TFA 926 mL, 0.35 mol) was added and the reaction was continued for 4 h. The reaction was filtered through celite and the solvent from the filtrate was removed in vacuo. The solids obtained were washed with saturated NaHCO$_{3(aq)}$ (500 mL), and H$_2$O (500 mL) then triturated with Methyl-t-Butyl Ether (500 mL) and then triturated again with methanol to afford 5-(3-Amino-benzyl)-1,3-dihydro-indol-2-one (30 g, 67%).

Library Reagent Table 2

| Library ID # | B |
|---|---|
| 01 | 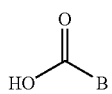 |
| 02 | 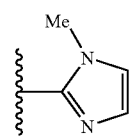 |
| 03 | 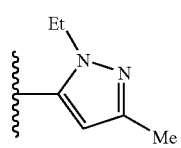 |
| 04 | 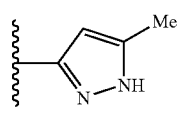 |
| 05 | 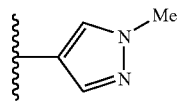 |
| 06 | CH$_3$ |
| 07 | 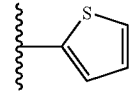 |
| 08 | 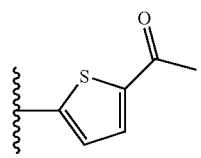 |

Library Reagent Table 2 -continued

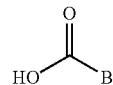

| Library ID # | B |
|---|---|
| 09 | 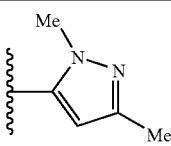 |
| 10 | 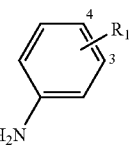 |

Library Reagent Table 3

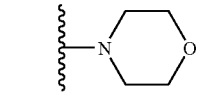

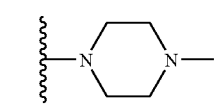

(wherein  above represents A in Formula I and II)

| Library ID # | R$_1$ substitution 3 | 4 |
|---|---|---|
| 1 | H | —N(morpholine) |
| 2 | H | —N(piperazine)N— |
| 4 | OH | OCH$_3$ |
| 5 | OH | CH$_3$ |
| 6 | OH | H |

General Stepwise Procedures:

Step 1: Amide Formation (A-01 through D-10).

Reagents from Library Reagent Table 2 were combined with reagents from Library Reagent Table 1 using the method described below to produce the amides listed in Library Reagent Table 4:

The requisite carboxylic acids (10 mmol) from Library Reagent Table 2 were treated with refluxing thionyl chloride (10 mL) for 2-3 h to form acid chlorides. After removing extra thionyl chloride under vacuum, the crude acid chlorides were reacted with scaffolds A-D (1 eq.) from Library Reagent Table 1 in refluxing THF (20 mL) overnight to produce amide products shown in Library Reagent Table 4. A total of 36 amides were prepared in 40-80% yield.

Library Reagent Table 4

| Library ID # | X | (position) | B |
|---|---|---|---|
| A-01 | C=O | 3″ | 1-methyl-imidazol-2-yl |
| A-02 | C=O | 3″ | 1-ethyl-3-methyl-pyrazol-5-yl |
| A-04 | C=O | 3″ | 1-methyl-pyrazol-4-yl |
| A-06 | C=O | 3″ | CH₃ |
| A-07 | C=O | 3″ | thiophen-2-yl |
| A-08 | C=O | 3″ | 5-acetyl-thiophen-2-yl |
| A-09 | C=O | 3″ | 1,3-dimethyl-pyrazol-5-yl |
| A-10 | C=O | 3″ | 1-tBu-3-methyl-pyrazol-5-yl |

-continued

Library Reagent Table 4

| Library ID # | X | (position) | B |
|---|---|---|---|
| B-02 | C=O | 4″ | 1-ethyl-3-methyl-pyrazol-5-yl |
| B-04 | C=O | 4″ | 1-methyl-pyrazol-4-yl |
| B-07 | C=O | 4″ | thiophen-2-yl |
| B-08 | C=O | 4″ | 5-acetyl-thiophen-2-yl |
| B-09 | C=O | 4″ | 1,3-dimethyl-pyrazol-5-yl |
| B-10 | C=O | 4″ | 1-tBu-3-methyl-pyrazol-5-yl |
| C-01 | CH₂ | 3″ | 1-methyl-imidazol-2-yl |
| C-02 | CH₂ | 3″ | 1-ethyl-3-methyl-pyrazol-5-yl |

-continued

Library Reagent Table 4

| Library ID # | X | (position) | B |
|---|---|---|---|
| C-03 | CH₂ | 3" | 5-methyl-1H-pyrazol-3-yl |
| C-04 | CH₂ | 3" | 1-methyl-1H-pyrazol-4-yl |
| C-05 | CH₂ | 3" | 1H-pyrazol-4-yl |
| C-06 | CH₂ | 3" | CH₃ |
| C-07 | CH₂ | 3" | thiophen-2-yl |
| C-08 | CH₂ | 3" | 5-acetylthiophen-2-yl |
| C-09 | CH₂ | 3" | 1,3-dimethyl-1H-pyrazol-5-yl |
| C-10 | CH₂ | 3" | 1-tBu-3-methyl-1H-pyrazol-5-yl |
| D-01 | CH₂ | 4" | 1-methyl-1H-imidazol-2-yl |

-continued

Library Reagent Table 4

| Library ID # | X | (position) | B |
|---|---|---|---|
| D-02 | CH₂ | 4" | 1-ethyl-3-methyl-1H-pyrazol-5-yl |
| D-03 | CH₂ | 4" | 5-methyl-1H-pyrazol-3-yl |
| D-04 | CH₂ | 4" | 1-methyl-1H-pyrazol-4-yl |
| D-05 | CH₂ | 4" | 1H-pyrazol-4-yl |
| D-06 | CH₂ | 4" | CH₃ |
| D-07 | CH₂ | 4" | thiophen-2-yl |
| D-08 | CH₂ | 4" | 5-acetylthiophen-2-yl |
| D-09 | CH₂ | 4" | 1,3-dimethyl-1H-pyrazol-5-yl |
| D-10 | CH₂ | 4" | 1-tBu-3-methyl-1H-pyrazol-5-yl |

Step 2: Formylation (A-01-F Through D-10-F).

The compounds listed in Library Reagent Table 4 were combined with Ethyl formate using the method described below to produce the formylated oxindoles listed in Library Reagent Table 5:

To a mixture of amide (5 mmol, see Library Reagent Table 4) and ethyl formate (50 mmol) in 10 mL of anhydrous ethyl alcohol, was added 21% wt sodium ethoxide in ethyl alcohol (10 mmol). The resulting reaction mixture was heated at 65° C. for 1.5 h. After cooling to room temperature, the reaction was acidified to pH 3-4 with 2 M HCl$_{(aq)}$, and the resulting mixture was concentrated to remove most of the ethanol. The precipitate that formed was collected by filtration, washed with water (5 mL×3) and dried under vacuum to give the desired product (ca. 90% yield). The product (e.g. General Scheme, A-01-F, See Library Reagent Table 5) obtained was used in step 3 without further purification.

Library Reagent Table 5

| Library ID # | X | (position) | B |
|---|---|---|---|
| A-01-F | C=O | 3" | *N-methylimidazol-2-yl* |
| A-02-F | C=O | 3" | *1-ethyl-3-methyl-pyrazol-5-yl* |
| A-04-F | C=O | 3" | *1-methyl-pyrazol-4-yl* |
| A-06-F | C=O | 3" | CH$_3$ |
| A-07-F | C=O | 3" | *thiophen-2-yl* |
| A-08-F | C=O | 3" | *5-acetyl-thiophen-2-yl* |
| A-09-F | C=O | 3" | *1,3-dimethyl-pyrazol-5-yl* |
| A-10-F | C=O | 3" | *1-tBu-3-methyl-pyrazol-5-yl* |
| B-02-F | C=O | 4" | *1-ethyl-3-methyl-pyrazol-5-yl* |
| B-04-F | C=O | 4" | *1-methyl-pyrazol-4-yl* |

-continued

Library Reagent Table 5

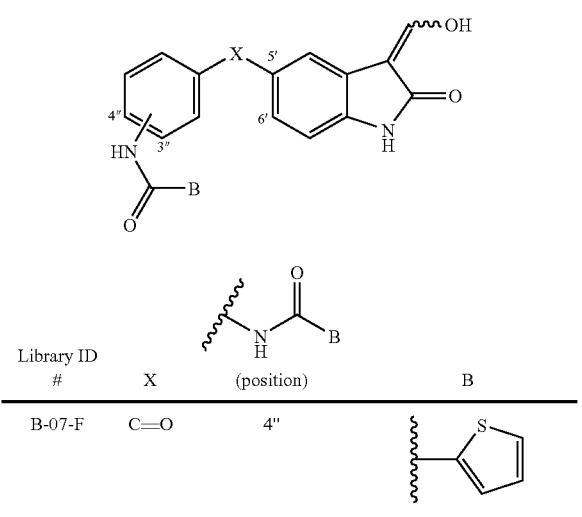

| Library ID # | X | (position) | B |
|---|---|---|---|
| B-07-F | C=O | 4" | thiophene |
| B-08-F | C=O | 4" | acetylthiophene |
| B-09-F | C=O | 4" | 1-Me-3-Me-pyrazole |
| B-10-F | C=O | 4" | 1-tBu-3-Me-pyrazole |
| C-01-F | CH₂ | 3" | 1-Me-imidazole |
| C-02-F | CH₂ | 3" | 1-Et-3-Me-pyrazole |

-continued

Library Reagent Table 5

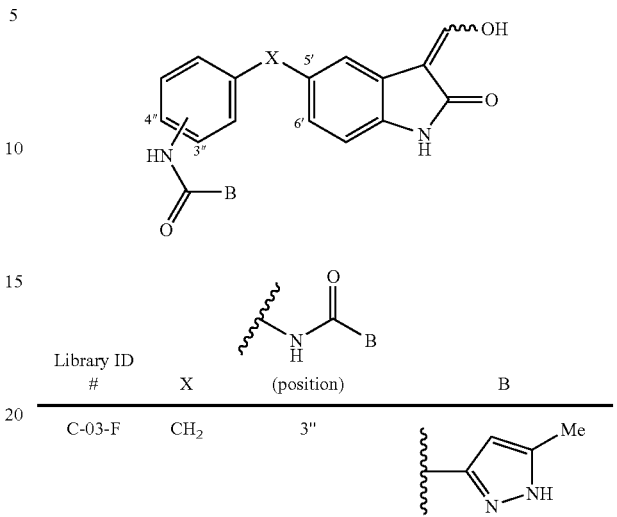

| Library ID # | X | (position) | B |
|---|---|---|---|
| C-03-F | CH₂ | 3" | 5-Me-1H-pyrazole |
| C-04-F | CH₂ | 3" | 1-Me-pyrazole |
| C-05-F | CH₂ | 3" | 1H-pyrazole |
| C-06-F | CH₂ | 3" | CH₃ |
| C-07-F | CH₂ | 3" | thiophene |
| C-08-F | CH₂ | 3" | acetylthiophene |
| C-09-F | CH₂ | 3" | 1-Me-3-Me-pyrazole |

-continued

Library Reagent Table 5

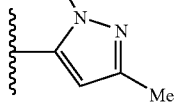

| Library ID # | X | (position) | B |
|---|---|---|---|
| C-10-F | CH$_2$ | 3" | 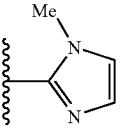 |
| D-01-F | CH$_2$ | 4" | 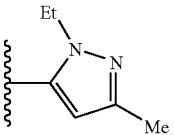 |
| D-02-F | CH$_2$ | 4" | 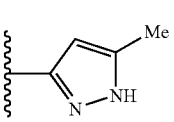 |
| D-03-F | CH$_2$ | 4" | 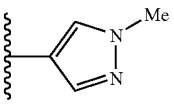 |
| D-04-F | CH$_2$ | 4" | 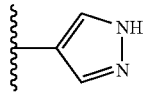 |
| D-05-F | CH$_2$ | 4" | 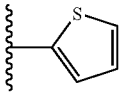 |
| D-06-F | CH$_2$ | 4" | CH$_3$ |

-continued

Library Reagent Table 5

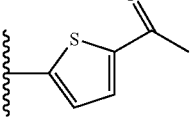

| Library ID # | X | (position) | B |
|---|---|---|---|
| D-07-F | CH$_2$ | 4" | 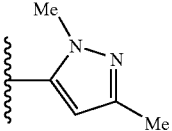 |
| D-08-F | CH$_2$ | 4" | 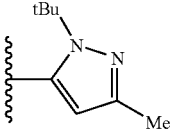 |
| D-09-F | CH$_2$ | 4" | |
| D-10-F | CH$_2$ | 4" | |

Step 3: Aniline Coupling (A-01-F1 Through D-10-F6)

Reagents from Library Reagent Table 5 were combined with reagents from Library Reagent Table 3 using the method described below to produce the materials listed in Library I Product Table:

To each reaction vial was added 100 to 120 mg of the hydroxymethylene-oxindoles from Library Reagent Table 5 (e.g. General Scheme, A-01-F) in 2 ml of THF/DMF (3/1 v/v) and an aniline (2 eq.) from Library Reagent Table 3 in 2 ml of THF/DMF (3/1, v/v). The reaction vial was capped and heated at 65° C. overnight after which time the reaction was allowed to cool to r.t. Subsequently the solvent was evaporated in a SpeedVac to yield the desired compounds, Examples 93 through 200 (e.g. General Scheme, A-01-F1, see Library I Product Table).

Library I Product Table

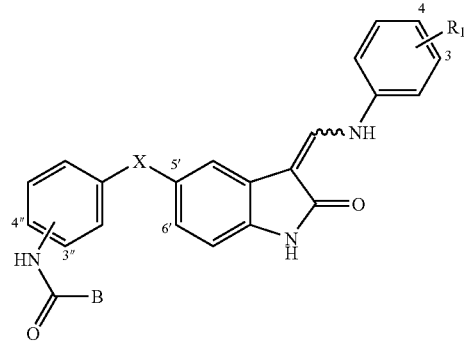

(Wherein X in the General Scheme above represents X in Formula II, (C=O)—B in the General Scheme above represents X'B in the Formula II, and 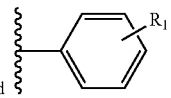 in the General Scheme above represents A in Formula II)

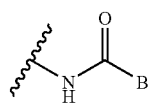

| Example # | Library ID # | R₁ subsititution 3 | R₁ subsititution 4 | X | position | B |
|---|---|---|---|---|---|---|
| 93 | A-01-F1 | H | morpholine (N-linked) | C=O | 3" | 1-Me-imidazol-2-yl |
| 94 | A-01-F2 | H | 4-methylpiperazin-1-yl | C=O | 3" | 1-Me-imidazol-2-yl |
| 95 | A-01-F4 | OH | OCH₃ | C=O | 3" | 1-Me-imidazol-2-yl |
| 96 | A-01-F5 | OH | CH₃ | C=O | 3" | 1-Me-imidazol-2-yl |
| 97 | A-02-F4 | OH | OCH₃ | C=O | 3" | 1-Et-3-Me-pyrazol-5-yl |
| 98 | A-04-F1 | H | morpholine (N-linked) | C=O | 3" | 1-Me-pyrazol-4-yl |

-continued
Library I Product Table

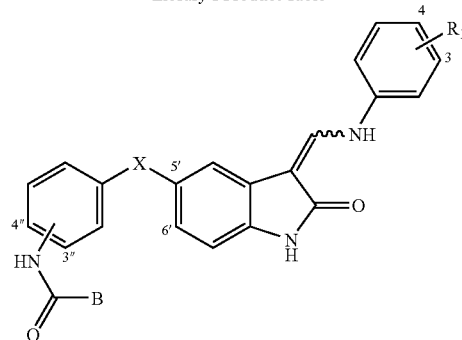

(Wherein X in the General Scheme above represents X in Formula II, (C=O)—B in the General Scheme above represents X′B in the Formula II, and 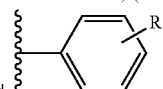 in the General Scheme above represents A in Formula II)

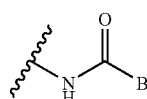

| Example # | Library ID # | R₁ substitution 3 | 4 | X | position | B |
|---|---|---|---|---|---|---|
| 99 | A-04-F2 | H | piperazinyl | C=O | 3″ | N-methylpyrazolyl |
| 100 | A-04-F6 | OH | H | C=O | 3″ | N-methylpyrazolyl |
| 101 | A-06-F2 | H | piperazinyl | C=O | 3″ | CH₃ |
| 102 | A-06-F4 | OH | OCH₃ | C=O | 3″ | CH₃ |
| 103 | A-07-F1 | H | morpholinyl | C=O | 3″ | thienyl |
| 104 | A-07-F2 | H | piperazinyl | C=O | 3″ | thienyl |
| 105 | A-07-F4 | OH | OCH₃ | C=O | 3″ | thienyl |
| 106 | A-08-F1 | H | morpholinyl | C=O | 3″ | acetylthienyl |

-continued

Library I Product Table

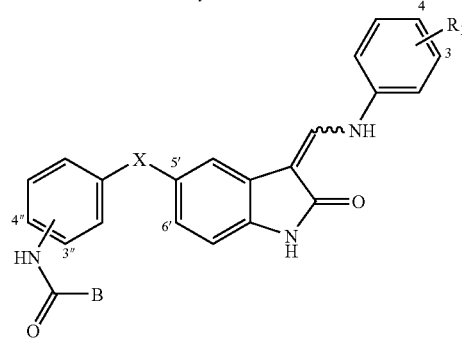

(Wherein X in the General Scheme above represents X in Formula II, (C═O)—B in the General Scheme above represents X′B in the Formula II, and 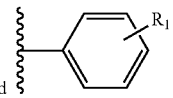 in the General Scheme above represents A in Formula II)

| Example # | Library ID # | R₁ subsititution 3 | 4 | X | 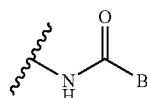 position | B |
|---|---|---|---|---|---|---|
| 107 | A-08-F2 | H | piperazinyl-Me | C═O | 3″ | 2-acetyl-thiophen-5-yl |
| 108 | A-09-F1 | H | morpholinyl | C═O | 3″ | 1,3-dimethyl-pyrazol-5-yl |
| 109 | A-09-F2 | H | piperazinyl-Me | C═O | 3″ | 1,3-dimethyl-pyrazol-5-yl |
| 110 | A-09-F4 | OH | OCH₃ | C═O | 3″ | 1,3-dimethyl-pyrazol-5-yl |
| 111 | A-10-F1 | H | morpholinyl | C═O | 3″ | 1-tBu-3-methyl-pyrazol-5-yl |
| 112 | A-10-F2 | H | piperazinyl-Me | C═O | 3″ | 1-tBu-3-methyl-pyrazol-5-yl |

-continued

Library I Product Table

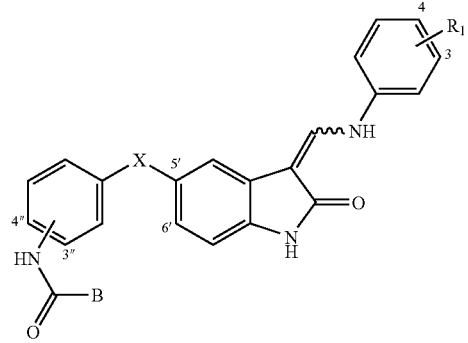

(Wherein X in the General Scheme above represents X in Formula II, (C=O)—B in the General Scheme above represents X'B in the Formula II, and 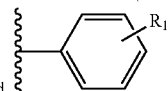 in the General Scheme above represents A in Formula II)

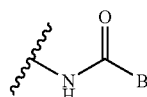

| Example # | Library ID # | R₁ substitution 3 | R₁ substitution 4 | X | position | B |
|---|---|---|---|---|---|---|
| 113 | A-10-F4 | OH | OCH₃ | C=O | 3" | tBu-pyrazole-Me |
| 114 | A-10-F5 | OH | CH₃ | C=O | 3" | tBu-pyrazole-Me |
| 115 | A-10-F6 | OH | H | C=O | 3" | tBu-pyrazole-Me |
| 116 | B-02-F4 | OH | OCH₃ | C=O | 4" | Et-pyrazole-Me |
| 117 | B-04-F1 | H | morpholine | C=O | 4" | Me-pyrazole |
| 118 | B-04-F2 | H | N-methylpiperazine | C=O | 4" | Me-pyrazole |

-continued

Library I Product Table

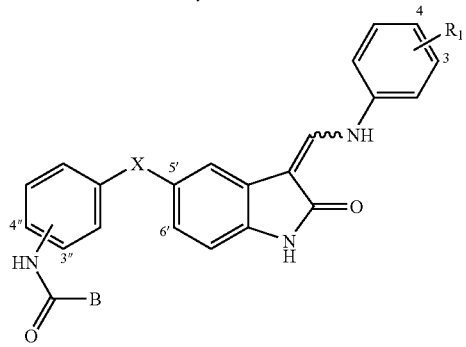

(Wherein X in the General Scheme above represents X in Formula II, (C=O)—B in the General Scheme above represents X'B in the Formula II, and 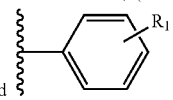 in the General Scheme above represents A in Formula II)

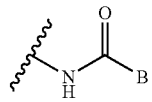

| Example # | Library ID # | R₁ substitution 3 | R₁ substitution 4 | X | position | B |
|---|---|---|---|---|---|---|
| 119 | B-07-F1 | H | morpholine (N-linked) | C=O | 4" | 2-thienyl |
| 120 | B-07-F2 | H | 4-methylpiperazin-1-yl | C=O | 4" | 2-thienyl |
| 121 | B-07-F4 | OH | OCH₃ | C=O | 4" | 2-thienyl |
| 122 | B-08-F1 | H | morpholine (N-linked) | C=O | 4" | 5-acetylthiophen-2-yl |
| 123 | B-08-F2 | H | 4-methylpiperazin-1-yl | C=O | 4" | 5-acetylthiophen-2-yl |
| 124 | B-09-F1 | H | morpholine (N-linked) | C=O | 4" | 1,3-dimethyl-1H-pyrazol-5-yl |

-continued

Library I Product Table

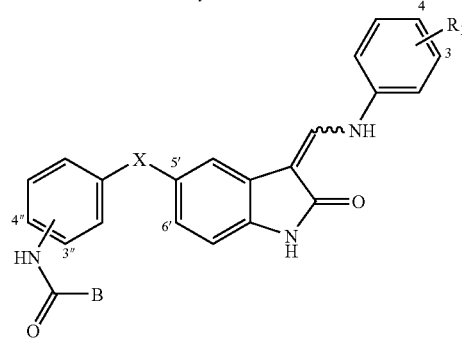

(Wherein X in the General Scheme above represents X in Formula II, (C=O)—B in the General Scheme above represents X'B in the Formula II, and 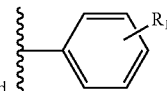 in the General Scheme above represents A in Formula II)

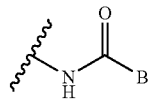

| Example # | Library ID # | R₁ substitution 3 | 4 | X | position | B |
|---|---|---|---|---|---|---|
| 125 | B-09-F2 | H | piperazine | C=O | 4" | 1,3-dimethylpyrazole |
| 126 | B-10-F1 | H | morpholine | C=O | 4" | 1-tBu-3-methylpyrazole |
| 127 | B-10-F2 | H | piperazine | C=O | 4" | 1-tBu-3-methylpyrazole |
| 128 | B-10-F4 | OH | OCH₃ | C=O | 4" | 1-tBu-3-methylpyrazole |
| 129 | B-10-F6 | OH | H | C=O | 4" | 1-tBu-3-methylpyrazole |
| 130 | C-01-F1 | H | morpholine | CH₂ | 3" | 1-methylimidazole |

-continued

Library I Product Table

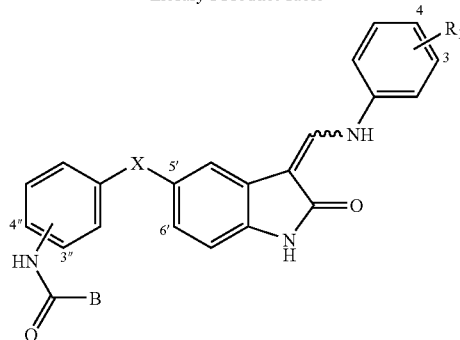

(Wherein X in the General Scheme above represents X in Formula II, (C=O)—B in the General Scheme above represents X'B in the Formula II, and 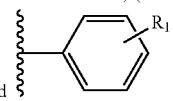 in the General Scheme above represents A in Formula II)

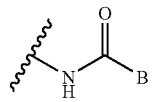

| Example # | Library ID # | R₁ substitution 3 | 4 | X | position | B |
|---|---|---|---|---|---|---|
| 131 | C-01-F2 | H | piperazine-N-Me | CH₂ | 3" | 1-Me-imidazol-2-yl |
| 132 | C-01-F4 | OH | OCH₃ | CH₂ | 3" | 1-Me-imidazol-2-yl |
| 133 | C-01-F5 | OH | CH₃ | CH₂ | 3" | 1-Me-imidazol-2-yl |
| 134 | C-01-F6 | OH | H | CH₂ | 3" | 1-Me-imidazol-2-yl |
| 135 | C-02-F1 | H | morpholino | CH₂ | 3" | 1-Et-3-Me-pyrazol-5-yl |
| 136 | C-02-F2 | H | piperazine-N-Me | CH₂ | 3" | 1-Et-3-Me-pyrazol-5-yl |

-continued

Library I Product Table

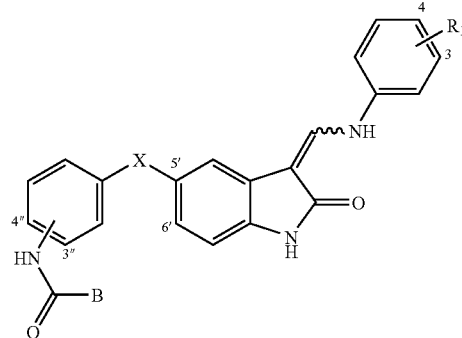

(Wherein X in the General Scheme above represents X in Formula II, (C=O)—B in the General Scheme above represents X'B in the Formula II, and 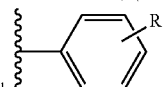 in the General Scheme above represents A in Formula II)

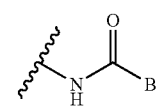

| Example # | Library ID # | R₁ substitution 3 | 4 | X | position | B |
|---|---|---|---|---|---|---|
| 137 | C-02-F4 | OH | OCH₃ | CH₂ | 3" | Et-pyrazole-Me |
| 138 | C-03-F1 | H | morpholine | CH₂ | 3" | Me-pyrazole-NH |
| 139 | C-03-F2 | H | N-methylpiperazine | CH₂ | 3" | Me-pyrazole-NH |
| 140 | C-03-F4 | OH | OCH₃ | CH₂ | 3" | Me-pyrazole-NH |
| 141 | C-03-F5 | OH | CH₃ | CH₂ | 3" | Me-pyrazole-NH |
| 142 | C-03-F6 | OH | H | CH₂ | 3" | Me-pyrazole-NH |
| 143 | C-04-F1 | H | morpholine | CH₂ | 3" | N-Me-pyrazole |

-continued

Library I Product Table

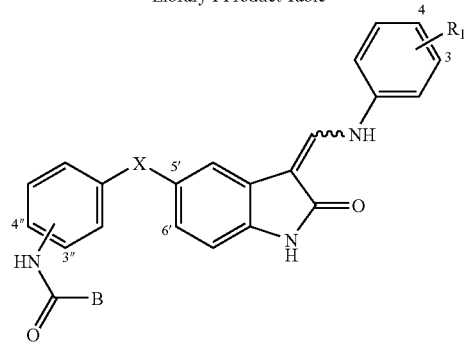

(Wherein X in the General Scheme above represents X in Formula II, (C=O)—B in the General Scheme above represents X'B in the Formula II, and 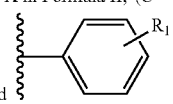 in the General Scheme above represents A in Formula II)

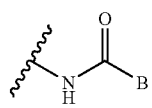

| Example # | Library ID # | R₁ substitution 3 | 4 | X | position | B |
|---|---|---|---|---|---|---|
| 144 | C-04-F2 | H | ⟨piperazine⟩ | CH₂ | 3″ | ⟨N-Me pyrazole⟩ |
| 145 | C-04-F4 | OH | OCH₃ | CH₂ | 3″ | ⟨N-Me pyrazole⟩ |
| 146 | C-04-F6 | OH | H | CH₂ | 3″ | ⟨N-Me pyrazole⟩ |
| 147 | C-05-F1 | H | ⟨morpholine⟩ | CH₂ | 3″ | ⟨NH pyrazole⟩ |
| 148 | C-05-F2 | H | ⟨piperazine⟩ | CH₂ | 3″ | ⟨NH pyrazole⟩ |
| 149 | C-05-F5 | OH | CH₃ | CH₂ | 3″ | ⟨NH pyrazole⟩ |
| 150 | C-05-F6 | OH | H | CH₂ | 3″ | ⟨NH pyrazole⟩ |
| 151 | C-06-F1 | H | ⟨morpholine⟩ | CH₂ | 3″ | CH₃ |

-continued

Library I Product Table

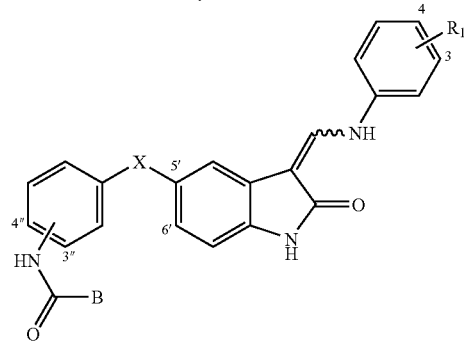

(Wherein X in the General Scheme above represents X in Formula II, (C=O)—B in the General Scheme above represents X'B in the Formula II, and 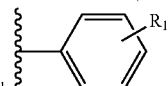 in the General Scheme above represents A in Formula II)

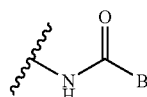

| Example # | Library ID # | R₁ substitution 3 | R₁ substitution 4 | X | position | B |
|---|---|---|---|---|---|---|
| 152 | C-06-F2 | H | piperazinyl | $CH_2$ | 3" | $CH_3$ |
| 153 | C-06-F4 | OH | $OCH_3$ | $CH_2$ | 3" | $CH_3$ |
| 154 | C-06-F5 | OH | $CH_3$ | $CH_2$ | 3" | $CH_3$ |
| 155 | C-06-F6 | OH | H | $CH_2$ | 3" | $CH_3$ |
| 156 | C-07-F1 | H | morpholinyl | $CH_2$ | 3" | thienyl |
| 157 | C-07-F2 | H | piperazinyl | $CH_2$ | 3" | thienyl |
| 158 | C-07-F4 | OH | $OCH_3$ | $CH_2$ | 3" | thienyl |
| 159 | C-07-F5 | OH | $CH_3$ | $CH_2$ | 3" | thienyl |
| 160 | C-07-F6 | OH | H | $CH_2$ | 3" | thienyl |

-continued

Library I Product Table

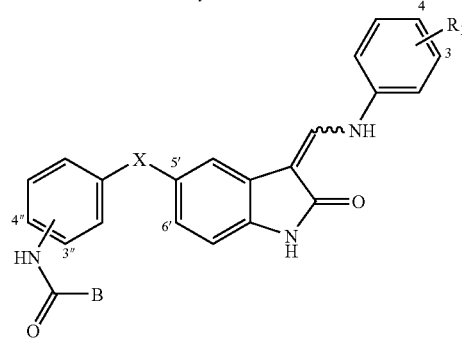

(Wherein X in the General Scheme above represents X in Formula II, (C=O)—B in the General Scheme above represents X'B in the Formula II, and 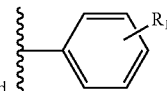 in the General Scheme above represents A in Formula II)

| Example # | Library ID # | $R_1$ subsitiution 3 | 4 | X | 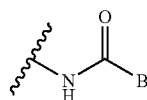 position | B |
|---|---|---|---|---|---|---|
| 161 | C-08-F1 | H | morpholine-N-yl | $CH_2$ | 3″ | 2-acetylthiophen-5-yl |
| 162 | C-08-F2 | H | 4-methylpiperazin-1-yl | $CH_2$ | 3″ | 2-acetylthiophen-5-yl |
| 163 | C-09-F1 | H | morpholine-N-yl | $CH_2$ | 3″ | 1,3-dimethylpyrazol-5-yl |
| 164 | C-09-F2 | H | 4-methylpiperazin-1-yl | $CH_2$ | 3″ | 1,3-dimethylpyrazol-5-yl |
| 165 | C-09-F4 | OH | $OCH_3$ | $CH_2$ | 3″ | 1,3-dimethylpyrazol-5-yl |
| 166 | C-09-F5 | OH | $CH_3$ | $CH_2$ | 3″ | 1,3-dimethylpyrazol-5-yl |

-continued
Library I Product Table

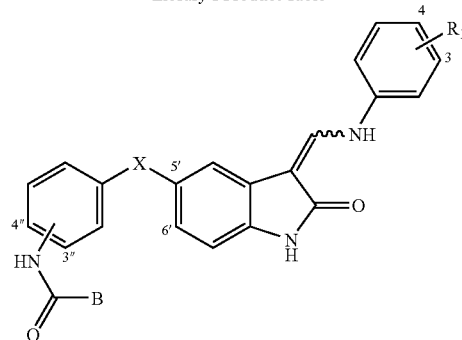

(Wherein X in the General Scheme above represents X in Formula II, (C=O)—B in the General Scheme above represents X'B in the Formula II, and 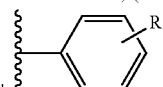 in the General Scheme above represents A in Formula II)

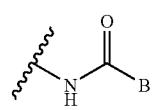

| Example # | Library ID # | R₁ subsititution 3 | 4 | X | position | B |
|---|---|---|---|---|---|---|
| 167 | C-09-F6 | OH | H | CH₂ | 3" | Me-pyrazole-Me |
| 168 | C-10-F2 | H | piperazine | CH₂ | 3" | tBu-pyrazole-Me |
| 169 | C-10-F6 | OH | H | CH₂ | 3" | tBu-pyrazole-Me |
| 170 | D-01-F1 | H | morpholine | CH₂ | 4" | Me-imidazole |
| 171 | D-01-F4 | OH | OCH₃ | CH₂ | 4" | Me-imidazole |
| 172 | D-01-F6 | OH | H | CH₂ | 4" | Me-imidazole |

-continued

Library I Product Table

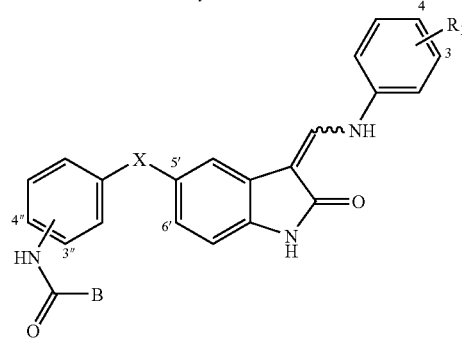

(Wherein X in the General Scheme above represents X in Formula II, (C=O)—B in the General Scheme above represents X'B in the Formula II, and 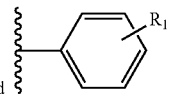 in the General Scheme above represents A in Formula II)

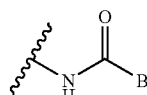

| Example # | Library ID # | $R_1$ substitution 3 | $R_1$ substitution 4 | X | position | B |
|---|---|---|---|---|---|---|
| 173 | D-02-F1 | H | morpholine (N-linked) | $CH_2$ | 4" | 1-Et, 3-Me pyrazol-5-yl |
| 174 | D-02-F4 | OH | $OCH_3$ | $CH_2$ | 4" | 1-Et, 3-Me pyrazol-5-yl |
| 175 | D-02-F6 | OH | H | $CH_2$ | 4" | 1-Et, 3-Me pyrazol-5-yl |
| 176 | D-03-F2 | H | 4-methylpiperazin-1-yl | $CH_2$ | 4" | 5-Me-1H-pyrazol-3-yl |
| 177 | D-03-F4 | OH | $OCH_3$ | $CH_2$ | 4" | 5-Me-1H-pyrazol-3-yl |
| 178 | D-04-F2 | H | 4-methylpiperazin-1-yl | $CH_2$ | 4" | 1,5-dimethylpyrazol-4-yl |
| 179 | D-04-F4 | OH | $OCH_3$ | $CH_2$ | 4" | 1,5-dimethylpyrazol-4-yl |

-continued

Library I Product Table

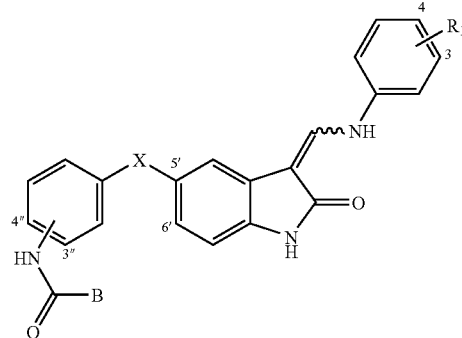

(Wherein X in the General Scheme above represents X in Formula II, (C=O)—B in the General Scheme above represents X'B in the Formula II, and 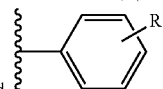 in the General Scheme above represents A in Formula II)

| Example # | Library ID # | R₁ substitution 3 | R₁ substitution 4 | X | 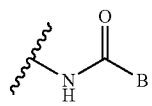 position | B |
|---|---|---|---|---|---|---|
| 180 | D-04-F5 | OH | CH₃ | CH₂ | 4" | 1-Me-pyrazol-4-yl |
| 181 | D-04-F6 | OH | H | CH₂ | 4" | 1-Me-pyrazol-4-yl |
| 182 | D-05-F1 | H | morpholino | CH₂ | 4" | 1H-pyrazol-4-yl |
| 183 | D-05-F2 | H | piperazinyl | CH₂ | 4" | 1H-pyrazol-4-yl |
| 184 | D-06-F1 | H | morpholino | CH₂ | 4" | CH₃ |
| 185 | D-06-F2 | H | piperazinyl | CH₂ | 4" | CH₃ |
| 186 | D-06-F6 | OH | H | CH₂ | 4" | CH₃ |
| 187 | D-07-F2 | H | piperazinyl | CH₂ | 4" | thiophen-2-yl |

-continued

Library I Product Table

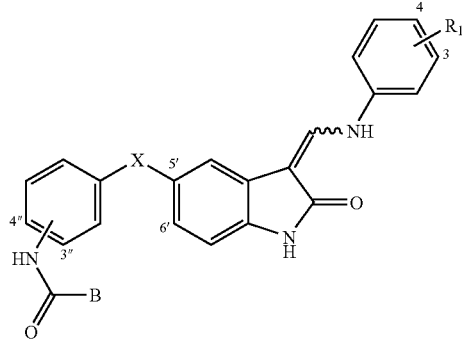

(Wherein X in the General Scheme above represents X in Formula II, (C=O)—B in the General Scheme above represents X'B in the Formula II, and 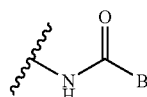 in the General Scheme above represents A in Formula II)

| Example # | Library ID # | R₁ subsitition 3 | R₁ subsitition 4 | X | 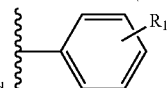 position | B |
|---|---|---|---|---|---|---|
| 188 | D-07-F4 | OH | OCH₃ | CH₂ | 4" | thiophen-2-yl |
| 189 | D-07-F5 | OH | CH₃ | CH₂ | 4" | thiophen-2-yl |
| 190 | D-08-F1 | H | morpholin-4-yl | CH₂ | 4" | 5-acetylthiophen-2-yl |
| 191 | D-08-F2 | H | 4-methylpiperazin-1-yl | CH₂ | 4" | 5-acetylthiophen-2-yl |
| 192 | D-09-F1 | H | morpholin-4-yl | CH₂ | 4" | 1,3-dimethyl-1H-pyrazol-5-yl |
| 193 | D-09-F2 | H | 4-methylpiperazin-1-yl | CH₂ | 4" | 1,3-dimethyl-1H-pyrazol-5-yl |

-continued

Library I Product Table

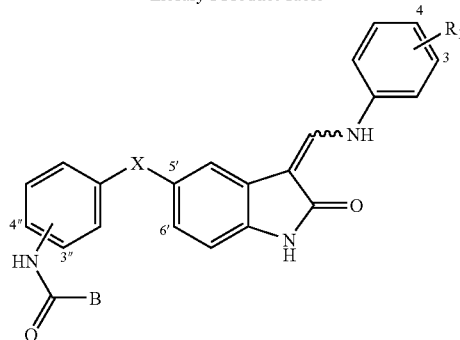

(Wherein X in the General Scheme above represents X in Formula II, (C=O)—B in the General Scheme above represents X'B in the Formula II, and 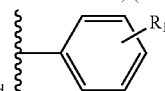 in the General Scheme above represents A in Formula II)

| Example # | Library ID # | R₁ subsitutution 3 | R₁ subsitutution 4 | X | 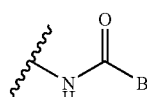 position | B |
|---|---|---|---|---|---|---|
| 194 | D-09-F4 | OH | OCH₃ | CH₂ | 4" | Me-N-N, Me (pyrazole) |
| 195 | D-09-F5 | OH | CH₃ | CH₂ | 4" | Me-N-N, Me (pyrazole) |
| 196 | D-10-F1 | H | morpholine (N-O) | CH₂ | 4" | tBu-N-N, Me (pyrazole) |
| 197 | D-10-F2 | H | N-methylpiperazine | CH₂ | 4" | tBu-N-N, Me (pyrazole) |
| 198 | D-10-F4 | OH | OCH₃ | CH₂ | 4" | tBu-N-N, Me (pyrazole) |

-continued

Library I Product Table

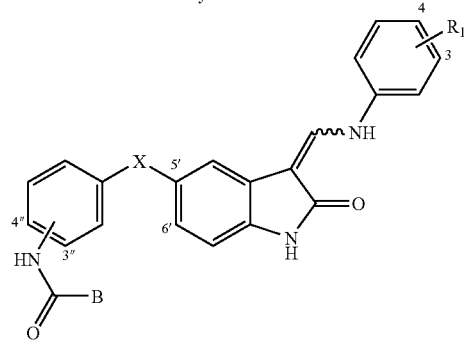

(Wherein X in the General Scheme above represents X in Formula II, (C=O)—B in the General Scheme above represents X'B in the Formula II, and 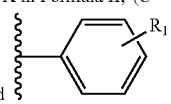 in the General Scheme above represents A in Formula II)

| Example # | Library ID # | R₁ substitution 3 | R₁ substitution 4 | X | position | 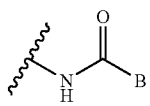 B |
|---|---|---|---|---|---|---|
| 199 | D-10-F5 | OH | CH₃ | CH₂ | 4″ | tBu-pyrazole-Me |
| 200 | D-10-F6 | OH | H | CH₂ | 4″ | tBu-pyrazole-Me |

Procedures for Library II: the Library of Compounds Examples 209 through 323 General Synthetic Procedure: The general synthetic route to the compounds prepared in the Library was similar in all cases to the procedures followed in the preparation of the individually prepared compounds (Examples 15-92 & 201-208, see General Scheme for overview).

General Scheme:

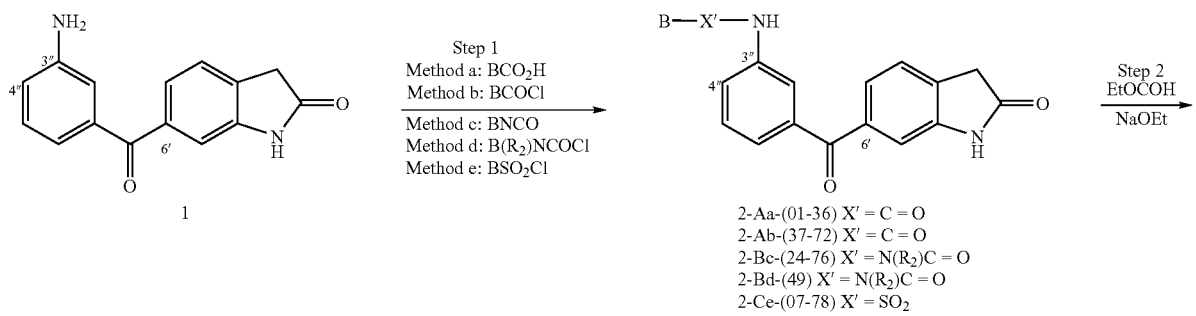

-continued

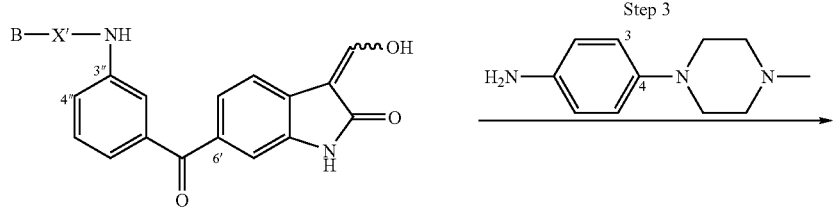

3-Aa-(01-36) X' = C = O
3-Ab-(37-72) X' = C = O
3-Bc-(24-76) X' = N(R$_2$)C = O
3-Bd-(49) X' = N(R$_2$)C = O
3-Ce-(07-78) X' = SO$_2$

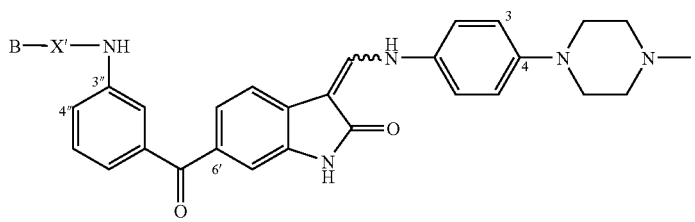

4-Aa-(01-36) X' = C = O
4-Ab-(37-72) X' = C = O
4-Bc-(24-76) X' = N(R$_2$)C = O
4-Bd-(49) X' = N(R$_2$)C = O
4-Ce-(07-78) X' = SO$_2$ (Wherein X'—B in the General Scheme above represents X'—B in Formula I, and

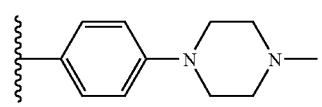

in the General Scheme above represents A in Formula I)

General Stepwise Procedures and Reagent Tables for the Preparation of Library II (not limited to but including, Examples 209-323).

Tables of Reagents:

Library Reagent Table 6

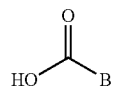

| Library ID # | B |
|---|---|
| a-01 | 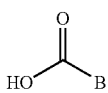 |
| a-02 | 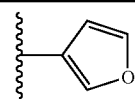 |

Library Reagent Table 6

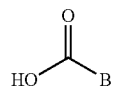

| Library ID # | B |
|---|---|
| a-03 | 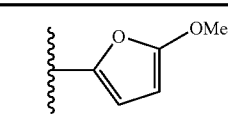 |
| a-04 | 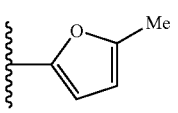 |
| a-05 | 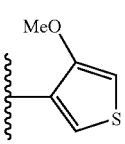 |
| a-06 | 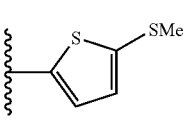 |
| a-07 | 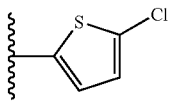 |

-continued
Library Reagent Table 6
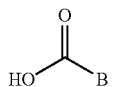
| Library ID # | B |
|---|---|
| a-08 | 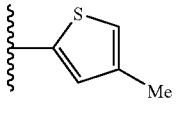 |
| a-09 | 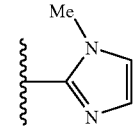 |
| a-10 | 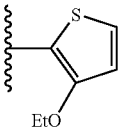 |
| a-11 | 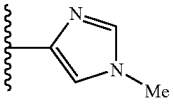 |
| a-12 | 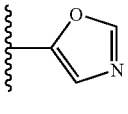 |
| a-13 | 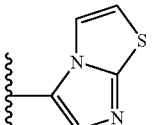 |
| a-14 | 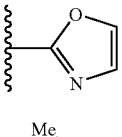 |
| a-15 | 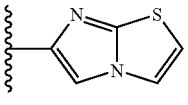 |
| a-16 | 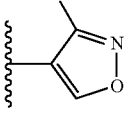 |
| a-17 | 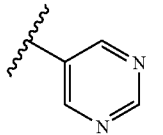 |
| a-18 | 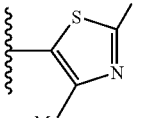 |
-continued
Library Reagent Table 6
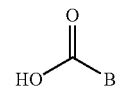
| Library ID # | B |
|---|---|
| a-19 | 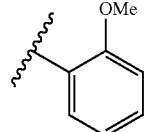 |
| a-20 | 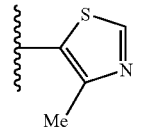 |
| a-21 | 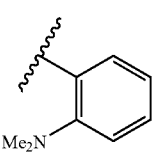 |
| a-22 | 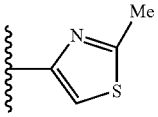 |
| a-23 | 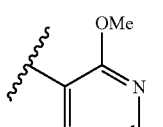 |
| a-24 | 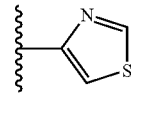 |
| a-25 | 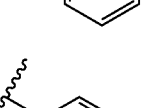 |
| a-26 | 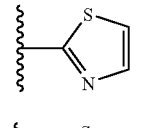 |
| a-27 | 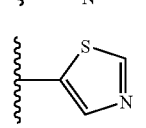 |

-continued
Library Reagent Table 6
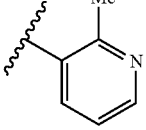
| Library ID # | B |
|---|---|
| a-28 | 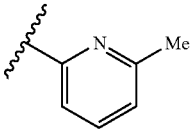 |
| a-29 | 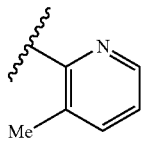 |
| a-30 | 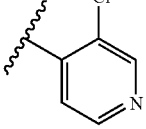 |
| a-31 | 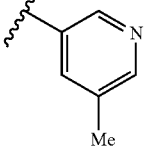 |
| a-32 | 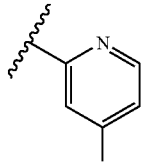 |
| a-33 | 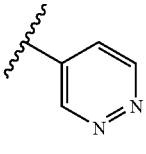 |
| a-34 | 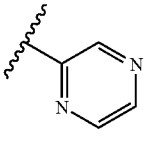 |
| a-35 | 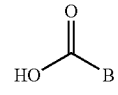 |
-continued
Library Reagent Table 6
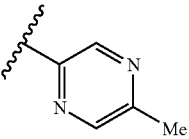
| Library ID # | B |
|---|---|
| a-36 | 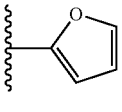 |
Library Reagent Table 7
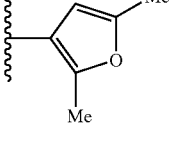
| Library ID # | B |
|---|---|
| b-37 | 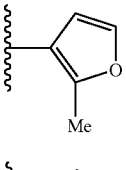 |
| b-38 | 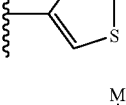 |
| b-39 | 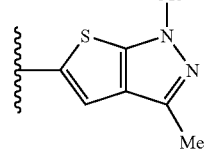 |
| b-40 | 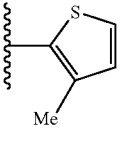 |
| b-41 |  |
| b-42 |  |

-continued

Library Reagent Table 7

![structure: ClC(=O)-B]

| Library ID # | B |
|---|---|
| b-43 | 2,5-dimethyl... 5-methylthiophen-2-yl (thiophene with Me at 5-position) |
| b-44 | 3,5-dimethylisoxazol-4-yl |
| b-45 | 5-methylisoxazol-3-yl |
| b-46 | 1-methyl-1H-imidazol-5-yl |
| b-47 | 4-methyl-1,2,3-thiadiazol-5-yl |
| b-48 | 1-methyl-1H-pyrrol-2-yl |
| b-49 | phenyl |
| b-50 | 3,5-difluorophenyl |
| b-51 | 2-chlorophenyl |

-continued

Library Reagent Table 7

![structure: ClC(=O)-B]

| Library ID # | B |
|---|---|
| b-52 | 3-chlorophenyl |
| b-53 | 4-chlorophenyl |
| b-54 | 2-methoxyphenyl |
| b-55 | 3-methoxyphenyl |
| b-56 | 4-methoxyphenyl |
| b-57 | 3,5-dimethoxyphenyl |
| b-58 | 3,4-dimethoxyphenyl |
| b-59 | 2-methylphenyl |
| b-60 | 3-methylphenyl |

-continued
Library Reagent Table 7
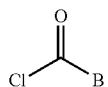
| Library ID # | B |
|---|---|
| b-61 | 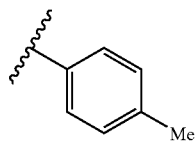 |
| b-62 | 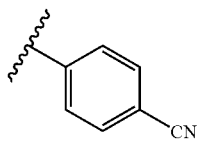 |
| b-63 | 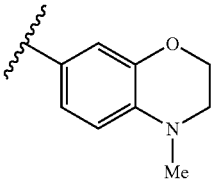 |
| b-64 | 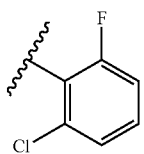 |
| b-65 | 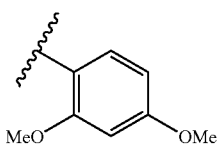 |
| b-66 | 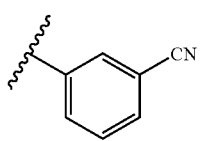 |
| b-67 | 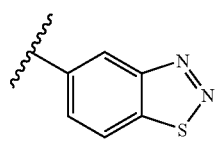 |
| b-68 | 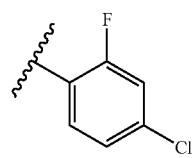 |
-continued
Library Reagent Table 7
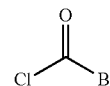
| Library ID # | B |
|---|---|
| b-69 | 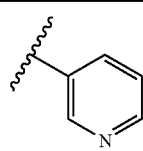 |
| b-70 | 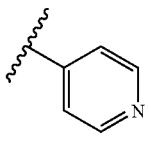 |
| b-71 | 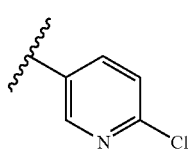 |
| b-72 | 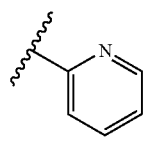 |
Library Reagent Table 8
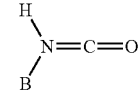
| Library ID # | B |
|---|---|
| c-24 | 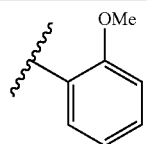 |
| c-40 | 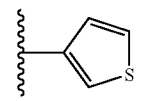 |
| c-49 | 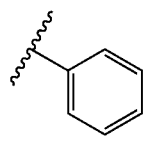 |

-continued
Library Reagent Table 8
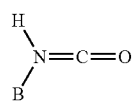
| Library ID # | B |
|---|---|
| c-50 | 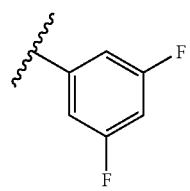 |
| c-51 | 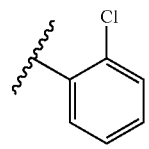 |
| c-52 | 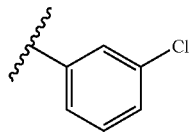 |
| c-53 | 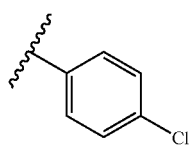 |
| c-54 | 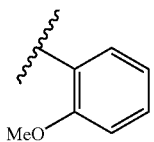 |
| c-55 | 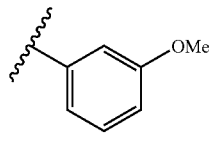 |
| c-56 | 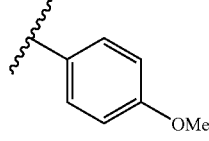 |
| c-57 | 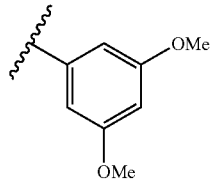 |
-continued
Library Reagent Table 8
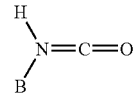
| Library ID # | B |
|---|---|
| c-58 | 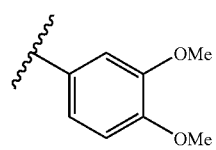 |
| c-59 | 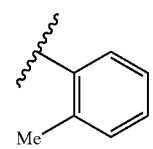 |
| c-60 | 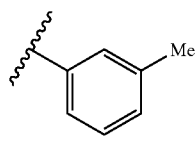 |
| c-61 | 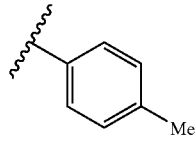 |
| c-62 | 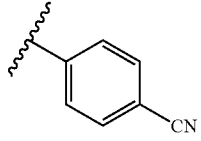 |
| c-65 | 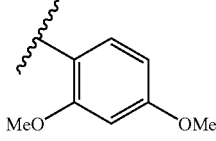 |
| c-66 | 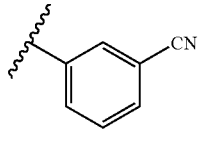 |
| c-68 | 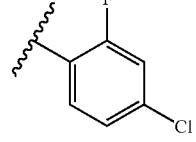 |
| c-73 | 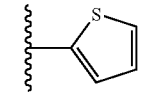 |

-continued
Library Reagent Table 8
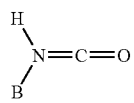
| Library ID # | B |
|---|---|
| c-74 | 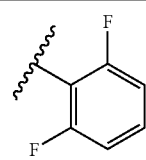 |
| c-75 | 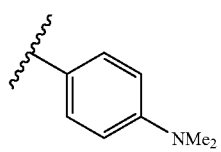 |
| c-76 | 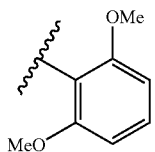 |
Library Reagent Table 9
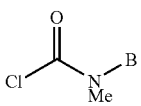
| Library ID # | B |
|---|---|
| d-49 | 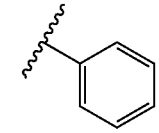 |
Library Reagent Table 10
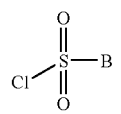
| Library ID # | B |
|---|---|
| e-07 | 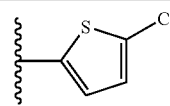 |
-continued
Library Reagent Table 10
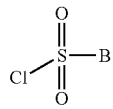
| Library ID # | B |
|---|---|
| e-20 | 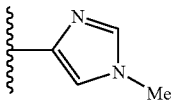 |
| e-38 | 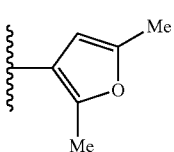 |
| e-40 | 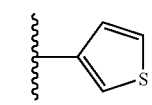 |
| e-44 | 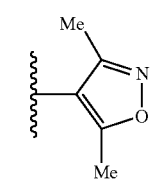 |
| e-50 | 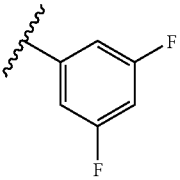 |
| e-51 | 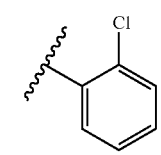 |
| e-52 | 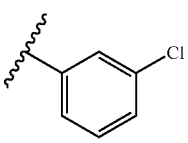 |
| e-53 | 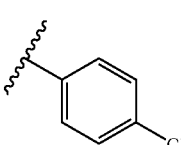 |
| e-55 | 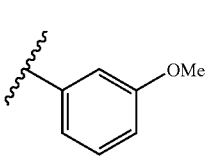 |

-continued

Library Reagent Table 10

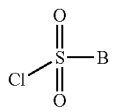

| Library ID # | B |
|---|---|
| e-56 | 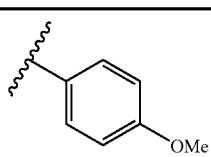 |
| e-59 | 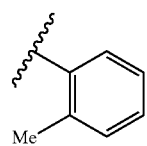 |
| e-60 | 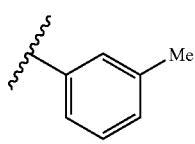 |
| e-61 | 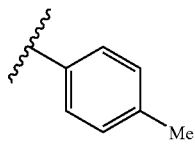 |
| e-62 | 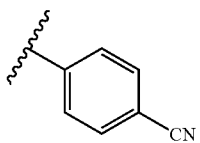 |
| e-66 | 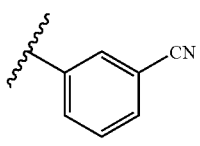 |
| e-73 | 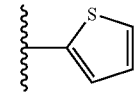 |
| e-77 | 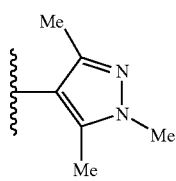 |
| e-78 | 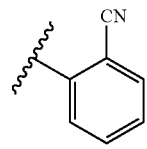 |

Step 1: Aniline Derivatization (2-Aa-01 Through 2-Ce-78)

The compounds listed in Library Reagent Tables 6-10 were combined with scaffold 1,6-(3-Amino-benzoyl)-1,3-dihydro-indol-2-one, from Library Reagent Table 1 (see Procedures for the Preparation of Library I section, or Example 40) using the methods described below to produce the amides, ureas and sulfonamides listed in Library Reagent Table 11:

Method a: Coupling with Carboxylic Acids (2-Aa-01 through 2-Aa-36)

Reagents from Library Reagent Table 6 were combined with scaffold 1,6-(3-Amino-benzoyl)-1,3-dihydro-indol-2-one, from Library Reagent Table 1 using the methods described below to produce the amides listed in Library Reagent Table 11:

To each reaction vial (40 mL) was added scaffold 1 (151 mg, 0.6 mmol), a carboxylic acid (0.75 mmol, see Reagent Table 6), HOBT (121 mg, 0.9 mmol), and anhydrous DMF (4 mL). To each of the above reaction mixtures was added EDC (172 mg, 0.9 mmol). Each reaction was shaken at r.t. for 20 hours. Each reaction mixture was evaporated in a Savant SpeedVac and the resulting residue from each was stirred in 20 mL of water. The solid that formed in each case was collected and washed once with water (20 mL), and then dried in a 40 mL vial under vacuum for 24 hours to provide the amides, 2-Aa-01 through 2-Aa-36, shown in Library Reagent Table 11.

Method b: Coupling with Acid Chlorides (2-Ab-37 through 2-Ab-72)

Reagents from Library Reagent Table 7 were combined with scaffold 1,6-(3-Amino-benzoyl)-1,3-dihydro-indol-2-one, from Library Reagent Table 1 using the methods described below to produce the amides listed in Library Reagent Table 11:

To each reaction vial (40 mL) was added scaffold 1 (151 mg, 0.6 mmol) and anhydrous THF (10 mL). An acid chloride (0.75 mmol, see Library Reagent Table 7) was then added to the reaction vial. The reaction vial was flushed with argon, capped, and heated at 65° C. overnight. The reaction was cooled to r.t. and the THF was evaporated in a Savant Speed-Vac and the resulting residue from each was stirred in 20 mL of water. The solid that formed in each case was collected and washed once with water (20 mL), and then dried in a 40 mL vial under vacuum for 24 hours to provide the amides, 2-Ab-37 through 2-Ab-72, shown in Library Reagent Table 11.

Method c: Reaction with Isocyanates (2-Bc-24 through 2-Bc-76)

Reagents from Library Reagent Table 8 were combined with scaffold 1,6-(3-Amino-benzoyl)-1,3-dihydro-indol-2-one, from Library Reagent Table 1 using the methods described below to produce the amides listed in Library Reagent Table 11:

To each reaction vial (40 mL) was added scaffold 1 (151 mg, 0.6 mmol), anhydrous THF (10 mL), and an isocyanate (0.75 mmol, see Library Reagent Table 8). The vial was flushed with argon, capped and heated at 65° C. overnight. The reaction was cooled to r.t. and the THF was evaporated in a Savant SpeedVac and the resulting residue from each was stirred in 20 mL of water. The solid that formed in each case was collected and washed once with water (20 mL), and then dried in a 40 mL vial under vacuum for 24 hours to provide the ureas, 2-Bc-24 through 2-Bc-76, shown in Library Reagent Table 11.

Method d: Reaction with Chlorocarbamates (2-Bd-49).

The compound from Library Reagent Table 9 were combined with scaffold 1,6-(3-Amino-benzoyl)-1,3-dihydro-indol-2-one, from Library Reagent Table 1 using the methods described below to produce the urea, 2-Bd-49, listed in Library Reagent Table 11:

To each reaction vial (40 mL) was added scaffold 1 (151 mg, 0.6 mmol), anhydrous dioxane (7 mL), anhydrous DMSO (1 mL), NMM (1.5 mmol), and a chlorocarbamate (0.75 mmol, see Library Reagent Table 9). Each vial was flushed with argon, capped, and heated at 70° C. overnight. The reaction was cooled to r.t. and the each reaction was evaporated in a Savant SpeedVac and the resulting residue from each was stirred in 20 mL of water. The solid that formed in each case was collected and washed once with water (20 mL), and then dried in a 40 mL vial under vacuum for 24 hours to provide the urea, 2-Bd-49, shown in Library Reagent Table 11.

Method e: Reaction with Sulfonyl Chlorides (2-Ce-07 through 2-Ce-78).

Reagents from Library Reagent Table 10 were combined with reagent 1 from Library Reagent Table 1 using the methods described below to produce the amides listed in Library Reagent Table 11:

To each reaction vial (40 mL) was added scaffold 1 (151 mg, 0.6 mmol), anhydrous dioxane (7 mL), anhydrous DMSO (1 mL), NMM (1.5 mmol), and a sulfonyl chloride (0.75 mmol, see Library Reagent Table 10). Each reaction vial was flushed with argon, capped, and shaken at r.t. overnight. Each reaction was evaporated in a Savant SpeedVac and the resulting residue from each was stirred in 20 mL of water. The solid that formed in each case was collected and washed once with water (20 mL), and then dried in a 40 mL vial under vacuum for 24 hours to provide the ureas, 2-Ce-07 through 2-Ce-78, shown in Library Reagent Table 11.

Library Reagent Table 11

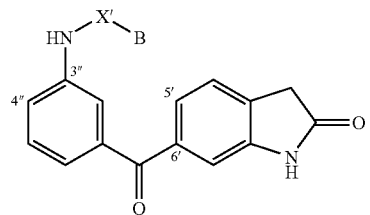

| Library ID # | X' | HN X'B (position) | B |
|---|---|---|---|
| 2-Aa-01 | C=O | 3" | (3-furyl) |
| 2-Aa-02 | C=O | 3" | (3-methylfuran-2-yl) |
| 2-Aa-03 | C=O | 3" | (5-methoxyfuran-2-yl) |
| 2-Aa-04 | C=O | 3" | (5-methylfuran-2-yl) |
| 2-Aa-05 | C=O | 3" | (4-methoxythiophen-3-yl) |
| 2-Aa-06 | C=O | 3" | (5-methylthiothiophen-2-yl) |
| 2-Aa-07 | C=O | 3" | (5-chlorothiophen-2-yl) |
| 2-Aa-08 | C=O | 3" | (4-methylthiophen-2-yl) |
| 2-Aa-09 | C=O | 3" | (3-ethoxythiophen-2-yl) |
| 2-Aa-10 | C=O | 3" | (oxazol-5-yl) |
| 2-Aa-11 | C=O | 3" | (oxazol-2-yl) |

-continued
Library Reagent Table 11
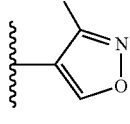
| Library ID # | X' | HN X'B (position) | B |
|---|---|---|---|
| 2-Aa-12 | C=O | 3" | 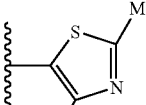 |
| 2-Aa-13 | C=O | 3" | 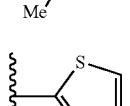 |
| 2-Aa-14 | C=O | 3" | 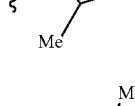 |
| 2-Aa-15 | C=O | 3" | 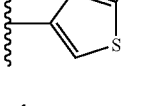 |
| 2-Aa-16 | C=O | 3" | 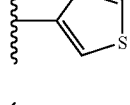 |
| 2-Aa-17 | C=O | 3" | 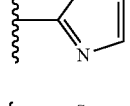 |
| 2-Aa-18 | C=O | 3" | 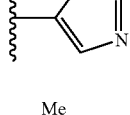 |
| 2-Aa-19 | C=O | 3" | 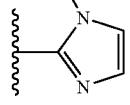 |
| 2-Aa-20 | C=O | 3" | 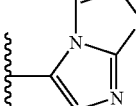 |
-continued
Library Reagent Table 11
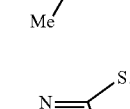
| Library ID # | X' | HN X'B (position) | B |
|---|---|---|---|
| 2-Aa-21 | C=O | 3" | 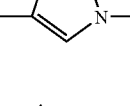 |
| 2-Aa-22 | C=O | 3" | 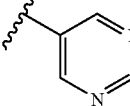 |
| 2-Aa-23 | C=O | 3" | 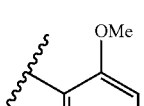 |
| 2-Aa-24 | C=O | 3" | 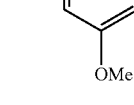 |
| 2-Aa-25 | C=O | 3" | 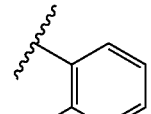 |
| 2-Aa-26 | C=O | 3" | |
| 2-Aa-27 | C=O | 3" | |

-continued

Library Reagent Table 11

| Library ID # | X' | HN X'B (position) | B |
|---|---|---|---|
| 2-Aa-28 | C=O | 3" | 2-methylpyridin-3-yl |
| 2-Aa-29 | C=O | 3" | 6-methylpyridin-2-yl |
| 2-Aa-30 | C=O | 3" | 3-methylpyridin-2-yl |
| 2-Aa-31 | C=O | 3" | 3-chloropyridin-4-yl |
| 2-Aa-32 | C=O | 3" | 5-methylpyridin-3-yl |
| 2-Aa-33 | C=O | 3" | 4-chloropyridin-2-yl |
| 2-Aa-34 | C=O | 3" | pyridazin-4-yl |
| 2-Aa-35 | C=O | 3" | pyrazin-2-yl |
| 2-Aa-36 | C=O | 3" | 5-methylpyrazin-2-yl |
| 2-Ab-37 | C=O | 3" | furan-2-yl |
| 2-Ab-38 | C=O | 3" | 2,5-dimethylfuran-3-yl |
| 2-Ab-39 | C=O | 3" | 2-methylfuran-3-yl |
| 2-Ab-40 | C=O | 3" | thiophen-3-yl |
| 2-Ab-41 | C=O | 3" | 1,3-dimethylthieno[2,3-c]pyrazol-5-yl |
| 2-Ab-42 | C=O | 3" | 3-methylthiophen-2-yl |
| 2-Ab-43 | C=O | 3" | 5-methylthiophen-2-yl |

-continued
Library Reagent Table 11
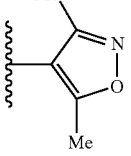
| Library ID # | X' | HN X'B (position) | B |
|---|---|---|---|
| 2-Ab-44 | C=O | 3" | 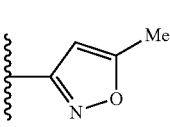 |
| 2-Ab-45 | C=O | 3" | 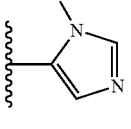 |
| 2-Ab-46 | C=O | 3" | 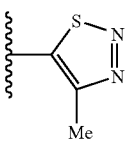 |
| 2-Ab-47 | C=O | 3" | 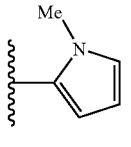 |
| 2-Ab-48 | C=O | 3" | 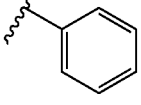 |
| 2-Ab-49 | C=O | 3" | 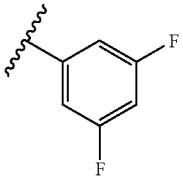 |
| 2-Ab-50 | C=O | 3" | 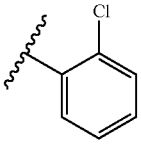 |
| 2-Ab-51 | C=O | 3" | 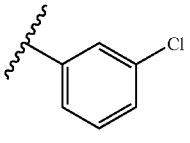 |
-continued
Library Reagent Table 11
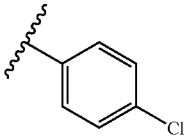
| Library ID # | X' | HN X'B (position) | B |
|---|---|---|---|
| 2-Ab-52 | C=O | 3" | 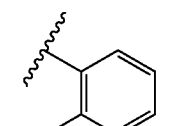 |
| 2-Ab-53 | C=O | 3" | 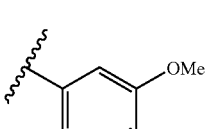 |
| 2-Ab-54 | C=O | 3" | 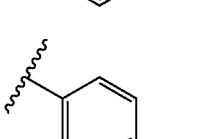 |
| 2-Ab-55 | C=O | 3" | 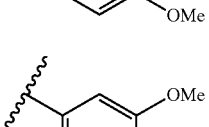 |
| 2-Ab-56 | C=O | 3" | 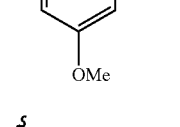 |
| 2-Ab-57 | C=O | 3" | 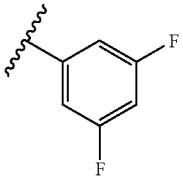 |
| 2-Ab-58 | C=O | 3" | 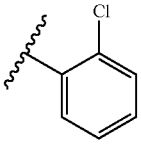 |
| 2-Ab-59 | C=O | 3" | 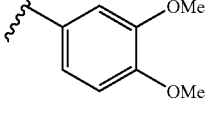 |

-continued
Library Reagent Table 11
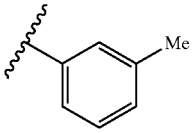
| Library ID # | X' | HN X'B (position) | B |
|---|---|---|---|
| 2-Ab-60 | C=O | 3" | 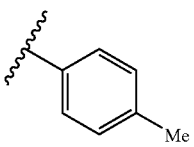 |
| 2-Ab-61 | C=O | 3" | 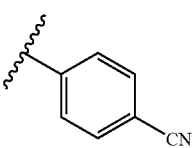 |
| 2-Ab-62 | C=O | 3" | 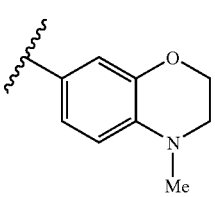 |
| 2-Ab-63 | C=O | 3" | 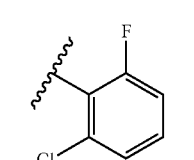 |
| 2-Ab-64 | C=O | 3" | 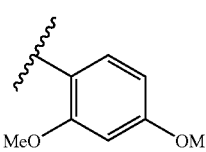 |
| 2-Ab-65 | C=O | 3" | 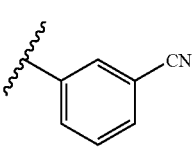 |
| 2-Ab-66 | C=O | 3" | 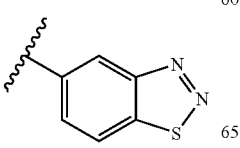 |
| 2-Ab-67 | C=O | 3" | 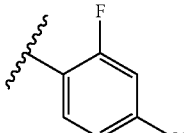 |
-continued
Library Reagent Table 11
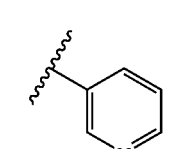
| Library ID # | X' | HN X'B (position) | B |
|---|---|---|---|
| 2-Ab-68 | C=O | 3" | 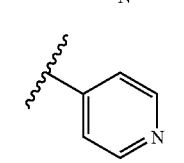 |
| 2-Ab-69 | C=O | 3" | 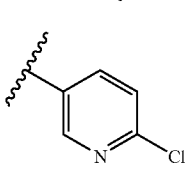 |
| 2-Ab-70 | C=O | 3" | 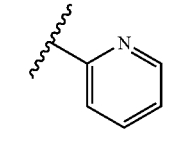 |
| 2-Ab-71 | C=O | 3" | 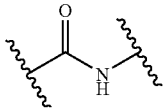 |
| 2-Ab-72 | C=O | 3" | 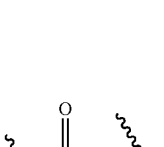 |
| 2-Bc-24 | 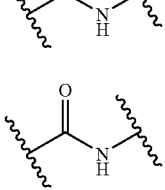 | 3" | 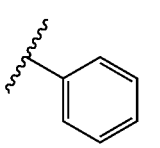 |
| 2-Bc-40 | | 3" | |
| 2-Bc-49 | | 3" | |

-continued
Library Reagent Table 11
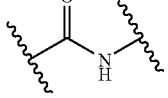
| Library ID # | X' | HN X'B (position) | B |
|---|---|---|---|
| 2-Bc-50 | 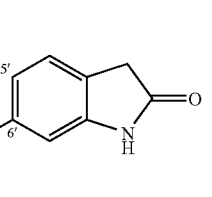 | 3" | 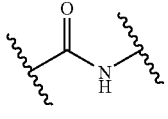 |
| 2-Bc-51 | 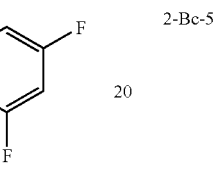 | 3" | 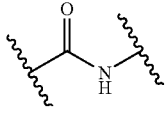 |
| 2-Bc-52 | 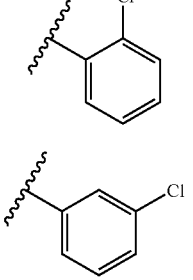 | 3" | 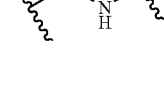 |
| 2-Bc-53 | 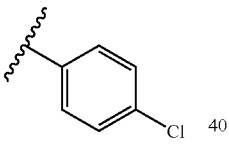 | 3" | 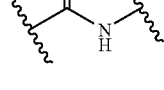 |
| 2-Bc-54 | 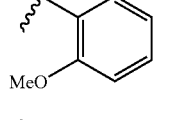 | 3" | 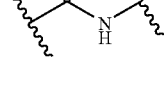 |
| 2-Bc-55 | 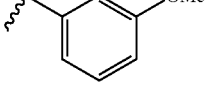 | 3" | 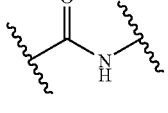 |
| 2-Bc-56 | 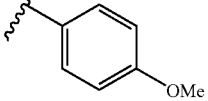 | 3" | 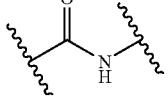 |
| 2-Bc-57 | 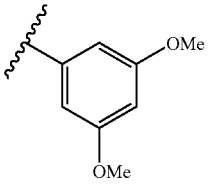 | 3" | 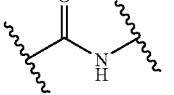 |
-continued
Library Reagent Table 11
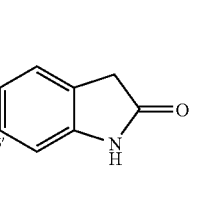
| Library ID # | X' | HN X'B (position) | B |
|---|---|---|---|
| 2-Bc-58 | 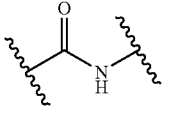 | 3" | 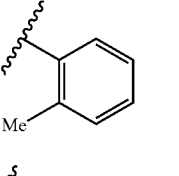 |
| 2-Bc-59 | 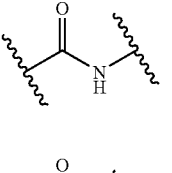 | 3" | 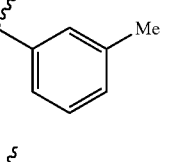 |
| 2-Bc-60 | 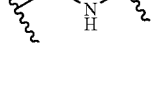 | 3" | 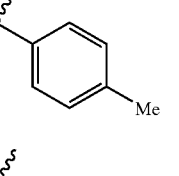 |
| 2-Bc-61 | 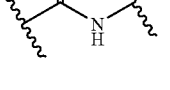 | 3" | 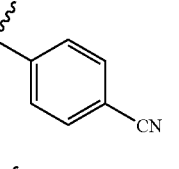 |
| 2-Bc-62 | 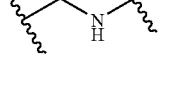 | 3" | 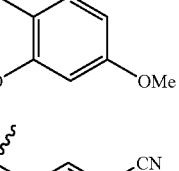 |
| 2-Bc-65 | 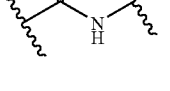 | 3" | 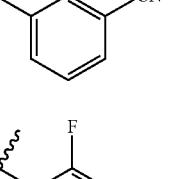 |
| 2-Bc-66 | 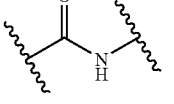 | 3" | 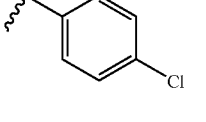 |
| 2-Bc-68 | | 3" | |

-continued

Library Reagent Table 11

| Library ID # | X' | HN X'B (position) | B |
|---|---|---|---|
| 2-Bc-73 | -C(O)NH- | 3" | 2-thienyl |
| 2-Bc-74 | -C(O)NH- | 3" | 2,6-difluorophenyl |
| 2-Bc-75 | -C(O)NH- | 3" | 4-(NMe₂)phenyl |
| 2-Bc-76 | -C(O)NH- | 3" | 2,6-dimethoxyphenyl |
| 2-Bd-49 | -C(O)N(Me)- | 3" | phenyl |
| 2-Ce-07 | -SO₂- | 3" | 5-chloro-2-thienyl |
| 2-Ce-20 | -SO₂- | 3" | 1-methylimidazol-4-yl |
| 2-Ce-38 | -SO₂- | 3" | 2,5-dimethylfuran-3-yl |
| 2-Ce-40 | -SO₂- | 3" | 3-thienyl |

-continued

Library Reagent Table 11

| Library ID # | X' | HN X'B (position) | B |
|---|---|---|---|
| 2-Ce-44 | -SO₂- | 3" | 3,5-dimethylisoxazol-4-yl |
| 2-Ce-50 | -SO₂- | 3" | 3,5-difluorophenyl |
| 2-Ce-51 | -SO₂- | 3" | 2-chlorophenyl |
| 2-Ce-52 | -SO₂- | 3" | 3-chlorophenyl |
| 2-Ce-53 | -SO₂- | 3" | 4-chlorophenyl |
| 2-Ce-55 | -SO₂- | 3" | 3-methoxyphenyl |
| 2-Ce-56 | -SO₂- | 3" | 4-methoxyphenyl |

Library Reagent Table 11

Structure: HN-X'-B substituent on aniline (3" position) connected via carbonyl (C=O) to 6' position of oxindole (indolin-2-one).

| Library ID # | X' | HN X'B (position) | B |
|---|---|---|---|
| 2-Ce-59 | S(=O)₂ | 3" | 2-methylphenyl |
| 2-Ce-60 | S(=O)₂ | 3" | 3-methylphenyl |
| 2-Ce-61 | S(=O)₂ | 3" | 4-methylphenyl |
| 2-Ce-62 | S(=O)₂ | 3" | 4-cyanophenyl |
| 2-Ce-66 | S(=O)₂ | 3" | 3-cyanophenyl |
| 2-Ce-73 | S(=O)₂ | 3" | 2-thienyl |
| 2-Ce-77 | S(=O)₂ | 3" | 1,3,5-trimethylpyrazol-4-yl |
| 2-Ce-78 | S(=O)₂ | 3" | 2-cyanophenyl |

The total amount of each crude product obtained from Step 1, listed in the above table, was used directly in Step 2 without further purification.

Step 2: Formylation (3-Aa-01 Through 3-Ce-78)

The compounds listed in Library Reagent Table 11 were combined with Ethyl Formate using the method described below to produce the formylated oxindoles 3-Aa-01 through 3-Ce-78 listed in Library Reagent Table 12:

To each reaction vial (40 mL) containing an oxindole from Step 1, 2-Aa-01 through 2-Ce-78 in Library Reagent Table 11, was added absolute ethanol (6 mL) and ethyl formate (0.5 mL, 10 eq.). The reaction vials were flushed with argon before a solution of sodium ethoxide in ethanol (21 wt. %, 0.5 mL, 2 eq.) was added. The vials were then capped.

For each of the amides 2-Aa-01 through 2-Ab-72 (all products from Step 1, Method a, and Step 1, Method b—see Library Reagent Table 11), the reactions were shaken at r.t. for two days. The reactions using the ureas 2-Bc-24 through 2-Bd-49 (all products from Step 1, Method c and Step 1, Method d; see Library Reagent Table 11) were shaken at r.t. for four days. For each of the reactions involving sulfonamides 2-Ce-07 through 2-Ce-78 (all products from Step 1, Method e; see Library Reagent Table 11), the reactions were run at 60° C. overnight.

Workup procedure for all reactions: To each reaction vial was added 1M HCl$_{(aq)}$ (1.3 mL) and water (20 mL). The precipitates that formed in each case were collected by filtration and dried under vacuum to provide the hydroxymethylene-oxindoles listed in Library Reagent Table 12 (3-Aa-01 through 3-Ce-78).

Library Reagent Table 12

Structure: HN-X'-B substituent on aniline (3" position) connected via carbonyl to 6' position of 3-(hydroxymethylene)oxindole.

| Library ID # | X' | HN X'B (position) | B |
|---|---|---|---|
| 3-Aa-01 | C=O | 3" | 3-furyl |
| 3-Aa-02 | C=O | 3" | 3-methylfuran-2-yl |
| 3-Aa-03 | C=O | 3" | 5-methoxyfuran-2-yl |
| 3-Aa-04 | C=O | 3" | 5-methylfuran-2-yl |

-continued

Library Reagent Table 12

| Library ID # | X' | HN X'B (position) | B |
|---|---|---|---|
| 3-Aa-05 | C=O | 3" | 3-methoxythiophen-4-yl |
| 3-Aa-06 | C=O | 3" | 5-(methylthio)thiophen-2-yl |
| 3-Aa-07 | C=O | 3" | 5-chlorothiophen-2-yl |
| 3-Aa-08 | C=O | 3" | 4-methylthiophen-2-yl |
| 3-Aa-09 | C=O | 3" | 3-ethoxythiophen-2-yl |
| 3-Aa-10 | C=O | 3" | oxazol-5-yl |
| 3-Aa-11 | C=O | 3" | oxazol-2-yl |
| 3-Aa-12 | C=O | 3" | 3-methylisoxazol-4-yl |
| 3-Aa-13 | C=O | 3" | 2,4-dimethylthiazol-5-yl |

-continued

Library Reagent Table 12

| Library ID # | X' | HN X'B (position) | B |
|---|---|---|---|
| 3-Aa-14 | C=O | 3" | 4-methylthiazol-5-yl |
| 3-Aa-15 | C=O | 3" | 2-methylthiazol-4-yl |
| 3-Aa-16 | C=O | 3" | thiazol-4-yl |
| 3-Aa-17 | C=O | 3" | thiazol-2-yl |
| 3-Aa-18 | C=O | 3" | thiazol-5-yl |
| 3-Aa-19 | C=O | 3" | 1-methylimidazol-2-yl |
| 3-Aa-20 | C=O | 3" | 1-methylimidazol-4-yl |
| 3-Aa-21 | C=O | 3" | 6-methylimidazo[2,1-b]thiazol-5-yl |
| 3-Aa-22 | C=O | 3" | imidazo[2,1-b]thiazol-6-yl |

Library Reagent Table 12

| Library ID # | X' | HN X'B (position) | B |
|---|---|---|---|
| 3-Aa-23 | C=O | 3" | pyrimidin-5-yl |
| 3-Aa-24 | C=O | 3" | 2,5-dimethoxyphenyl |
| 3-Aa-25 | C=O | 3" | 2-(dimethylamino)phenyl |
| 3-Aa-26 | C=O | 3" | 2-methoxypyridin-3-yl |
| 3-Aa-27 | C=O | 3" | 6-methylpyridin-3-yl |
| 3-Aa-28 | C=O | 3" | 2-methylpyridin-3-yl |
| 3-Aa-29 | C=O | 3" | 6-methylpyridin-2-yl |
| 3-Aa-30 | C=O | 3" | 3-methylpyridin-2-yl |

Library Reagent Table 12

| Library ID # | X' | HN X'B (position) | B |
|---|---|---|---|
| 3-Aa-31 | C=O | 3" | 3-chloropyridin-4-yl |
| 3-Aa-32 | C=O | 3" | 5-methylpyridin-3-yl |
| 3-Aa-33 | C=O | 3" | 4-chloropyridin-2-yl |
| 3-Aa-34 | C=O | 3" | pyridazin-4-yl |
| 3-Aa-35 | C=O | 3" | pyrazin-2-yl |
| 3-Aa-36 | C=O | 3" | 5-methylpyrazin-2-yl |
| 3-Ab-37 | C=O | 3" | furan-2-yl |
| 3-Ab-38 | C=O | 3" | 2,5-dimethylfuran-3-yl |

-continued
Library Reagent Table 12
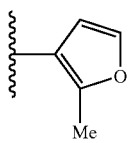
| Library ID # | X' | HN X'B (position) | B |
|---|---|---|---|
| 3-Ab-39 | C=O | 3" | 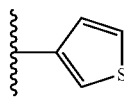 |
| 3-Ab-40 | C=O | 3" | 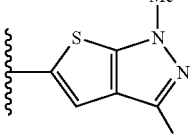 |
| 3-Ab-41 | C=O | 3" | 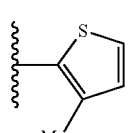 |
| 3-Ab-42 | C=O | 3" | 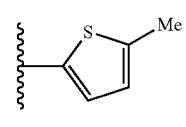 |
| 3-Ab-43 | C=O | 3" | 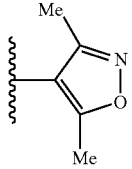 |
| 3-Ab-44 | C=O | 3" | 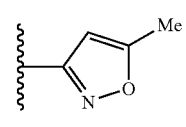 |
| 3-Ab-45 | C=O | 3" | 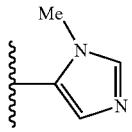 |
| 3-Ab-46 | C=O | 3" | 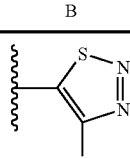 |
-continued
Library Reagent Table 12
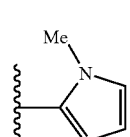
| Library ID # | X' | HN X'B (position) | B |
|---|---|---|---|
| 3-Ab-47 | C=O | 3" | 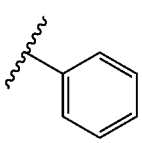 |
| 3-Ab-48 | C=O | 3" | 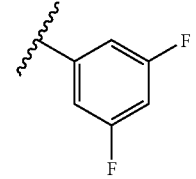 |
| 3-Ab-49 | C=O | 3" | 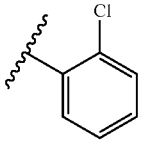 |
| 3-Ab-50 | C=O | 3" | 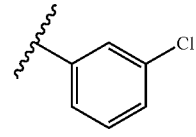 |
| 3-Ab-51 | C=O | 3" | 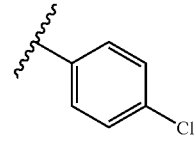 |
| 3-Ab-52 | C=O | 3" | 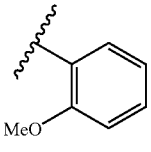 |
| 3-Ab-53 | C=O | 3" | |
| 3-Ab-54 | C=O | 3" | |

-continued
Library Reagent Table 12
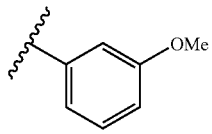
| Library ID # | X' | HN X'B (position) | B |
|---|---|---|---|
| 3-Ab-55 | C=O | 3" | 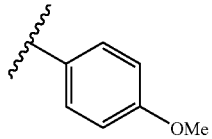 |
| 3-Ab-56 | C=O | 3" | 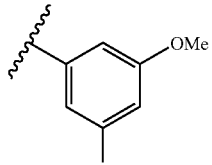 |
| 3-Ab-57 | C=O | 3" | 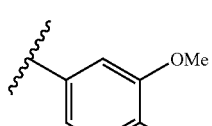 |
| 3-Ab-58 | C=O | 3" | 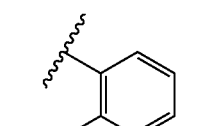 |
| 3-Ab-59 | C=O | 3" | 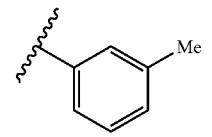 |
| 3-Ab-60 | C=O | 3" | 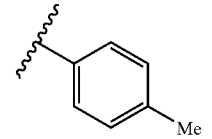 |
| 3-Ab-61 | C=O | 3" | 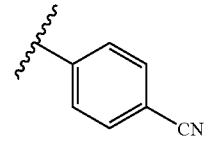 |
| 3-Ab-62 | C=O | 3" | 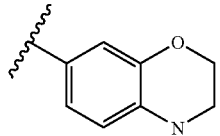 |
-continued
Library Reagent Table 12
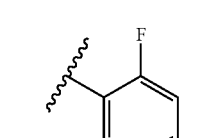
| Library ID # | X' | HN X'B (position) | B |
|---|---|---|---|
| 3-Ab-63 | C=O | 3" | 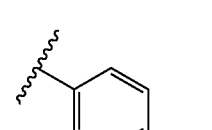 |
| 3-Ab-64 | C=O | 3" | 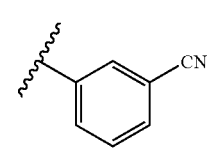 |
| 3-Ab-65 | C=O | 3" | 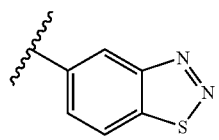 |
| 3-Ab-66 | C=O | 3" | 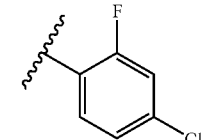 |
| 3-Ab-67 | C=O | 3" | 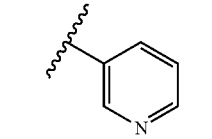 |
| 3-Ab-68 | C=O | 3" | 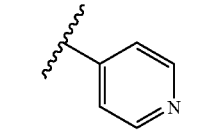 |
| 3-Ab-69 | C=O | 3" | 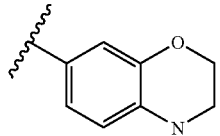 |
| 3-Ab-70 | C=O | 3" | 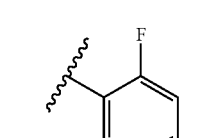 |

-continued

Library Reagent Table 12

| Library ID # | X' | HN X'B (position) | B |
|---|---|---|---|
| 3-Ab-71 | C=O | 3" | 2-chloropyridin-5-yl |
| 3-Ab-72 | C=O | 3" | pyridin-2-yl |
| 3-Bc-24 | -C(O)NH- | 3" | 2,5-dimethoxyphenyl |
| 3-Bc-40 | -C(O)NH- | 3" | thiophen-3-yl |
| 3-Bc-49 | -C(O)NH- | 3" | phenyl |
| 3-Bc-50 | -C(O)NH- | 3" | 3,5-difluorophenyl |
| 3-Bc-51 | -C(O)NH- | 3" | 2-chlorophenyl |
| 3-Bc-52 | -C(O)NH- | 3" | 3-chlorophenyl |

-continued

Library Reagent Table 12

| Library ID # | X' | HN X'B (position) | B |
|---|---|---|---|
| 3-Bc-53 | -C(O)NH- | 3" | 4-chlorophenyl |
| 3-Bc-54 | -C(O)NH- | 3" | 2-methoxyphenyl |
| 3-Bc-55 | -C(O)NH- | 3" | 3-methoxyphenyl |
| 3-Bc-56 | -C(O)NH- | 3" | 4-methoxyphenyl |
| 3-Bc-57 | -C(O)NH- | 3" | 3,5-dimethoxyphenyl |
| 3-Bc-58 | -C(O)NH- | 3" | 3,4-dimethoxyphenyl |
| 3-Bc-59 | -C(O)NH- | 3" | 2-methylphenyl |
| 3-Bc-60 | -C(O)NH- | 3" | 3-methylphenyl |

-continued

Library Reagent Table 12

| Library ID # | X' | HN X'B (position) | B |
|---|---|---|---|
| 3-Bc-61 | -C(O)NH- | 3" | 4-Me-phenyl |
| 3-Bc-62 | -C(O)NH- | 3" | 4-CN-phenyl |
| 3-Bc-65 | -C(O)NH- | 3" | 2,4-diMeO-phenyl |
| 3-Bc-66 | -C(O)NH- | 3" | 3-CN-phenyl |
| 3-Bc-68 | -C(O)NH- | 3" | 2-F,4-Cl-phenyl |
| 3-Bc-73 | -C(O)NH- | 3" | 2-thienyl |
| 3-Bc-74 | -C(O)NH- | 3" | 2,6-diF-phenyl |
| 3-Bc-75 | -C(O)NH- | 3" | 4-NMe₂-phenyl |

-continued

Library Reagent Table 12

| Library ID # | X' | HN X'B (position) | B |
|---|---|---|---|
| 3-Bc-76 | -C(O)NH- | 3" | 2,6-diMeO-phenyl |
| 3-Bd-49 | -C(O)N(Me)- | 3" | phenyl |
| 3-Ce-07 | -S(O)₂- | 3" | 5-Cl-2-thienyl |
| 3-Ce-20 | -S(O)₂- | 3" | 1-Me-imidazol-4-yl |
| 3-Ce-38 | -S(O)₂- | 3" | 2,5-diMe-furan-3-yl |
| 3-Ce-40 | -S(O)₂- | 3" | 3-thienyl |
| 3-Ce-44 | -S(O)₂- | 3" | 3,5-diMe-isoxazol-4-yl |
| 3-Ce-50 | -S(O)₂- | 3" | 3,5-diF-phenyl |

Library Reagent Table 12

(Structure: hydroxymethylene-oxindole with HN-X'-B substituent at 3" position on phenyl ring attached via carbonyl at 6' to oxindole)

| Library ID # | X' | HN X'B (position) | B |
|---|---|---|---|
| 3-Ce-51 | -S(=O)(=O)- | 3" | 2-Cl-phenyl |
| 3-Ce-52 | -S(=O)(=O)- | 3" | 3-Cl-phenyl |
| 3-Ce-53 | -S(=O)(=O)- | 3" | 4-Cl-phenyl |
| 3-Ce-55 | -S(=O)(=O)- | 3" | 3-OMe-phenyl |
| 3-Ce-56 | -S(=O)(=O)- | 3" | 4-OMe-phenyl |
| 3-Ce-59 | -S(=O)(=O)- | 3" | 2-Me-phenyl |
| 3-Ce-60 | -S(=O)(=O)- | 3" | 3-Me-phenyl |
| 3-Ce-61 | -S(=O)(=O)- | 3" | 4-Me-phenyl |
| 3-Ce-62 | -S(=O)(=O)- | 3" | 4-CN-phenyl |
| 3-Ce-66 | -S(=O)(=O)- | 3" | 3-CN-phenyl |
| 3-Ce-73 | -S(=O)(=O)- | 3" | 2-thienyl |
| 3-Ce-77 | -S(=O)(=O)- | 3" | 1,3,5-trimethylpyrazol-4-yl |
| 3-Ce-78 | -S(=O)(=O)- | 3" | 2-CN-phenyl |

The crude products obtained from Step 2, listed in the above table were used directly in Step 3 without further purification.

Step 3: Amine Addition (4-Aa-01 Through 4-Ce-78)

The compounds listed in Library Reagent Table 12 were combined with 4-(4-Methyl-piperazin-1-yl)-phenylamine, see Library ID # 2, Library Reagent Table 3 (in Procedures for the Preparation of Library I), using the method described below to produce the products listed in Library Reagent Table 12 (Examples 209-323):

To each reaction vial (8 mL) was added 100 mg of a crude hydroxymethylene-oxindole from Library Reagent Table 12 (3-Aa-01 through 3-Ce-78), anhydrous THF (3 mL), anhydrous DMF (1 mL), and 4-(4-Methyl-piperazin-1-yl)-phenylamine (70 mg). Each reaction vial was capped and, under an argon atmosphere, was heated maintaining a 70° C. temperature overnight. After removal of the reaction solvents, the crude products listed in Library II Product Table (4-Aa-01 through 4-Ce-78) obtained were submitted for RP-HPLC purification.

Library II Product Table
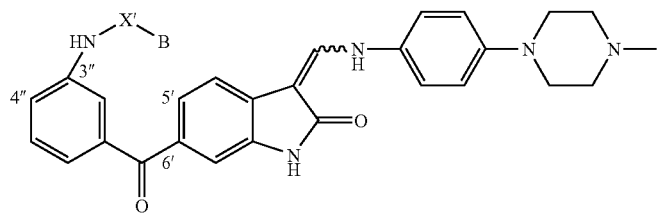
Wherein X'-B is equivalent to X'-B in Formula I
| Example # | Library ID # | X' | HN X'B position | B |
|---|---|---|---|---|
| 209 | 4-Aa-01 | C=O | 3" | 3-furyl |
| 210 | 4-Aa-02 | C=O | 3" | 3-Me-2-furyl |
| 211 | 4-Aa-03 | C=O | 3" | 5-OMe-2-furyl |
| 212 | 4-Aa-04 | C=O | 3" | 5-Me-2-furyl |
| 213 | 4-Aa-05 | C=O | 3" | 4-MeO-3-thienyl |
| 214 | 4-Aa-06 | C=O | 3" | 5-SMe-2-thienyl |
| 215 | 4-Aa-07 | C=O | 3" | 5-Cl-2-thienyl |
| 216 | 4-Aa-08 | C=O | 3" | 4-Me-2-thienyl |
| 217 | 4-Aa-09 | C=O | 3" | 3-EtO-2-thienyl |

-continued
Library II Product Table
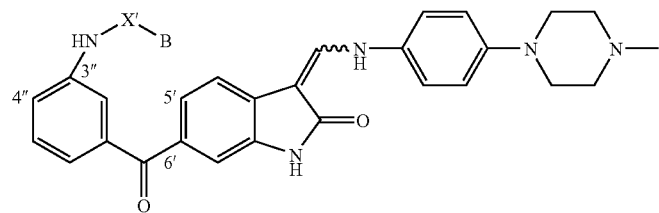
Wherein X'-B is equivalent to X'-B in Formula I
| Example # | Library ID # | X' | HN X'B position | B |
|---|---|---|---|---|
| 218 | 4-Aa-10 | C=O | 3" | oxazol-5-yl |
| 219 | 4-Aa-11 | C=O | 3" | oxazol-2-yl |
| 220 | 4-Aa-12 | C=O | 3" | 3-methylisoxazol-4-yl |
| 221 | 4-Aa-13 | C=O | 3" | 2,4-dimethylthiazol-5-yl |
| 222 | 4-Aa-14 | C=O | 3" | 4-methylthiazol-5-yl |
| 223 | 4-Aa-15 | C=O | 3" | 2-methylthiazol-4-yl |
| 224 | 4-Aa-16 | C=O | 3" | thiazol-4-yl |
| 225 | 4-Aa-17 | C=O | 3" | thiazol-2-yl |
| 226 | 4-Aa-18 | C=O | 3" | thiazol-5-yl |

-continued
Library II Product Table
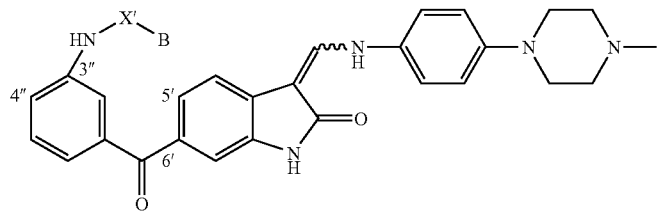
Wherein X'-B is equivalent to X'-B in Formula I
| Example # | Library ID # | X' | HN X'B position | B |
|---|---|---|---|---|
| 227 | 4-Aa-19 | C=O | 3" | 1-methylimidazol-2-yl |
| 228 | 4-Aa-20 | C=O | 3" | 1-methylimidazol-5-yl |
| 229 | 4-Aa-21 | C=O | 3" | 6-methylimidazo[2,1-b]thiazol-5-yl |
| 230 | 4-Aa-22 | C=O | 3" | imidazo[2,1-b]thiazol-6-yl |
| 231 | 4-Aa-23 | C=O | 3" | pyrimidin-5-yl |
| 232 | 4-Aa-24 | C=O | 3" | 2,5-dimethoxyphenyl |
| 233 | 4-Aa-25 | C=O | 3" | 2-(dimethylamino)phenyl |
| 234 | 4-Aa-26 | C=O | 3" | 2-methoxypyridin-3-yl |

-continued
Library II Product Table
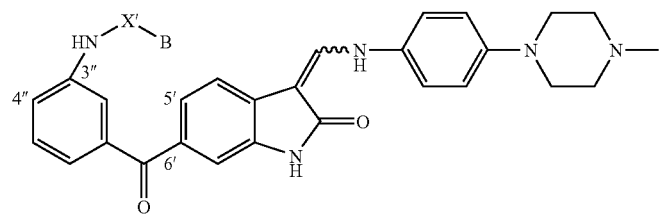
Wherein X'-B is equivalent to X'-B in Formula I
| Example # | Library ID # | X' | HN X'B position | B |
|---|---|---|---|---|
| 235 | 4-Aa-27 | C=O | 3" | 5-(6-methylpyridyl) |
| 236 | 4-Aa-28 | C=O | 3" | 3-(2-methylpyridyl) |
| 237 | 4-Aa-29 | C=O | 3" | 2-(6-methylpyridyl) |
| 238 | 4-Aa-30 | C=O | 3" | 2-(3-methylpyridyl) |
| 239 | 4-Aa-31 | C=O | 3" | 4-(3-chloropyridyl) |
| 240 | 4-Aa-32 | C=O | 3" | 3-(5-methylpyridyl) |
| 241 | 4-Aa-33 | C=O | 3" | 2-(4-chloropyridyl) |

-continued
Library II Product Table
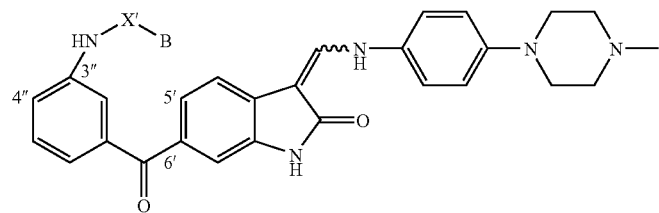
Wherein X'-B is equivalent to X'-B in Formula I
| Example # | Library ID # | X' | HN X'B position | B |
|---|---|---|---|---|
| 242 | 4-Aa-34 | C=O | 3" | pyridazinyl |
| 243 | 4-Aa-35 | C=O | 3" | pyrazinyl |
| 244 | 4-Aa-36 | C=O | 3" | 5-methylpyrazinyl |
| 245 | 4-Ab-37 | C=O | 3" | 2-furyl |
| 246 | 4-Ab-38 | C=O | 3" | 2,5-dimethylfuryl |
| 247 | 4-Ab-39 | C=O | 3" | 2-methylfuryl |
| 248 | 4-Ab-40 | C=O | 3" | 3-thienyl |
| 249 | 4-Ab-41 | C=O | 3" | 1,3-dimethylthieno[2,3-c]pyrazolyl |

-continued
Library II Product Table
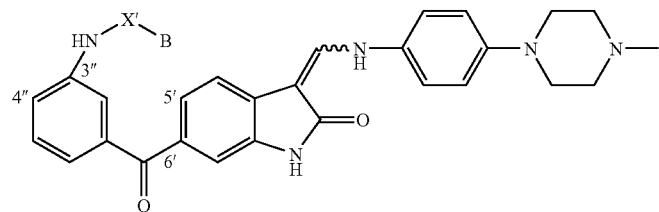
Wherein X'-B is equivalent to X'-B in Formula I
| Example # | Library ID # | X' | HN X'B position | B |
|---|---|---|---|---|
| 250 | 4-Ab-42 | C=O | 3" | 3-methylthiophen-2-yl |
| 251 | 4-Ab-43 | C=O | 3" | 5-methylthiophen-2-yl |
| 252 | 4-Ab-44 | C=O | 3" | 3,5-dimethylisoxazol-4-yl |
| 253 | 4-Ab-45 | C=O | 3" | 5-methylisoxazol-3-yl |
| 254 | 4-Ab-46 | C=O | 3" | 1-methylimidazol-5-yl |
| 255 | 4-Ab-47 | C=O | 3" | 4-methyl-1,2,3-thiadiazol-5-yl |
| 256 | 4-Ab-48 | C=O | 3" | 1-methylpyrrol-2-yl |
| 257 | 4-Ab-49 | C=O | 3" | phenyl |

-continued
Library II Product Table
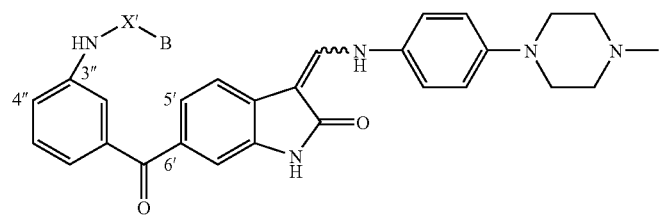
Wherein X'-B is equivalent to X'-B in Formula I
| Example # | Library ID # | X' | HN X'B position | B |
|---|---|---|---|---|
| 258 | 4-Ab-50 | C=O | 3" | 3,5-difluorophenyl |
| 259 | 4-Ab-51 | C=O | 3" | 2-chlorophenyl |
| 260 | 4-Ab-52 | C=O | 3" | 3-chlorophenyl |
| 261 | 4-Ab-53 | C=O | 3" | 4-chlorophenyl |
| 262 | 4-Ab-54 | C=O | 3" | 2-methoxyphenyl |
| 263 | 4-Ab-55 | C=O | 3" | 3-methoxyphenyl |
| 264 | 4-Ab-56 | C=O | 3" | 4-methoxyphenyl |

-continued
Library II Product Table
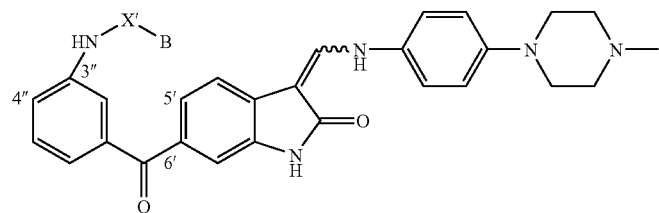
Wherein X'-B is equivalent to X'-B in Formula I
| Example # | Library ID # | X' | HN X'B position | B |
|---|---|---|---|---|
| 265 | 4-Ab-57 | C=O | 3" | 3,5-dimethoxyphenyl |
| 266 | 4-Ab-58 | C=O | 3" | 3,4-dimethoxyphenyl |
| 267 | 4-Ab-59 | C=O | 3" | 2-methylphenyl |
| 268 | 4-Ab-60 | C=O | 3" | 3-methylphenyl |
| 269 | 4-Ab-61 | C=O | 3" | 4-methylphenyl |
| 270 | 4-Ab-62 | C=O | 3" | 4-cyanophenyl |
| 271 | 4-Ab-63 | C=O | 3" | 4-methyl-3,4-dihydro-2H-benzo[1,4]oxazin-7-yl |

-continued
Library II Product Table
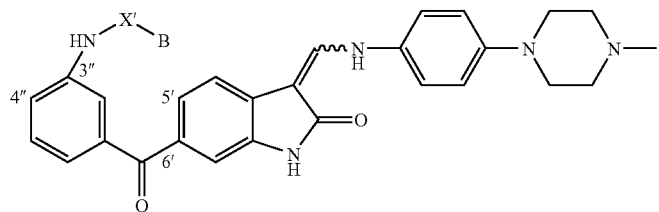
Wherein X'-B is equivalent to X'-B in Formula I
| Example # | Library ID # | X' | HN X'B position | B |
|---|---|---|---|---|
| 272 | 4-Ab-64 | C=O | 3" | 2-F, 6-Cl phenyl |
| 273 | 4-Ab-65 | C=O | 3" | 2,4-dimethoxyphenyl |
| 274 | 4-Ab-66 | C=O | 3" | 3-cyanophenyl |
| 275 | 4-Ab-67 | C=O | 3" | benzothiadiazol-5-yl |
| 276 | 4-Ab-68 | C=O | 3" | 2-F, 4-Cl phenyl |
| 277 | 4-Ab-69 | C=O | 3" | pyridin-3-yl |
| 278 | 4-Ab-70 | C=O | 3" | pyridin-4-yl |
| 279 | 4-Ab-71 | C=O | 3" | 6-chloropyridin-3-yl |

-continued
Library II Product Table
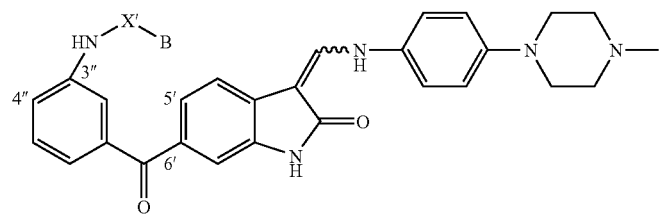
Wherein X'-B is equivalent to X'-B in Formula I
| Example # | Library ID # | X' | HN X'B position | B |
|---|---|---|---|---|
| 280 | 4-Ab-72 | C=O | 3" | 2-pyridyl |
| 281 | 4-Bc-73 | -C(O)-NH- | 3" | 2-thienyl |
| 282 | 4-Bc-40 | -C(O)-NH- | 3" | 3-thienyl |
| 283 | 4-Bc-49 | -C(O)-NH- | 3" | phenyl |
| 284 | 4-Bc-74 | -C(O)-NH- | 3" | 2,6-difluorophenyl |
| 285 | 4-Bc-51 | -C(O)-NH- | 3" | 2-chlorophenyl |
| 286 | 4-Bc-52 | -C(O)-NH- | 3" | 3-chlorophenyl |
| 287 | 4-Bc-53 | -C(O)-NH- | 3" | 4-chlorophenyl |

-continued
Library II Product Table
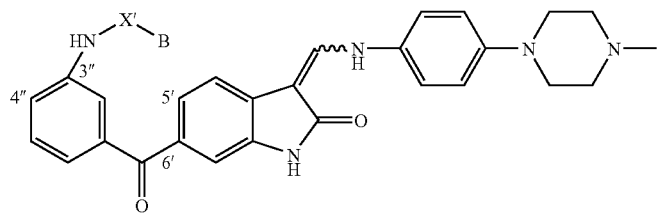
Wherein X'-B is equivalent to X'-B in Formula I
| Example # | Library ID # | X' | HN X'B position | B |
|---|---|---|---|---|
| 288 | 4-Bc-54 | —C(O)NH— | 3" | 2-MeO-phenyl |
| 289 | 4-Bc-55 | —C(O)NH— | 3" | 3-MeO-phenyl |
| 290 | 4-Bc-56 | —C(O)NH— | 3" | 4-MeO-phenyl |
| 291 | 4-Bc-65 | —C(O)NH— | 3" | 3,4-(MeO)₂-phenyl |
| 292 | 4-Bc-59 | —C(O)NH— | 3" | 2-Me-phenyl |
| 293 | 4-Bc-60 | —C(O)NH— | 3" | 3-Me-phenyl |
| 294 | 4-Bc-61 | —C(O)NH— | 3" | 4-Me-phenyl |
| 295 | 4-Bc-66 | —C(O)NH— | 3" | 3-CN-phenyl |

-continued
Library II Product Table
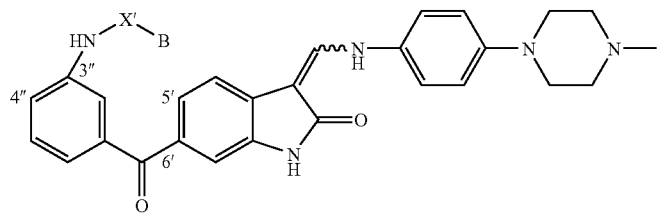
Wherein X'-B is equivalent to X'-B in Formula I
| Example # | Library ID # | X' | HN X'B position | B |
|---|---|---|---|---|
| 296 | 4-Bc-62 | -C(O)NH- | 3" | 4-CN-phenyl |
| 297 | 4-Bc-75 | -C(O)NH- | 3" | 4-NMe₂-phenyl |
| 298 | 4-Bc-50 | -C(O)NH- | 3" | 3,5-difluorophenyl |
| 299 | 4-Bc-57 | -C(O)NH- | 3" | 3,5-dimethoxyphenyl |
| 300 | 4-Bc-58 | -C(O)NH- | 3" | 3,4-dimethoxyphenyl |
| 301 | 4-Bc-68 | -C(O)NH- | 3" | 2-F-4-Cl-phenyl |
| 302 | 4-Bc-24 | -C(O)NH- | 3" | 2,5-dimethoxyphenyl |

-continued
Library II Product Table
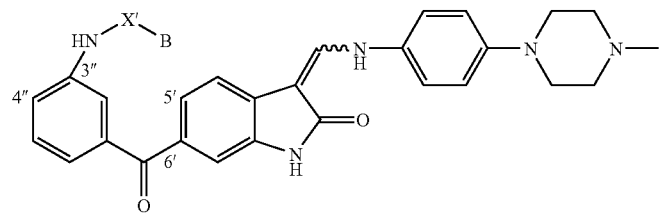
Wherein X'-B is equivalent to X'-B in Formula I
| Example # | Library ID # | X' | HN X'B position | B |
|---|---|---|---|---|
| 303 | 4-Bc-76 | —C(O)NH— | 3" | 2,6-dimethoxyphenyl |
| 304 | 4-Ce-38 | —SO₂— | 3" | 2,5-dimethylfuran-3-yl |
| 305 | 4-Ce-73 | —SO₂— | 3" | thiophen-2-yl |
| 306 | 4-Ce-40 | —SO₂— | 3" | thiophen-3-yl |
| 307 | 4-Ce-07 | —SO₂— | 3" | 5-chlorothiophen-2-yl |
| 308 | 4-Ce-44 | —SO₂— | 3" | 3,5-dimethylisoxazol-4-yl |
| 309 | 4-Ce-20 | —SO₂— | 3" | 1-methylimidazol-5-yl |
| 310 | 4-Ce-77 | —SO₂— | 3" | 1,3,5-trimethylpyrazol-4-yl |

-continued
Library II Product Table
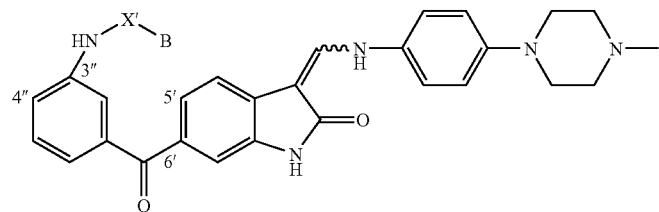
Wherein X'-B is equivalent to X'-B in Formula I
| Example # | Library ID # | X' | HN X'B position | B |
|---|---|---|---|---|
| 311 | 4-Ce-51 | —S(O)₂— | 3" | 2-Cl-C₆H₄ |
| 312 | 4-Ce-52 | —S(O)₂— | 3" | 3-Cl-C₆H₄ |
| 313 | 4-Ce-53 | —S(O)₂— | 3" | 4-Cl-C₆H₄ |
| 314 | 4-Ce-56 | —S(O)₂— | 3" | 4-OMe-C₆H₄ |
| 315 | 4-Ce-61 | —S(O)₂— | 3" | 4-Me-C₆H₄ |
| 316 | 4-Ce-78 | —S(O)₂— | 3" | 2-CN-C₆H₄ |
| 317 | 4-Ce-66 | —S(O)₂— | 3" | 3-CN-C₆H₄ |
| 318 | 4-Ce-62 | —S(O)₂— | 3" | 4-CN-C₆H₄ |

-continued

Library II Product Table

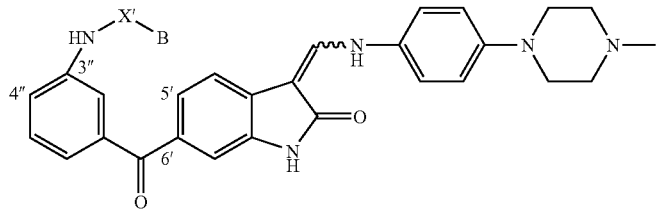

Wherein X'-B is equivalent to X'-B in Formula I

| Example # | Library ID # | X' | HN X'B position | B |
|---|---|---|---|---|
| 319 | 4-Ce-59 | —S(O)₂— | 3" | 2-Me-phenyl |
| 320 | 4-Ce-50 | —S(O)₂— | 3" | 3,5-difluorophenyl |
| 321 | 4-Ce-55 | —S(O)₂— | 3" | 3-OMe-phenyl |
| 322 | 4-Ce-60 | —S(O)₂— | 3" | 3-Me-phenyl |
| 323 | 4-Bd-49 | —C(O)N(Me)— | 3" | phenyl |

Example 324

4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 200 mg, 0.497 mmol) and THF (5 mL). To the resulting solution was added 3-(4-Amino-phenyl)-propionic acid (82.4 mg, 0.499 mmol), and the mixture was stirred for 24 h at 65° C. Subsequently, the reaction mixture was cooled to room temperature and the yellow precipitate that had formed was filtered. The solid collected was washed with ~10 mL of 0° C. iPrOH affording the title compound in 33% yield (0.092 g, 0.163 mmol).

Example 325

2,5-Dimethyl-2H-pyrazole-3-carboxylic acid {3-[3-({4-[3-(4-methyl-piperazin-1-yl)-propylamino]-phenylamino}-methylene)-2-oxo-2,3-dihydro-1H-indole-6-carbonyl]-phenyl}-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]- amide (as prepared in Example 60, 100 mg, 0.249 mmol) and THF (2.5 mL). To the resulting solution was added N-[3-(4-Methyl-piperazin-1-yl)-propyl]-benzene-1,4-diamine (prepared below, 86.2 mg, 0.347 mmol), and the mixture was stirred for 24 h at 65° C. The reaction mixture was cooled to room temperature and then diluted with Hexanes (~40 mL). The black precipitate that formed was removed by filtration and the filtrate was concentrated in vacuo. The crude residue was dissolved in EtOAc (~5 mL) and triturated with Hexane (~50 mL) to give a yellow precipitate. The precipitate was filtered and washed with 0° C. i-prOH (~5 mL) yielding 51% (0.0802 g, 0.127 mmol) of the title compound.

The N-[3-(4-Methyl-piperazin-1-yl)-propyl]-benzene-1,4-diamine is prepared from p-fluoronitrobenzene by using the following multiple step procedure:

Step 1: [3-(4-Methyl-piperazin-1-yl)-propyl]-(4-nitro-phenyl)-amine

A 100 mL round bottom flask was dried in an oven overnight and cooled to room temperature under $Ar_{(g)}$. The flask was charged with fluoronitrobenzene (0.187 mL, 1.77 mmol), 3-(4-Methyl-piperazin-1-yl)-propylamine (0.361 g, 2.30 mmol) and dioxane (9.0 mL). To the resulting solution diisopropyl ethyl amine (0.463 mL, 2.66 mmol) was added dropwise and allowed to stir at 105° C. for 48 h. The mixture was extracted with EtOAc (3x~30 mL), and with brine (2x~30 mL). The combined organic layers were then dried over anhydrous $Na_2SO_4$, filtered and concentrated in vacuo. The crude mixture was then purified over silica (10% MeOH/90% $CHCl_3$) affording a yellow solid (0.365 g, 1.31 mmol, 74% yield).

Step 2: N-[3-(4-Methyl-piperazin-1-yl)-propyl]-benzene-1,4-diamine

A 50 mL round bottom flask was charged with [3-(4-Methyl-piperazin-1-yl)-propyl]-(4-nitro-phenyl)-amine (as prepared in step 1 above; 0.365 g, 1.31 mmol) and EtOH (5 mL). Hydrazine Hydrate (0.286 mL, 9.17 mmol) was then added to the solution. Excess RaNi was then added in dropwise until gas evolution from the solution ceased. The suspension was then allowed to stir for an additional 45 minutes at 65° C. The suspension was cooled to room temperature and then filtered over celite. The celite was washed with MeOH (~20 mL) and the combined organic solutions were then concentrated in vacuo affording pure N-[3-(4-Methyl-piperazin-1-yl)-propyl]-benzene-1,4-diamine as a light brown oil (0.269 g, 1.09 mmol, 83% yield).

Example 326

2,5-Dimethyl-2H-pyrazole-3-carboxylic acid [3-(3-{[4-(2-morpholin-4-yl-ethylamino)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2.5 mL). To the resulting solution was added N-(2-Morpholin-4-yl-ethyl)-benzene-1,4-diamine (prepared below, 77.1 mg, 0.348 mmol), and the mixture was stirred for 24 h at 65° C. The reaction mixture was cooled to room temperature and then diluted with Hexanes (~40 mL). The black precipitate that formed was removed by filtration and the filtrate was concentrated in vacuo. The crude residue was dissolved in EtOAc (~5 mL) and triturated with Hexane (~50 mL) to give a yellow precipitate. The precipitate was filtered and washed with 0° C. i-prOH (~5 mL) yielding 45% (0.0677 g, 0.112 mmol) of the title compound.

The N-(2-Morpholin-4-yl-ethyl)-benzene-1,4-diamine is prepared from p-fluoronitrobenzene by using the following multiple step procedure:

Step 1: (2-Morpholin-4-yl-ethyl)-(4-nitro-phenyl)-amine

A 50 mL round bottom flask was dried in an oven overnight and cooled to room temperature under $Ar_{(g)}$. The flask was charged with fluoronitrobenzene (0.187 mL, 1.77 mmol), 2-Morpholin-4-yl-ethylamine (0.299 g, 2.30 mmol) and dioxane (9.0 mL). To the solution, diisopropyl ethyl amine (0.463 mL, 2.66 mmol) was added dropwise and allowed to stir at 105° C. for 48 h. The mixture was extracted with EtOAc (3x~30 mL), and with brine (2x~30 mL). The combined organic layers were then dried over anhydrous $Na_2SO_4$, filtered and concentrated in vacuo. The crude mixture was then purified over silica (10% MeOH/90% $CHCl_3$) affording (2-Morpholin-4-yl-ethyl)-(4-nitro-phenyl)-amine as a yellow solid (0.315 g, 1.26 mmol, 71% yield).

Step 2:
N-(2-Morpholin-4-yl-ethyl)-benzene-1,4-diamine

A 50 mL round bottom flask was charged with (2-Morpholin-4-yl-ethyl)-(4-nitro-phenyl)-amine (0.315 g, 1.26 mmol) and EtOH (5 mL). Hydrazine Hydrate (0.278 mL, 8.82 mmol) was then added to the solution. Excess RaNi was then added in dropwise until gas evolution ceased. The suspension was then allowed to stir for an additional 1 h at 65° C. The suspension was cooled to room temperature and then was filtered over celite. The celite was washed with MeOH (~20 mL) and the combined organic solutions were then concentrated in vacuo affording pure N-(2-Morpholin-4-yl-ethyl)-benzene-1,4-diamine as a light purple oil (0.220 g, 0.995 mmol, 79% yield).

Example 327

2,5-Dimethyl-2H-pyrazole-3-carboxylic acid [3-(2-oxo-3-{[4-(2-pyrrolidin-1-yl-ethylamino)-phenylamino]-methylene}-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2.5 mL). To the resulting solution was added N-(2-Pyrrolidin-1-yl-ethyl)-benzene-1,4-diamine (prepared below, 70.8 mg, 0.345 mmol), and the mixture was stirred for 24 h at 65° C. The reaction mixture was cooled to room temperature and then diluted with Hexanes (~40 mL). The black precipitate that formed was removed by filtration and the filtrate was concentrated in vacuo. The crude residue was dissolved in EtOAc (~5 mL) and triturated with Hexane (~50 mL) to give a yellow precipitate. The precipitate was filtered and washed with 0° C. i-prOH (~5 mL) yielding 25% (0.0366 g, 0.062 mmol) of the title compound.

The N-(2-Pyrrolidin-1-yl-ethyl)-benzene-1,4-diamine is prepared from p-fluoronitrobenzene by using the following multiple step procedure:

Step 1: (4-Nitro-phenyl)-(2-pyrrolidin-1-yl-ethyl)-amine

A 50 mL round bottom flask was dried in an oven overnight and cooled to room temperature under $Ar_{(g)}$. The flask was charged with fluoronitrobenzene (0.187 mL, 1.77 mmol), 2-Pyrrolidin-1-yl-ethylamine (0.201 g, 2.30 mmol) and dioxane (9.0 mL). To the solution, diisopropyl ethyl amine (0.463 mL, 2.66 mmol) was added dropwise and allowed to stir at 105° C. for 48 h. The mixture was extracted with EtOAc (3×~30 mL), and with brine (2×~30 mL). The combined organic layers were then dried over anhydrous $Na_2SO_4$, filtered and concentrated in vacuo. The crude mixture was then purified over silica (10% MeOH/90% $CHCl_3$) affording (4-Nitro-phenyl)-(2-pyrrolidin-1-yl-ethyl)-amine as a yellow solid (0.352 g, 1.50 mmol, 85% yield).

Step 2: N-(2-Pyrrolidin-1-yl-ethyl)-benzene-1,4-diamine

A 25 mL round bottom flask was charged with (4-Nitro-phenyl)-(2-pyrrolidin-1-yl-ethyl)-amine (0.352 g, 1.50 mmol) and EtOH (5 mL). Hydrazine Hydrate (0.326 mL, 10.5 mmol) was then added to the solution. Excess RaNi was then added in dropwise until gas evolution ceased. The suspension was then allowed to stir for an additional 1 h at 65° C. The suspension was cooled to room temperature and then was filtered over celite. The celite was washed with MeOH (~20 mL) and the combined organic solutions were then concentrated in vacuo affording pure N-(2-Pyrrolidin-1-yl-ethyl)-benzene-1,4-diamine as a light purple oil (0.219 g, 1.07 mmol, 71% yield).

Example 328

5-Chloro-1-methyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 5-Chloro-1-methyl-1H-pyrazole-4-carboxylic acid [3-(3-hydroxymethylene-2-oxo-2,3-dihydro-1H-indole-6-carbonyl)-phenyl]-amide (prepared below, 100 mg, 0.237 mmol) and THF (2.5 mL). To the resulting solution was added 4-(4-methyl-piperazin-1-yl)-phenylamine (59.2 mg, 0.309 mmol), and the mixture was stirred for 24 h at 65° C. Subsequently, the reaction mixture was cooled to room temperature and diluted with EtOAc (5 mL) and Hexanes (40 mL). The precipitate that formed was then filtered and washed with acetone (5 mL) to afford the title compound in 71% yield (0.100 g, 0.168 mmol).

The 5-Chloro-1-methyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 5-Chloro-1-methyl-1H-pyrazole-4-carboxylic acid [3-(2-oxo-2,3-dihydro-1H-indole-6-carbonyl)-phenyl]-amide A dry flask was charged with 5-Chloro-1-methyl-1H-pyrazole-4-carbonyl chloride (0.200 g, 1.1 mmol) was dissolved in THF (10 mL). 6-(3-Amino-benzoyl)-1,3-dihydro-indol-2-one (as prepared in Example 40, 0.178 g, 0.706 mmol) was added to the THF solution of the acid chloride, and the mixture was allowed to reflux for overnight. The reaction mixture was then allowed to cool to room temperature. The room temperature reaction mixture was filtered. The solid residue was washed with 0° C. THF (10 mL) to afford the 5-Chloro-1-methyl-1H-pyrazole-4-carboxylic acid [3-(2-oxo-2,3-dihydro-1H-indole-6-carbonyl)-phenyl]-amide as a solid (0.199 g, 0.504 mmol, 71%).

Step 2: 5-Chloro-1-methyl-1H-pyrazole-4-carboxylic acid [3-(3-hydroxymethylene-2-oxo-2,3-dihydro-1H-indole-6-carbonyl)-phenyl]-amide 5-Chloro-1-methyl-1H-pyrazole-4-carboxylic acid [3-(2-oxo-2,3-dihydro-1H-indole-6-carbonyl)-phenyl]-amide (0.150 g, 0.380 mmol) and ethyl formate (0.090 mL, 1.12 mmol) were dissolved in anhydrous ethanol (4 mL). The resulting solution was treated in dropwise fashion with a 21 wt % solution of sodium ethoxide in ethanol (0.7 mL, 1.9 mmol). This reaction mixture was heated at 78° C. for 0.5 h, producing a black oil. Subsequently, the reaction mixture was cooled to room temperature, and then the reaction pH was adjusted to pH 1 with dropwise addition of 1M $HCl_{(aq)}$ causing the formation of a tan precipitate. The suspension was filtered and the solids were subsequently washed with 0° C. EtOH to afford the pure 5-Chloro-1-methyl-1H-pyrazole-4-carboxylic acid [3-(3-hydroxymethylene-2-oxo-2,3-dihydro-1H-indole-6-carbonyl)-phenyl]-amide (0.105 g, 0.248 mmol, 65%).

Example 329

2,5-Dimethyl-2H-pyrazole-3-carboxylic acid (3-{3-[(4-aminomethyl-phenylamino)-methylene]-2-oxo-2,3-dihydro-1H-indole-6-carbonyl}-phenyl)-amide A dry 100 mL round bottom flask equipped with an $Ar_{(g)}$ inlet was charged with {4-[(6-{3-[(2,5-Dimethyl-2H-pyrazole-3-carbonyl)-amino]-benzoyl}-2-oxo-1,2-dihydro-indol-3-ylidenemethyl)-amino]-benzyl}-carbamic acid tert-butyl ester (as prepared in Example 203, 0.113 g, 0.186 mmol) and $CH_2Cl_2$ (0.622 mL). The resulting solution was cooled to 0° C. in an ice bath. TFA (0.015 mL) was then added and the reaction mixture was allowed to stir at 0° C. for 30 minutes after which the bath was removed and the reaction was allowed to stir at room temperature for an additional 1 h. Subsequently the reaction mixture was neutralized with saturated $NaHCO_{3(aq)}$ and then washed with EtOAc (3×20 mL). The combined organic layer was then dried over anhydrous $Na_2SO_4$, filtered and concentrated in vacuo. The crude residue was chromatographed over silica (5% MeOH/95% $CHCl_3$) to afford pure 2,5-Dimethyl-2H-pyrazole-3-carboxylic acid (3-{3-[(4-aminomethyl-phenylamino)-methylene]-2-oxo-2,3-dihydro-1H-indole-6-carbonyl}-phenyl)-amide in 61% yield (0.057 g, 0.113 mmol).

Example 330

2,5-Dimethyl-2H-pyrazole-3-carboxylic acid [3-(3-{[4-(2-hydroxy-ethyl)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 300 mg, 0.746 mmol) and THF (7.5 mL). To the resulting solution was added 2-(4-amino-phenyl)-ethanol (120 mg, 0.875 mmol), and the mixture was stirred for 24 h at 65° C. Subsequently, the reaction mixture was cooled to room temperature and the resulting suspension was filtered. The solids collected were washed with 0° C. iPrOH (5 mL) and set aside. The filtrate was concentrated in vacuo and the residue obtained was dissolved in EtOAc (5 mL). The resulting solution was triturated with Hexanes (~50 mL) to yield a precipitate. This precipitate was then filtered and washed with 0° C. iPrOH (5 mL). The solids collected were combined with those previously set aside to afford the title compound in 20% yield (0.078 g, 0.149 mmol).

Example 331

2,5-Dimethyl-2H-pyrazole-3-carboxylic acid (3-{3-[(4-hydroxymethyl-phenylamino)-methylene]-2-oxo-2,3-dihydro-1H-indole-6-carbonyl}-phenyl)-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 300 mg, 0.746 mmol) and THF (7.5 mL). To the resulting solution was added (4-aminophenyl)-methanol (133 mg, 0.955 mmol), and the mixture was stirred for 24 h at 65° C. Subsequently, the reaction mixture was cooled to room temperature and the resulting suspension was filtered. The solids collected were washed with 0° C. iPrOH (5 mL) and set aside. The filtrate was concentrated in vacuo and the residue obtained was dissolved in EtOAc (5 mL). The resulting solution was triturated with Hexanes (~50 mL) to yield a precipitate. This precipitate was then filtered and washed with 0° C. iPrOH (5 mL). The solids collected were combined with those previously set aside to afford the title compound in 24% yield (0.091 g, 0.179 mmol).

Example 332

Dimethylamino-acetic acid 4-[(6-{3-[(2,5-dimethyl-2H-pyrazole-3-carbonyl)-amino]-benzoyl}-2-oxo-1,2-dihydro-indol-3-ylidenemethyl)-amino]-benzyl ester In a dry 50 mL round bottomed flask, 2,5-Dimethyl-2H-pyrazole-3-carboxylic acid (3-{3-[(4-hydroxymethyl-phenylamino)-methylene]-2-oxo-2,3-dihydro-1H-indole-6-carbonyl}-phenyl)-amide (as prepared in Example 331, 0.020 mg, 0.039 mmol) was dissolved in DMF (1 mL), under $Ar_{(g)}$. Dimethylaminoacetyl chloride hydrochloride (9.32 mg, 0.059 mmol) was then added followed by triethylamine (0.016 mL, 0.117 mmol). The mixture was stirred at room temperature for 2 hours after which the reaction mixture was partitioned between EtOAc (~5 mL) and brine (~5 mL). The organic layer was extracted with brine (3×5 mL). The organic layers were combined and then concentrated in vacuo. The crude residue was then chromatographed over silica (EtOAc/MeOH gradiant was used starting from 1% MeOH up to 5% MeOH). The pure product was isolated as a yellow solid (15.5 mg, 0.026 mmol, 67%).

Example 333

2,5-Dimethyl-2H-pyrazole-3-carboxylic acid [3-(3-{[4-(4-hydroxy-piperidin-1-yl)-phenylamino]-methylene}-2-oxo-2,3-dihydro-1H-indole-6-carbonyl)-phenyl]-amide A small screw cap test tube was charged with 2,5-Dimethyl-2H-pyrazole-3-carboxylic acid [3-(3-hydroxymethylene-2-oxo-2,3-dihydro-1H-indole-6-carbonyl)-phenyl]-amide (as prepared in Example 60, 100 mg, 0.249 mmol) and THF (2.5 mL). To the resulting solution was 1-(4-aminophenyl)-piperidin-4-ol (prepared below, 48.3 mg, 0.251 mmol), and the mixture was stirred for 24 h at 65° C. Subsequently, the reaction mixture was cooled to room temperature and diluted with EtOAc (5 mL) and Hexanes (40 mL). The precipitate that formed was then filtered and washed with 0° C. iPrOH (5 mL) to afford the title compound in 24% yield (0.034 g, 0.06 mmol).

The 1-(4-Amino-phenyl)-piperidin-4-ol is prepared from p-fluoronitrobenzene by using the following multiple step procedure:

Step 1: 1-(4-Nitro-phenyl)-piperidin-4-ol

A 100 mL round bottom flask was dried in an oven overnight and cooled to room temperature under $Ar_{(g)}$. The flask was charged with fluoronitrobenzene (0.500 mL, 4.71 mmol), Piperidin-4-ol (0.619 g, 2.30 mmol) and dioxane (9.0 mL). To the resulting solution, diisopropyl ethyl amine (0.463 mL, 6.12 mmol) was added dropwise, and the reaction was allowed to stir at 105° C. for 48 h. The mixture was extracted with EtOAc (3×~50 mL), and brine (2×~50 mL). The combined organic layers were then dried over anhydrous $Na_2SO_4$, filtered and concentrated in vacuo. The crude mixture was then purified over silica (10% MeOH/90% $CHCl_3$) affording a yellow solid (0.742 g, 3.34 mmol, 71% yield).

Step 2: 1-(4-Amino-phenyl)-piperidin-4-ol

A 50 mL round bottom flask was charged with [3-(4-Methyl-piperazin-1-yl)-propyl]-(4-nitro-phenyl)-amine (0.742 g, 3.34 mmol) and dissolved into EtOH (20 mL). Hydrazine Hydrate (0.642 mL, 20.04 mmol) was then added. Excess RaNi was then added in dropwise until the solution stopped bubbling. The suspension was then allowed to stir for an additional 15 minutes at 65° C. The suspension was cooled to rt and then filtered over celite. The celite was washed with MeOH (~20 mL) and the combined organic solutions were then concentrated in vacuo. The crude oil was then purified over silica (3% Chloroform/Hexanes to 10% Chloroform/Hexanes) affording pure 1-(4-amino-phenyl)-piperidin-4-ol as a light brown oil in 51% yield (0.327 g, 1.71 mmol).

Example 334

2,5-Dimethyl-2H-pyrazole-3-carboxylic acid (3-{3-[(4-hydroxycarbamoyl-phenylamino)-methylene]-2-oxo-2,3-dihydro-1H-indole-6-carbonyl}-phenyl)-amide In a dry 25 mL round bottomed flask under $Ar_{(g)}$, 4-[(6-{3-[(2,5-Dimethyl-2H-pyrazole-3-carbonyl)-amino]-benzoyl}-2-oxo-1,2-dihydro-indol-3-ylidenemethyl)-amino]-benzoic acid (as prepared in Example 77, 50 mg, 0.094 mmol) was dissolved in DMF (1 mL). The resulting solution was treated sequentially with 1,1'-Carbonyldiimidazole (19.9 mg, 0.122 mmol) then triethylamine (0.039 mL, 0.282 mmol). After allowing the reaction mixture to stir for 45 min, O-hydroxylamine hydrochloride (11.4 mg, 0.188 mmol) was added, and the resulting reaction mixture was stirred at room temperature for 2 h. The crude reaction mixture was partitioned between EtOAc (~3 mL), sat. $NaHCO_3$ (~3 mL) and Brine (~3 mL). The organics were dried over anhydrous $Na_2SO_4$ and then concentrated in vacuo. The crude residue was then chromatographed over silica (EtOAc/MeOH gradient was used starting from 1% MeOH up to 5% MeOH). Pure 2,5-Dimethyl-2H- pyrazole-3-carboxylic acid (3-{3-[(4-hydroxycarbamoyl-phenylamino)-methylene]-2-oxo-2,3-dihydro-1H-indole-6-carbonyl}-phenyl)-amide was isolated as a yellow solid in 61% yield (30.7 mg, 0.057 mmol).

Example 335

Isopropyl 4-[4-({(Z)-[6-(3-{[(1,3-dimethyl-1H-pyrazol-5-yl)carbonyl]amino}benzoyl)-2-oxo-1,2-dihydro-3H-indol-3-ylidene]methyl}amino)phenyl]butanoate In a dry 50 mL round bottomed flask, 4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid (as prepared in Example 324, 50 mg, 0.088 mmol) was dissolved into DMF (1 mL), under $Ar_{(g)}$. PyBOP (60 mg, 0.115 mmol) was then added followed by triethyl amine (0.04 mL, 0.266 mmol) and O-methylhydroxylamine hydrochloride (22 mg, 0.264 mmol). The mixture was stirred at room temperature for 2 h after which the reaction mixture was partitioned between EtOAc (~10 mL) and brine (~10 mL). The organic layer was extracted with brine (3×~10 mL). The organic layers were combined and then concentrated in vacuo. The crude mixture was then chromatographed over silica (EtOAc/MeOH gradiant was used starting from 1% MeOH up to 5% MeOH). The title compound was isolated in pure form as a yellow solid (27.8 mg, 0.046 mmol, 53%).

Example 336

2,5-Dimethyl-2H-pyrazole-3-carboxylic acid (3-{3-[1-[4-(3-methoxycarbamoyl-propyl)-phenylamino]-meth-(Z)-ylidene]-2-oxo-2,3-dihydro-1H-indole-6-carbonyl}-phenyl)-amide In a dry 50 mL round bottomed flask, 4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid (as prepared in Example 324, 100 mg, 0.176 mmol) was dissolved into dioxane (2 mL), under $Ar_{(g)}$. Ethyl chloroformate (20 mg, 0.264 mmol) was then added and the reaction was allowed to stir at room temperature for 4 hours. Isopropanol (1 mL) was then added to the reaction mixture and allowed to stir for an additional 2 hours. The reaction mixture was partitioned between EtOAc (~25 mL) and brine (~25 mL). The organic layer was extracted with brine (3×~25 mL). The organic layers were combined and then concentrated in vacuo. The crude mixture was then chromatographed over silica (EtOAc/MeOH gradiant was used starting from 1% MeOH up to 5% MeOH). The pure 2,5-Dimethyl-2H-pyrazole-3-carboxylic acid (3-{3-[1-[4-(3-methoxycarbamoyl-propyl)-phenylamino]-meth-(Z)-ylidene]-2-oxo-2,3-dihydro-1H-indole-6-carbonyl}-phenyl)-amide was isolated as a yellow solid (48.2 mg, 0.079 mmol, 45%).

Example 337

2-Ethyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-Ethyl-2H-pyrazole-3-carboxylic acid [3-(3-hydroxymethylene-2-oxo-2,3-dihydro-1H-indole-6-carbonyl)-phenyl]-amide (prepared below, 100 mg, 0.249 mmol) and THF (2.5 mL). To the resulting solution was added 4-(4-methyl-piperazin-1-yl)-phenylamine (47.9 mg, 0.250 mmol), and the mixture was stirred for 24 h at 65° C. Subsequently, the reaction mixture was cooled to room temperature and concentrated in vacuo. The solid residue was redissolved in EtOAc (~5 mL) and Hexane (~40 mL) was added to the solution. The precipitate that formed was collected by filtration and washed with 0° C. iPrOH (10 mL) to afford the title compound in 36% yield (0.0515 g, 0.089 mmol).

The 2-Ethyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-Ethyl-2H-pyrazole-3-carboxylic acid [3-(2-oxo-2,3-dihydro-1H-indole-6-carbonyl)-phenyl]-amide A dry flask was charged with 2-Ethyl-2H-pyrazole-3-carboxylic acid (0.111 g, 0.792 mmol) and thionyl chloride (5 mL) and allowed to stir at 79° C. for 3 h. The thionyl chloride was then removed by concentration in vacuo. The crude acid chloride was cooled to room temperature, and then dissolved in THF (8 mL). 6-(3-Amino-benzoyl)-1,3-dihydro-indol-2-one (as prepared in Example 40, 0.200 g, 0.793 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 2-Ethyl-2H-pyrazole-3-carboxylic acid [3-(2-oxo-2,3-dihydro-1H-indole-6-carbonyl)-phenyl]-amide as a solid (0.200 g, 0.534 mmol, 68%).

Step 2: 2-Ethyl-2H-pyrazole-3-carboxylic acid [3-(3-hydroxymethylene-2-oxo-2,3-dihydro-1H-indole-6-carbonyl)-phenyl]-amide 2-Ethyl-2H-pyrazole-3-carboxylic acid [3-(2-oxo-2,3-dihydro-1H-indole-6-carbonyl)-phenyl]-amide (0.200 g, 0.534 mmol) and ethyl formate (0.13 mL, 1.6 mmol) were dissolved in anhydrous ethanol (5 mL). The resulting solution was treated in dropwise fashion with a 21 wt % solution of sodium ethoxide in ethanol (1.0 mL, 2.68 mmol). This reaction mixture was heated at 78° C. for 0.5 h, producing a black oil. Subsequently, the reaction mixture was cooled to room temperature, and then the reaction pH was adjusted to pH 1 with dropwise addition of 1M $HCl_{(aq)}$ causing the formation of a tan precipitate. The suspension was filtered and the tan solid collected was washed with 0° C. EtOH yielding the pure 2-Ethyl-2H-pyrazole-3-carboxylic acid [3-(3-hydroxymethylene-2-oxo-2,3-dihydro-1H-indole-6-carbonyl)-phenyl]-amide (0.1247 g, 0.310 mmol, 58%).

Example 338

2-Phenyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-Phenyl-2H-pyrazole-3-carboxylic acid [3-(3-hydroxymethylene-2-oxo-2,3-dihydro-1H-indole-6-carbonyl)-phenyl]-amide (prepared below, 100 mg, 0.222 mmol) and THF (2.5 mL). To the resulting solution was added 4-(4-methyl-piperazin-1-yl)-phenylamine (42.2 mg, 0.221 mmol), and the mixture was stirred for 24 h at 65° C. Subsequently, the reaction mixture was cooled to room temperature and concentrated in vacuo. The solid residue was redissolved in EtOAc (5 mL) and Hexane (40 mL) was added to the solution. The precipitate that formed was collected by filtration and washed with 0° C. iPrOH (10 mL) to afford the title compound in 81% yield (0.112 g, 0.180 mmol).

The 2-Phenyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-Phenyl-2H-pyrazole-3-carboxylic acid [3-(2-oxo-2,3-dihydro-1H-indole-6-carbonyl)-phenyl]-amide A dry flask was charged with 2-Phenyl-2H-pyrazole-3-carbonyl chloride (0.164 g, 0.794 mmol) and THF (8 mL). 6-(3-Amino-benzoyl)-1,3-dihydro-indol-2-one (as prepared in Example 40, 0.200 g, 0.793 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 2-Phenyl-2H-pyrazole-3-carboxylic acid [3-(2-oxo-2,3-dihydro-1H-indole-6-carbonyl)-phenyl]-amide as a solid (0.255 g, 0.600 mmol, 76%).

Step 2: 2-Phenyl-2H-pyrazole-3-carboxylic acid [3-(3-hydroxymethylene-2-oxo-2,3-dihydro-1H-indole-6-carbonyl)-phenyl]-amide 2-Phenyl-2H-pyrazole-3-carboxylic acid [3-(2-oxo-2,3-dihydro-1H-indole-6-carbonyl)-phenyl]-amide (0.250 g, 0.5918 mmol) and ethyl formate (0.142 mL, 1.77 mmol) were dissolved in anhydrous ethanol (6 mL). The resulting solution was treated in dropwise fashion with a 21 wt % solution of sodium ethoxide in ethanol (1.1 mL, 2.95 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a gray precipitate. The suspension was filtered and the gray solid collected was washed with 0° C. EtOH yielding the pure 2-Phenyl-2H-pyrazole-3-carboxylic acid [3-(3-hydroxymethylene-2-oxo-2,3-dihydro-1H-indole-6-carbonyl)-phenyl]-amide (0.189 g, 0.420 mmol, 71%).

Example 339

1-Ethyl-3-methyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 1-Ethyl-3-methyl-1H-pyrazole-4-carboxylic acid [3-(3-hydroxymethylene-2-oxo-2,3-dihydro-1H-indole-6-carbonyl)-phenyl]-amide (prepared below, 100 mg, 0.2401 mmol) and THF (2.5 mL). To the resulting solution was added 4-(4-methyl-piperazin-1-yl)-phenylamine (45.7 mg, 0.240 mmol), and the mixture was stirred for 24 h at 65° C. Subsequently, the reaction mixture was cooled to room temperature and concentrated in vacuo. The solid residue was redissolved in EtOAc (~5 mL) and Hexane (~40 mL) was added to the solution. The precipitate that formed was collected by filtration and washed with 0° C. iPrOH (10 mL) to afford the title compound in 58% yield (0.0821 g, 0.139 mmol).

1-Ethyl-3-methyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-Phenyl-2H-pyrazole-3-carboxylic acid [3-(2-oxo-2,3-dihydro-1H-indole-6-carbonyl)-phenyl]-amide A dry flask was charged with 1-Ethyl-3-methyl-1H-pyrazole-4-carboxylic acid (0.122 g, 0.791 mmol) and thionyl chloride (5 mL) and allowed to stir at 79° C. for 3 h. The thionyl chloride was then removed by concentration in vacuo. The crude acid chloride was cooled to room temperature, and then dissolved in THF (8 mL). 6-(3-Amino-benzoyl)-1,3-dihydro-indol-2-one (as prepared in Example 40, 0.200 g, 0.793 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 2-Phenyl-2H-pyrazole-3-carboxylic acid [3-(2-oxo-2,3-dihydro-1H-indole-6-carbonyl)-phenyl]-amide as a solid (0.249 g, 0.640 mmol, 81%).

Step 2: 1-Ethyl-3-methyl-1H-pyrazole-4-carboxylic acid [3-(3-hydroxymethylene-2-oxo-2,3-dihydro-1H-indole-6-carbonyl)-phenyl]-amide 2-Phenyl-2H-pyrazole-3-carboxylic acid [3-(2-oxo-2,3-dihydro-1H-indole-6-carbonyl)-phenyl]-amide (0.240 g, 0.6179 mmol) and ethyl formate (0.148 mL, 1.84 mmol) were dissolved in anhydrous ethanol (6 mL). The resulting solution was treated in dropwise fashion with a 21 wt % solution of sodium ethoxide in ethanol (1.2 mL, 3.21 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a tan precipitate. The suspension was filtered and the tan solid collected was washed with 0° C. EtOH yielding the pure 1-Ethyl-3-methyl-1H-pyrazole-4-carboxylic acid [3-(3-hydroxymethylene-2-oxo-2,3-dihydro-1H-indole-6-carbonyl)-phenyl]-amide (0.2084 g, 0.500 mmol, 81%).

Example 340

1,3,5-Trimethyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 1,3,5-Trimethyl-1H-pyrazole-4-carboxylic acid [3-(3-hydroxymethylene-2-oxo-2,3-dihydro-1H-indole-6-carbonyl)-phenyl]-amide (prepared below, 100 mg, 0.2401 mmol) and THF (2.5 mL). To the resulting solution was added 4-(4-methyl-piperazin-1-yl)-phenylamine (45.9 mg, 0.240 mmol), and the mixture was stirred for 24 h at 65° C. Subsequently, the reaction mixture was cooled to room temperature and concentrated in vacuo. The solid residue was redissolved in EtOAc (~5 mL) and Hexane (~40 mL) was added to the solution. The precipitate that formed was collected by filtration and washed with 0° C. iPrOH (10 mL) to afford the title compound in 59% yield (0.0835 g, 0.142 mmol).

1,3,5-Trimethyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 1,3,5-Trimethyl-1H-pyrazole-4-carboxylic acid [3-(2-oxo-2,3-dihydro-1H-indole-6-carbonyl)-phenyl]-amide A dry flask was charged with 1,3,5-Trimethyl-1H-pyrazole-4-carboxylic acid (0.122 g, 0.791 mmol) and thionyl chloride (5 mL) and allowed to stir at 79° C. for 3 h. The thionyl chloride was then removed by concentration in vacuo. The crude acid chloride was cooled to room temperature, and then dissolved in THF (8 mL). 6-(3-Amino-benzoyl)-1,3-dihydro-indol-2-one (as prepared in Example 40, 0.200 g, 0.793 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 1,3,5-Trimethyl-1H-pyrazole-4-carboxylic acid [3-(2-oxo-2,3-dihydro-1H-indole-6-carbonyl)-phenyl]-amide as a solid (0.169 g, 0.440 mmol, 56%).

Step 2: 1,3,5-Trimethyl-1H-pyrazole-4-carboxylic acid [3-(3-hydroxymethylene-2-oxo-2,3-dihydro-1H-indole-6-carbonyl)-phenyl]-amide 1,3,5-Trimethyl-1H-pyrazole-4-carboxylic acid [3-(2-oxo-2,3-dihydro-1H-indole-6-carbonyl)-phenyl]-amide (0.150 g, 0.3862 mmol) and ethyl formate (0.093 mL, 1.16 mmol) were dissolved in anhydrous ethanol (4 mL). The resulting solution was treated in dropwise fashion with a 21 wt % solution of sodium ethoxide in ethanol (0.72 mL, 1.93 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a tan precipitate. The suspension was filtered and the tan solid collected was washed with 0° C. EtOH yielding the pure 1,3,5-Trimethyl-1H-pyrazole-4-carboxylic acid [3-(3-hydroxymethylene-2-oxo-2,3-dihydro-1H-indole-6-carbonyl)-phenyl]-amide (0.1271 g, 0.305 mmol, 79%).

Example 341

1-tert-Butyl-5-methyl-1H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 1-tert-Butyl-5-methyl-1H-pyrazole-3-carboxylic acid [3-(3-hydroxymethylene-2-oxo-2,3-dihydro-1H-indole-6-carbonyl)-phenyl]-amide (prepared below, 179 mg, 0.4027 mmol) and THF (4 mL). To the resulting solution was added 4-(4-methyl-piperazin-1-yl)-phenylamine (77.2 mg, 0.404 mmol), and the mixture was stirred for 24 h at 65° C. Subsequently, the reaction mixture was cooled to room temperature and concentrated in vacuo. The solid residue was redissolved in EtOAc (~5 mL) and Hexane (~40 mL) was added to the solution. The precipitate that formed was collected by filtration and washed with 0° C. iPrOH (10 mL) to afford the title compound in 38% yield (0.0945 g, 0.153 mmol).

The 1-tert-Butyl-5-methyl-1H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 1-tert-Butyl-5-methyl-1H-pyrazole-3-carboxylic acid [3-(2-oxo-2,3-dihydro-1H-indole-6-carbonyl)-phenyl]-amide A dry flask was charged with 1-tert-Butyl-5-methyl-1H-pyrazole-3-carbonyl chloride (0.207 g, 1.032 mmol) and THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 1-tert-Butyl-5-methyl-1H-pyrazole-3-carboxylic acid [3-(2-oxo-2,3-dihydro-1H-indole-6-carbonyl)-phenyl]-amide as a solid (0.206 g, 0.490 mmol, 48%).

Step 2: 1-tert-Butyl-5-methyl-1H-pyrazole-3-carboxylic acid [3-(3-hydroxymethylene-2-oxo-2,3-dihydro-1H-indole-6-carbonyl)-phenyl]-amide 1-tert-Butyl-5-methyl-1H-pyrazole-3-carboxylic acid [3-(2-oxo-2,3-dihydro-1H-indole-6-carbonyl)-phenyl]-amide (0.200 g, 0.4802 mmol) and ethyl formate (0.115 mL, 1.43 mmol) were dissolved in anhydrous ethanol (5 mL). The resulting solution was treated in dropwise fashion with a 21 wt % solution of sodium ethoxide in ethanol (0.895 mL, 2.4 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a brown precipitate. The suspension was filtered and the brown solid collected was washed with 0° C. EtOH yielding the pure 1-tert-Butyl-5-methyl-1H-pyrazole-3-carboxylic acid [3-(3-hydroxymethylene-2-oxo-2,3-dihydro-1H-indole-6-carbonyl)-phenyl]-amide (0.1814 g, 0.408 mmol, 85%).

Example 342

4-Chloro-1-ethyl-1H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 4-Chloro-1-ethyl-1H-pyrazole-3-carboxylic acid [3-(3-hydroxymethylene-2-oxo-2,3-dihydro-1H-indole-6-carbonyl)-phenyl]-amide (prepared below, 85 mg, 0.1946 mmol) and THF (2.0 mL). To the resulting solution was added 4-(4-methyl-piperazin-1-yl)-phenylamine (37.3 mg, 0.195 mmol), and the mixture was stirred for 24 h at 65° C. Subsequently, the reaction mixture was cooled to room temperature and concentrated in vacuo. The solid residue was redissolved in EtOAc (~5 mL) and Hexane (~50 mL) was added to the solution. The precipitate that formed was collected by filtration and washed with acetone (10 mL) to afford the title compound in 43% yield (0.051 g, 0.084 mmol).

4-Chloro-1-ethyl-1H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 4-Chloro-1-ethyl-1H-pyrazole-3-carboxylic acid [3-(2-oxo-2,3-dihydro-1H-indole-6-carbonyl)-phenyl]-amide A dry flask was charged with 4-Chloro-1-ethyl-1H-pyrazole-3-carboxylic acid (0.179 g, 1.03 mmol) and thionyl chloride (5 mL) and allowed to stir at 79° C. for 3 h. The thionyl chloride was then removed by concentration in vacuo. The crude acid chloride was cooled to room temperature, and then dissolved in THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 4-Chloro-1-ethyl-1H-pyrazole-3-carboxylic acid [3-(2-oxo-2,3-dihydro-1H-indole-6-carbonyl)-phenyl]-amide as a solid (0.227 g, 0.560 mmol, 54%).

Step 2: 4-Chloro-1-ethyl-1H-pyrazole-3-carboxylic acid [3-(3-hydroxymethylene-2-oxo-2,3-dihydro-1H-indole-6-carbonyl)-phenyl]-amide 4-Chloro-1-ethyl-1H-pyrazole-3-carboxylic acid [3-(2-oxo-2,3-dihydro-1H-indole-6-carbonyl)-phenyl]-amide (0.150 g, 0.3669 mmol) and ethyl formate (0.088 mL, 1.1 mmol) were dissolved in anhydrous ethanol (4 mL). The resulting solution was treated in dropwise fashion with a 21 wt % solution of sodium ethoxide in ethanol (0.68 mL, 1.82 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a tan precipitate. The suspension was filtered and the tan solid collected was washed with 0° C. EtOH yielding the pure 4-Chloro-1-ethyl-1H-pyrazole-3-carboxylic acid [3-(3-hydroxymethylene-2-oxo-2,3-dihydro-1H-indole-6-carbonyl)-phenyl]-amide (0.0865 g, 0.198 mmol, 54%).

Example 343

4-{4-[(6-{3-[(4-Chloro-1-ethyl-1H-pyrazole-3-carbonyl)-amino]-benzoyl}-2-oxo-1,2-dihydro-indol-3-ylidenemethyl)-amino]-phenyl}-butyric acid A small screw cap test tube was charged with 4-Chloro-1-ethyl-1H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide (as prepared in Example 342, 100 mg, 0.229 mmol) and THF (2.5 mL). To the resulting solution was added 4-(4-Amino-phenyl)-butyric acid (41.4 mg, 0.231 mmol), and the mixture was stirred for 24 h at 65° C. Subsequently, the reaction mixture was cooled to room temperature and diluted with EtOAc (~5 mL) and Hexane (~40 mL). The solid that precipitated was collected by filtration and washed with 0° C. acetone (~10 mL) affording the title compound in 45% yield (0.061 g, 0.102 mmol).

Example 344

4-Chloro-1-ethyl-1H-pyrazole-3-carboxylic acid (3-{2-oxo-3-[(4-pyrrolidin-1-ylmethyl-phenylamino)-methylene]-2,3-dihydro-1H-indole-6-carbonyl}-phenyl)-amide A small screw cap test tube was charged with 4-Chloro-1-ethyl-1H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide (as prepared in Example 342, 100 mg, 0.229 mmol) and THF (2.5 mL). To the resulting solution was added 4-Pyrrolidin-1-ylmethyl-phenylamine (40.3 mg, 0.229 mmol), and the mixture was stirred for 24 h at 65° C. Subsequently, the reaction mixture was cooled to room temperature and diluted with EtOAc (~5 mL) and Hexane (~40 mL). The solid that precipitated was collected by filtration and washed with 0° C. acetone (~10 mL) affording the title compound in 31% yield (0.043 g, 0.072 mmol).

Example 345

5-Ethyl-1-methyl-1H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 5-Ethyl-1-methyl-1H-pyrazole-3-carboxylic acid [3-(3-hydroxymethylene-2-oxo-2,3-dihydro-1H-indole-6-carbonyl)-phenyl]-amide (prepared below, 61 mg, 0.1465 mmol) and THF (2.0 mL). To the resulting solution was added 4-(4-methyl-piperazin-1-yl)-phenylamine (27.7 mg, 0.145 mmol), and the mixture was stirred for 24 h at 65° C. Subsequently, the reaction mixture was cooled to room temperature and concentrated in vacuo. The solid residue was recrystallized with ~5 mL of i-prOH affording the title compound in 12% yield (0.010 g, 0.017 mmol).

The 5-Ethyl-1-methyl-1H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 5-Ethyl-1-methyl-1H-pyrazole-3-carboxylic acid [3-(2-oxo-2,3-dihydro-1H-indole-6-carbonyl)-phenyl]-amide A dry flask was charged with 5-Ethyl-1-methyl-1H-pyrazole-3-carboxylic acid (0.159 g, 1.03 mmol) and thionyl chloride (5 mL) and allowed to stir at 79° C. for 3 h. The thionyl chloride was then removed by concentration in vacuo. The crude acid chloride was cooled to room temperature, and then dissolved in THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and filtered. The solid residue was washed with 0° C. THF and collected to afford the 5-Ethyl-1-methyl-1H-pyrazole-3-carboxylic acid [3-(2-oxo-2,3-dihydro-1H-indole-6-carbonyl)-phenyl]-amide as a solid (0.248 g, 0.64 mmol, 62%).

Step 2: 5-Ethyl-1-methyl-1H-pyrazole-3-carboxylic acid [3-(3-hydroxymethylene-2-oxo-2,3-dihydro-1H-indole-6-carbonyl)-phenyl]-amide 5-Ethyl-1-methyl-1H-pyrazole-3-carboxylic acid [3-(2-oxo-2,3-dihydro-1H-indole-6-carbonyl)-phenyl]-amide (0.240 g, 0.6179 mmol) and ethyl formate (0.148 mL, 1.84 mmol) were dissolved in anhydrous ethanol (6 mL). The resulting solution was treated in dropwise fashion with a 21 wt % solution of sodium ethoxide in ethanol (1.2 mL, 3.21 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a tan precipitate. The suspension was filtered and the solids were washed with 0° C. EtOH to afford the pure 5-Ethyl-1-methyl-1H-pyrazole-3-carboxylic acid [3-(3-hydroxymethylene-2-oxo-2,3-dihydro-1H-indole-6-carbonyl)-phenyl]-amide (0.2187 g, 0.525 mmol, 85%).

Example 346

3-{4-[(6-{3-[(5-Ethyl-1-methyl-1H-pyrazole-3-carbonyl)-amino]-benzoyl}-2-oxo-1,2-dihydro-indol-3-ylidenemethyl)-amino]-phenyl}-propionic acid A small screw cap test tube was charged with 5-Ethyl-1-methyl-1H-pyrazole-3-carboxylic acid [3-(3-hydroxymethylene-2-oxo-2,3-dihydro-1H-indole-6-carbonyl)-phenyl]-amide (as prepared in Example 345, 60 mg, 0.1441 mmol) and THF (2.0 mL). To the resulting solution was added 3-(4-Amino-phenyl)-propionic acid (24.2 mg, 0.146 mmol), and the mixture was stirred for 24 h at 65° C. Subsequently, the reaction mixture was cooled to room temperature and diluted with EtOAc (~5 mL) and Hexane (~40 mL). The solid that precipitated was collected by filtration and washed with 0° C. iPrOH (~10 mL) affording the title compound in 41% yield (0.033 g, 0.059 mmol).

Example 347

5-Ethyl-1-methyl-1H-pyrazole-3-carboxylic acid (3-{2-oxo-3-[(4-pyrrolidin-1-ylmethyl-phenylamino)-methylene]-2,3-dihydro-1H-indole-6-carbonyl}-phenyl)-amide A small screw cap test tube was charged with 5-Ethyl-1-methyl-1H-pyrazole-3-carboxylic acid [3-(3-hydroxymethylene-2-oxo-2,3-dihydro-1H-indole-6-carbonyl)-phenyl]-amide (as prepared in Example 345, 70 mg, 0.1681 mmol) and THF (2.0 mL). To the resulting solution was added 4-Pyrrolidin-1-ylmethyl-phenylamine (30.1 mg, 0.171 mmol), and the mixture was stirred for 24 h at 65° C. Subsequently, the reaction mixture was cooled to room temperature and diluted with EtOAc (~5 mL) and Hexane (~40 mL). The solid that precipitated was collected by filtration and washed with 0° C. iPrOH (~10 mL) affording the title compound in 18% yield (0.018 g, 0.031 mmol).

Example 348

5-tert-Butyl-2-methyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 5-tert-Butyl-2-methyl-2H-pyrazole-3-carboxylic acid [3-(3-hydroxymethylene-2-oxo-2,3-dihydro-1H-indole-6-carbonyl)-phenyl]-amide (prepared below, 128 mg, 0.288 mmol) and THF (3.0 mL). To the resulting solution was added 4-(4-methyl-piperazin-1-yl)-phenylamine (54.8 mg, 0.286 mmol), and the mixture was stirred for 24 h at 65° C. Subsequently, the reaction mixture was cooled to room temperature and diluted with EtOAc (~5 mL) and Hexane (~40 mL). The precipitate that formed was collected by filtration and washed with 0° C. iPrOH (~10 mL) to afford the title compound in 29% yield (0.051 g, 0.083 mmol).

The 5-tert-Butyl-2-methyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 5-tert-Butyl-2-methyl-2H-pyrazole-3-carboxylic acid [3-(2-oxo-2,3-dihydro-1H-indole-6-carbonyl)-phenyl]-amide A dry flask was charged with 5-tert-Butyl-2H-pyrazole-3-carbonyl chloride (0.207 g, 1.03 mmol) and THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and subsequently vacuum filtered. The solid was washed with 0° C. THF (~5 mL) and collected to afford the 5-tert-Butyl-2-methyl-2H-pyrazole-3-carboxylic acid [3-(2-oxo-2,3-dihydro-1H-indole-6-carbonyl)-phenyl]-amide as a solid (0.390 g, 0.94 mmol, 91%).

Step 2: 5-tert-Butyl-2-methyl-2H-pyrazole-3-carboxylic acid [3-(3-hydroxymethylene-2-oxo-2,3-dihydro-1H-indole-6-carbonyl)-phenyl]-amide 5-tert-Butyl-2-methyl-2H-pyrazole-3-carboxylic acid [3-(2-oxo-2,3-dihydro-1H-indole-6-carbonyl)-phenyl]-amide (0.350 g, 0.8404 mmol) and ethyl formate (0.20 mL, 2.50 mmol) were dissolved in anhydrous ethanol (8 mL). The resulting solution was treated in dropwise fashion with a 21 wt % solution of sodium ethoxide in ethanol (1.6 mL, 4.29 mmol). This reaction mixture was heated at 78° C. for 0.5 h, producing a black oil. Subsequently, the reaction mixture was cooled to room temperature, and then the reaction pH was adjusted to pH 1 with dropwise addition of 1M $HCl_{(aq)}$ causing the formation of a brown precipitate. The suspension was filtered and the brown solid collected was washed with 0° C. EtOH yielding the pure 5-tert-Butyl-2-methyl-2H-pyrazole-3-carboxylic acid [3-(3-hydroxymethylene-2-oxo-2,3-dihydro-1H-indole-6-carbonyl)-phenyl]-amide (0.2428 g, 0.546 mmol, 65%).

Example 349

2-Isopropyl-2H-pyrazole-3-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 2-Isopropyl-2H-pyrazole-3-carboxylic acid [3-(3-hydroxymethylene-2-oxo-2,3-dihydro-1H-indole-6-carbonyl)-phenyl]-amide (prepared below, 138 mg, 0.3314 mmol) and THF (3.3 mL). To the resulting solution was added 4-(4-methyl-piperazin-1-yl)-phenylamine (63.3 mg, 0.331 mmol), and the mixture was stirred for 24 h at 65° C. Subsequently, the reaction mixture was cooled to room temperature and diluted with EtOAc (~5 mL) and Hexane (~40 mL). The precipitate that formed was collected by filtration and washed with 0° C. iPrOH (~10 mL) to afford the title compound in 65% yield (0.127 g, 0.215 mmol).

The 2-Isopropyl-2H-pyrazole-3-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 2-Isopropyl-2H-pyrazole-3-carboxylic acid [3-(2-oxo-2,3-dihydro-1H-indole-6-carbonyl)-phenyl]-amide A dry flask was charged with 2-Isopropyl-2H-pyrazole-3-carboxylic acid (0.159 g, 1.03 mmol) and thionyl chloride (5 mL) and allowed to stir at 79° C. for 3 h. The thionyl chloride was then removed by concentration in vacuo. The crude acid chloride was cooled to room temperature, and then dissolved in THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and filtered. The solid residue was washed with 0° C. THF and collected to afford the 2-Isopropyl-2H-pyrazole-3-carboxylic acid [3-(2-oxo-2,3-dihydro-1H-indole-6-carbonyl)-phenyl]-amide as a solid (0.328 g, 0.84 mmol, 82%).

Step 2: 2-Isopropyl-2H-pyrazole-3-carboxylic acid [3-(3-hydroxymethylene-2-oxo-2,3-dihydro-1H-indole-6-carbonyl)-phenyl]-amide 2-Isopropyl-2H-pyrazole-3-carboxylic acid [3-(2-oxo-2,3-dihydro-1H-indole-6-carbonyl)-phenyl]-amide (0.300 g, 0.7723 mmol) and ethyl formate (0.185 mL, 2.30 mmol) were dissolved in anhydrous ethanol (8 mL). The resulting solution was treated in dropwise fashion with a 21 wt % solution of sodium ethoxide in ethanol (1.44 mL, 3.86 mmol). This reaction mixture was heated at 78° C. for 0.5 h, producing a black oil. Subsequently, the reaction mixture was cooled to room temperature, and then the reaction pH was adjusted to pH 1 with dropwise addition of 1M $HCl_{(aq)}$ causing the formation of a tan precipitate. The suspension was filtered and the solids were washed with 0° C. EtOH to afford the pure 2-Isopropyl-2H-pyrazole-3-carboxylic acid [3-(3-hydroxymethylene-2-oxo-2,3-dihydro-1H-indole-6-carbonyl)-phenyl]-amide (0.267 g, 0.641 mmol, 83%).

Example 350

1,5-Dimethyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 1,5-Dimethyl-1H-pyrazole-4-carboxylic acid [3-(3-hydroxymethylene-2-oxo-2,3-dihydro-1H-indole-6-carbonyl)-phenyl]-amide (prepared below, 134 mg, 0.333 mmol) and THF (3.3 mL). To the resulting solution was added 4-(4-methyl-piperazin-1-yl)-phenylamine (64.2 mg, 0.336 mmol), and the mixture was stirred for 24 h at 65° C. Subsequently, the reaction mixture was cooled to room temperature and concentrated in vacuo. The residue was dissolved in EtOAc (~5 mL) and the resulting solution was triturated with Hexanes (~40 mL). The precipitate that formed was collected by filtration and washed with 0° C. iPrOH (~10 mL) to afford the title compound in 11% yield (0.021 g, 0.036 mmol).

The 1,5-Dimethyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 1,5-Dimethyl-1H-pyrazole-4-carboxylic acid [3-(2-oxo-2,3-dihydro-1H-indole-6-carbonyl)-phenyl]-amide A dry flask was charged with 1,5-Dimethyl-1H-pyrazole-4-carboxylic acid (0.144 g, 1.03 mmol) and thionyl chloride (5 mL) and allowed to stir at 79° C. for 3 h. The thionyl chloride was then removed by concentration in vacuo. The crude acid chloride was cooled to room temperature, and then dissolved in THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and filtered. The solid residue was washed with 0° C. THF and collected to afford the 1,5-Dimethyl-1H-pyrazole-4-carboxylic acid [3-(2-oxo-2,3-dihydro-1H-indole-6-carbonyl)-phenyl]-amide as a solid (0.177 g, 0.47 mmol, 46%).

Step 2: 1,5-Dimethyl-1H-pyrazole-4-carboxylic acid [3-(3-hydroxymethylene-2-oxo-2,3-dihydro-1H-indole-6-carbonyl)-phenyl]-amide 1,5-Dimethyl-1H-pyrazole-4-carboxylic acid [3-(2-oxo-2,3-dihydro-1H-indole-6-carbonyl)-phenyl]-amide (0.172 g, 0.4594 mmol) and ethyl formate (0.11 mL, 1.37 mmol) were dissolved in anhydrous ethanol (5 mL). The resulting solution was treated in dropwise fashion with a 21 wt % solution of sodium ethoxide in ethanol (0.86 mL, 2.3 mmol). This reaction mixture was heated at 78° C. for 0.5 h, producing a black oil. Subsequently, the reaction mixture was cooled to room temperature, and then the reaction pH was adjusted to pH 1 with dropwise addition of 1M $HCl_{(aq)}$ causing the formation of a brown precipitate. The suspension was filtered and the solids were washed with 0° C. EtOH to afford the pure 1,5-Dimethyl-1H-pyrazole-4-carboxylic acid [3-(3-hydroxymethylene-2-oxo-2,3-dihydro-1H-indole-6-carbonyl)-phenyl]-amide (0.136 g, 0.34 mmol, 74%).

Example 351

1-Ethyl-5-methyl-1H-pyrazole-4-carboxylic acid [3-(3-{[4-(4-methyl-piperazin-1-yl)-phenylamino]-methylene}-2-oxo-2,3-dihydro-1H-indole-6-carbonyl)-phenyl]-amide A small screw cap test tube was charged with 1-Ethyl-5-methyl-1H-pyrazole-4-carboxylic acid [3-(3-hydroxymethylene-2-oxo-2,3-dihydro-1H-indole-6-carbonyl)-phenyl]-amide (prepared below, 192 mg, 0.4611 mmol) and THF (4.6 mL). To the resulting solution was added 4-(4-methyl-piperazin-1-yl)-phenylamine (87.9 mg, 0.46 mmol), and the mixture was stirred for 24 h at 65° C. Subsequently, the reaction mixture was cooled to room temperature and concentrated in vacuo. The crude residue was purified by flash silica gel chromatography ($CHCl_3$:MeOH mix eluant with gradient of 1% MeOH to 15% MeOH) to afford the title compound in 16% yield (0.041 g, 0.072 mmol).

The 1-Ethyl-5-methyl-1H-pyrazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 1-Ethyl-5-methyl-1H-pyrazole-4-carboxylic acid [3-(2-oxo-2,3-dihydro-1H-indole-6-carbonyl)-phenyl]-amide A dry flask was charged with 1-Ethyl-5-methyl-1H-pyrazole-4-carboxylic acid (0.159 g, 1.03 mmol) and thionyl chloride (5 mL) and allowed to stir at 79° C. for 3 h. The thionyl chloride was then removed by concentration in vacuo. The crude acid chloride was cooled to room temperature, and then dissolved in THF (10 mL). 6-(3-Amino-benzoyl)-1,3-dihydro-indol-2-one (as prepared in Example 40, 0.260 g, 1.03 mmol) was added to the THF solution of the acid chloride, and the mixture was allowed to reflux overnight. The reaction mixture was then allowed to cool to room temperature and filtered. The solid residue was washed with 0° C. THF and collected to afford the 1-Ethyl-5-methyl-1H-pyrazole-4-carboxylic acid [3-(2-oxo-2,3-dihydro-1H-indole-6-carbonyl)-phenyl]-amide as a solid (0.236 g, 0.61 mmol, 59%).

Step 2: 1-Ethyl-5-methyl-1H-pyrazole-4-carboxylic acid [3-(3-hydroxymethylene-2-oxo-2,3-dihydro-1H-indole-6-carbonyl)-phenyl]-amide 1-Ethyl-5-methyl-1H-pyrazole-4-carboxylic acid [3-(2-oxo-2,3-dihydro-1H-indole-6-carbonyl)-phenyl]-amide (0.235 g, 0.605 mmol) and ethyl formate (0.145 mL, 1.80 mmol) were dissolved in anhydrous ethanol (5 mL). The resulting solution was treated in dropwise fashion with a 21 wt % solution of sodium ethoxide in ethanol (1.13 mL, 3.02 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a brown precipitate. The suspension was filtered and the solids were washed with 0° C. EtOH to afford the pure 1-Ethyl-5-methyl-1H-pyrazole-4-carboxylic acid [3-(3-hydroxymethylene-2-oxo-2,3-dihydro-1H-indole-6-carbonyl)-phenyl]-amide (0.199 g, 0.478 mmol, 79%).

Example 352

3-Methyl-thiophene-2-carboxylic acid (3-{2-oxo-3-[(4-pyrrolidin-1-ylmethyl-phenylamino)-methylene]-2,3-dihydro-1H-indole-6-carbonyl}-phenyl)-amide A small screw cap test tube was charged with 3-Methyl-thiophene-2-carboxylic acid [3-(3-hydroxymethylene-2-oxo-2,3-dihydro-1H-indole-6-carbonyl)-phenyl]-amide (prepared below, 200 mg, 0.4945 mmol) and THF (5.0 mL). To the resulting solution was added 4-Pyrrolidin-1-ylmethyl-phenylamine (87.1 mg, 0.494 mmol), and the mixture was stirred for 24 h at 65° C. Subsequently, the reaction mixture was cooled to room temperature and diluted with EtOAc (~5 mL) and Hexane (~40 mL). The precipitate that formed was collected by filtration and washed with 0° C. iPrOH (~5 mL) to afford the title compound in 52% yield (0.144 g, 0.256 mmol).

The 3-Methyl-thiophene-2-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 3-Methyl-thiophene-2-carboxylic acid [3-(2-oxo-2,3-dihydro-1H-indole-6-carbonyl)-phenyl]-amide A dry flask was charged with 3-Methyl-thiophene-2-carboxylic acid (0.500 g, 3.520 mmol) and thionyl chloride (10 mL) and allowed to stir at 79° C. for 3 h. The thionyl chloride was then removed by concentration in vacuo. The crude acid chloride was cooled to room temperature, and then dissolved in THF (35 mL). 6-(3-Amino-benzoyl)-1,3-dihydro-indol-2-one (as prepared in Example 40, 0.888 g, 3.517 mmol) was added to the THF solution of the acid chloride, and the mixture was allowed to reflux overnight. The reaction mixture was then allowed to cool to room temperature and filtered. The solid residue was washed with 0° C. THF and collected to afford the 3-Methyl-thiophene-2-carboxylic acid [3-(2-oxo-2,3-dihydro-1H-indole-6-carbonyl)-phenyl]-amide as a solid (0.940 g, 2.50 mmol, 71%).

Step 2: 3-Methyl-thiophene-2-carboxylic acid [3-(3-hydroxymethylene-2-oxo-2,3-dihydro-1H-indole-6-carbonyl)-phenyl]-amide 3-Methyl-thiophene-2-carboxylic acid [3-(2-oxo-2,3-dihydro-1H-indole-6-carbonyl)-phenyl]-amide (0.925 g, 2.4573 mmol) and ethyl formate (0.59 mL, 7.33 mmol) were dissolved in anhydrous ethanol (25 mL). The resulting solution was treated in dropwise fashion with a 21 wt % solution of sodium ethoxide in ethanol (4.583 mL, 12.28 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a tan precipitate. The suspension was filtered and the solids were washed with 0° C. EtOH to afford the pure 3-Methyl-thiophene-2-carboxylic acid [3-(3-hydroxymethylene-2-oxo-2,3-dihydro-1H-indole-6-carbonyl)-phenyl]-amide (0.6659 g, 1.65 mmol, 67%).

Example 353

4-{4-[(6-{3-[(3-Methyl-thiophene-2-carbonyl)-amino]-benzoyl}-2-oxo-1,2-dihydro-indol-3-ylidenemethyl)-amino]-phenyl}-butyric acid A small screw cap test tube was charged with 3-Methyl-thiophene-2-carboxylic acid [3-(3-hydroxymethylene-2-oxo-2,3-dihydro-1H-indole-6-carbonyl)-phenyl]-amide (as prepared in Example 352, 200 mg, 0.4945 mmol) and THF (5.0 mL). To the resulting solution was added 4-(4-Amino-phenyl)-butyric acid (88.6 mg, 0.494 mmol), and the mixture was stirred for 24 h at 65° C. Subsequently, the reaction mixture was cooled to room temperature and concentrated in vacuo. The crude residue was purified by flash silica gel chromatography (CHCl$_3$:MeOH mix eluant with gradient of 1% MeOH to 15% MeOH) to afford the title compound in 43% yield (0.120 g, 0.212 mmol).

Example 354

3-Methyl-furan-2-carboxylic acid [3-(2-oxo-3-{[4-(2-pyrrolidin-1-yl-ethyl)-phenylamino]-methylene}-2,3-dihydro-1H-indole-6-carbonyl)-phenyl]-amide A small screw cap test tube was charged with 3-Methyl-furan-2-carboxylic acid [3-(3-hydroxymethylene-2-oxo-2,3-dihydro-1H-indole-6-carbonyl)-phenyl]-amide (prepared below, 200 mg, 0.515 mmol) and THF (5.0 mL). To the resulting solution was added 4-(2-Pyrrolidin-1-yl-ethyl)-phenylamine (98 mg, 0.515 mmol), and the mixture was stirred for 24 h at 65° C. Subsequently, the reaction mixture was cooled to room temperature and concentrated in vacuo. The crude residue was purified by flash silica gel chromatography (EtOAc:MeOH mix eluant with gradient of 1% MeOH to 10% MeOH) to afford the title compound in 17% yield (0.049 g, 0.087 mmol).

The 3-Methyl-furan-2-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 3-Methyl-furan-2-carboxylic acid [3-(2-oxo-2,3-dihydro-1H-indole-6-carbonyl)-phenyl]-amide A dry flask was charged with 3-Methyl-furan-2-carboxylic acid (0.500 g, 3.96 mmol) and thionyl chloride (10 mL) and allowed to stir at 79° C. for 3 h. The thionyl chloride was then removed by concentration in vacuo. The crude acid chloride was cooled to room temperature, and then dissolved in THF (40 mL). 6-(3-Amino-benzoyl)-1,3-dihydro-indol-2-one (as prepared in Example 40, 1.00 g, 3.96 mmol) was added to the THF solution of the acid chloride, and the mixture was allowed to reflux overnight. The reaction mixture was then allowed to cool to room temperature and filtered. The solid residue was washed with 0° C. THF and collected to afford the 3-Methyl-furan-2-carboxylic acid [3-(2-oxo-2,3-dihydro-1H-indole-6-carbonyl)-phenyl]-amide as a solid (1.242 g, 3.45 mmol, 87%).

Step 2: 3-Methyl-furan-2-carboxylic acid [3-(3-hydroxymethylene-2-oxo-2,3-dihydro-1H-indole-6-carbonyl)-phenyl]-amide 3-Methyl-furan-2-carboxylic acid [3-(2-oxo-2,3-dihydro-1H-indole-6-carbonyl)-phenyl]-amide (1.200 g, 3.33 mmol) and ethyl formate (0.8 mL, 9.95 mmol) were dissolved in anhydrous ethanol (30 mL). The resulting solution was treated in dropwise fashion with a 21 wt % solution of sodium ethoxide in ethanol (6.2 mL, 16.63 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a light yellow precipitate. The suspension was filtered and the solids were washed with 0° C. EtOH to afford the pure 3-Methyl-furan-2-carboxylic acid [3-(3-hydroxymethylene-2-oxo-2,3-dihydro-1H-indole-6-carbonyl)-phenyl]-amide (0.931 g, 2.4 mmol, 72%).

Example 355

3-{4-[(6-{3-[(3-Methyl-furan-2-carbonyl)-amino]-benzoyl}-2-oxo-1,2-dihydro-indol-3-ylidenemethyl)-amino]-phenyl}-propionic acid A small screw cap test tube was charged with 3-Methyl-furan-2-carboxylic acid [3-(3-hydroxymethylene-2-oxo-2,3-dihydro-1H-indole-6-carbonyl)-phenyl]-amide (as prepared in Example 354, 200 mg, 0.515 mmol) and THF (5.0 mL). To the resulting solution was added 3-(4-Amino-phenyl)-propionic acid (85.1 mg, 0.515 mmol), and the mixture was stirred for 24 h at 65° C. Subsequently, the reaction mixture was cooled to room temperature and concentrated in vacuo. The crude residue was purified by flash silica gel chromatography (EtOAc:MeOH mix eluant with gradient of 1% MeOH to 10% MeOH) to afford the title compound in 57% yield (0.157 g, 0.293 mmol).

Example 356

3-Methyl-furan-2-carboxylic acid (3-{2-oxo-3-[(4-pyrrolidin-1-ylmethyl-phenylamino)-methylene]-2,3-dihydro-1H-indole-6-carbonyl}-phenyl)-amide A small screw cap test tube was charged with 3-Methyl-furan-2-carboxylic acid [3-(3-hydroxymethylene-2-oxo-2,3-dihydro-1H-indole-6-carbonyl)-phenyl]-amide (as prepared in Example 354, 100 mg, 0.2575 mmol) and THF (2.6 mL). To the resulting solution was added 4-Pyrrolidin-1-ylmethyl-phenylamine (45.4 mg, 0.258 mmol), and the mixture was stirred for 24 h at 65° C. Subsequently, the reaction mixture was cooled to room temperature and diluted with EtOAc (~5 mL) and Hexane (~40 mL). The precipitate that formed was collected by filtration and washed with 0° C. iPrOH (~5 mL) to afford the title compound in 43% yield (0.060 g, 0.11 mmol).

Example 357

3-{4-[(6-{3-[(5-Chloro-1-methyl-1H-pyrazole-4-carbonyl)-amino]-benzoyl}-2-oxo-1,2-dihydro-indol-3-ylidenemethyl)-amino]-phenyl}-propionic acid A small screw cap test tube was charged with 5-Chloro-1-methyl-1H-pyrazole-4-carboxylic acid [3-(3-hydroxymethylene-2-oxo-2,3-dihydro-1H-indole-6-carbonyl)-phenyl]-amide (as prepared in Example 328, 100 mg, 0.2365 mmol) and THF (2.5 mL). To the resulting solution was added 3-(4-Amino-phenyl)-propionic acid (39.1 mg, 0.237 mmol), and the mixture was stirred for 24 h at 65° C. Subsequently, the reaction mixture was cooled to room temperature and diluted with EtOAc (~5 mL) and Hexane (~50 mL). The precipitate that formed was collected by filtration and washed with acetone (~15 mL) to afford the title compound in 57% yield (0.077 g, 0.1351 mmol).

Example 358

5-Chloro-1-methyl-1H-pyrazole-4-carboxylic acid [3-(2-oxo-3-{[4-(2-pyrrolidin-1-yl-ethyl)-phenylamino]-methylene}-2,3-dihydro-1H-indole-6-carbonyl)-phenyl]-amide A small screw cap test tube was charged with 5-Chloro-1-methyl-1H-pyrazole-4-carboxylic acid [3-(3-hydroxymethylene-2-oxo-2,3-dihydro-1H-indole-6-carbonyl)-phenyl]-amide (as prepared in Example 328, 100 mg, 0.2365 mmol) and THF (2.5 mL). To the resulting solution was added 4-(2-Pyrrolidin-1-yl-ethyl)-phenylamine (45 mg, 0.236 mmol), and the mixture was stirred for 24 h at 65° C. Subsequently, the reaction mixture was cooled to room temperature and diluted with EtOAc (~5 mL) and Hexane (~50 mL). The precipitate that formed was collected by filtration and washed with acetone (~15 mL) to afford the title compound in 29% yield (0.041 g, 0.0689 mmol).

Example 359

3-{4-[(6-{3-[(3-Methyl-isoxazole-4-carbonyl)-amino]-benzoyl}-2-oxo-1,2-dihydro-indol-3-ylidenemethyl)-amino]-phenyl}-propionic acid A small screw cap test tube was charged with 3-Methyl-isoxazole-4-carboxylic acid [3-(3-hydroxymethylene-2-oxo-2,3-dihydro-1H-indole-6-carbonyl)-phenyl]-amide (prepared below, 100 mg, 0.257 mmol) and THF (2.5 mL). To the resulting solution was added 3-(4-Amino-phenyl)-propionic acid (42.4 mg, 0.257 mmol), and the mixture was stirred for 24 h at 65° C. Subsequently, the reaction mixture was cooled to room temperature and a yellow precipitate formed. The precipitate was filtered then washed with 0° C. iPrOH (~5 mL) to afford the title compound in 25% yield (0.034 g, 0.0634 mmol).

The 3-Methyl-isoxazole-4-carboxylic acid [3-(3-hydroxymethylene-2-oxo-2,3-dihydro-1H-indole-6-carbonyl)-phenyl]-amide was prepared from 3-nitrobenzoyl chloride using the following multiple step procedure:

Step 1: 3-Methyl-isoxazole-4-carboxylic acid [3-(2-oxo-2,3-dihydro-1H-indole-6-carbonyl)-phenyl]-amide A dry flask was charged with 3-Methyl-isoxazole-4-carboxylic acid (0.500 g, 3.9339 mmol) and thionyl chloride (10 mL) and allowed to stir at 79° C. for 3 h. The thionyl chloride was then removed by concentration in vacuo. The crude acid chloride was cooled to room temperature, and then dissolved in THF (39 mL). 6-(3-Amino-benzoyl)-1,3-dihydro-indol-2-one (as prepared in Example 40, 0.992 g, 3.932 mmol) was added to the THF solution of the acid chloride, and the mixture was allowed to reflux overnight. The reaction mixture was then allowed to cool to room temperature and filtered. The solid residue was washed with 0° C. THF (5 mL) and collected to afford the 3-Methyl-isoxazole-4-carboxylic acid [3-(2-oxo-2,3-dihydro-1H-indole-6-carbonyl)-phenyl]-amide as a solid (0.938 g, 2.60 mmol, 66%).

Step 2: 3-Methyl-isoxazole-4-carboxylic acid [3-(3-hydroxymethylene-2-oxo-2,3-dihydro-1H-indole-6-carbonyl)-phenyl]-amide 3-Methyl-isoxazole-4-carboxylic acid [3-(2-oxo-2,3-dihydro-1H-indole-6-carbonyl)-phenyl]-amide (0.935 g, 2.59 mmol) and ethyl formate (0.62 mL, 7.72 mmol) were dissolved in anhydrous ethanol (25 mL). The resulting solution was treated in dropwise fashion with a 21 wt % solution of sodium ethoxide in ethanol (4.83 mL, 12.94 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a brown precipitate. The suspension was filtered and the solids were washed with 0° C. EtOH to afford the pure 3-Methyl-isoxazole-4-carboxylic acid [3-(3-hydroxymethylene-2-oxo-2,3-dihydro-1H-indole-6-carbonyl)-phenyl]-amide (0.232 g, 0.595 mmol, 23%).

Example 360

3-Methyl-isoxazole-4-carboxylic acid [3-(2-oxo-3-{[4-(2-pyrrolidin-1-yl-ethyl)-phenylamino]-methylene}-2,3-dihydro-1H-indole-6-carbonyl)-phenyl]-amide A small screw cap test tube was charged with 3-Methyl-isoxazole-4-carboxylic acid [3-(3-hydroxymethylene-2-oxo-2,3-dihydro-1H-indole-6-carbonyl)-phenyl]-amide (as prepared in Example 359, 100 mg, 0.257 mmol) and THF (2.5 mL). To the resulting solution was added 4-(2-Pyrrolidin-1-yl-ethyl)-phenylamine (48.9 mg, 0.257 mmol), and the mixture was stirred for 24 h at 65° C. Subsequently, the reaction mixture was cooled to room temperature and diluted with EtOAc (~5 mL) and Hexane (~50 mL). The precipitate that formed was collected by filtration and washed with 0° C. iPrOH (~5 mL) to afford the title compound in 41% yield (0.059 g, 0.105 mmol).

Example 361

2-Methyl-N-(3-{2-oxo-3-[(4-pyrrolidin-1-ylmethyl-phenylamino)-methylene]-2,3-dihydro-1H-indole-6-carbonyl}-phenyl)-benzamide A small screw cap test tube was charged with N-[3-(3-Hydroxymethylene-2-oxo-2,3-dihydro-1H-indole-6-carbonyl)-phenyl]-2-methyl-benzamide (prepared below, 100 mg, 0.251 mmol) and THF (2.5 mL). To the resulting solution was added 4-Pyrrolidin-1-ylmethyl-phenylamine (44.2 mg, 0.251 mmol), and the mixture was stirred for 24 h at 65° C. Subsequently, the reaction mixture was cooled to room temperature and diluted with EtOAc (~5 mL) and Hexane (~40 mL). The precipitate that formed was collected by filtration and washed with acetone (~5 mL) to afford the title compound in 56% yield (0.078 g, 0.1401 mmol).

The N-[3-(3-Hydroxymethylene-2-oxo-2,3-dihydro-1H-indole-6-carbonyl)-phenyl]-2-methyl-benzamide was prepared from 3-nitrobenzoyl chloride using the following multiple step procedure:

Step 1: 2-Methyl-N-[3-(2-oxo-2,3-dihydro-1H-indole-6-carbonyl)-phenyl]-benzamide A dry flask was charged with 2-Methyl-benzoyl chloride (3.00 g, 19.41 mmol) and THF (200 mL). 6-(3-Amino-benzoyl)-1,3-dihydro-indol-2-one (as prepared in Example 40, 4.895 g, 19.4 mmol) was added to the THF solution of the acid chloride, and the mixture was allowed to reflux overnight. The reaction mixture was then allowed to cool to room temperature and filtered. The solid residue was washed with 0° C. THF (15 mL) and collected to afford the 2-Methyl-N-[3-(2-oxo-2,3-dihydro-1H-indole-6-carbonyl)-phenyl]-benzamide as a solid (5.174 g, 13.97 mmol, 72%).

Step 2: N-[3-(3-Hydroxymethylene-2-oxo-2,3-dihydro-1H-indole-6-carbonyl)-phenyl]-2-methyl-benzamide 2-Methyl-N-[3-(2-oxo-2,3-dihydro-1H-indole-6-carbonyl)-phenyl]-benzamide (5.00 g, 13.499 mmol) and ethyl formate (3.24 mL, 40.3 mmol) were dissolved in anhydrous ethanol (135 mL). The resulting solution was treated in dropwise fashion with a 21 wt % solution of sodium ethoxide in ethanol (25.2 mL, 67.47 mmol). This reaction mixture was heated at 78° C. for 0.5 h, producing a black oil. Subsequently, the reaction mixture was cooled to room temperature, and then the reaction pH was adjusted to pH 1 with dropwise addition of 1M HCl$_{(aq)}$ causing the formation of a light yellow precipitate. The suspension was filtered and the solids were washed with 0° C. EtOH to afford the pure N-[3-(3-Hydroxymethylene-2-oxo-2,3-dihydro-1H-indole-6-carbonyl)-phenyl]-2-methyl-benzamide (4.464 g, 11.2 mmol, 81%).

Example 362

4-[4-({6-[3-(2-Methyl-benzoylamino)-benzoyl]-2-oxo-1,2-dihydro-indol-3-ylidenemethyl}-amino)-phenyl]-butyric acid A small screw cap test tube was charged with N-[3-(3-Hydroxymethylene-2-oxo-2,3-dihydro-1H-indole-6-carbonyl)-phenyl]-2-methyl-benzamide (as prepared in Example 361, 100 mg, 0.251 mmol) and THF (2.5 mL). To the resulting solution was added 4-Pyrrolidin-1-ylmethyl-phenylamine (45 mg, 0.251 mmol), and the mixture was stirred for 24 h at 65° C. Subsequently, the reaction mixture was cooled to room temperature and concentrated in vacuo. The crude residue was purified by flash silica gel chromatography (EtOAc: MeOH mix eluant with gradient of 1% MeOH to 10% MeOH) to afford the title compound in 43% yield (0.060 g, 0.1072 mmol).

Example 363

2-Ethyl-5-methyl-2H-pyrazole-3-carboxylic acid (3-{2-oxo-3-[(4-pyrrolidin-1-ylmethyl-phenylamino)-methylene]-2,3-dihydro-1H-indole-6-carbonyl}-phenyl)-amide A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]- amide (as prepared in Example 69, 100 mg, 0.2401 mmol) and THF (3.0 mL). To the resulting solution was added 4-Pyrrolidin-1-ylmethyl-phenylamine (42.3 mg, 0.24 mmol), and the mixture was stirred for 24 h at 65° C. Subsequently, the reaction mixture was cooled to room temperature and diluted with EtOAc (~5 mL) and Hexane (~50 mL). The precipitate that formed was collected by filtration and washed with 0° C. iPrOH (~5 mL) to afford the title compound in 25% yield (0.035 g, 0.0609 mmol).

Example 364

4-{4-[(6-{3-[(2-Ethyl-5-methyl-2H-pyrazole-3-carbonyl)-amino]-benzoyl}-2-oxo-1,2-dihydro-indol-3-ylidenemethyl)-amino]-phenyl}-butyric acid A small screw cap test tube was charged with 2-Ethyl-5-methyl-2H-pyrazole-3-carboxylic acid [3-(3-hydroxymethylene-2-oxo-2,3-dihydro-1H-indole-6-carbonyl)-phenyl]-amide (as prepared in Example 69, 100 mg, 0.2401 mmol) and THF (3.0 mL). To the resulting solution was added 4-(4-Amino-phenyl)-butyric acid (43 mg, 0.24 mmol), and the mixture was stirred for 24 h at 65° C. Subsequently, the reaction mixture was cooled to room temperature and diluted with EtOAc (~5 mL) and Hexane (~50 mL). The precipitate that formed was collected by filtration and washed with 0° C. iPrOH (~5 mL) to afford the title compound in 29% yield (0.040 g, 0.0692 mmol).

Example 365

6-{3-[(2,5-Dimethyl-2H-pyrazol-3-ylmethyl)-amino]-benzoyl}-3-[1-[4-(4-methyl-piperazin-1-yl)-phenylamino]-meth-(Z)-ylidene]-1,3-dihydro-indol-2-one A small screw cap test tube was charged with 6-{3-[(2,5-Dimethyl-2H-pyrazol-3-ylmethyl)-amino]-benzoyl}-3-hydroxymethylene-1,3-dihydro-indol-2-one (prepared below, 0.045 g, 0.117 mmol) and THF (2 mL). To the resulting solution was added 4-(4-Methyl-piperazin-1-yl)-phenylamine (23 mg, 0.117 mmol), and the mixture was stirred for 24 h at 65° C. The reaction mixture was cooled to room temperature and the precipitate that formed was collected by filtration. The yellow solid was dissolved in 5 mL of a solvent mixture containing 98% EtOAc/2% i-prOH and washed with water (2×5 mL). The organic layers were combined, dried over anhydrous $Na_2SO_4$, filtered, and concentrated in vacuo. The crude residue was columned over silica (95/5, chloroform/Hexanes w/0.5% $NEt_3$ to afford the title compound in 39% yield (26 mg, 0.045 mmol).

The 6-[3-[(2,5-Dimethyl-2H-pyrazol-3-ylmethyl)-amino]-benzoyl]-3-hydroxymethylene-1,3-dihydro-indol-2-one was prepared from 3-nitrobenzoyl chloride using the following multiple step procedure:

Step 1: 6-{3-[(2,5-Dimethyl-2H-pyrazol-3-ylmethyl)-amino]-benzoyl}-1,3-dihydro-indol-2-one A dry round bottom flask was charged with 6-(3-Amino-benzoyl)-1,3-dihydro-indol-2-one (as prepared in Example 40, 0.300 g, 1.19 mmol), 1,3-Dimethyl-2H-pyrazole-5-carbaldehyde (0.191 g, 1.91 mmol) and acetic acid (0.3 mL). The mixture was allowed to stir for 4 h at room temperature. A 1M solution of sodium cyanoborohydride in THF (3.57 mL, 3.57 mmol) was then added and the mixture was allowed to stir for 45 minutes. The reaction mixture was poured into $H_2O$ (100 mL) and allowed to stir for 15 minutes. The resulting suspension was vacuum filtered and the filtrate was extracted with EtOAc (3×~100 mL). The organic layers were combined, dried over anhydrous $Na_2SO_4$, filtered and concentrated in vacuo to afford a yellow oil. The yellow oil was then chromatographed over silica which had been previously neutralized by flushing the column with the purification eluant (97/3, chloroform/methanol w/0.5% $NEt_3$) several times. This chromatographic purification resulted in the isolation of pure 6-{3-[(2,5-Dimethyl-2H-pyrazol-3-ylmethyl)-amino]-benzoyl}-1,3-dihydro-indol-2-one in 30% yield (0.128 g, 0.357 mmol).

Step 2: 6-{3-[(2,5-Dimethyl-2H-pyrazol-3-ylmethyl)-amino]-benzoyl}-3-hydroxymethylene-1,3-dihydro-indol-2-one 6-{3-[(2,5-Dimethyl-2H-pyrazol-3-ylmethyl)-amino]-benzoyl}-1,3-dihydro-indol-2-one (0.100 g, 0.278 mmol) and ethyl formate (0.066 mL, 0.834 mmol) were dissolved in anhydrous ethanol (0.600 mL). The resulting solution was treated in dropwise fashion with a 21 wt % solution of sodium ethoxide in ethanol (0.519 mL, 1.39 mmol). This reaction mixture was heated at 78° C. for 1 h, producing a black oil. The reaction mixture was cooled to room temperature, and then the reaction pH was adjusted to pH 1 with dropwise addition of 1M $HCl_{(aq)}$ causing the formation of a tan precipitate. The suspension was filtered yielding 6-{3-[(2,5-Dimethyl-2H-pyrazol-3-ylmethyl)-amino]-benzoyl}-3-hydroxymethylene-1,3-dihydro-indol-2-one as an orange solid in 42% yield (0.045 g, 0.117 mmol).

(prepared below, 0.021 g, 0.056 mmol)

Example 366

6-(3-Benzylamino-benzoyl)-3-[1-[4-(4-methyl-piperazin-1-yl)-phenylamino]-meth-(Z)-ylidene]-1,3-dihydro-indol-2-one A small screw cap test tube was charged with 6-(3-Benzylamino-benzoyl)-3-[1-hydroxy-meth-(Z)-ylidene]-1,3-dihydro-indol-2-one (prepared below, 0.021 g, 0.056 mmol) and THF (1 mL). To the resulting solution was added 4-(4-Methyl-piperazin-1-yl)-phenylamine (10.7 mg, 0.056 mmol), and the mixture was stirred for 24 h at 65° C. The reaction mixture was cooled to room temperature. The yellow solid was dissolved in 5 mL of a solvent mixture containing 98% EtOAc/2% i-prOH and washed with water (2×5 mL). The organic layers were combined, dried over anhydrous $Na_2SO_4$, filtered, and concentrated in vacuo. The crude residue was chromatographed over silica (95/5 chloroform/Hexanes w/0.5% $NEt_3$) to afford the title compound in 51% yield (15.5 mg, 0.028 mmol).

The 6-(3-Benzylamino-benzoyl)-3-[1-hydroxy-meth-(Z)-ylidene]-1,3-dihydro-indol-2-one was prepared from 3-nitrobenzoyl chloride using the following multiple step procedure:

Step 1: 6-[3-(benzylamino)benzoyl]-1,3-dihydro-2H-indol-2-one

A dry round bottom flask was charged with 6-(3-Amino-benzoyl)-1,3-dihydro-indol-2-one (as prepared in Example 40, 0.100 g, 0.397 mmol), benzaldehyde (0.042 g, 0.397 mmol) and acetic acid (0.1 mL). The mixture was allowed to stir for 5 hours at room temperature. A 1M solution of sodium cyanoborohydride in THF (1.19 mL, 1.19 mmol) was then added, and the mixture was allowed to stir for 45 minutes. Subsequently the reaction mixture was poured into H$_2$O (~30 mL) and allowed to stir for 15 minutes. The suspension was filtered and the filtrate was extracted with EtOAc (3×~10 mL). The organics were dried over anhydrous Na$_2$SO$_4$, filtered and concentrated in vacuo to afford a brown oil. The brown oil was then chromatographed over silica (97/3, chloroform/methanol w/0.5% NEt$_3$) to afford 6-[3-(benzylamino) benzoyl]-1,3-dihydro-2H-indol-2-one in 26% yield (0.035 g, 0.103 mmol).

Step 2: 6-(3-Benzylamino-benzoyl)-3-[1-hydroxy-meth-(Z)-ylidene]-1,3-dihydro-indol-2-one 6-[3-(benzylamino)benzoyl]-1,3-dihydro-2H-indol-2-one (0.057 g, 0.167 mmol) and ethyl formate (0.040 mL, 0.500 mmol) were dissolved in anhydrous ethanol (1.67 mL). The resulting solution was treated in dropwise fashion with a 21 wt % solution of sodium ethoxide in ethanol (0.310 mL, 0.833 mmol). This reaction mixture was heated at 78° C. for 1 h, producing a black oil. The reaction mixture was cooled to room temperature, and then the reaction pH was adjusted to pH 1 with dropwise addition of 1M HCl$_{(aq)}$ causing the formation of a tan precipitate. The suspension was filtered yielding 6-(3-Benzylamino-benzoyl)-3-[1-hydroxy-meth-(Z)-ylidene]-1,3-dihydro-indol-2-one as an orange solid (0.021 g, 0.056 mmol, 34%) which was carried on without further purification.

Procedures for Library III: The Library of Compounds not limited to but including, Examples 367 through 377

General Synthetic Procedure: The general synthetic route to the compounds prepared in the Library was similar in all cases to the procedures followed in the preparation of the individually prepared compounds (Examples 15-92 & 201-208, see General Scheme for overview).

Library III General Scheme:

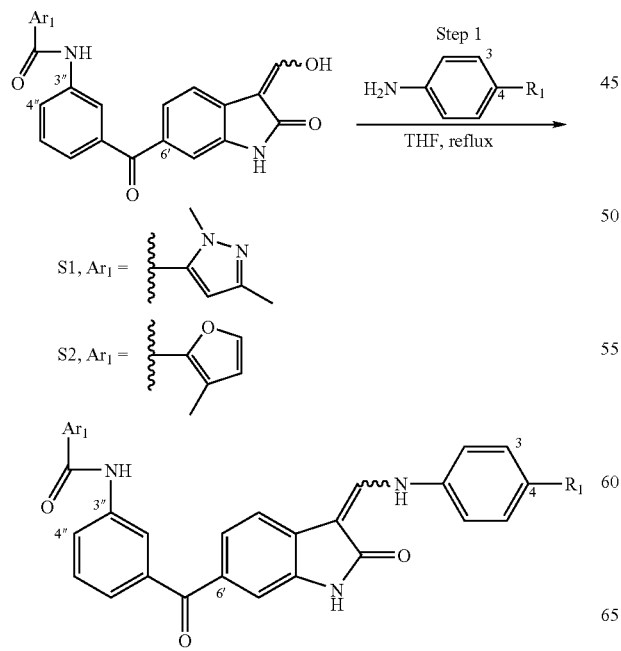

-continued
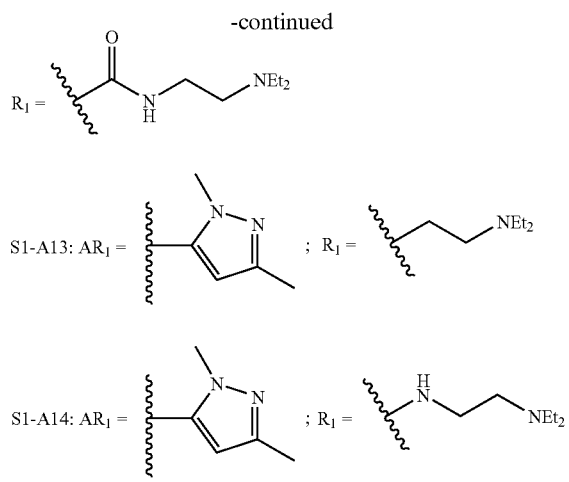
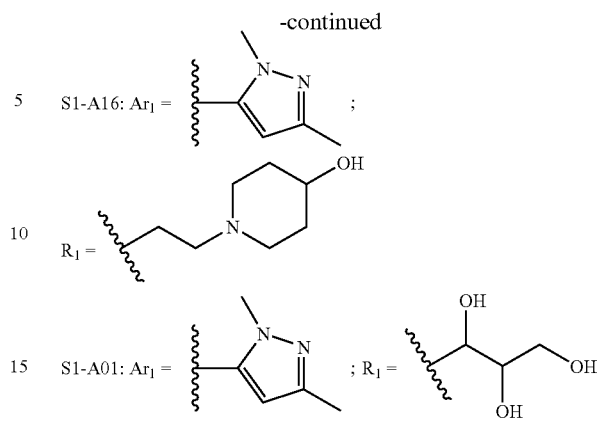
(wherein Ar₁—CO represents B—X' in Formula I)
| Example # | Library ID # | R₁ substitution 3 | R₁ substitution 4 | Ar₁ |
|---|---|---|---|---|
| 367 | S1, A04 | H | —CH₂NEt₂ | Me-pyrazole-Me |
| 368 | S1, A06 | H | piperidine-OH | Me-pyrazole-Me |
| 369 | S1, A12 | H | —NH(CH₂)₂NEt₂ | Me-pyrazole-Me |
| 370 | S1, A15 | H | piperazine-CH₂CH₂-O-CH₂CH₂OH | Me-pyrazole-Me |
| 371 | S1, A03 | H | —CONHCH₂CH₂NEt₂ | Me-pyrazole-Me |
| 372 | S2, A03 | H | —CONHCH₂CH₂NEt₂ | furan-Me |
Library Product Table III

Library Product Table III -continued

| Example # | Library ID # | R₁ substitution 3 | R₁ substitution 4 | Ar₁ |
|---|---|---|---|---|
| 373 | S1, A08 | H | —CH₂CONHCH₂CH₂NEt₂ | Me-pyrazole-Me |
| 374 | S1, A13 | H | —CH₂CH₂NEt₂ | Me-pyrazole-Me |
| 375 | S1, A14 | H | —CH₂CH₂CH₂NEt₂ | Me-pyrazole-Me |
| 376 | S1, A16 | H | —CH₂CH₂-N(piperidine)-OH | Me-pyrazole-Me |
| 377 | S1, A01 | H | —CH(OH)CH(OH)CH₂OH | Me-pyrazole-Me |

General Procedures for the Preparation of Library III (not limited to but including, Examples 367-377)

General coupling procedure of anilines with scaffolds S1 & S2, a table of products prepared via this method follows the method (Library Product Table III):

A mixture of Aniline (anilines, A-01 thru A-16, 1 equivalent) and Scaffold S1 or S2 (1 equivalent) was taken in anhydrous THF (0.125 M) and heated at 70° C. for 16 h. Solvent was evaporated under vacuum and the crude products were purified by preparative RP-HPLC to afford the final compounds listed in Library Product Table III.

The preparation of Example 367 serves as a specific example of the above general procedure:

Example 367

2,5-Dimethyl-2H-pyrazole-3-carboxylic acid (3-{3-[1-(4-diethylaminomethyl-phenylamino)-meth-(Z)-ylidene]-2-oxo-2,3-dihydro-1H-indole-6-carbonyl}-phenyl)-amide A mixture of 4-((diethylamino)methyl)aniline (A-04; 100 mg, 0.25 mmol, 1 equivalent) and N-(3-(3-(hydroxymethylene)-2-oxoindoline-6-carbonyl)phenyl)-1,3-dimethyl-1H-pyrazole-5-carboxamide (Scaffold S1; 50 mg, 0.25 mmol, 1 equivalent) was taken in anhydrous THF (2 mL, 0.125 M) and heated at 70° C. for 16 h. Solvent was evaporated under vacuum and the crude product was purified by preparative RP-HPLC. 2,5-Dimethyl-2H-pyrazole-3-carboxylic acid (3-{3-[1-(4-diethylaminomethyl-phenylamino)-meth-(Z)-ylidene]-2-oxo-2,3-dihydro-1H-indole-6-carbonyl}-phenyl)-amide (78 mg, 55%) was obtained as a brown powder.

Scaffolds S1 and S2 are prepared as shown in Examples 60 & 354 respectively. Most of the anilines used in the above general procedure were not commercial (Example 377 is an exception as it is commercial) and therefore required preparation. The anilines prepared were grouped by the synthetic method used for preparation and the experimental procedures for the grouped anilines are exemplified below:

Anilines used in Examples 367 and 368 were prepared by the following general method using the amines listed in Library Reagent Table 13 and p-Nitrobenzaldehyde:

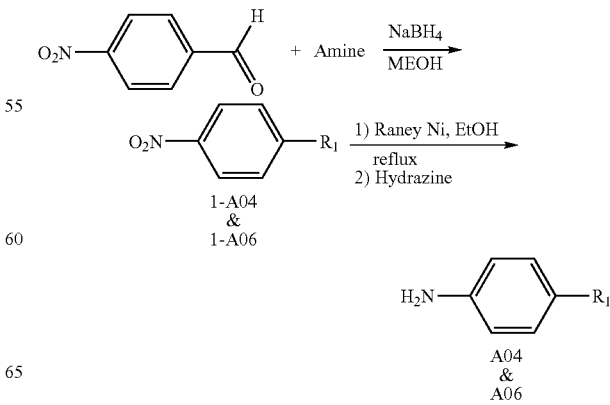

1-A04 & 1-A06

A04 & A06

Library Reagent Table 13

| Anilines used for Example # | Amine | Nitro-intermediate ID # | Aniline ID # | R₁ substitution |
|---|---|---|---|---|
| 367 | HNEt₂ | 1-A04 | A04 | —CH₂NEt₂ |
| 368 | HN⟨piperidine⟩-OH | 1-A06 | A06 | ⟨CH₂-piperidine-OH⟩ |

Step 1: General Reductive Amination Procedure[i]

A mixture of nitrobenzaldehyde (1 mmol) and amine (1 mmol) was stirred in anhydrous methanol (10 mL) under a nitrogen atmosphere for 3-4 h. Sodium borohydride (1.6 mmol) was added portion-wise so that temperature of the reaction mixture remained ambient. The mixture was stirred for 10 minutes before 1 N aqueous sodium hydroxide (2.5 mL) was added to quench the reaction. Dichloromethane (10 mL) was added followed by water (5 mL). The organic layer was separated and aqueous layer extracted with an additional portion of dichloromethane (5 mL). The combined organic solution was dried (Na₂SO₄), filtered, and evaporated to provide the required product.

Step 2: General Nitro Reduction Procedure

To a suspension of Nitrobenzene A04 or A06 (1.61 mmol) and Raney Ni (50 mg) in refluxing ethanol (10 mL) was added drop-wise anhydrous hydrazine (0.5 mL). After the addition was complete, the mixture was refluxed for an additional 20 minutes and then filtered through a pad of Celite. The Celite bed was washed with ethanol (100 mL) and the combined solution was evaporated under reduced pressure to provide pure aniline.

Specific Aniline, 4-Diethylaminomethyl-phenylamine, used in Example 367 serves as a specific example of the above general procedures:

Step 1: N-ethyl-N-(4-nitrobenzyl)ethanamine (1-A04)

To a solution of 2.11 g (14 mmol) of 4-nitrobenzaldehyde in 50 mL dichloroethane was added diethylamine (1.13 g, 15.4 mmol) followed by sodium triacetoxyborohydride (4.45 g, 21 mmol). The mixture was stirred at room temperature overnight. A solution of saturated aqueous sodium bicarbonate (25 mL) was added to the reaction mixture and the resulting solution was extracted with ethyl acetate (1×150 mL, 2×50 mL). The combined organic extract was dried (sodium sulfate), filtered, and solvent removed under reduced pressure to provide crude N-ethyl-N-(4-nitrobenzyl)ethanamine as an oil (4.0 g). The material was used in the next step without further purification.

Step 2: 4-Diethylaminomethyl-phenylamine (A04)

To a suspension of N-ethyl-N-(4-nitrobenzyl)ethanamine (335 mg, 1.61 mmol) and Raney Ni (50 mg) in refluxing ethanol (10 mL) was added drop-wise anhydrous hydrazine (0.5 mL). After the addition was complete, the mixture was refluxed for an additional 20 minutes and then filtered through a pad of Celite. The Celite bed was washed with ethanol (100 mL) and the combined solution was evaporated under reduced pressure to provide pure 4-((diethylamino)methyl)aniline (262 mg, 91%).

Anilines used in Examples 369 and 370 were prepared by the following general method using the amines listed in Library Reagent Table 14 and p-Fluoro-Nitrobenzene:

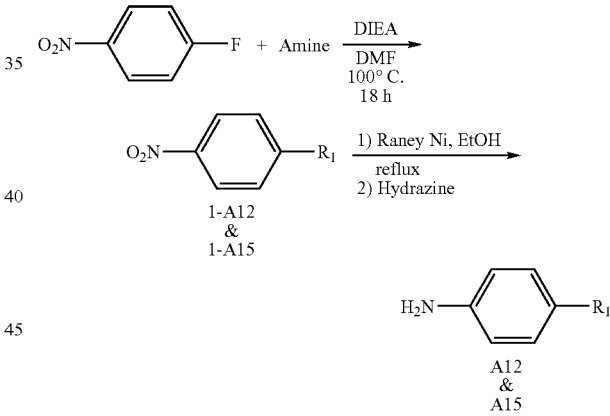

Library Reagent Table 14

| Example # anilines used for | Amine | Nitro-intermediate ID # | Aniline ID # | R₁ substitution |
|---|---|---|---|---|
| 369 | H₂NCH₂CH₂NEt₂ | 1-A12 | A12 | —HNCH₂CH₂NEt₂ |
| 370 | HN⟨piperazine⟩N-CH₂CH₂-O-CH₂CH₂-OH | 1-A15 | A15 | ⟨-N⟨piperazine⟩N-CH₂CH₂-O-CH₂CH₂-OH⟩ |

Step 1: General Procedure for the Nucleophilic Aromatic Substitution Reactions A mixture of 1-fluoro-4-nitrobenzene (2.00 g, 14.2 mmol, 1 equivalent), amine (21.3 mmol, 1.5 equivalents), and diisopropyl ethylamine (28.3 mmol, 2 equivalents) were heated at 110° C. in DMF (0.15 M) for 18 h. The mixture was cooled and poured onto crushed ice. The yellow solid that precipitated was isolated by filtration, washed with water, and dried under vacuum to provide pure compound. In cases where product did not precipitate, the aqueous suspension was extracted with dichloromethane (50 mL), washed with saturated aqueous brine solution (50 mL), dried over sodium sulfate, and the solvent evaporated to provide the product.

Step 2: General Nitro Reduction Procedure

To a suspension of Nitrobenzene 1-A12 or 1-A15 (1.61 mmol) and Raney Ni (50 mg) in refluxing ethanol (10 mL) was added drop-wise anhydrous hydrazine (0.5 mL). After the addition was complete, the mixture was refluxed for an additional 20 minutes and then filtered through a pad of Celite. The Celite bed was washed with ethanol (100 mL) and the combined solution was evaporated under reduced pressure to provide pure aniline.

Specific Examples of this two-step procedure have been shown previously (e.g. Example 325)

Anilines used in Examples 371, 372 and 373 were prepared by the following general method using the amines listed in Library Reagent Table 15 and either 4-nitrobenzoic acid (371, 372) or (4-Nitro-phenyl)-acetic acid (373):

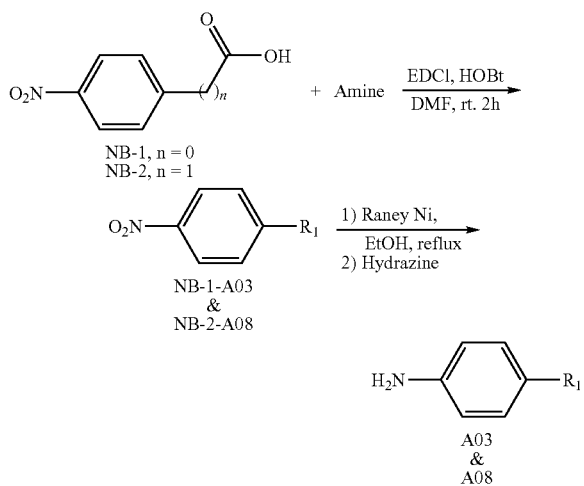

Step 1: General Procedure for Amidation Reactions

A mixture of nitrocarboxylic acid (NB-1 or NB-2; 1.2 equivalents), amine (A03 or A08; 1.1 equivalents), 1-(3-dimethylaminopropyl)-3-ethylcarbodiimide hydrochloride (1.2 equivalents), and 1-hydroxybenzotriazole hydrate (1.2 equivalents) in DMF (0.79 M) was stirred at room temperature for 4 hours. The mixture was diluted with dichloromethane (100 mL) and washed with aqueous saturated sodium bicarbonate solution (50 mL). The aqueous layer was re-extracted with dichloromethane (2×50 mL) and the combined organic solutions were dried ($Na_2SO_4$), filtered and evaporated under reduced pressure. The crude mixture was purified on silica gel column to provide the nitrobenzamide (NB-1-A03 or NB-2-A08).

Step 2: General Nitro Reduction Procedure

To a suspension of Nitrobenzene NB-1-A03 or NB-2-A08 (1.61 mmol) and Raney Ni (50 mg) in refluxing ethanol (10 mL) was added drop-wise anhydrous hydrazine (0.5 mL). After the addition was complete, the mixture was refluxed for an additional 20 minutes and then filtered through a pad of Celite. The Celite bed was washed with ethanol (100 mL) and the combined solution was evaporated under reduced pressure to provide pure aniline.

Specific Nitrobenzene, N-(2-(Diethylamino)-ethyl)-4-nitrobenzamide (A03), used in Examples 371 & 372 serves as a specific example of Step 1 in the above general procedures:

A mixture of 4-nitrobenzoic acid (2.00 g, 11.9 mmol), N,N-diethylethylene diamine (1.53 g, 13.16 mmol), 1-(3-dimethylaminopropyl)-3-ethylcarbodiimide hydrochloride (2.74 g, 14.35 mmol), and 1-hydroxybenzotriazole hydrate (2.19 g, 14.35 mmol) in 15 mL DMF was stirred at room temperature for 4 hours. The mixture was diluted with dichloromethane (100 mL) and washed with aqueous saturated sodium bicarbonate solution (50 mL). The aqueous layer was re-extracted with dichloromethane (2×50 mL) and the combined organic solutions were dried ($Na_2SO_4$), filtered and evaporated under reduced pressure. The crude mixture was purified on silica gel column to provide N-(2-(diethylamino)-ethyl)-4-nitrobenzamide as an amber colored oil (2.2 g 69%).

Anilines used in Examples 374, 375 and 376 were prepared by the following general method using the amines listed in Library Reagent Table 16 and either (4-Nitro-phenyl)-acetic acid (374, 376) or (4-Nitro-phenyl)-proprionic acid (375):

Library Reagent Table 15

| Example # anilines used for | Amine | Nitro-Carboxylic Acid used | Aniline ID # | $R_1$ substitution |
|---|---|---|---|---|
| 371 | $H_2NCH_2CH_2NEt_2$ | 4-Nitrobenzoic Acid | A03 | —$CONHCH_2CH_2NEt_2$ |
| 372 | $H_2NCH_2CH_2NEt_2$ | 4-Nitrobenzoic Acid | A03 | —$CONHCH_2CH_2NEt_2$ |
| 373 | $H_2NCH_2CH_2NEt_2$ | (4-Nitro-phenyl)-acetic acid | A08 | —$CH_2CONHCH_2CH_2NEt_2$ |

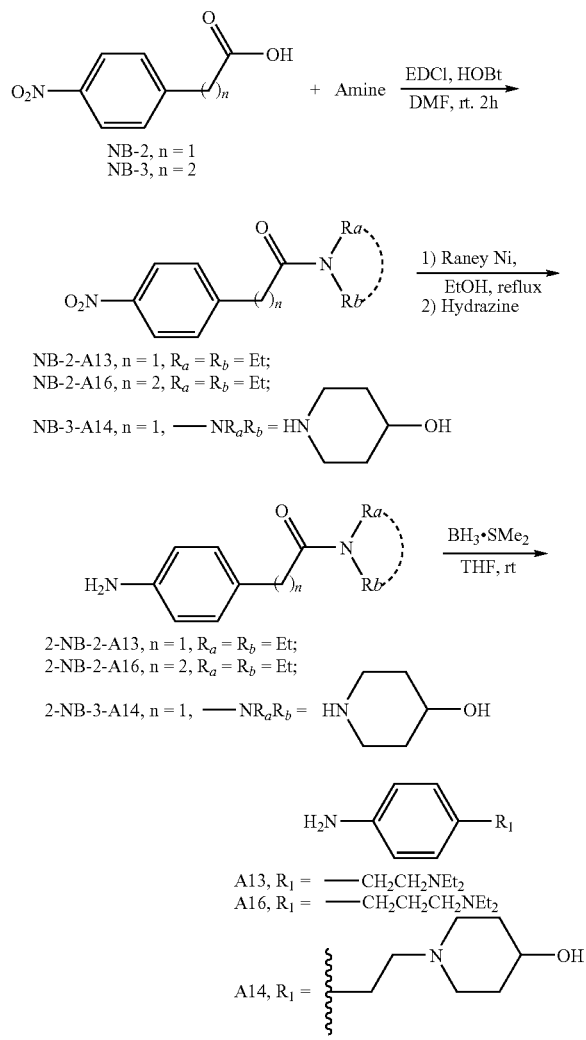

Step 1: General Procedure for Amidation Reactions

A mixture of nitrocarboxylic acid (NB-2 or NB-3; 1.2 equivalents), amine (A13, A14 or A16; 1.1 equivalents), 1-(3-dimethylaminopropyl)-3-ethylcarbodiimide hydrochloride (1.2 equivalents), and 1-hydroxybenzotriazole hydrate (1.2 equivalents) in DMF (0.79 M) was stirred at room temperature for 4 hours. The mixture was diluted with dichloromethane (100 mL) and washed with aqueous saturated sodium bicarbonate solution (50 mL). The aqueous layer was re-extracted with dichloromethane (2×50 mL) and the combined organic solution was dried ($Na_2SO_4$), filtered and evaporated under reduced pressure. The crude mixture was purified on silica gel column to provide the 4-nitrobenzamide (NB-2-A13, NB-2-A14 or NB-3-A16).

Step 2: General Nitro Reduction Procedure

To a suspension of Nitrobenzene (NB-2-A13, NB-2-A14 or NB-3-A16; 1.61 mmol) and Raney Ni (50 mg) in refluxing ethanol (10 mL) was added drop-wise anhydrous hydrazine (0.5 mL). After the addition was complete, the mixture was refluxed for an additional 20 minutes and then filtered through a pad of Celite. The Celite bed was washed with ethanol (100 mL) and the combined solution was evaporated under reduced pressure to provide pure 2-(4-aminophenyl)-acetamide (2-NB-2-A13, 2-NB-2-A14 or 2-NB-3-A16).

Step 3: General Amide Reduction Procedure

To a solution of 2-(4-aminophenyl)-acetamide (2-NB-2-A13, 2-NB-2-A14 or 2-NB-3-A16; 7.28 mmol, 1 equivalent) from Step 2 in anhydrous THF (15 mL, 0.5 M) kept at 0° C. was added a 2 M solution of borane dimethylsulfide in THF (14.5 mL, 3.98 equivalents) slowly. The reaction was allowed to warm to room temperature and stirred for 18 h. Hydrochloric acid (6N, 10 mL) was carefully added and the reaction was refluxed for 1 hour followed by cooling to room temperature and neutralization with 3N sodium hydroxide solution. Aqueous layer was separated and extracted with ethyl acetate (4×30 mL). Combined organic layer was dried over sodium sulfate, filtered and evaporated to provide the desired aniline (A13, A16, A14)

Library Reagent Table 16

| Example # anilines used for | Amine | Nitrocarboxylic Acid used | ID #: Nitro-benzamide-intermediate | ID #: Amino-benzamide-intermediate | Aniline ID # | $R_1$ substitution |
|---|---|---|---|---|---|---|
| 374 | $HNEt_2$ | (4-Nitro-phenyl)-acetic acid | NB-2-A13 | 2-NB-2-A13 | A13 | —$CH_2CH_2NEt_2$ |
| 376 | HN⟨piperidine⟩OH | (4-Nitro-phenyl)-acetic acid | NB-2-A16 | 2-NB-2-A16 | A16 | —CH₂—N⟨piperidine⟩—O |
| 375 | $HNEt_2$ | (4-Nitro-phenyl)-proprionic acid | NB-3-A14 | 2-NB-3-A14 | A14 | —$CH_2CH_2CH_2NEt_2$ |

Specific Aniline, 4-(2-(Diethylamino)ethyl)aniline, used in Example 374 serves as a specific example of Step 3 in the above general procedure:

To a solution of 2-(4-aminophenyl)-N,N-diethylacetamide, (2-NB-2-A13; 1.5 g, 7.28 mmol) from Step 2 in anhydrous THF (15 mL) kept at 0° C. was added a 2 M solution of borane dimethylsulfide in THF (14.5 mL, 29 mmol) slowly. The reaction was allowed to warm to room temperature and stirred for 18 h. Hydrochloric acid (6N, 10 mL) was carefully added and the reaction was refluxed for 1 hour followed by cooling to room temperature and neutralization with 3N sodium hydroxide solution. Aqueous layer was separated and extracted with ethyl acetate (4×30 mL). Combined organic layer was dried over sodium sulfate, filtered and evaporated to provide 4-(2-(diethylamino)ethyl)aniline as a light-brown oil (1.25 g, 86%).

Procedures for the Preparation of TKI Ocular Implants

Powder Blending

The drug, TKI, was stored at room temperature with minimal light exposure, and polymers, utilized for the matrix, were stored at 5° C. and allowed to equilibrate to room temperature prior to use. Both the TKI and the polymer were used as received. Formulations, listed in Table 1, were blended in a stainless steel mixing capsule with two stainless steel balls and placed in a Retsch mill at 30 cps or Turbula blender at 96 rpm for 5 to 15 minutes. Depending on the starting materials, formulations underwent four to six blending cycles at five to fifteen minutes each. Between blending cycles, a stainless steel spatula was used to dislodge material from the inside surfaces of the mixing vessel.

Powder Compaction

A die with a 720 μm opening was attached to a stainless steel extrusion barrel, and the barrel was inserted into the powder compactor assembly. The powder compactor is set to 50 psi, and the powder is added to the barrel in small increments using a stainless steel powder funnel. After the addition of each increment, the pneumatic compactor was actuated to compress the added powder. This process was repeated until the extrusion barrel was full.

Extrusion

A piston extruder was set to temperature and allowed to equilibrate. The extrusion temperature was chosen based on drug-load and polymer. The extrusion temperature was adjusted for each formulation to produce smooth, uniform-looking filaments. After the extruder temperature equilibrated, the piston extrusion barrel was inserted into the extruder, and a thermocouple was inserted to measure the temperature at the surface of the barrel. After the barrel temperature equilibrated, the piston was inserted into the barrel and the piston speed was set at 0.0025 in/min. The first 2-4 inches of extrudate was discarded. Afterwards, 3-5-inch pieces were cut directly into a centrifuge tube. Samples were labeled and stored in a sealed foil pouch containing desiccant. Formulations with higher drug load required higher extrusion temperatures. Polymers with higher intrinsic viscosities required higher extrusion temperatures than polymers with lower intrinsic viscosities. Lactide-glycolide co-polymers with a higher lactide percentage (75:25) required a lower processing temperature than polymers with a lower lactide percentage (50:50). Formulation information and extrusion temperatures are listed in Table A.

| Formulation Notebook Number | Example Number | % Drug Load | Polymer 1 | % Polymer 1 | Polymer 2 | % Polymer 2 |
|---|---|---|---|---|---|---|
| 7526-122G | Example 206 | 60 | RG755 | 40 | n/a | n/a |
| 7526-123G | Example 206 | 40 | RG755 | 60 | n/a | n/a |
| 7526-124G | Example 206 | 60 | RG752 | 40 | n/a | n/a |
| 7526-125G | Example 206 | 40 | RG752 | 60 | n/a | n/a |
| 7526-126G | Example 206 | 50 | RG504 | 50 | n/a | n/a |
| 7526-127G | Example 206 | 30 | RG504 | 70 | n/a | n/a |
| 7526-128G | Example 206 | 50 | RG755 | 25 | RG752 | 25 |
| 7526-129G | Example 206 | 50 | RG755 | 25 | RG504 | 25 |
| 8092-089G | Example 206 | 40 | RG755 | 60 | n/a | n/a |
| 8092-090G | Example 206 | 50 | RG504 | 50 | n/a | n/a |
| 8092-091G | Example 206 | 50 | RG755 | 25 | RG504 | 25 |
| 8092-015G | Example 324 | 50 | RG502 | 25 | RG502H | 25 |
| 8092-016G | Example 324 | 60 | RG104 | 10 | RG502 | 15 |
| 8092-017G | Example 324 | 50 | RG502 | 25 | RG502H | 22 |
| 8092-018G | Example 324 | 50 | RG104 | 10 | RG502 | 15 |
| 8092-072G | Example 324 | 40 | RG104 | 20 | RG502 | 15 |
| 8092-073G1 | Example 324 | 40 | RG104 | 20 | RG502 | 15 |
| 8092-073G2 | Example 324 | 40 | RG104 | 20 | RG502 | 15 |
| 8092-073G3 | Example 324 | 40 | RG104 | 20 | RG502 | 15 |
| 8092-074G | Example 324 | 40 | RG104 | 20 | RG502 | 15 |
| 8092-075G | Example 324 | 40 | RG104 | 20 | RG502 | 15 |
| 7526-164G | Example 355 | 15 | RG752S | 85 | n/a | n/a |
| 7526-165G | Example 355 | 15 | RG755 | 85 | n/a | n/a |
| 7526-166G | Example 355 | 50 | RG752S | 50 | n/a | n/a |
| 7526-167G | Example 355 | 50 | RG755 | 50 | n/a | n/a |
| 7526-168G | Example 355 | 30 | RG502 | 70 | n/a | n/a |
| 7526-169G | Example 355 | 30 | RG505 | 70 | n/a | n/a |
| 7526-170G | Example 355 | 40 | Rg752s | 30 | RG504 | 30 |
| 7526-171G | Example 355 | 40 | RG755 | 30 | RG504 | 30 |
| 8328-046G | Example 355 | 45 | RG755 | 45 | n/a | n/a |
| 8328-047G | Example 355 | 45 | RG755 | 45 | n/a | n/a |
| 8387-001G | Example 355 | 50 | RG755 | 50 | n/a | n/a |
| 8092-156G | Example 378 | 15 | RG752S | 85 | | |
| 8092-157G | Example 378 | 50 | RG752S | 50 | | |
| 8092-158G | Example 378 | 50 | RG755 | 50 | | |

-continued

| Formulation Notebook Number | | | | | Nozzel Used (micrometer) | Extrusion Temperature (degrees centigrade) | Processing |
|---|---|---|---|---|---|---|---|
| 8092-159G | Example 378 | 40 | R104 | 20 | RG502 | 15 | |
| 8092-160G | Example 378 | 40 | R104 | 20 | RG502 | 15 | |
| 8092-161G | Example 378 | 40 | R104 | 40 | RG502 | 20 | |

| Formulation Notebook Number | Polymer 3 | % Polymer 3 | Additive | % Additive | Nozzel Used (micrometer) | Extrusion Temperature (degrees centigrade) | Processing |
|---|---|---|---|---|---|---|---|
| 7526-122G | n/a | n/a | n/a | n/a | 400 | 87 | n/a |
| 7526-123G | n/a | n/a | n/a | n/a | 400 | 90 | n/a |
| 7526-124G | n/a | n/a | n/a | n/a | 420 | 97 | n/a |
| 7526-125G | n/a | n/a | n/a | n/a | 400 | 90 | n/a |
| 7526-126G | n/a | n/a | n/a | n/a | 400 | 97 | n/a |
| 7526-127G | n/a | n/a | n/a | n/a | 400 | 92 | n/a |
| 7526-128G | n/a | n/a | n/a | n/a | 420 | 94 | n/a |
| 7526-129G | n/a | n/a | n/a | n/a | 400 | 98 | n/a |
| 8092-089G | n/a | n/a | n/a | n/a | 420 | 81 | n/a |
| 8092-090G | n/a | n/a | n/a | n/a | 400 | 92 | n/a |
| 8092-091G | n/a | n/a | n/a | n/a | 400 | 102 | n/a |
| 8092-015G | n/a | n/a | n/a | n/a | 480 | 75 | n/a |
| 8092-016G | RG502H | 25 | n/a | n/a | 440 | 75 | n/a |
| 8092-017G | n/a | n/a | Mg(OH)2 | 3 | 500 | 76 | n/a |
| 8092-018G | RG502H | 22 | Mg(OH)2 | 3 | 500 | 75 | n/a |
| 8092-072G | RG502H | 19 | Mg(OH)2 | 6 | 500 | 77 | Milled TKI with additive first |
| 8092-073G1 | RG502H | 19 | CaCO3 | 6 | 480 | 68 | Milled TKI with additive first |
| 8092-073G2 | RG502H, | 19 | CaCO3 | 6 | 480 | 68 | n/a |
| 8092-073G3 | RG502H | 19 | CaCO3 | 6 | 480 | 68 | n/a |
| 8092-074G | RG502H, | 19 | Mannitol | 6 | 440 | 63 | Milled TKI with additive first |
| 8092-075G | RG502H | 19 | PEG3350 | 6 | 420 | 58 | Milled TKI with additive first |
| 7526-164G | n/a | n/a | n/a | n/a | 500 | 76 | n/a |
| 7526-165G | n/a | n/a | n/a | n/a | 500 | 96 | n/a |
| 7526-166G | n/a | n/a | n/a | n/a | 500 | 81 | n/a |
| 7526-167G | n/a | n/a | n/a | n/a | 500 | 81 | n/a |
| 7526-168G | n/a | n/a | n/a | n/a | 500 | 80 | n/a |
| 7526-169G | n/a | n/a | n/a | n/a | 500 | 79 | n/a |
| 7526-170G | n/a | n/a | n/a | n/a | 500 | 80 | n/a |
| 7526-171G | n/a | n/a | n/a | n/a | 500 | 82 | n/a |
| 8328-046G | n/a | n/a | Mg(OH)2 | 10 | 440 | 91 | n/a |
| 8328-047G | n/a | n/a | MgCO3 | 10 | 440 | 91 | n/a |
| 8387-001G | n/a | n/a | n/a | n/a | 440 | 95.3 | n/a |
| 8092-156G | | | | | 420 | 75 | n/a |
| 8092-157G | | | | | 440 | 75 | n/a |
| 8092-158G | | | | | 420 | 95 | n/a |
| 8092-159G | RG502H | 19 | Mg(OH)2 | 6 | 440 | 76 | n/a |
| 8092-160G | RG502H | 19 | Mannitol | 6 | 420 | 80 | n/a |
| 8092-161G | | | | | 440 | 83 | n/a |

In Table A, Example Number refers to the TKI prepared in the above-numbered example and utilized as the API (active pharmaceutical ingredient) in the ocular implant tested.

The polymers utilized in such ocular implants are as follows:

| Resomer | Monomer ratio | i.v. dL/g (MW) |
|---|---|---|
| RG502 | 50:50 poly (D,L-lactide-co-glycolide) | 0.2 |
| RG502H | 50:50 poly (D,L-lactide-co-glycolide) | 0.2 |
| RG504 | 50:50 poly (D,L-lactide-co-glycolide) | 0.5 |
| RG505 | 50:50 poly (D,L-lactide-co-glycolide) | 0.7 |
| RG509 | 50:50 poly (D,L-lactide-co-glycolide) | 1.6 |
| RG752 | 75:25 poly (D,L-lactide-co-glycolide) | 0.2 |
| RG752S | 50:50 poly (D,L-lactide-co-glycolide) | 0.2 |
| RG755 | 50:50 poly (D,L-lactide-co-glycolide) | 0.6 (40000) |
| R104 | poly (D,L-lactide) | (3500) |

The release rate was determined by the below procedure and certain of the release studies were reported in FIGS. 1 through 3, below.

The in vitro release study was carried out in an incubator at 37° C. shaking at 120 rpm.

The release medium was 0.02% Polysorbate 80 containing 10 mM phosphate buffered saline, pH7.4. The medium and implants were placed in 20 mL scintillation vials. At given time points, the medium containing released drug was collected and replaced with fresh medium. The concentration of the compound in the release medium was analyzed using HPLC.

The results reported in FIG. 1 show that 2,5-Dimethyl-2H-pyrazole-3-carboxylic acid (3-{2-oxo-3-[(4-pyrrolidin-1-yl-methyl-phenylamino)-methylene]-2,3-dihydro-1H-indole-6-carbonyl}-phenyl)-amide (Example 206) may be formulated into an ocular composite that releases from about 10 to about 60 microgram of the TKI within 30 days. The above results are equivalent to a release of from 2-12% of the TKI from the ocular implant in 30 days. Also, it can be seen that this TKI can be formulated into an ocular composite that continues to release the TKI for more then six (6) months.

The results reported in FIG. 2 show that 4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid (Example 324) may be formulated into an ocular composite that releases from about 2 to about 10 ug. of the TKI within 30 days. The above results are equivalent to a release of 2-8% of the TKI within 30 days. Also, it can be seen that this TKI can be formulated into an ocular composite that continues to release the TKI for more then six (6) months.

The results reported in FIG. 3 show that 3-{4-[(6-{3-[(3-Methyl-furan-2-carbonyl)-amino]-benzoyl}-2-oxo-1,2-dihydro-indol-3-ylidenemethyl)-amino]-phenyl}-propionic acid, sodium salt (Example 378) may be formulated into an ocular composite that releases from about 130 to about 160 ug. of the TKI within 10 days. The above results are equivalent to a release of 29-35% of the TKI within 30 days. Also, it can be seen that this TKI can be formulated into a ocular composite that continues to release the TKI for more then six (6) months.

As a result of the testing of the composites of this invention it has been found that the most preferred composites are exemplified by a formulation comprising of 50% RG755 (polymer) and 50% of the TKI compound of Example 378. This formulation releases Example 378 at a rate between 7 microgram per day and 2.5 microgram per day for approximately 50 days with a minimal burst release at day 1.

Another preferred composite of the present invention comprises of 50% RG504 polymer and 50% of Example 206. This formulation releases Example 206 at a rate between 5 microgram per day and 0.5 microgram per day for approximately 50 days with a minimal burst release at day 1.

All references cited herein are hereby incorporated by reference in their entirety.

The foregoing description details specific methods and compositions that can be employed to practice the present invention, and represents the best mode contemplated. However, it is apparent for one of ordinary skill in the art that further compositions with the desired pharmacological properties can be prepared in an analogous manner. Similarly, different pharmaceutical compositions may be prepared and used with substantially the same result. Thus, however detailed the foregoing may appear in text, it should not be construed as limiting the overall scope hereof.

The invention claimed is:
1. An ocular implant comprising:
a tyrosine kinase inhibitor and a polymer matrix that releases drug at a rate effective to sustain release of an amount of the tyrosine kinase inhibitor from the implant for at least about one week after the implant is placed in an eye, wherein said tyrosine kinase inhibitor is a compound
represented by the following general formula:

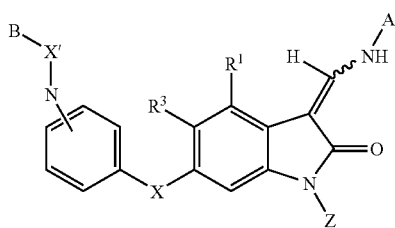

I

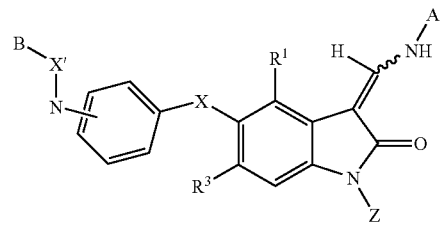

II wherein
X is selected from the group consisting of C=O, C=S, $CR^4R^5$, O, S, NH, and $NR^4$;
Z is selected from the group consisting of hydrogen, $C_1$ to $C_8$ alkyl, phenyl, hydroxymethyl, —$CH_2$—N(—$CH_2CH_2W\ CH_2CH_2$—), $COCH_3$, $CH_2CH_2OH$, and $CH_2CH_2CH_2OH$;
W is selected from the group consisting of O, S, $CH_2$ and $NCH_3$;
$R^1$ is selected from the group consisting of hydrogen and $CH_3$;
$R^3$ is selected from the group consisting of hydrogen, halogen, $C_1$ to $C_8$ alkyl, phenyl, hydroxymethyl, $COCH_3$, $CH_2CH_2OH$, $CH_2CH_2CH_2OH$ and $[C(R^2)_2]_cN(R^2)_2$, wherein $R^2$ is selected from the group consisting of hydrogen, halogen, $NO_2$, CN, $C_1$ to $C_4$ alkyl or aryl, and $N(R^2)_2$ may form a 3 to 7 membered heterocyclic ring, and said heterocyclic ring may be substituted with one or more of $R^2$; and $[C(R^2)_2]_c$ may form a 3 to 7 membered carbocyclic or heterocyclic ring;
$R^4$ and $R^5$ may be selected from the group consisting of hydrogen, halogen, $NO_2$, CN, $C_1$ to $C_8$ alkyl and aryl; or $CR^4R^5$ may form a 3 to 7 membered carbocyclic or heterocyclic ring;
A is

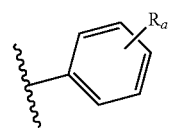

wherein,
R is selected from the group consisting of hydrogen, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, $HN$—$C(O)OR^2$, $(CR^7R^8)_cOC(O)(CR^7R^8)_cN(R^2)_2$, $(CR^7R^8)_cN(R^2)_2$, $SO_2$ $(CR^7R^8)_cN(R^2)_2$, $OP(O)(OR^2)_2$, $OC(O)OR^2$, $OCH_2O$, HN—CH=CH, —$N(COR^2)CH_2CH_2$, HC=N—NH, N=CH—S, $O(CR^7R^8)_d$—$R^6$, $(CR^7R^8)_c$—$R^6$ and $(CR^7R^8)_cNR_2(CR^7R^8)_dR^6$ wherein $R^6$ is selected from the group consisting of halogen, 3-fluoropyrrolidinyl, piperidinyl, 4-fluoropiperidinyl, N-methylpiperazinyl, 2,6-dimethylmorpholinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl) ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, and ethanolamine; provided said alkyl or phenyl radicals may be substituted with one or two halo, hydroxy or lower alkyl amino radicals or said alkyl radicals may include enchained nitrogen or oxygen atoms, and wherein $R^7$ and $R^8$ may be selected from the group consisting of H, hydroxyl, halogen, and $C_1$ to $C_4$ alkyl and $CR^7R^8$ may form a carbocyclic ring of from 3 to 6 carbons;

X' is selected from the group consisting of

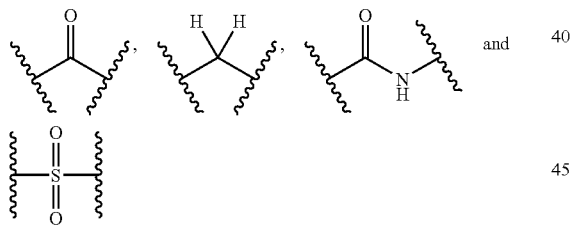

and

B may be selected from the group consisting of hydrogen, hydroxy, $C_1$ to $C_8$ alkyl, aryl and $CR^4R^5$ wherein $CR^4R^5$ may form a 3 to 7 membered carbocyclic or heterocyclic ring;

a is 0 or an integer of from 1 to 5, preferably 1 to 3;

c is 0 or an integer of from 1 to 4, d is an integer of from 2 to 5;

the wavy line represents a E or Z bond and pharmaceutically acceptable salts thereof.

2. The implant of claim 1 wherein said polymer is a biodegradable polymer.

3. The implant of claim 1 wherein X is C=O or $CR^4R^5$.

4. The implant of claim 1 wherein $R^4$ and $R^5$ are hydrogen.

5. The implant of claim 1 wherein B is a 5 or 6 membered aryl radical represented by formula III below:

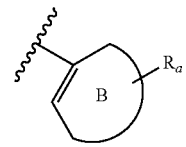

wherein said aryl radical is selected from the group consisting of:

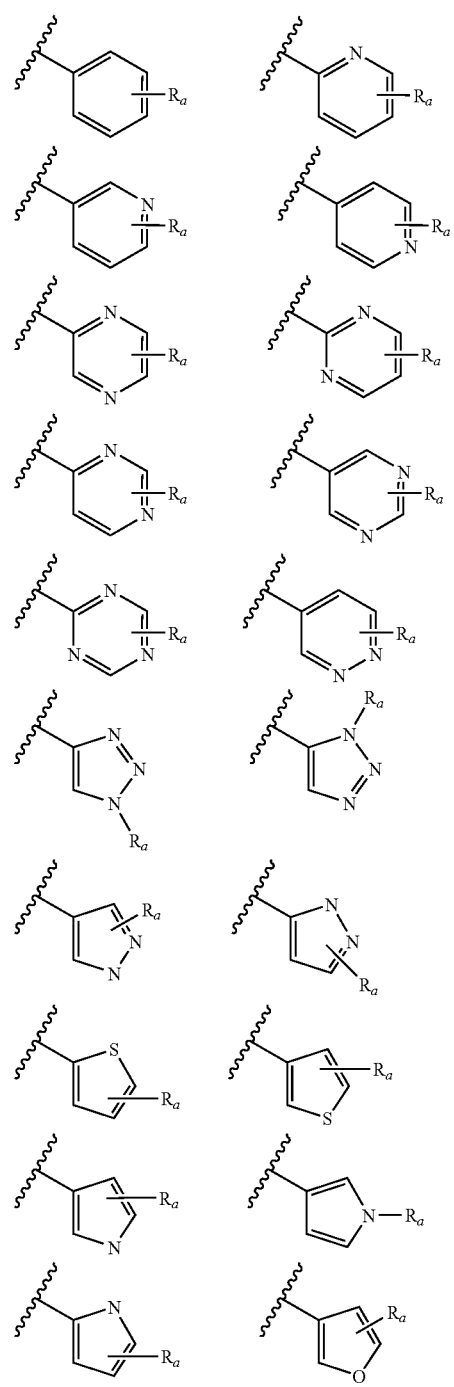

-continued

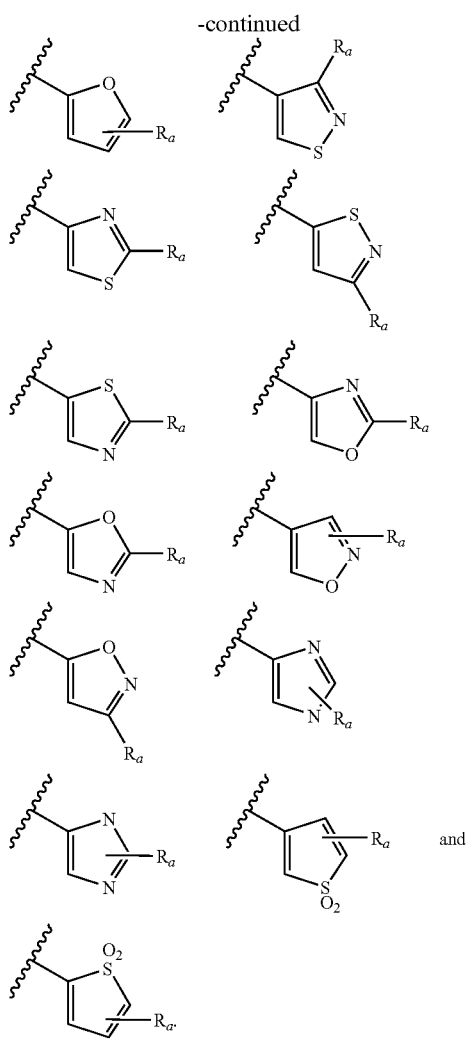

6. The implant of claim 1, further comprising an additional ophthalmically acceptable therapeutic agent.

7. The implant of claim 1, wherein the tyrosine kinase inhibitor is dispersed within the biodegradable polymer matrix.

8. The implant of claim 1, wherein the matrix comprises at least one polymer selected from the group consisting of polylactides, poly (lactide-co-glycolides), polycaprolactones, and mixtures thereof.

9. The implant of claim 1, wherein the polymeric carrier is a poly-lactide-co-glycolide (PLGA) polymer.

10. The implant of claim 2, wherein the biodegradable polymer matrix is a PLGA.

11. The implant of claim 1 wherein the polymer matrix is a viscous aqueous carrier.

12. The implant of claim 11, wherein the polymer matrix is a hyaluronic acid.

13. The implant of claim 1, wherein the polymer matrix comprises a polymer selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, and combinations thereof.

14. The implant of claim 1, wherein the implant comprises a first portion comprising a mixture of the tyrosine kinase inhibitor and a biodegradable polymer, and a different second portion comprising a biodegradable polymer substantially free of the tyrosine kinase inhibitor.

15. The implant of claim 1, wherein the matrix comprises a single type of polymer, and the implant releases the tyrosine kinase inhibitor for about 70 days at a substantially linear rate.

16. The implant of claim 1, wherein the matrix releases drug at a rate effective to sustain release of an amount of the tyrosine kinase inhibitor from the implant for more than one month from the time the implant is placed in the vitreous of the eye.

17. The implant of claim 1, wherein the implant is structured to be placed in the vitreous of the eye.

18. The implant of claim 1, wherein the tyrosine kinase inhibitor is provided in an amount from about 40% by weight to about 70% by weight of the implant, and the biodegradable polymer matrix comprises a poly (lactide-co-glycolide) in an amount from about 30% by weight to about 60% by weight of the implant.

19. The implant of claim 1 formed as a rod, a wafer, or a particle.

20. The implant of claim 1 which is formed by an extrusion process.

21. The implant of claim 1 wherein said compound is selected from the group consisting of
2,5-Dimethyl-2H-pyrazole-3-carboxylic acid (3-{2-oxo-3-[(4-pyrrolidin-1-ylmethyl-phenylamino)-methylene]-2,3-dihydro-1H-indole-6-carbonyl}-phenyl)-amide
3-{4-[(6-{3-[(3-Methyl-furan-2-carbonyl)-amino]-benzoyl}-2-oxo-1,2-dihydro-indol-3-ylidenemethyl)-amino]-phenyl}-propionic acid
4-{4-[(6-{3-[(2,5-Dimethyl-2H-pyrazole-3-carbonyl)-amino]-benzoyl}-2-oxo-1,2-dihydro-indol-3-ylidenemethyl)-amino]-phenyl}-butyric acid.

22. A method of treating an ocular condition of an eye of a patient, comprising the step of placing a biodegradable intraocular implant in an eye of the patient, the implant comprising a tyrosine kinase inhibitor and a biodegradable polymer matrix, wherein the implant degrades at a rate effective to sustain release of an amount of the tyrosine kinase inhibitor from the implant effective to treat the ocular condition and the tyrosine kinase inhibitor the compound of claim 1.

23. The method of claim 22, wherein the method is effective to treat a retinal ocular condition.

24. The method of claim 22, wherein the ocular condition is glaucoma.

25. The method of claim 22, wherein the ocular condition is proliferative vitreoretinopathy.

26. The method of claim 22, wherein the implant is placed in the posterior of the eye.

27. The method of claim 22, wherein the implant is placed in the eye with a trocar.

28. The method of claim 22, wherein the implant is placed in the eye with a syringe.

29. The method of claim 22, further comprising a step of administering a therapeutic agent in addition to the tyrosine kinase inhibitor to the patient.

30. The implant of claim 1 wherein said compound is a pharmaceutically acceptable salt.

31. The implant of claim 30 wherein said compound is 3-{4-[(6-{3-[(3-Methyl-furan-2-carbonyl)-amino]-benzoyl}-2-oxo-1,2-dihydro-indol-3-ylidenemethyl)-amino]-phenyl}-propionic acid, sodium salt.

* * * * *

UNITED STATES PATENT AND TRADEMARK OFFICE
CERTIFICATE OF CORRECTION

PATENT NO. : 7,749,530 B2
APPLICATION NO. : 12/317469
DATED : July 6, 2010
INVENTOR(S) : Lon T. Spada et al.

It is certified that error appears in the above-identified patent and that said Letters Patent is hereby corrected as shown below:

Title page, Item (56), in column 2, under "Other Publications", line 5, delete "Oncogen" and insert -- Oncogene --, therefor.

In column 1, line 12, after "reference" insert -- . --.

In column 2, line 49-50, delete "Oncogen" and insert -- Oncogene --, therefor.

In column 3, line 31, after "pH 7.4" insert -- . --.

In column 3, line 35-36, after "pH 7.4" insert -- . --.

In column 4, line 51-52, delete "$(CR^7R^8)N(R^2)_2$" and insert -- $(CR^7R^8)_cN(R^2)_2$ --, therefor.

In column 4, line 52, delete "$(CR^7R^8)_cN(R^2)_2$" and insert -- $(CR^7R^8)_cN(R^2)_2,$ --, therefor.

In column 5, line 47, delete "e.g" and insert -- e.g. --, therefor.

In column 7, line 20, after "thereof" insert -- . --.

In column 8, line 41, delete "Opthalmol" and insert -- Ophthalmol --, therefor.

In column 9, line 5, delete "serpignous" and insert -- serpiginous --, therefor.

In column 9, line 12, delete "telangiectasis," and insert -- telangiectasia, --, therefor.

In column 9, line 44, delete "veal" and insert -- uveal --, therefor.

In column 11, line 47, delete "e.g" and insert -- e.g. --, therefor.

In column 16, line 56, after "solution" insert -- ; --.

Signed and Sealed this

Twenty-sixth Day of October, 2010

David J. Kappos
*Director of the United States Patent and Trademark Office*

In column 17, line 7, after "phase" insert -- ; --.

In column 17, line 20, after "suspension" insert -- ; --.

In column 18, line 27, delete "The" and insert -- the --, therefor.

In column 26, line 34, after "Formula I" insert -- . --.

In column 141, line 63, delete "(2 mL," and insert -- (21 mL, --, therefor.

In column 145, line 10, delete "(4.4 mL," and insert -- (4.41 mL, --, therefor.

In column 154, line 10-11, delete "(0.78 mL," and insert -- (0.781 mL, --, therefor.

In column 156, line 15, delete "-H-" and insert -- -1H- --, therefor.

In column 169, line 57, after "vacuo" insert -- . --.

In column 311, line 8, delete "diispropyl" and insert -- diisopropyl --, therefor.

In column 312, line 17, delete "(0.7 mL," and insert -- (0.71 mL, --, therefor.

In column 324, line 30, delete "(0.20 mL," and insert -- (0.201 mL, --, therefor.

In column 329, line 20, delete "(6.2 mL," and insert -- (6.21 mL, --, therefor.

In column 331, line 20, delete "(0.62 mL," and insert -- (0.621 mL, --, therefor.

In column 333, line 52, delete "6-[3-" and insert -- 6-{3- --, therefor.

In column 333, line 53, delete "benzoyl]-" and insert -- benzoyl}- --, therefor.

In column 336, line 15-20, delete " " and insert -- --, therefor.

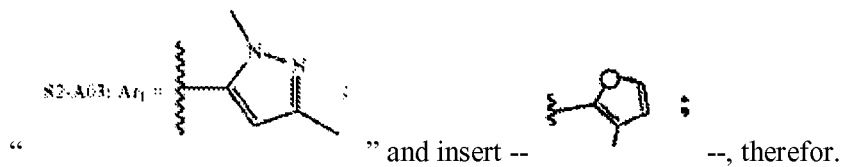

In column 337, line 15, delete " " and insert -- --.

In column 339, line 41, after "377)" insert -- : --.

In column 344, line 54, delete "proprionic" and insert -- propionic --, therefor.

CERTIFICATE OF CORRECTION (continued)
U.S. Pat. No. 7,749,530 B2

In column 346, line 43, after "A14)" insert -- . --.

In column 349-350, line 6, delete "Nozzel" and insert -- Nozzle --, therefor.